US011795223B2

(12) United States Patent
Cao et al.

(10) Patent No.: US 11,795,223 B2
(45) Date of Patent: Oct. 24, 2023

(54) COMBINATION THERAPIES FOR TREATING MYELODYSPLASTIC SYNDROMES AND ACUTE MYELOID LEUKEMIA

(71) Applicant: Forty Seven, Inc., Foster City, CA (US)

(72) Inventors: Yinuo Cao, Mountain View, CA (US); Mark Ping Chao, Mountain View, CA (US); Ravindra Majeti, Palo Alto, CA (US); Roy Louis Maute, Menlo Park, CA (US); Chris Hidemi Mizufune Takimoto, Menlo Park, CA (US); Kelly Tran, East Palo Alto, CA (US)

(73) Assignee: Forty Seven, Inc., Foster City, CA (US)

(*) Notice: Subject to any disclaimer, the term of this patent is extended or adjusted under 35 U.S.C. 154(b) by 48 days.

(21) Appl. No.: 17/072,681

(22) Filed: Oct. 16, 2020

(65) Prior Publication Data
US 2021/0115140 A1 Apr. 22, 2021

Related U.S. Application Data

(60) Provisional application No. 63/031,438, filed on May 28, 2020, provisional application No. 62/944,851, filed on Dec. 6, 2019, provisional application No. 62/916,949, filed on Oct. 18, 2019.

(51) Int. Cl.
*C07K 16/28* (2006.01)
*A61K 31/706* (2006.01)
*A61P 35/02* (2006.01)
*A61K 39/395* (2006.01)
*A61K 39/00* (2006.01)

(52) U.S. Cl.
CPC ........ *C07K 16/2803* (2013.01); *A61K 31/706* (2013.01); *A61P 35/02* (2018.01); *C07K 16/2896* (2013.01); *A61K 39/395* (2013.01); *A61K 2039/505* (2013.01); *A61K 2039/545* (2013.01)

(58) Field of Classification Search
CPC ............ C07K 16/2803; C07K 16/2896; C07K 2317/24; C07K 2317/76; A61K 31/706; A61K 2039/505; A61K 2039/545; A61K 2039/572; A61K 2039/575; A61K 2039/585; A61K 39/39; A61K 45/06; A61K 39/3955; A61K 2300/00; A61P 35/02
See application file for complete search history.

(56) References Cited

U.S. PATENT DOCUMENTS

2016/0008429 A1* 1/2016 Willingham ............ A61P 35/00
424/133.1
2018/0071302 A1 3/2018 Abella et al.

FOREIGN PATENT DOCUMENTS

WO WO-2018/237168 A1 12/2018
WO WO-2021/076908 A1 4/2021

OTHER PUBLICATIONS

NCT03248479, Clinical trial, version published May 30, 2018, https://clinicaltrials.gov/ct2/show/NCT03248479 (Year: 2018).*
Khan C, Pathe N, Fazal S, Lister J, Rossetti JM. Azacitidine in the management of patients with myelodysplastic syndromes. Ther Adv Hematol. Dec. 2012;3(6):355-73. doi: 10.1177/2040620712464882. PMID: 23606938; PMCID: PMC3627328. (Year: 2012).*
Gilead (Gilead, "Magrolimab Demonstrates Clinical Responses in Ongoing Phase 1b Trial of Previously Untreated Acute Myeloid Leukemia Patients", Press Release, Dec. 6, 2020) (Year: 2020).*
Vyas (EHA Library. Jun. 15, 2018; 214718; PF232) (Year: 2018).*
David P. Steensma, Case Study: TP53-Mutated Myelodysplastic Syndrome, Advances in Hematologic Malignancies Issue 9, Fall 2018 (Year: 2018).*
Welch JS et al, TP53 and Decitabine in Acute Myeloid Leukemia and Myelodysplastic Syndromes. N Engl J Med. Nov. 24, 2016;375(21):2023-2036. (Year: 2016).*
Zeidan AM, et al., Phase 1 study of anti-CD47 monoclonal antibody CC-90002 in patients with relapsed/refractory acute myeloid leukemia and high-risk myelodysplastic syndromes. Ann Hematol. Mar. 2022; 101(3):557-569. (Year: 2022).*
Rami S. Komrokji, David A Sallman, Najla Al Ali, Eric Padron, Kendra Sweet, Jeffrey E. Lancet, Alan F List; Outcome of Myelodysplastic Syndrome Patients with TP53 Mutation Treated with Hypomethylating Agents. Blood 2017; 130 (Supplement 1): 1687. (Year: 2017).*
2022. Tolerability and Efficacy of the First-in-Class Anti-CD47 Antibody Magrolimab Combined with Azacitidine in Frontline TP53m AML Patients: Phase 1b Results, American Society of Clinical Oncology 2022 Annual Meeting, Jun. 3-7, 2022, Chicago, IL.
International Search Report for PCT/US2020/056011 (Combination Therapies for Treating Myelodysplastic Syndromes and Acute Myeloid Leukemia, filed Oct. 16, 2020) received by ISA/EP, 5 pages (Jan. 28, 2021).
Sallman, D.A. et al., The first-in-class anti-CD47 antibody Hu5F9-G4 is active and well tolerated alone or with azacititdine in AML and MDS patients: Initial phase 1b results, Journal of Clinical Oncology, 37(15):7009-7009 (2019).

(Continued)

Primary Examiner — Hong Sang
(74) Attorney, Agent, or Firm — Choate, Hall & Stewart LLP; Rolando Medina; Melissa M. Adams

(57) ABSTRACT

Methods, kits, and compositions are provided herein that can be used to treat hematopoietic disorders using an anti-CD47 agent such as an antibody and a hypomethylating agent, such as azacitidine.

12 Claims, 6 Drawing Sheets
Specification includes a Sequence Listing.

(56) References Cited

OTHER PUBLICATIONS

Sallman, David A., Case Presentation: ManagingTP53-MutantMDS, Clinical Lymphoma Myeloma and Leukemia, 19(1):S73-S74 (2014).
Written Opinion for PCT/US2020/056011 (Combination Therapies for Treating Myelodysplastic Syndromes and Acute Myeloid Leukemia, filed Oct. 16, 2020) received by ISA/EP, 6 pages (Jan. 28, 2021).
2022, Magrolimab in Combination with Azacitidine for Untreated Higher Risk Myelodysplastic Syndrome (HR-MDS): 5F9005 Phase 1b Study Results, Presented at American Society of Clinical Oncology, Jun. 3-7, Chicago, IL.
2022, Magrolimab in Combination with Azacitidine for Untreated Higher Risk Myelodysplastic Syndrome (HR-MDS): 5F9005 Phase 1b Study Results, Presented at the Society of Hematological Oncology, Sep. 28-Oct. 1, Houston, TX.
2022, Tolerability and Efficacy of the First-in-Class Anti-CD47 Antibody Magrolimab Combined with Azacitidine in Patients with Frontline TP53m AML: Phase 1b Results, Presented at the Society of Hematological Oncology, Sep. 28-Oct. 1, Houston, TX.
Montalban-Bravo, G. and Garcia-Manero, G., Myelodysplastic syndromes: 2018 update on diagnosis, risk-stratification and management, Am J Hematol., 93:129-147 (2018).
Sallman, D. A. et al., Magrolimab in combination with azacitidine in patients with higher-risk myelodysplastic syndromes: final results of a phase Ib study, Journal of Clinical Oncology, 12 pages, (2023).
Sallman, D.A. et al., The first-in-class anti-CD47 antibody magrolimab (5F9) in combination with azacitidine is effective in MDS and AML patients: ongoing phase 1B results, Blood, 134 (Supplemental_1): 569, 4 pages, (2019).

\* cited by examiner

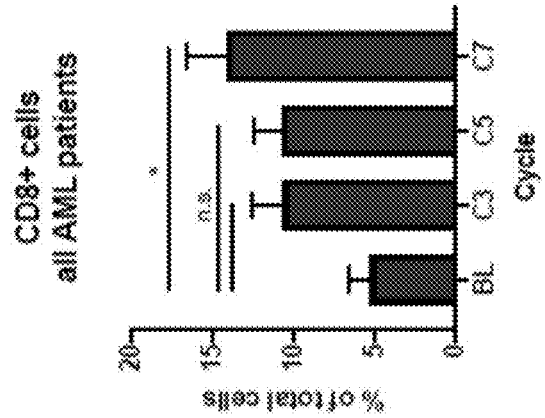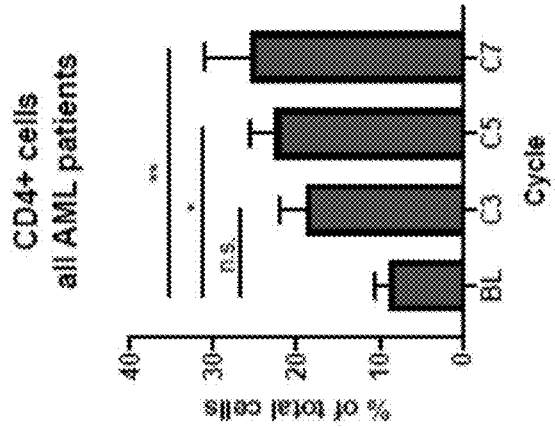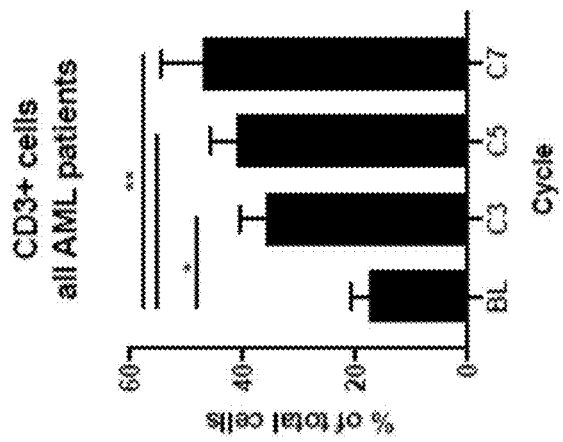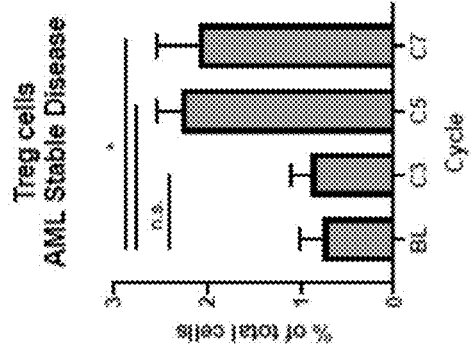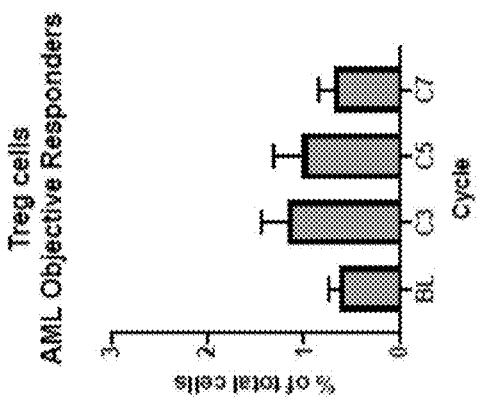

COMBINATION THERAPIES FOR TREATING MYELODYSPLASTIC SYNDROMES AND ACUTE MYELOID LEUKEMIA

CROSS REFERENCE TO RELATED APPLICATIONS

This application claims benefit of U.S. Provisional Application No. 62/916,949, filed Oct. 18, 2019; U.S. Provisional Application No. 62/944,851, filed Dec. 6, 2019; and U.S. Provisional Application No. 63/031,438, filed May 28, 2020; each of which is hereby incorporated by reference in its entirety for all purposes.

SEQUENCE LISTING

The instant application contains a Sequence Listing which has been submitted via EFS-Web and is hereby incorporated by reference in its entirety. Said ASCII copy, created on Oct. 9, 2020, is named FSI-006_P3C_SL, and is 145,290 bytes in size.

BACKGROUND

CD47 has been identified as a key molecule mediating cancer cell evasion of phagocytosis by the innate immune system. CD47 appears to be an important means by which cancer cells, including cancer stem cells, overcome oftentimes intrinsic expression of their prophagocytic, "eat me," signals. The progression from normal cell to cancer cell can involve changes in genes and/or gene expression that trigger programmed cell death (PCD) and programmed cell removal (PCR). Many of the steps in cancer progression subvert multiple mechanisms of PCD, and expression of anti-phagocytic signal, CD47, may represent an important checkpoint.

CD47 serves as the ligand for SIRPα, which is expressed on phagocytic cells including macrophages and dendritic cells. When SIRPα is activated by CD47 binding, it initiates a signal transduction cascade resulting in inhibition of phagocytosis. In this way, CD47 functions as an anti-phagocytic signal by delivering a dominant inhibitory signal to phagocytic cells.

Acute myeloid leukemia (AML) is a common hematological malignancy whose incidence rises from 3:100,000 in young adults to greater than 20:100,000 in older adults. For patients <60 years of age, overall survival (OS) is 40 to 50%, but is only 5% for patients >60 years of age. The majority of newly diagnosed patients with AML are over the age of 60. In this patient population, standard induction chemotherapy is often not an option due to increased treatment-related mortality as a result of age and co-morbidities. Standard of care for AML patients unfit for combination chemotherapy is treatment with hypomethylating agents (azacitidine or decitabine) or low dose cytarabine. Despite these frontline treatments, median OS is only about 10 months. In all types of AML, disease relapse is common despite an initial therapeutic response and is the most common reason for death. Standard chemotherapy and allogeneic stem cell transplant (when used) often fail to eradicate all tumor-propagating cells and select for chemotherapy-resistant leukemia-propagating subclones. Patients refractory to salvage therapy are treated palliatively, as current treatment options are extremely limited. These patients have a median survival of 2 months. In addition, patients with newly diagnosed intermediate or higher-risk myelodysplastic syndrome (MDS) and those who relapse after standard care have a poor prognosis and high risk of progression to AML. Therefore, there is an urgent need for new treatment modalities for relapsed/refractory (R/R) AML and MDS patients, newly diagnosed AML patients ineligible for induction chemotherapy based on age and co-morbidities, and newly diagnosed intermediate/high/very high risk MDS patients.

SUMMARY

In one aspect, provided herein are methods of treating a hematopoietic disorder in a subject, wherein the subject has at least one p53 mutation, comprising: (a) administering an isolated antibody that inhibits binding between CD47 and SIRPα; and (b) administering a hypomethylating agent to the subject.

In one aspect, provided herein are methods of treating a hematopoietic disorder in a subject comprising: (a) administering an isolated antibody that inhibits binding between CD47 and SIRPα; and (b) administering a hypomethylating agent to the subject, wherein the subject is determined or has been determined to have at least one p53 mutation.

In one aspect, provided herein are methods of treating a hematopoietic disorder in a subject comprising: determining or having determined the presence of at least one p53 mutation in the subject; and administering or having administered to the subject (i) an isolated antibody that inhibits binding between CD47 and SIRPα and (ii) a hypomethylating agent.

In some embodiments, determining the presence of at least one p53 mutation comprises a DNA assay, an RNA assay or a protein assay.

In some embodiments, if the at least one p53 mutation is present, the antibody and a hypomethylating agent are administered to the subject.

In some embodiments, the antibody is an anti-CD47 antibody or an anti-SIRPα antibody.

In some embodiments, the anti-CD47 antibody is administered to the subject at a dose of greater than or equal to 10 mg of antibody per kg of body weight.

In some embodiments, the hypomethylating agent is azacitidine or decitabine.

In some embodiments, the hypomethylating agent is azacitidine.

In some embodiments, the hematopoietic disorder is a blood pre-cancer.

In some embodiments, the hematopoietic disorder is a blood cancer.

In some embodiments, the hematopoietic disorder is myelodysplastic syndrome (MDS).

In some embodiments, the hematopoietic disorder is acute myeloid leukemia (AML).

In some embodiments, the hematopoietic disorder is clonal hematopoiesis (CH), clonal hematopoiesis of indeterminant potential (CHIP), age-related clonal hematopoiesis (ARCH), idiopathic cytopenias of undetermined significance (ICUS), or clonal cytopenia of undetermined significance (CCUS).

In some embodiments, the p53 mutation comprises at least one of a missense mutation, a nonsense mutation, a frameshift mutation, an intronic mutation, a truncating mutation, a mutation in the DNA binding domain, or a mutation in the tetramerization domain.

In some embodiments, the p53 mutation comprises a mutation in the DNA binding domain.

In some embodiments, the subject is relapsed or refractory to at least 1, 2, 3, 4, 5, 6, 7, 8, 9, 10 or greater than 10 prior lines of cancer therapy.

In some embodiments, the anti-CD47 antibody comprises Hu5F9-G4.

In some embodiments, the anti-CD47 antibody consists of Hu5F9-G4.

In some embodiments, the anti-SIRPα antibody comprises at least one of Hu1H9-G1, Hu1H9-G4, Hu3C2-G1, Hu3C2-G4, 9B11-G1, 9B11-G4, 7E11-G1, and 7E11-G4.

In some embodiments, the anti-SIRPα antibody consists of an antibody selected from the group consisting of Hu1H9-G1, Hu1H9-G4, Hu3C2-G1, Hu3C2-G4, 9B11-G1, 9B11-G4, 7E11-G1, and 7E11-G4.

In some embodiments, the anti-CD47 antibody is administered at a dose of at least 10-30, 20-30, 10, 15, 20, or 30 mg of antibody per kg of body weight.

In some embodiments, the antibody is administered intravenously.

In some embodiments, the azacitidine is administered at a dose of at least 75 mg/m$^2$.

In some embodiments, the azacitidine is administered intravenously, subcutaneously, or orally.

In some embodiments, the anti-CD47 antibody is administered to the subject in a first cycle comprising a priming dose of at least 1 mg of antibody per kg of body weight on days 1 and 4, followed by a dose of at least 15 mg of antibody per kg of body weight on day 8, and followed by a dose of at least 30 mg of antibody per kg of body weight on day 15.

In some embodiments, the anti-CD47 antibody is administered to the subject in a first cycle comprising a priming dose of at least 1 mg of antibody per kg of body weight on days 1 and 4, followed by a dose of at least 15 mg of antibody per kg of body weight on day 8, and followed by a dose of at least 30 mg of antibody per kg of body weight once every week on days 15 and 22.

In some embodiments, the method further comprises a loading dose of at least 30 mg of antibody per kg of body weight on day 11.

In some embodiments, the first cycle is 4 weeks in duration.

In some embodiments, the azacitidine is administered to the subject at a dose of at least 75 mg/m2 on each of days 1-7 of the first cycle.

In some embodiments, the azacitidine is administered to the subject at a dose of at least 75 mg/m2 on each of days 1-5 of the first cycle.

In some embodiments, the anti-CD47 antibody is administered to the subject in a second cycle comprising a dose of at least 30 mg of antibody per kg of body weight once every four weeks.

In some embodiments, the anti-CD47 antibody is administered to the subject in a second cycle comprising a dose of at least 30 mg of antibody per kg of body weight once every two weeks.

In some embodiments, the anti-CD47 antibody is administered to the subject in a second cycle comprising a dose of at least 30 mg of antibody per kg of body weight once every week.

In some embodiments, the anti-CD47 antibody is administered to the subject in a second cycle comprising a dose of at least 30 mg of antibody per kg of body weight twice weekly.

In some embodiments, wherein the second cycle is 4 weeks in duration.

In some embodiments, the anti-CD47 antibody is administered to the subject in a third cycle comprising a dose of at least 30 mg of antibody per kg of body weight once every four weeks.

In some embodiments, the anti-CD47 antibody is administered to the subject in a third cycle comprising a dose of at least 30 mg of antibody per kg of body weight once every two weeks.

In some embodiments, the anti-CD47 antibody is administered to the subject in a third cycle comprising a dose of at least 30 mg of antibody per kg of body weight once every week.

In some embodiments, the anti-CD47 antibody administered to the subject in a third cycle comprising a dose of at least 30 mg of antibody per kg of body weight twice weekly.

In some embodiments, the anti-CD47 antibody is administered to the subject in a first cycle comprising a priming dose of at least 1 mg of antibody per kg of body weight on day 1, followed by a dose of at least 30 mg of antibody per kg of body weight on days 8, 15, and 22.

In some embodiments, the anti-CD47 antibody is administered to the subject in a second cycle comprising a dose of at least 60 mg of antibody per kg of body weight once every two weeks on day 1 and 15.

In some embodiments, the second cycle is 4 weeks in duration.

In some embodiments, the azacitidine is administered to the subject at a dose of at least 75 mg/m2 on each of days 1-7 of the second cycle.

In some embodiments, the azacitidine is administered to the subject at a dose of at least 75 mg/m2 on each of days 1-5 of the second cycle.

In some embodiments, the anti-CD47 antibody administered to the subject in a third cycle comprising a dose of at least 60 mg of antibody per kg of body weight once every four weeks.

In some embodiments, the third cycle is 4 weeks in duration.

In some embodiments, the azacitidine is administered to the subject at a dose of at least 75 mg/m2 on each of days 1-7 of the third cycle.

In some embodiments, the azacitidine is administered to the subject at a dose of at least 75 mg/m2 on each of days 1-5 of the third cycle.

In some embodiments, the subject is or has been determined to be refractory to azacitidine, decitabine, or cytarabine prior to administration of the antibody and the method results in a reversal of refractoriness to azacitidine, decitabine, or cytarabine.

In some embodiments, the administration of the antibody and hypomethylating agent reduces the p53 mutational burden in the subject relative to the p53 mutational burden present in the subject prior to the administration.

In some embodiments, the method further comprises assessing the p53 mutational burden in the subject after at least one cycle of administration of the antibody and the hypomethylating agent.

In some embodiments, the method further comprises administering at least an additional cycle of the antibody and the hypomethylating agent if the p53 mutational burden has decreased.

In some embodiments, the administration of the antibody and hypomethylating agent reduces the level of leukemia stem cells present in the bone marrow of the subject as compared to the level of leukemia stem cells present in the bone marrow of the subject before the administration.

In some embodiments, the method further comprises assessing the level of leukemia stem cells present in the bone marrow of the subject after at least one cycle of administration of the antibody and the hypomethylating agent.

In some embodiments, the method further comprises administering at least an additional cycle of the antibody and the hypomethylating agent if the amount of leukemia stem cells has decreased.

In some embodiments, the subject is a human subject, and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on days 11, 15, and 22, and (4) administering a dose of at least 75 mg/m2 of azacitidine on each of days 1-7; and the second cycle comprising (1) administering a dose of at least 30 mg of anti-CD47 antibody per kg of body weight once every week on days 1, 8, 15, and 22, and (2) administering a dose of at least 75 mg/m2 of azacitidine on each of days 1-7.

In some embodiments, the second cycle is repeated as one or more additional cycles without limit or until a clinical benefit is reduced or lost or no longer observed.

In some embodiments, a third cycle of four weeks comprises (1) administering a dose of at least 30 mg of anti-CD47 antibody per kg of body weight once every two weeks on days 1 and 15, and (2) administering a dose of at least 75 mg/m2 of azacitidine on each of days 1-7.

In some embodiments, a third cycle of four weeks comprises (1) administering a dose of at least 30 mg of anti-CD47 antibody per kg of body weight once every week on days 1, 8, 15, and 22 and (2) administering a dose of at least 75 mg/m2 of azacitidine on each of days 1-7.

In some embodiments, the third cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In some embodiments, the subject is a human subject, and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on days 15 and 22, and (4) administering a dose of at least 75 mg/m2 of azacitidine on each of days 1-7; and the second cycle comprising (1) administering a dose of at least 30 mg of anti-CD47 antibody per kg of body weight once every week on days 1, 8, 15, and 22, and (2) administering a dose of at least 75 mg/m2 of azacitidine on each of days 1-7.

In some embodiments, the second cycle is repeated as one or more additional cycles without limit or until a clinical benefit is reduced or lost or no longer observed.

In some embodiments, a third cycle of four weeks comprises (1) administering a dose of at least 30 mg of anti-CD47 antibody per kg of body weight once every two weeks on days 1 and 15, and (2) administering a dose of at least 75 mg/m2 of azacitidine on each of days 1-7.

In some embodiments, the third cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In some embodiments, the subject is a human subject, and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1, (2) administering a dose of at least 30 mg of anti-CD47 antibody per kg of body weight on Days 8, 15, and 22, and (3) administering a dose of at least 75 mg/m2 of azacitidine on each of days 1-7; and the second cycle comprising (1) administering a dose of at least 60 mg of anti-CD47 antibody per kg of body weight once every two weeks on days 1 and 15, (2) administering a dose of at least 75 mg/m2 of azacitidine on each of days 1-7.

In some embodiments, the second cycle is repeated as one or more additional cycles without limit or until a clinical benefit is reduced or lost or no longer observed.

In some embodiments, a third cycle of four weeks comprises (1) administering a dose of at least 60 mg of anti-CD47 antibody per kg of body weight once every four weeks on day 1, and (2) administering a dose of at least 75 mg/m2 of azacitidine on each of days 1-7.

In some embodiments, the third cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In some embodiments, the subject is a human subject, and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1, (2) administering a dose of at least 30 mg of anti-CD47 antibody per kg of body weight on Days 8, 15, and 22, and (3) administering a dose of at least 75 mg/m$^2$ of azacitidine on each of days 1-7; and the second cycle comprising (1) administering a dose of at least 60 mg of anti-CD47 antibody per kg of body weight once every four weeks on day 1, and (2) administering a dose of at least 75 mg/m$^2$ of azacitidine on each of days 1-7. In some embodiments, the anti-CD47 antibody is administered intravenously. In some embodiments, the subject has low risk MDS. In some embodiments, the second cycle is repeated as one or more additional cycles without limit or until a clinical benefit is reduced or lost or no longer observed.

In some embodiments, the subject is a human subject, and the method comprises administering the anti-CD47 antibody and the azacitidine to the subject for at least two distinct cycles of four weeks each, the first cycle comprising (1) administering a priming dose of anti-CD47 antibody in the range of 80 mg to 800 mg (e.g., 80 mg to 400 mg, e.g., 80 mg to 200 mg, e.g., 80 mg, 100 mg, 160 mg, 200 mg, 240 mg, 320 mg, 400 mg) on Day 1, (2) administering a dose of at least 2400 mg of anti-CD47 antibody on Days 8, 15, and 22, and (3) administering a dose of at least 75 mg/m$^2$ of azacitidine on each of days 1-7; and the second cycle comprising (1) administering a dose of at least 4800 mg of anti-CD47 antibody once every four weeks on day 1, and (2) administering a dose of at least 75 mg/m² of azacitidine on each of days 1-7. In some embodiments, the anti-CD47 antibody is administered intravenously. In some embodiments, the subject has low risk MDS. In some embodiments, the second cycle is repeated as one or more additional cycles without limit or until a clinical benefit is reduced or lost or no longer observed.

In some embodiments, the subject is a human subject, and the method comprises administering the anti-CD47 antibody and the azacitidine to the subject for at least three distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on one or both of days 11 and 15; and 22, and (4) administering a dose of at least 75 mg/m² of azacitidine on each of days 1-7; the second cycle comprising (1) administering a dose of at least 30 mg of anti-CD47 antibody per kg of body weight once every week on days 1, 8, 15, and 22, and (2) administering a dose of at least 75 mg/m² of azacitidine on each of days 1-7; and the third cycle comprising (1) administering a dose of at least 30 mg of anti-CD47 antibody per kg of body weight once every week on days 1 and 15, and (2) administering a dose of at least 75 mg/m² of azacitidine on each of days 1-7. In some embodiments, the anti-CD47 antibody is administered intravenously. In some embodiments, the subject has high risk MDS or AML. In some embodiments, the third cycle is repeated as one or more additional cycles without limit or until a clinical benefit is reduced or lost or no longer observed. In some embodiments, the subject is a human subject, and the method comprises administering the anti-CD47 antibody and the azacitidine to the subject for at least three distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 30 mg of anti-CD47 antibody per kg of body weight on Days 8, 15, and 22, and (3) administering a dose of at least 75 mg/m² of azacitidine on each of days 1-7; the second cycle comprising (1) administering a dose of at least 30 mg of anti-CD47 antibody per kg of body weight once every week on days 1, 8, 15, and 22, and (2) administering a dose of at least 75 mg/m² of azacitidine on each of days 1-7; and the third cycle comprising (1) administering a dose of at least 30 mg of anti-CD47 antibody per kg of body weight once every week on days 1 and 15, and (2) administering a dose of at least 75 mg/m² of azacitidine on each of days 1-7. In some embodiments, the anti-CD47 antibody is administered intravenously. In some embodiments, the subject has high risk MDS or AML. In some embodiments, the third cycle is repeated as one or more additional cycles without limit or until a clinical benefit is reduced or lost or no longer observed.

In some embodiments, a fourth cycle of four weeks comprises (1) administering a dose of at least 30 mg of anti-CD47 antibody per kg of body weight once every two weeks on days 1 and 15, and (2) administering a dose of at least 75 mg/m² of azacitidine on each of days 1-7.

In some embodiments, the fourth cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In some embodiments, the subject is a human subject, and the method comprises administering the anti-CD47 antibody and the azacitidine to the subject for at least three distinct cycles of four weeks each, the first cycle comprising (1) administering a priming dose of anti-CD47 antibody in the range of 80 mg to 800 mg (e.g., 80 mg to 400 mg, e.g., 80 mg to 200 mg, e.g., 80 mg, 100 mg, 160 mg, 200 mg, 240 mg, 320 mg, 400 mg) on Day 1 and 4, (2) administering a dose of at least 1200 mg of anti-CD47 antibody on day 8, (3) administering a dose of at least 2400 mg of anti-CD47 antibody on days 15 and 22, and (4) administering a dose of at least 75 mg/m² of azacitidine on each of days 1-7; the second cycle comprising (1) administering a dose of at least 2400 mg of anti-CD47 antibody per kg of body weight once every week on days 1, 8, 15, and 22, and (2) administering a dose of at least 75 mg/m² of azacitidine on each of days 1-7; and the third cycle comprising (1) administering a dose of at least 2400 mg of anti-CD47 antibody once every other week on days 1 and 15, and (2) administering a dose of at least 75 mg/m² of azacitidine on each of days 1-7. In some embodiments, the anti-CD47 antibody is administered intravenously. In some embodiments, the subject has high risk MDS or AML. In some embodiments, the third cycle is repeated as one or more additional cycles without limit or until a clinical benefit is reduced or lost or no longer observed.

In some embodiments, the subject is a human subject having a myelodysplastic syndrome (MDS), wherein the wherein the subject has at least one p53 mutation, and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on days 11, 15, and 22, and (4) administering a dose of at least 75 mg/m2 of azacitidine on each of days 1-7; and the second cycle comprising (1) administering a dose of at least 30 mg of anti-CD47 antibody per kg of body weight once every week on days 1, 8, 15, and 22, and (2) administering a dose of at least 75 mg/m2 of azacitidine on each of days 1-7.

In some embodiments, the second cycle is repeated as one or more additional cycles without limit or until a clinical benefit is reduced or lost or no longer observed.

In some embodiments, a third cycle of four weeks comprises (1) administering a dose of at least 30 mg of anti-CD47 antibody per kg of body weight once every four weeks on day 1, and (2) administering a dose of at least 75 mg/m2 of azacitidine on each of days 1-7.

In some embodiments, a third cycle of four weeks comprises (1) administering a dose of at least 30 mg of anti-CD47 antibody per kg of body weight once every two weeks on days 1 and 15, and (2) administering a dose of at least 75 mg/m2 of azacitidine on each of days 1-7.

In some embodiments, a third cycle of four weeks comprises (1) administering a dose of at least 30 mg of anti-CD47 antibody per kg of body weight once every week on days 1, 8, 15, and 22 and (2) administering a dose of at least 75 mg/m2 of azacitidine on each of days 1-7.

In some embodiments, the third cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In some embodiments, the subject is a human subject having acute myeloid leukemia (AML), wherein the subject has at least one p53 mutation and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on days 11, 15, and 22, and (4) administering a dose of at least 75 mg/m2 of azacitidine on each of days 1-7; and the second cycle comprising (1) administering a dose of at least 30 mg of anti-CD47 antibody per kg of body weight once every week on days 1, 8, 15, and 22, and (2) administering a dose of at least 75 mg/m2 of azacitidine on each of days 1-7.

In some embodiments, the second cycle is repeated as one or more additional cycles without limit or until a clinical benefit is reduced or lost or no longer observed.

In some embodiments, a third cycle of four weeks comprises (1) administering a dose of at least 30 mg of anti-CD47 antibody per kg of body weight once every four weeks on day 1, and (2) administering a dose of at least 75 mg/m2 of azacitidine on each of days 1-7.

In some embodiments, a third cycle of four weeks comprises (1) administering a dose of at least 30 mg of anti-CD47 antibody per kg of body weight once every two weeks on days 1 and 15, and (2) administering a dose of at least 75 mg/m2 of azacitidine on each of days 1-7.

In some embodiments, a third cycle of four weeks comprises (1) administering a dose of at least 30 mg of anti-CD47 antibody per kg of body weight once every week on days 1, 8, 15, and 22 and (2) administering a dose of at least 75 mg/m2 of azacitidine on each of days 1-7.

In some embodiments, the third cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In another aspect, provided herein are methods of treating a hematopoietic disorder in a subject, wherein the subject is a human subject, wherein the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on days 15 and 22, and (4) administering a dose of at least 75 mg/m$^2$ of azacitidine on each of days 1-7; and the second cycle comprising (1) administering a dose of at least 30 mg of anti-CD47 antibody per kg of body weight once every week on days 1, 8, 15, and 22, and (2) administering a dose of at least 75 mg/m$^2$ of azacitidine on each of days 1-7.

In some embodiments, the second cycle is repeated as one or more additional cycles without limit or until a clinical benefit is reduced or lost or no longer observed.

In some embodiments, a third cycle of four weeks comprises (1) administering a dose of at least 30 mg of anti-CD47 antibody per kg of body weight once every four weeks on day 1.

In some embodiments, a third cycle of four weeks comprises (1) administering a dose of at least 30 mg of anti-CD47 antibody per kg of body weight once every two weeks on days 1 and 15.

In some embodiments, a third cycle of four weeks comprises (1) administering a dose of at least 30 mg of anti-CD47 antibody per kg of body weight once every week on days 1, 8, 15, and 22.

In some embodiments, the third cycle of four weeks further comprises administering a dose of at least 75 mg/m$^2$ of azacitidine on each of days 1-7.

In some embodiments, the third cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In another aspect, provided herein are methods of treating a hematopoietic disorder in a subject, wherein the subject is a human subject, and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1, (2) administering a dose of at least 30 mg of anti-CD47 antibody per kg of body weight on Days 8, 15, and 22, and (3) administering a dose of at least 75 mg/m$^2$ of azacitidine on each of days 1-7; and the second cycle comprising (1) administering a dose of at least 60 mg of anti-CD47 antibody per kg of body weight once every two weeks on days 1 and 15, (2) administering a dose of at least 75 mg/m$^2$ of azacitidine on each of days 1-7.

In some embodiments, the second cycle is repeated as one or more additional cycles without limit or until a clinical benefit is reduced or lost or no longer observed.

In some embodiments, a third cycle of four weeks comprises (1) administering a dose of at least 60 mg of anti-CD47 antibody per kg of body weight once every four weeks on day 1.

In some embodiments, a third cycle of four weeks comprises (1) administering a dose of at least 60 mg of anti-CD47 antibody per kg of body weight once every two weeks on days 1 and 15.

In some embodiments, a third cycle of four weeks comprises (1) administering a dose of at least 60 mg of anti-CD47 antibody per kg of body weight once every week on days 1, 8, 15, and 22.

In some embodiments, the third cycle of four weeks further comprises administering a dose of at least 75 mg/m$^2$ of azacitidine on each of days 1-7.

In another aspect, provided herein are methods of treating a hematopoietic disorder in a subject comprising: determining or having determined a T cell infiltration level in the bone marrow in the subject; and administering or having administered to the subject (i) an isolated antibody that inhibits binding between CD47 and SIRPα and (ii) a hypomethylating agent.

In some embodiments, determining the T cell infiltration level comprises a DNA assay, an RNA assay or a protein assay.

In some embodiments, the assay is selected from the group consisting of: T cell receptor sequencing, reverse transcription quantitative polymerase chain reaction, RNA sequencing, RNA hybridization, fluorescence-based flow cytometry, time of flight mass cytometry, or immunoblot.

In some embodiments, the administration of the antibody and hypomethylating agent alters the T cell infiltration level in the bone marrow as compared to the T cell infiltration level in the bone marrow before administration.

In some embodiments, the administration increases the T cell infiltration level and the T cells are CD8+ CTLs or CD4+T helper (Th) cells.

In some embodiments, the administration decreases the T cell infiltration level and the T cells are FOXP3$^+$ Treg cells.

In some embodiments, the administration decreases the level of FOXP3$^+$ Treg cells in the T cell infiltration in the bone marrow.

In some embodiments, the administration decreases the in situ development of FOXP3+ Treg cells in the bone marrow.

In some embodiments, the method further comprises assessing the T cell infiltration level in the bone marrow in the subject after at least one cycle of administration of the antibody and the hypomethylating agent.

In some embodiments, the method further comprises administering at least an additional cycle of the antibody and the hypomethylating agent if the T cell infiltration level in the bone marrow has been increased and the T cells are CD8+ CTLs or CD4+T helper (Th) cells.

In some embodiments, the method further comprises administering at least an additional cycle of the antibody and the hypomethylating agent if the T cell infiltration level in the bone marrow has been decreased and the T cells are FOXP3$^+$ Treg cells.

In some embodiments, the antibody is an anti-CD47 antibody or an anti-SIRPα antibody.

In some embodiments, the anti-CD47 antibody is administered to the subject at a dose of greater than or equal to 1 mg of antibody per kg of body weight.

In some embodiments, the hypomethylating agent is azacitidine or decitabine.

In some embodiments, the hematopoietic disorder is a blood pre-cancer or a blood cancer.

In some embodiments, the hematopoietic disorder is acute myeloid leukemia (AML) or myelodysplastic syndrome (MDS).

In some embodiments, the subject is a human subject, wherein the T cell infiltration level in the bone marrow of the subject is or has been determined subject, and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on days 11, 15, and 22, and (4) administering a dose of at least 75 mg/m$^2$ of azacitidine on each of days 1-7; and the second cycle comprising (1) administering a dose of at least 30 mg of anti-CD47 antibody per kg of body weight once every week on days 1, 8, 15, and 22, and (2) administering a dose of at least 75 mg/m$^2$ of azacitidine on each of days 1-7.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 6A shows an increase in total T cells after Hu5F9-G4 and azacytidine therapy. FIG. 6B shows an increase in CD4+ T cells after Hu5F9-G4 and azacytidine therapy. FIG. 6C shows an increase in CD8+ T cells after Hu5F9-G4 and azacytidine therapy. FIG. 6D shows no significant change in Treg T cells in the objective responder population after Hu5F9-G4 and azacytidine therapy. FIG. 6E shows a significant increase in Treg T cells in the stable disease population after Hu5F9-G4 and azacytidine therapy.

DETAILED DESCRIPTION

Definitions

Figure 1:
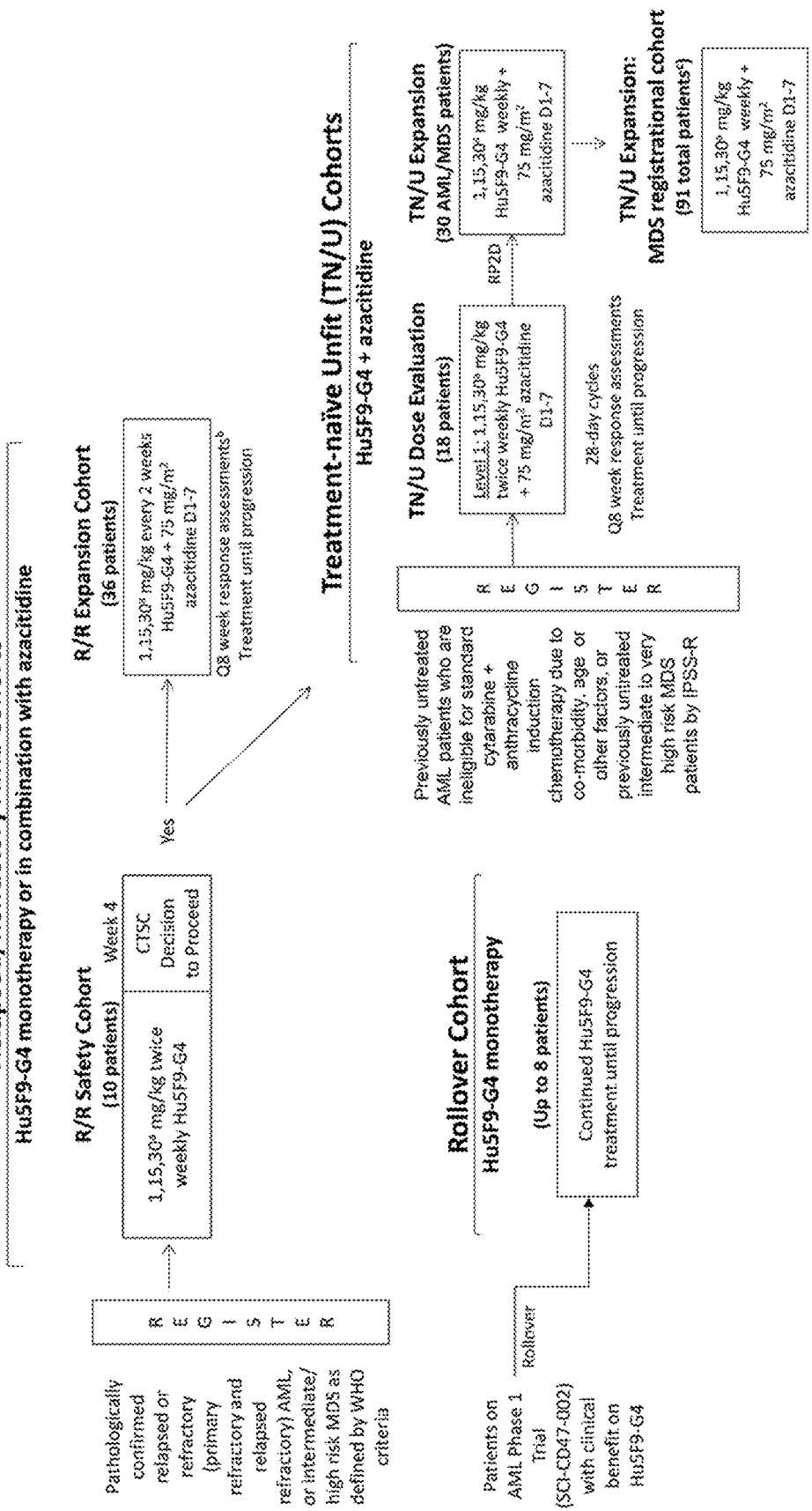
FIG. 1 shows the study design schema for a Phase 1b Trial of Hu5F9-G4 Monotherapy or Hu5F9-G4 in Combination with Azacitidine in Patients with Hematological Malignancies.

Terms used in the claims and specification are defined as set forth below unless otherwise specified.

The term "ameliorating" refers to any therapeutically beneficial result in the treatment of a disease state, e.g., a cancer disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

Antibodies

The methods described herein include administration of an antibody or antibodies, e.g., administration of an anti-CD47 antibody or an anti-SIRPα antibody. As described above, the term "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')2, Fab, Fv and rIgG). The term also refers to recombinant single chain Fv fragments (scFv). The term antibody also includes bivalent or bispecific molecules, diabodies, triabodies, and tetrabodies.

An antibody for use in the methods as described herein includes antibodies that inhibit binding between CD47 and SIRPα. In some embodiments, an antibody that inhibits binding between CD47 and SIRPα is an anti-CD47 antibody. In some embodiments, an antibody that inhibits binding between CD47 and SIRPα is an anti-SIRPα antibody. In some embodiments, an anti-CD47 antibody as disclosed herein is used to inhibit binding between CD47 and SIRPα. In some embodiments, an anti-SIRPα antibody as disclosed herein is used to inhibit binding between CD47 and SIRPα. In some embodiments, an antibody that inhibits binding between CD47 and SIRPα is a monoclonal antibody.

Selection of antibodies may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

In some embodiments, the antibodies provided herein comprise an antibody fragment. In some embodiments, the antibodies provided herein consist of an antibody fragment. In some embodiments, the antibodies provided herein consist essentially of an antibody fragment. In some aspects, the antibody fragment is an Fv fragment. In some aspects, the antibody fragment is a Fab fragment. In some aspects, the antibody fragment is a F(ab')2 fragment. In some aspects, the antibody fragment is a Fab' fragment. In some aspects, the antibody fragment is an scFv (sFv) fragment. In some aspects, the antibody fragment is an scFv-Fc fragment. In some aspects, the antibody fragment is a fragment of a single domain antibody.

In some embodiments, an antibody fragment provided herein is derived from an illustrative antibody provided herein. In some embodiments, an antibody fragments provided herein is not derived from an illustrative antibody provided herein and may, for example, be isolated de novo according to the methods provided herein for obtaining antibody fragments.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

In some embodiments, the antibodies provided herein comprise a light chain. In some aspects, the light chain is a kappa light chain. In some aspects, the light chain is a lambda light chain.

In some embodiments, the antibodies provided herein comprise a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

As an alternative to the use of an antibody comprising a human Fc region with reduced affinity for an Fcγ receptor, an antibody can be engineered to lack Fc sequences, e.g., by producing an antibody fragment such as a F(ab')2 fragment. To generate an F(ab)2 fragment, the purified antibody is suspended with Pierce F(ab')2 Preparation pepsin immobilized on settled resin, according to the manufacturer's instructions. Pepsin digestion typically produces a F(ab')2 fragment (110 kDa by SDS-PAGE under non-reducing conditions) and numerous small peptides of the Fc portion. The resulting F(ab')2 fragment is composed of a pair of Fab' units connected by two disulfide bonds. The Fc fragment is extensively degraded and separated from F(ab')2 by dialysis, gel filtration, or ion exchange chromatography.

In certain aspects, an antibody comprises a human Fc region comprising at least one modification that reduces binding to a human Fc receptor.

In some embodiments, the antibodies provided herein are monoclonal antibodies. In some embodiments, the antibodies provided herein are polyclonal antibodies.

In some embodiments, the antibodies provided herein comprise a chimeric antibody. In some embodiments, the antibodies provided herein consist of a chimeric antibody. In some embodiments, the antibodies provided herein consist essentially of a chimeric antibody. In some embodiments, the antibodies provided herein comprise a humanized antibody. In some embodiments, the antibodies provided herein consist of a humanized antibody. In some embodiments, the antibodies provided herein consist essentially of a humanized antibody. In some embodiments, the antibodies provided herein comprise a human antibody. In some embodiments, the antibodies provided herein consist of a human antibody. In some embodiments, the antibodies provided herein consist essentially of a human antibody.

In some embodiments, the antibodies provided herein comprise an alternative scaffold. In some embodiments, the antibodies provided herein consist of an alternative scaffold. In some embodiments, the antibodies provided herein consist essentially of an alternative scaffold. Any suitable alternative scaffold may be used. In some aspects, the alternative scaffold is selected from an Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer.

Antibodies of interest may be tested for their ability to induce ADCC (antibody-dependent cellular cytotoxicity) or ADCP (antibody dependent cellular phagocytosis). Antibody-associated ADCC activity can be monitored and quantified through detection of either the release of label or lactate dehydrogenase from the lysed cells, or detection of reduced target cell viability (e.g. Annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.).

In some embodiments, the methods described herein include administration of antibodies with sequences described herein; e.g., the heavy chain, light chain, and/or CDR sequences described herein. The sequences of the administered antibodies can be, e.g., at least 95, 96, 97, 98, 99, or 100% identical to the sequences described herein.

It is known that when an antibody is expressed in cells, the antibody is modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (See Journal of Pharmaceutical Sciences, 2008, Vol. 97, p. 2426-2447, incorporated by reference in its entirety). In some embodiments, an antibody is an antibody or antigen-binding fragment thereof which has undergone posttranslational modification. Examples of an antibody or antigen-binding fragment thereof which have undergone posttranslational modification include an antibody or antigen-binding fragments thereof which have undergone pyroglutamylation at the N terminal of the heavy chain variable region and/or deletion of lysine at the C terminal of the heavy chain. It is known in the art that such posttranslational modification due to pyroglutamylation at the N terminal and deletion of lysine at the C terminal does not have any influence on the activity of the antibody or fragment thereof (Analytical Biochemistry, 2006, Vol. 348, p. 24-39, incorporated by reference in its entirety).

In some embodiments, the Fc region or Fc domain of the directed antibody comprise amino acid modifications that promote an increased serum half-life of the anti-binding molecule. Mutations that increase the half-life of an antibody have been described. In one embodiment, the Fc region or Fc domain of one or both of the CD3-targeting heavy chain and the HIV antigen-targeting heavy chain comprise a methionine to tyrosine substitution at position 252 (EU numbering), a serine to threonine substitution at position 254 (EU numbering), and a threonine to glutamic acid substitution at position 256 (EU numbering). See, e.g., U.S. Pat. No. 7,658,921. This type of mutant, designated as a "YTE mutant" exhibits a four-fold increased half-life relative to wild-type versions of the same antibody (Dall'Acqua, et al., J Biol Chem, 281: 23514-24 (2006); Robbie, et al., Antimicrob Agents Chemotherap., 57(12):6147-6153 (2013)). In certain embodiments, the Fc region or Fc domain of one or both of the CD3-targeting heavy chain and the HIV antigen-targeting heavy chain comprise an IgG constant domain comprising one, two, three or more amino acid substitutions of amino acid residues at positions 251-257, 285-290, 308-314, 385-389, and 428-436 (EU numbering). Alternatively, M428L and N434S ("LS") substitutions can increase the pharmacokinetic half-life of the multi-specific antigen binding molecule. In other embodiments, the Fc region or Fc domain of one or both of the CD3-targeting heavy chain and the HIV antigen-targeting heavy chain comprise a M428L and N434S substitution (EU numbering). In other embodiments, the Fc region or Fc domain of one or both of the CD3-targeting heavy chain and the HIV antigen-targeting heavy chain comprise T250Q and M428L (EU numbering) mutations. In other embodiments, the Fc region or Fc domain of one or both of the CD3-targeting heavy chain and the HIV antigen-targeting heavy chain comprise H433K and N434F (EU numbering) mutations.

In some embodiments, the Fc region or Fc domain of the antibody comprise posttranslational and/or amino acid modifications that increase effector activity, e.g., have improved FcγIIIa binding and increased antibody-dependent cellular cytotoxicity (ADCC). In some embodiments, the Fc region or Fc domain of the antibody comprises DE modifications (i.e., S239D and I332E by EU numbering) in the Fc region. In some embodiments, the Fc region or Fc domain of the antibody comprises DEL modifications (i.e., S239D, I332E and A330L by EU numbering) in the Fc region. In some embodiments, the Fc region or Fc domain of the antibody comprises DEA modifications (i.e., S239D, I332E and G236A by EU numbering) in the Fc region. In some embodiments, the Fc region or Fc domain of the antibody comprises DEAL modifications (i.e., S239D, I332E, G236A and A330L by EU numbering) in the Fc region. See, e.g., U.S. Pat. Nos. 7,317,091; 7,662,925; 8,039,592; 8,093,357; 8,093,359; 8,383,109; 8,388,955; 8,735,545; 8,858,937; 8,937,158; 9,040,041; 9,353,187; 10,184,000; and 10,584, 176. Additional amino acid modifications that increase effector activity, e.g., have improved FcγIIIa binding and increased antibody-dependent cellular cytotoxicity (ADCC) include without limitation (EU numbering) F243L/R292P/ Y300L/V305I/P396L; S298A/E333A/K334A; or L234Y/ L235Q/G236W/S239M/H268D/D270E/S298A on a first Fc domain and D270E/K326D/A330M/K334E on a second Fc domain. Amino acid mutations that increase C1q binding and complement-dependent cytotoxicity (CDC) include without limitation (EU numbering) S267E/H268F/S324T or K326W/E333S. Fc region mutations that enhance effector activity are reviewed in, e.g., Wang, et al., *Protein Cell* (2018) 9(1): 63-73; and Saunders, *Front Immunol.* (2019) 10:1296.

In other embodiments, the antibody or antigen-binding fragment thereof has modified glycosylation, which, e.g., may be introduced post-translationally or through genetic engineering. In some embodiments, the antibody or antigen-binding fragment thereof is afucosylated, e.g., at a glycosylation site present in the antibody or antigen-binding fragment thereof. Most approved monoclonal antibodies are of the IgG1 isotype, where two N-linked biantennary complex-type oligosaccharides are bound to the Fc region. The Fc region exercises the effector function of ADCC through its interaction with leukocyte receptors of the FcγR family. Afucosylated monoclonal antibodies are monoclonal antibodies engineered so that the oligosaccharides in the Fc region of the antibody do not have any fucose sugar units.

Anti-CD47 Agents

The methods described herein include administration of an anti-CD47 agent. In some embodiments, the anti-CD47 agent is an anti-CD47 antibody.

CD47 (IAP, MER6, OA3; NCBI Gene ID: 961; UniProt Q08722) is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2008) Mol Cell. 31(2):266-77; Hatherley et al. (2007) J.B.C. 282:14567-75; and the role of SIRPα cis dimerization in CD47 binding is discussed by Lee et al. (2010) J.B.C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

The term "anti-CD47 agent" or "agent that provides for CD47 blockade" refers to any agent that reduces the binding of CD47 (e.g., on a target cell) to a CD47 ligand such as SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

In some embodiments, the subject anti-CD47 antibody specifically binds CD47 and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα and such an antibody can be referred to as a "non-blocking anti-CD47 antibody." A suitable anti-CD47 antibody that is an "anti-CD47 agent" can be referred to as a "CD47-blocking antibody". Non-limiting examples of suitable antibodies include clones B6H12, 5F9, 8B6, and C3 (for example as described in International Patent Publication WO2011143624, published Jan. 19, 2012, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

In some embodiments an anti-CD47 antibody comprises a human IgG Fc region, e.g. an IgG1, IgG2a, IgG2b, IgG3, IgG4 constant region. In one embodiment the IgG Fc region is an IgG4 constant region. The IgG4 hinge may be stabilized by the amino acid substitution S241P (see Angal et al. (1993) Mol. Immunol. 30(1):105-108, herein specifically incorporated by reference).

In some embodiments, the anti-CD47 antibody competes for binding to CD47 with Hu5F9-G4. In some embodiments, the anti-CD47 binds to the same CD47 epitope as Hu5F9-G4.

In some embodiments, an antibody binds human CD47 with a KD of less than or equal to about 1, 1-6, 1-5, 1-4, 1-3, 2, 3, 4, 5, 6, 7, 8, 9, or $10 \times 10^{-9}$ M, as measured by Biacore assay.

In some embodiments, an anti-CD47 antibody is administered at a dose of 10-30, 20-30, 10, 20, or 30 mg of antibody per kg of body weight.

In some embodiments, an anti-CD47 antibody results in greater than or equal to 90% receptor saturation, optionally 90-100, 90, 91, 92, 93, 94, 95, 96, 97, 98, 99, or 100% receptor saturation, optionally wherein receptor saturation is measured using flow cytometry or an equivalent assay.

An anti-CD47 antibody can be formulated in a pharmaceutical composition with a pharmaceutically acceptable excipient.

An anti-CD47 antibody can be administered intravenously.

An anti-CD47 agent can include a SIRPα agent that includes SIRPα or a portion thereof. For example, an anti-CD47 agent can include a SIRPα-based Fc fusion. See, e.g., Kipp Weiskopf, et al. Science 341, 88 (2013), herein incorporated by reference.

An anti-CD47 agent can include a SIRPα agent disclosed in WO2014094122, herein incorporated by reference, in its entirety, for all purposes. For example, a SIRPα agent can include the sequence of SEQ ID NO: 3, 25, or 26 as disclosed in WO2014094122; each of which is herein incorporated by reference.

An anti-CD47 agent can include a SIRPα agent disclosed in WO2017177333, herein incorporated by reference, in its entirety, for all purposes. For example, a SIRPα agent can include the sequence of SEQ ID NO: 3 or 8 as disclosed in WO2017177333; each of which is herein incorporated by reference.

An anti-CD47 agent can include a SIRPα agent disclosed in WO2016023040, herein incorporated by reference, in its entirety, for all purposes. For example, a SIRPα agent can include the sequence of SEQ ID NO: 78-85, 98-104, 107-113, 116-122, 135-137, or 152-159 as disclosed in WO2016023040; each of which is herein incorporated by reference.

An anti-CD47 agent can include a SIRPα agent disclosed in WO2017027422, herein incorporated by reference, in its entirety, for all purposes. For example, a SIRPα agent can include the sequence of SEQ ID NO: 3-34 as disclosed in WO2017027422; each of which is herein incorporated by reference.

CD47 Antibodies

In some embodiments, the methods described herein include administration of the anti-CD47 antibody Hu5F9-G4. Hu5F9-G4 is also known as magrolimab. In some embodiments, the methods described herein include administration of the anti-CD47 antibody magrolimab. In some embodiments, the methods described herein include administration of an anti-CD47 antibody with sequences (light chain, heavy chain, variable light chain domain, variable heavy chain domain, and/or CDR) at least 97%, at least 98%, at least 99% or 100% identical to the sequences of Hu5f9-G4. Table 1 contains the sequence of the Hu5f9-G4 antibody heavy and light chains (SEQ ID NOs: 50 and 51, respectively), the VH and VL CDRs according to the Kabat CDR definition (SEQ ID NOs: 52-57 and 133), the VH and VL CDRs according to the IMGT CDR definition (SEQ ID NOs: 134-139), the VH and VL CDRs according to the Chothia CDR definition (SEQ ID NOs: 140-145), the VH and VL CDRs according to the Honegger CDR definition (SEQ ID NOs: 146-151), and the variable heavy and light chain sequences (SEQ ID NOs: 131 and 132). Further suitable anti CD-47 antibodies include clones B6H12, 5F9, 8B6, C3, and huC3 (for example as described in International Patent Publication WO2011143624, herein specifically incorporated by reference). The 5F9 variable heavy chain domain is provided as SEQ ID NO: 58, and the 5F9 variable light chain domain is provided as SEQ ID NO: 59. The HuB6H12 variable heavy chain domain is provided as SEQ ID NO: 60, and the HuB6H12 variable light chain domain is provided as SEQ ID NO: 61. The 8B6 variable heavy chain domain is provided as SEQ ID NO: 62, and the HuB6H12 variable light chain domain is provided as SEQ ID NO: 63. The C3 variable heavy chain domain is provided as SEQ ID NO: 64, and the C3 variable light chain domain is provided as SEQ ID NO: 65. HuC3 variable heavy chain domains are provided as SEQ ID NO: 66 and 67, and huC3 variable light chain domains are provided as SEQ ID NO: 68 and 69. An anti-CD47 antibody can comprise: a heavy chain sequence of SEQ ID NO: 50 and a light chain of sequence of SEQ ID NO: 51. An anti-CD47 antibody can comprise: a VH sequence of SEQ ID NO: 58 and a VL sequence of SEQ ID NO: 59. An anti-CD47 antibody can comprise: a VH sequence of SEQ ID NO: 60 and a VL sequence of SEQ ID NO: 61. An anti-CD47 antibody can comprise: a VH sequence of SEQ ID NO: 62 and a VL sequence of SEQ ID NO: 63. An anti-CD47 antibody can comprise: a VH sequence of SEQ ID NO: 64 and a VL sequence of SEQ ID NO: 65. An anti-CD47 antibody can comprise: a VH sequence of SEQ ID NO: 66 or 67 and a VL sequence of SEQ ID NO: 68 or 69.

Anti-CD47 antibody heavy chain variable regions are disclosed as SEQ ID NOs: 5-30 and anti-CD47 antibody light chain variable regions are disclosed as SEQ ID NOs: 31-47 in U.S. Patent Publication US 20140140989, published May 22, 2014, and International Patent Publication WO2013119714, published Aug. 15, 2013, both of which are herein incorporated by reference in their entirety. Suitable anti-CD47 variable heavy chain domains are provided as SEQ ID NOs: 70-95 and anti-CD47 variable light chain domains are provided as SEQ ID NOs: 96-112. An anti-CD47 antibody can comprise a VH sequence of SEQ ID NO: 70-95. An anti-CD47 antibody can comprise a VL sequence of SEQ ID NO: 96-112. An anti-CD47 antibody can comprise a VH sequence of SEQ ID NO: 70-95 and a VL sequence of SEQ ID NO: 96-112.

An anti-CD47 antibody can comprise a VH sequence of SEQ ID NO: 113-115. An anti-CD47 antibody can comprise a VL sequence of SEQ ID NO: 116-118. An anti-CD47 antibody can comprise a VH sequence of SEQ ID NO: 113-115 and a VL sequence of SEQ ID NO: 116-118.

TABLE 1

| SEQ ID NO | Description and Sequence |
|---|---|
| 50 | Hu5f9-G4 Antibody Heavy Chain — QVQLVQSGAEVKKPGASVKVSCKASGYTFTNYNMHWVRQAPGQRLEWMGTIYPGND DTSYNQKFKDRVTITADTSASTAYMELSSLRSEDTAVYYCARGGYRAMDYWGQGTL VTVSSASTKGPSVFPLAPCSRSTSESTAALGCLVKDYFPEPVTVSWNSGALTSGVH TFPAVLQSSGLYSLSSVVTVPSSSLGTKTYTCNVDHKPSNTKVDKRVESKYGPPCP PCPAPEFLGGPSVFLFPPKPKDTLMISRTPEVTCVVVDVSQEDPEVQFNWYVDGVE VHNAKTKPREEQFNSTYRVVSVLTVLHQDWLNGKEYKCKVSNKGLPSSIEKTISKA KGQPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLGK |
| 51 | Hu5f9-G4 Antibody Light chain — DIVMTQSPLSLPVTPGEPASISCRSSQSIVYSNGNTYLGWYLQKPGQSPQLLIYKV SNRFSGVPDRFSGSGSGTDFTLKISRVEAEDVGVYYCFQGSHVPYTFGQGTKLEIK RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 52 | Hu5f9-G4 VH CDR1 — NYNMH |
| 53 | Hu5f9-G4 VH CDR2 — TIYPGNDDTSYNQKFKD |
| 54 | Hu5f9-G4 VH CDR3 — GGYRAMDY |
| 55 | Hu5f9-G4 VL CDR1 — RSSQSIVYSNGNTYL |
| 56 | Hu5f9-G4 VL CDR2 — KVSNRFS |
| 57 | Hu5f9-G4 VL CDR3 — FQGSHVPYT |
| 131 | Hu5f9-G4 VH — QVQLVQSGAEVKKPGASVKVSCKASGYTFTNYNMHWVRQAPGQRLEWMGTIYPGND DTSYNQKFKDRVTITADTSASTAYMELSSLRSEDTAVYYCARGGYRAMDYWGQGTL VTVSS |
| 132 | Hu5f9-G4 VL — DIVMTQSPLSLPVTPGEPASISCRSSQSIVYSNGNTYLGWYLQKPGQSPQLLIYKV SNRFSGVPDRFSGSGSGTDFTLKISRVEAEDVGVYYCFQGSHVPYTFGQGTKLEIK |
| 133 | Hu5f9-G4 VL CDR1 — RSSQSIVYSNGNTYLG |
| 134 | Hu5f9-G4 VH CDR1 — GYTFTNYN |
| 135 | Hu5f9-G4 VH CDR2 — IYPGNDDT |
| 136 | Hu5f9-G4 VH CDR3 — ARGGYRAMDY |
| 137 | Hu5f9-G4 VL CDR1 — QSIVYSNGNTY |
| 138 | Hu5f9-G4 VL CDR2 — KVS |
| 139 | Hu5f9-G4 VL CDR3 — FQGSHVPYT |
| 140 | Hu5f9-G4 VH CDR1 — GYTFTNY |
| 141 | Hu5f9-G4 VH CDR2 — PGND |

TABLE 1-continued

| SEQ ID NO | Description and Sequence |
|---|---|
| 142 | Hu5f9-G4 VH CDR3 GYRAMD |
| 143 | Hu5f9-G4 VL CDR1 SQSIVYSNGNTY |
| 144 | Hu5f9-G4 VL CDR2 KVS |
| 145 | Hu5f9-G4 VL CDR3 GSHVPY |
| 146 | Hu5f9-G4 VH CDR1 ASGYTFTNYN |
| 147 | Hu5f9-G4 VH CDR2 IYPGNDDTSYNQKFKDR |
| 148 | Hu5f9-G4 VH CDR3 GGYRAMD |
| 149 | Hu5f9-G4 VL CDR1 SSQSIVYSNGNTY |
| 150 | Hu5f9-G4 VL CDR2 KVSNRFSGVPDR |
| 151 | Hu5f9-G4 VL CDR3 GSHVPY |

Additional CD47 inhibitors or anti-CD47 agents include, without limitation, anti-CD47 mAbs (Vx-1004), anti-human CD47 mAbs (CNTO-7108), CC-90002, CC-90002-ST-001, humanized anti-CD47 antibody (Hu5F9-G4; magrolimab), NI-1701, NI-1801, RCT-1938, ALX-148, TTI-621, RRx-001, DSP-107, VT-1021, TTI-621, TTI-622, IMM-02, SGN-CD47M, and Lemzoparlimab.

In some embodiments, an anti-CD47 agent comprises a bispecific antibody. In some embodiments, an anti-CD47 agent comprises a bispecific anti-CD47 antibody. Examples of bi-specific antibodies targeting CD47 include, but are not limited to, IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33). Additional monospecific and bispecific anti-CD47 antibodies include, but are not limited to, BI-188, TJC-4, SHR-1603, HLX-24, LQ-001, IMC-002, ZL-1201, IMM-01, B6H12, GenSci-059, TAY-018, PT-240, 1F8-GMCSF, SY-102, and KD-015.

Additional anti-CD47 agents, such as antibodies, are described in WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188 and WO2020009725, each of which are herein incorporated by reference in their entirety.

Anti-SIRPα Agents

The methods described herein include administration of an anti-SIRPα agent or inhibitor.

In some embodiments, the anti-SIRPα agent is an anti-SIRPα antibody that specifically binds to SIRPα. In some aspects, the SIRPα is human SIRPα (NCBI Gene ID: 140885; UniProt P78324).

In some embodiments, the anti-SIRPα agent is a SIRPα inhibitor. Such inhibitors include, but are not limited to, AL-008, RRx-001, and CTX-5861.

In some embodiments, the anti-SIRPα agent is an anti-SIRPα antibodies. Such antibodies include, but are not limited to, FSI-189, ES-004, BI765063, ADU1805, and CC-95251.

Additional anti-SIRPα agents, inhibitors, and antibodies are described in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752, each of which are herein incorporated by reference in their entirety.

In some embodiments, anti-SIRPα antibodies provided herein specifically bind to the extracellular domain of SIRPα. The SIRPα may be expressed on the surface of any suitable target cell. In some embodiments, the target cell is a professional antigen presenting cell. In some embodiments, the target cell is a macrophage. An antibody can be pan-specific for human SIRPα isotypes. An antibody can be specific for a human SIRPα isotype.

In certain embodiments an antibody is 1H9. In certain embodiments an antibody is 3C2.

In some embodiments, an antibody provided herein inhibits binding of SIRPα to one or more ligands of SIRPα.

In certain aspects, an antibody does not bind to SIRPγ. In certain aspects, an antibody does not substantially bind to SIRPγ.

In some embodiments, an antibody fragment provided herein competes for binding to SIRPα with 1H9 and/or 3C2. In some embodiments, a fragment of an antibody provided herein binds the same epitope of SIRPα as such antibody.

In some aspects, an antibody disclosed herein is pan-specific for human SIRPα isotypes. An antibody disclosed herein, such as 1H9, can bind to multiple human SIRPα isotypes including one or more of V1, V2, and V1/V5. Exemplary V1 sequence shown in SEQ ID NO:48. Exemplary V2 sequence shown in SEQ ID NO:49. See also Polymorphism in Sirpa modulates engraftment of human hematopoietic stem cells. Nature Immunology, 8; 1313, 2007. An antibody disclosed herein can bind to each of human SIRPα isotypes V1 and V2. An antibody disclosed herein can bind to human SIRPα isotype V1, including homozygous. An antibody disclosed herein can bind to human SIRPα isotype V2, including homozygous. An antibody disclosed herein can bind to human SIRPα isotypes V1/V5 (heterozygous). An antibody disclosed herein, such as 1H9, can bind to multiple human SIRPα isotypes including each of V1, V2, and V1/V5. Such antibodies can include 1H9 and 3C2, including humanized and/or Fc engineered versions of such antibodies. 1H9 can bind to each of human SIRPα isotypes V1 and V2. 1H9 can bind to human SIRPα isotype V1, including homozygous. 1H9 can bind to human SIRPα isotype V2, including homozygous. 1H9 can bind to human SIRPα isotypes V1/V5 (heterozygous). 1H9 can bind to multiple human SIRPα isotypes including each of V1, V2, and V1/V5. Binding to the human SIRPα variants can be measured using assays known in the art including PCR and/or flow cytometry. For example, a given sample can be genotyped to determine SIRP status and binding to SIRP can be determined using flow cytometry.

In certain aspects, an antibody competes for binding to human SIRPα with an antibody selected from 1H9 and 3C2. In certain aspects, an antibody binds to the same human SIRPα epitope as bound by 1H9 or 3C2. In certain aspects, an antibody binds to an overlapping human SIRPα epitope as bound by 1H9 or 3C2. In certain aspects, an antibody binds to a distinct human SIRPα epitope as bound by 1H9 or 3C2.

In certain aspects, an antibody does not compete for binding to human SIRPα with KWar antibody.

In certain aspects, an antibody partially competes for binding to human SIRPα with KWar antibody.

In certain aspects, an antibody inhibits binding of human CD47 to human SIRPα.

In certain aspects, an antibody inhibits binding of human SP-A to human SIRPα.

In certain aspects, an antibody inhibits binding of human SP-D to human SIRPα.

In certain aspects, an antibody binds to rhesus monkey SIRPα.

In certain aspects, an antibody binds to cynomolgus SIRPα.

In some embodiments, a SIRPα antibody is an antibody that competes with an illustrative antibody provided herein, e.g., 1H9 and/or 3C2. In some aspects, the antibody that competes with the illustrative antibody provided herein binds the same epitope as an illustrative antibody provided herein.

In some embodiments, a subject anti-CD47 agent is a "high affinity SIRPα reagent", which includes SIRPα-derived polypeptides and analogs thereof. High affinity SIRPα reagents are described in international application WO2013109752A1, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with 1 g molecules. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

SIRPα Antibodies

In some embodiments, an antibody binds human SIRPα with a KD of less than or equal to about 1, 1-6, 1-5, 1-4, 1-3, 2, 3, 4, 5, 6, 7, 8, 9, or $10 \times 10^{-9}$ M, as measured by Biacore assay.

An antibody can comprise: a CDR-H1 comprising the sequence set forth in SEQ ID NO:1; a CDR-H2 comprising the sequence set forth in SEQ ID NO:2; a CDR-H3 comprising the sequence set forth in SEQ ID NO:3; a CDR-L1 comprising the sequence set forth in SEQ ID NO:4; a CDR-L2 comprising the sequence set forth in SEQ ID NO:5; and a CDR-L3 comprising the sequence set forth in SEQ ID NO:6.

An antibody can comprise: a VH sequence of SEQ ID NO:7 and a VL sequence of SEQ ID NO:8.

An antibody can comprise: a heavy chain of SEQ ID NO:17 and a light chain of SEQ ID NO:18.

An antibody can comprise: a CDR-H1 comprising the sequence set forth in SEQ ID NO:9; a CDR-H2 comprising the sequence set forth in SEQ ID NO:10; a CDR-H3 comprising the sequence set forth in SEQ ID NO:11; a CDR-L1 comprising the sequence set forth in SEQ ID NO:12; a CDR-L2 comprising the sequence set forth in SEQ ID NO:13; and a CDR-L3 comprising the sequence set forth in SEQ ID NO:14.

An antibody can comprise: a VH sequence of SEQ ID NO:15 and a VL sequence of SEQ ID NO:16.

An antibody can comprise: a heavy chain of SEQ ID NO:19 and a light chain of SEQ ID NO:20.

An antibody can comprise: a CDR-H1 comprising the sequence set forth in SEQ ID NO:21; a CDR-H2 comprising the sequence set forth in SEQ ID NO:22; a CDR-H3 comprising the sequence set forth in SEQ ID NO:23; a CDR-L1 comprising the sequence set forth in SEQ ID NO:24; a CDR-L2 comprising the sequence set forth in SEQ ID NO:25; and a CDR-L3 comprising the sequence set forth in SEQ ID NO:26.

An antibody can comprise: a VH sequence of SEQ ID NO:27 and a VL sequence of SEQ ID NO:28.

An antibody can comprise: a CDR-H1 comprising the sequence set forth in SEQ ID NO:29; a CDR-H2 comprising the sequence set forth in SEQ ID NO:30; a CDR-H3 comprising the sequence set forth in SEQ ID NO:31; a CDR-L1 comprising the sequence set forth in SEQ ID NO:32; a CDR-L2 comprising the sequence set forth in SEQ ID NO:33; and a CDR-L3 comprising the sequence set forth in SEQ ID NO:34.

An antibody can comprise: a VH sequence of SEQ ID NO:35 and a VL sequence of SEQ ID NO:36.

In certain aspects, an antibody can comprise one or more CDRs of 1H9. In certain aspects, an antibody can comprise all CDRs of 1H9. In certain aspects, an antibody can comprise one or more variable sequences of 1H9. In certain aspects, an antibody can comprise each variable sequence of 1H9. In certain aspects, an antibody can comprise the heavy chain of 1H9. In certain aspects, an antibody can comprise the light chain of 1H9. In certain aspects, an antibody can comprise the heavy chain and the light chain of 1H9. In certain aspects, an antibody is 1H9.

In certain aspects, an antibody can comprise one or more CDRs of 3C2. In certain aspects, an antibody can comprise all CDRs of 3C2. In certain aspects, an antibody can comprise one or more variable sequences of 3C2. In certain aspects, an antibody can comprise each variable sequence of 3C2. In certain aspects, an antibody can comprise the heavy chain of 3C2. In certain aspects, an antibody can comprise the light chain of 3C2. In certain aspects, an antibody can comprise the heavy chain and the light chain of 3C2. In certain aspects, an antibody is 3C2.

In certain aspects, an antibody can comprise one or more CDRs of 9B11. In certain aspects, an antibody can comprise all CDRs of 9B11. In certain aspects, an antibody can comprise one or more variable sequences of 9B11. In certain aspects, an antibody can comprise each variable sequence of 9B11. In certain aspects, an antibody can comprise the heavy chain of 9B11. In certain aspects, an antibody can comprise the light chain of 9B11. In certain aspects, an antibody can comprise the heavy chain and the light chain of 9B11. In certain aspects, an antibody is 9B11.

In certain aspects, an antibody can comprise one or more CDRs of 7E11. In certain aspects, an antibody can comprise all CDRs of 7E11. In certain aspects, an antibody can comprise one or more variable sequences of 7E11. In certain aspects, an antibody can comprise each variable sequence of 7E11. In certain aspects, an antibody can comprise the heavy chain of 7E11. In certain aspects, an antibody can comprise the light chain of 7E11. In certain aspects, an antibody can comprise the heavy chain and the light chain of 7E11. In certain aspects, an antibody is 7E11.

Anti-SIRPα antibody heavy chain variable domains are also provided as SEQ ID NOs: 119-125. Anti-SIRPα antibody light chain variable domains are also provided as SEQ ID NOs: 126-128. Anti-SIRPα antibody heavy chain variable regions are disclosed as SEQ ID NOs: 24, 25, 26, 27, 28, 29, and 30 and anti-SIRPα antibody light chain variable regions are disclosed as SEQ ID NOs: 31, 32 and 33 in U.S. Patent Publication US 20190127477, published May 5, 2019, herein incorporated by reference in its entirety.

Anti-SIRPα antibody heavy chain variable regions are disclosed as SEQ ID NOs: 7, 10, 14, 16, 18, 30, 75, 78, 80, 82, 84, 86, and 88 and anti-SIRPα antibody light chain variable regions are disclosed as SEQ ID NOs: 8, 20, 22, 24, 26, 28, 32, 76, 90, 92, 94, 96, 98, 100, and 104 in U.S. Patent Publication US 20180312587, published Nov. 1, 2018, herein incorporated by reference in its entirety.

Anti-SIRPα antibody heavy chain variable regions are disclosed as SEQ ID NO: 26, 81, 83 and anti-SIRPα antibody light chain variable regions are disclosed as SEQ ID NOs: 25, 39-41 in International Patent Publication WO2019183266A1, published Sep. 26, 2019, herein incorporated by reference in its entirety.

In some embodiments, an antibody provided herein comprises a sequence having at least about 50%, 60%, 70%, 80%, 90%, 95%, or 99% identity to an illustrative sequence provided in SEQ ID NOs: 1-36. In some embodiments, an antibody provided herein comprises a sequence provided in SEQ ID NOs: 1-36, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

Additional Agents for Combination Therapies

Additional agents, such as small molecules, antibodies, adoptive cellular therapies and chimeric antigen receptor T cells (CAR-T), checkpoint inhibitors, and vaccines, that are appropriate for treating hematological malignancies can be administered in combination with the anti-CD47 agents as described herein. Additional immunotherapeutic agents for hematological malignancies are described in Dong S et al, J Life Sci (Westlake Village). 2019 June; 1(1): 46-52; and Cuesta-Mateos C Et al, Front. Immunol. 8:1936. doi: 10.3389/fimmu.2017.01936, each of which are hereby incorporated by reference in their entirety.

In various embodiments, an anti-CD47 agent or an anti-SIRPα agent as described herein, is combined with one or more additional therapeutic agents, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (mono- and multi-specific antibodies and fragments thereof in any format (e.g., including without limitation DARTs®, Duobodies®, BiTEs®, BiKEs, TriKEs, XmAbs®, TandAbs®, scFvs, Fabs, Fab derivatives)), bispecific antibodies, non-immunoglobulin antibody mimetics (e.g., including without limitation adnectins, affibody molecules, affilins, affimers, affitins, alphabodies, anticalins, peptide aptamers, armadillo repeat proteins (ARMs), atrimers, avimers, designed ankyrin repeat proteins (DARPins®), fynomers, knottins, Kunitz domain peptides, monobodies, and nanoCLAMPs), antibody-drug conjugates (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

In various embodiments, an anti-CD47 agent or an anti-SIRPα agent as described herein, is combined with one or more additional therapeutic agents including, without limitation, an inhibitor, agonist, antagonist, ligand, modulator, stimulator, blocker, activator or suppressor of a target (e.g., polypeptide or polynucleotide) including without limitation: Abelson murine leukemia viral oncogene homolog 1 gene (ABL, such as ABL1), Acetyl-CoA carboxylase (such as ACC1/2), activated CDC kinase (ACK, such as ACK), Adenosine deaminase, adenosine receptor (such as A2BR, A2aR, A3aR), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, 4-1BB ligand (CD137L), Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C—C motif) receptor (such as CCR2, CCR4, CCR5, CCR8), chemokine (C—X—C motif) receptor (such as CXCR1, CXCR2, CXCR3 and CXCR4), Chemokine CC21 ligand, Cholecystokinin CCK2 receptor, Chorionic gonadotropin, c-Kit (tyrosine-protein kinase Kit or CD117), CISH (Cytokine-inducible SH2-containing protein), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e (CEACAM6), CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COP9 signalosome subunit 5, CSF-1 (colony-stimulating factor 1 receptor), CSF2 gene, CTLA-4 (cytotoxic T-lymphocyte protein 4) receptor, C-type lectin domain protein 9A (CLEC9A), Cyclin D1, Cyclin G, cyclin-dependent kinases (CDK, such as CDK1, CDK12, CDK1B, CDK2-9), cyclooxygenase (such as COX1, COX2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, DEAD-box helicase 6 (DDX6), Death receptor 5 (DR5, TRAILR2), Death receptor 4 (DR4, TRAILR1), Delta-like protein ligand (such as 3, 4), Deoxyribonuclease, Deubiquitinating enzymes (DUBs), Dickkopf-1 ligand, dihydrofolate reductase (DHFR), Dihydropyrimidine dehydrogenase, Dipeptidyl peptidase IV, discoidin domain receptor (DDR, such as DDR1), Diacylglycerol kinase zeta (DGKZ), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, E3 ubiquitin-protein ligase (such as RNF128, CBL-B), echinoderm microtubule like protein 4, EGFR tyrosine kinase receptor, Elastase, Elongation factor 1 alpha 2, Elongation factor 2, Endoglin, Endonuclease, endoplasmic reticulum aminopeptidase (ERAP, such as ERAP 1, ERAP2), Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Hypoxia-inducible factor prolyl hydroxylase (HIF-PH or EGLN), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heme oxygenase 1 (HO1), Heme oxygenase 2 (HO2), Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOTIL), histone deacetylase (HDAC, such as 1, 2, 3, 6, 10, 11), Histone H1, Histone H3, HLA class I antigen (A-2 alpha), HLA class II antigen, HLA class I antigen alpha G (HLA-G), Non-classical HLA, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha (HIF1α), Imprinted Maternally Expressed Transcript (H19) gene, mitogen-activated protein kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1 and IDO2), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, Interleukin 35 (IL-35), isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukocyte immunoglobulin-like receptor subfamily B member 1 (ILT2), Leukocyte immunoglobulin-like receptor subfamily B member 2 (ILT4), Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), 5-Lipoxygenase (5-LOX), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, NLRP3 (NACHT LRR PYD domain protein 3) modulators, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly (ADP-ribose) polymerase (PARP, such as PARP1, PARP2 and PARP3, PARP7, and mono-PARPs), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), Prostaglandin E2 synthase, prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, RosI tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Secreted phospholipase A2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, Stabilin-1 (STAB1), STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Suppressor of cytokine signaling modulators (SOCS), Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, Three prime repair exonuclease 1 (TREX1), Three prime repair exonuclease 2 (TREX2), Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, transferrin (TF), transforming growth factor alpha (TGFα), transforming growth factor beta (TGFB) and isoforms thereof, TGF beta 2 ligand, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), tryptophan 2,3-dioxygenase (TDO), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tumor specific neoantigens, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E2I (UBE2I, UBC9), Ubiquitin-specific-processing protease 7 (USP7), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase, Mer (Mer tyrosine kinase receptor modulators), YAP (Yes-associated protein modulators)es, Wee-1 protein kinase, Werner Syndrome RecQ Like Helicase (WRN), Wilms' tumor antigen 1, Wilms' tumor protein, WW domain containing transcription regulator protein 1 (TAZ), X-linked inhibitor of apoptosis protein, Zinc finger protein transcription factor or any combination thereof.

In various embodiments, an anti-CD47 agent or an anti-SIRPα agent as described herein, is combined with one or more additional therapeutic agents that may be categorized by their mechanism of action into, for example, the following groups: anti-metabolites/anti-cancer agents, such as pyrimidine analogs floxuridine, capecitabine, cytarabine, CPX-351 (liposomal cytarabine, daunorubicin), and TAS-118; Alpha 1 adrenoceptor/Alpha 2 adrenoceptor antagonists, such as phenoxybenzamine hydrochloride (injectable, pheochromocytoma); Androgen receptor antagonists, such as nilutamide; anti-cadherin antibodies, such as HKT-288; anti-leucine-rich repeat containing 15 (LRRC15) antibodies, such as ABBV-085. ARGX-110; angiotensin receptor blockers, nitric oxide donors; antisense oligonucleotides, such as AEG35156, IONIS-KRAS-2.5Rx, EZN-3042, RX-0201, IONIS-AR-2.5Rx, BP-100 (prexigebersen), IONIS-STAT3-2.5Rx; anti-angiopoietin (ANG)-2 antibodies, such as MEDI3617, and LY3127804; anti-ANG-1/ANG-2 antibodies, such as AMG-780; anti-CSF1R antibodies, such as emactuzumab, LY3022855, AMG-820, FPA-008 (cabiralizumab); anti-endoglin antibodies, such as TRC105 (carotuximab); anti-ERBB antibodies, such as CDX-3379, HLX-02, seribantumab; anti-HER2 antibodies, such as HERCEPTIN® (trastuzumab), trastuzumab biosimimar, margetuximab, MEDI4276, BAT-8001, Pertuzumab (Perjeta), RG6264, ZW25 (a bispecific HER2-directed antibody targeting the extracellular domains 2 and 4; Cancer Discov. 2019 January; 9(1):8; PMID: 30504239); anti-HLA-DR antibodies, such as IMMU-114; anti-IL-3 antibodies, such as JNJ-56022473; anti-TNF receptor superfamily member 18 (TNFRSF18, GITR; NCBI Gene ID: 8784) antibodies, such as MK-4166, MEDI1873, FPA-154, INCAGN-1876, TRX-518, BMS-986156, MK-1248, GWN-323; and those described, e.g. in Intl. Patent Publ. Nos. WO 2017/096179, WO 2017/096276, WO 2017/096189; and WO 2018/089628; anti-EphA3 antibodies, such as KB-004; anti-CD37 antibodies, such as otlertuzumab (TRU-016); anti-FGFR-3 antibodies, such as LY3076226, B-701; anti-FGFR-2 antibodies, such as GAL-F2; anti-C5 antibodies, such as ALXN-1210; anti-EpCAM antibodies, such as VB4-845; anti-CEA antibodies, such as RG-7813; anti-Carcinoembryonic-antigen-related-cell-adhesion-molecule-6 (CEACAM6, CD66C) antibodies, such as BAY-1834942, NEO-201 (CEACAM 5/6); anti-GD2 antibodies, such as APN-301; anti-interleukin-17 (IL-17) antibodies, such as CJM-112; anti-interleukin-1 beta antibodies, such as canakinumab (ACZ885), VPM087; anti-carbonic anhydrase 9 (CA9, CAIX) antibodies, such as TX-250; anti-Mucin 1 (MUC1) antibodies, such as gatipotuzumab, Mab-AR-20.5; anti-KMA antibodies, such as MDX-1097; anti-CD55 antibodies, such as PAT-SC1; anti-c-Met antibodies, such as ABBV-399; anti-PSMA antibodies, such as ATL-101; anti-CD100 antibodies, such as VX-15; anti-EPHA3 antibodies, such as fibatuzumab; anti-APRIL antibodies, such as BION-1301; anti-fibroblast activation protein (FAP)/IL-2R antibodies, such as RG7461; anti-fibroblast activation protein (FAP)/TRAIL-R2 antibodies, such as RG7386; anti-fucosyl-GM1 antibodies, such as BMS-986012; anti-IL-8 (Interleukin-8) antibodies, such as HuMax-Inflam; anti-myostatin inhibitors, such as landogrozumab; anti-delta-like protein ligand 3 (DDL3) antibodies, such as rovalpituzumab tesirine; anti-DLL4 (delta like ligand 4) antibodies, such as demcizumab; anti-clusterin antibodies, such as AB-16B5; anti-Ephrin-A4 (EFNA4) antibodies, such as PF-06647263; anti-mesothelin antibodies, such as BMS-986148, Anti-MSLN-MMAE; anti-sodium phosphate cotransporter 2B (NaP2B) antibodies, such as lifastuzumab; anti-TGFb antibodies, such as SAR439459; anti-transforming growth factor-beta (TGF-beta) antibodies, such as ABBV-151, LY3022859, NIS793, XOMA 089; purine analogs, folate antagonists (such as pralatrexate), cladribine, pentostatin, fludarabine and related inhibitors; antiproliferative/antimitotic agents including natural products, such as vinca alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide); DNA damaging agents, such as actinomycin, amsacrine, busulfan, carboplatin, chlorambucil, cisplatin, cyclophosphamide (CYTOXAN®), dactinomycin, daunorubicin, doxorubicin, DEBDOX, epirubicin, iphosphamide, melphalan, merchlorethamine, mitomycin C, mitoxantrone, nitrosourea, procarbazine, taxol, Taxotere, teniposide, etoposide, and triethylenethiophosphoramide; DNA-hypomethylating agents, such as guadecitabine (SGI-110), ASTX727; antibiotics such as dactinomycin, daunorubicin, doxorubicin, idarubicin, anthracyclines, mitoxantrone, bleomycins, plicamycin (mithramycin); enzymes such as L-asparaginase which systemically metabolizes L-asparagine and deprives cells which do not have the capacity to synthesize their own asparagine; DNAi oligonucleotides targeting Bcl-2, such as PNT2258; agents that activate or reactivate latent human immunodeficiency virus (HIV), such as panobinostat and romidepsin; asparaginase stimulators, such as crisantaspase (Erwinase®) and GRASPA (ERY-001, ERY-ASP), calaspargase pegol, pegaspargase; pan-Trk, ROS1 and ALK inhibitors, such as entrectinib, TPX-0005; anaplastic lymphoma kinase (ALK) inhibitors, such as alectinib, ceritinib, alecensa (RG7853), ALUNBRIG® (brigatinib); antiproliferative/antimitotic alkylating agents, such as nitrogen mustard cyclophosphamide and analogs (e.g., melphalan, chlorambucil, hexamethylmelamine, thiotepa), alkyl nitrosoureas (e.g., carmustine) and analogs, streptozocin, and triazenes (e.g., dacarbazine); antiproliferative/antimitotic antimetabolites, such as folic acid analogs (methotrexate); platinum coordination complexes (e.g., cisplatin, oxiloplatinim, and carboplatin), procarbazine, hydroxyurea, mitotane, and aminoglutethimide; hormones, hormone analogs (e.g., estrogen, tamoxifen, goserelin, bicalutamide, and nilutamide), and aromatase inhibitors (e.g., letrozole and anastrozole); antiplatelet agents; anticoagulants such as heparin, synthetic heparin salts, and other inhibitors of thrombin; fibrinolytic agents such as tissue plasminogen activator, streptokinase, urokinase, aspirin, dipyridamole, ticlopidine, and clopidogrel; antimigratory agents; antisecretory agents (e.g., breveldin); immunosuppressives, such as tacrolimus, sirolimus, azathioprine, and mycophenolate; growth factor inhibitors, and vascular endothelial growth factor inhibitors; fibroblast growth factor inhibitors, such as FPA14; AMP activated protein kinase stimulators, such as metformin hydrochloride; ADP ribosyl cyclase-1 inhibitors, such as daratumumab (DARZALEX®); Caspase recruitment domain protein-15 stimulators, such as mifamurtide (liposomal); CCR5 chemokine antagonists, such as MK-7690 (vicriviroc); CDC7 protein kinase inhibitors, such as TAK-931; Cholesterol side-chain cleavage enzyme inhibitors, such as ODM-209; Dihydropyrimidine dehydrogenase/Orotate phosphoribosyltransferase inhibitors, such as Cefesone (tegafur+gimeracil+oteracil potassium); DNA polymerase/Ribonucleotide reductase inhibitors, such as clofarabine; DNA interference oligonucleotides, such as PNT2258, AZD-9150; Estrogen receptor modulators, such as bazedoxifene; Estrogen receptor agonists/Progesterone receptor antagonists, such as TRI-CYCLEN LO (norethindrone+ethinyl estradiol); HLA class I antigen A-2 alpha modulators, such as FH-MCVA2TCR; HLA class I antigen A-2 alpha/MART-1 melanoma antigen modulators, such as MART-1 F5 TCR engineered PBMC; Human Granulocyte Colony Stimulating Factors, such as PF-06881894; GNRH receptor agonists, such as leuprorelin acetate, leuprorelin acetate sustained release depot (ATRIGEL), triptorelin pamoate, goserelin acetate; GNRH receptor antagonists, such as elagolix, relugolix, degarelix; Endoplasmin modulators, such as anlotinib; H+K+ ATPase inhibitors, such as omeprazole, esomeprazole; ICAM-1/CD55 modulators, such as cavatak (V-937); IL-15/IL-12 modulators, such as SAR441000; Interleukin 23A inhibitors, such as guselkumab; Lysine specific histone demethylase 1 inhibitors, such as CC-90011; IL-12 Mrna, such as MEDI1191; RIG-I modulators, such as RGT-100; NOD2 modulators, such as SB-9200, and IR-103; Progesterone receptor agonists, such as levonorgestrel; Protein cereblon modulators, such as CC-92480, CC-90009; Protein cereblon modulators/DNA binding protein Ikaros inhibitors/Zinc finger binding protein Aiolos inhibitors, such as iberdomide; Retinoid X receptor modulators, such as alitretinoin, bexarotene (oral formulation); RIP-1 kinase inhibitors, such as GSK-3145095; selective oestrogen receptor degraders, such as AZD9833; SUMO inhibitors, such as TAK-981; Thrombopoietin receptor agonists, such as eltrombopag; Thyroid hormone receptor agonists, such as levothyroxine sodium; TNF agonists, such as tasonermin; Tyrosine phosphatase substrate 1 inhibitors, such as CC-95251; HER2 inhibitors, such as neratinib, tucatinib (ONT-380); EGFR/ErbB2/Ephb4 inhibitors, such as tesevatinib; EGFR/HER2 inhibitors, such as TAK-788; EGFR family tyrosine kinase receptor inhibitors, such as DZD-9008; EGFR/ErbB-2 inhibitors, such as varlitinib; mutant selective EGFR inhibitors, such as PF-06747775, EGF816 (nazartinib), ASP8273, ACEA-0010, BI-1482694; epha2 inhibitors, such as MM-310; polycomb protein (EED) inhibitors, such as MAK683; DHFR inhibitor/Folate transporter 1 modulator/Folate receptor antagonist, such as pralatrexate; DHFR/GAR transformylase/Thymidylate synthase/Transferase inhibitors, such as pemetrexed disodium; p38 MAP kinase inhibitors, such as ralimetinib; PRMT inhibitors, such as MS203, PF-06939999, GSK3368715, GSK3326595; Sphingosine kinase 2 (SK2) inhibitors, such as opaganib; Nuclear erythroid 2-related factor 2 stimulators, such as omaveloxolone (RTA-408); Tropomyosin receptor kinase (TRK) inhibitors, such as LOXO-195, ONO-7579; Mucin 1 inhibitors, such as GO-203-2C; MARCKS protein inhibitors, such as BIO-11006; Folate antagonists, such as arfolitixorin; Galectin-3 inhibitors, such as GR-MD-02; Phosphorylated P68 inhibitors, such as RX-5902; CD95/TNF modulators, such as ofranergene obadenovec; pan-PIM kinase inhibitors, such as INCB-053914; IL-12 gene stimulators, such as EGEN-001, tavokinogene telseplasmid; Heat shock protein HSP90 inhibitors, such as TAS-116, PEN-866;

VEGF/HGF antagonists, such as MP-0250; VEGF ligand inhibitors, such as bevacizumab biosimilar; VEGF receptor antagonists/VEGF ligand inhibitors, such as ramucirumab; VEGF-1/VEGF-2/VEGF-3 receptor antagonists; such as fruquintinib; VEGF-1/VEGF-2 receptor modulators, such as HLA-A2402/HLA-A0201 restricted epitope peptide vaccine; Placenta growth factor ligand inhibitor/VEGF-A ligand inhibitor, such as aflibercept; SYK tyrosine kinase/JAK tyrosine kinase inhibitors, such as ASN-002; Trk tyrosine kinase receptor inhibitors, such as larotrectinib sulfate; JAK3/JAK1/TBK1 kinase inhibitors, such as CS-12912; IL-24 antagonist, such as AD-IL24; NLRP3 (NACHT LRR PYD domain protein 3) modulators, such as BMS-986299; RIG-I agonists, such as RGT-100; Aerolysin stimulators, such as topsalysin; P-Glycoprotein 1 inhibitors, such as HM-30181A; CSF-1 antagonists, such as ARRY-382, BLZ-945; CCR8 inhibitors, such as JTX-1811, 1-309, SB-649701, HG-1013, RAP-310; anti-Mesothelin antibodies, such as SEL-403; Thymidine kinase stimulators, such as aglatimagene besadenovec; Polo-like kinase 1 inhibitors, such as PCM-075, onvansertib; NAE inhibitors, such as pevonedistat (MLN-4924), TAS-4464; Pleiotropic pathway modulators, such as avadomide (CC-122); Amyloid protein binding protein-1 inhibitorS/Ubiquitin ligase modulators, such as pevonedistat; FoxM1 inhibitors, such as thiostrepton; UBA1 inhibitors, such as TAK-243; Src tyrosine kinase inhibitors, such as VAL-201; VDAC/HK inhibitors, such as VDA-1102; Elf4a inhibitors, such as rohinitib, eFT226; TP53 gene stimulators, such as ad-p53; Retinoic acid receptor agonists, such as tretinoin; Retinoic acid receptor alpha (RARa) inhibitors, such as SY-1425; SIRT3 inhibitors, such as YC8-02; Stromal cell-derived factor 1 ligand inhibitors, such as olaptesed pegol (NOX-A12); IL-4 receptor modulators, such as MDNA-55; Arginase-I stimulators, such as pegzilarginase; Topoisomerase I inhibitors, such as irinotecan hydrochloride, Onivyde; Topoisomerase I inhibitor/hypoxia inducible factor-1 alpha inhibitors, such as PEG-SN38 (firtecan pegol); Hypoxia inducible factor-1 alpha inhibitors, such as PT-2977, PT-2385; CD122 (IL-2 receptor) agonists, such as proleukin (aldesleukin, IL-2); pegylated IL-2 (eg NKTR-214); modified variants of IL-2 (eg THOR-707); TLR7/TLR8 agonist, such as NKTR-262; TLR7 agonists, such as DS-0509, GS-9620, LHC-165, TMX-101 (imiquimod); p53 tumor suppressor protein stimulators such as kevetrin; Mdm4/Mdm2 p53-binding protein inhibitors, such as ALRN-6924; kinesin spindle protein (KSP) inhibitors, such as filanesib (ARRY-520); CD80-fc fusion protein inhibitors, such as FPT-155; Menin and mixed lineage leukemia (MLL) inhibitors such as KO-539; Liver x receptor agonists, such as RGX-104; IL-10 agonists, such as Pegilodecakin (AM-0010); VEGFR/PDGFR inhibitors, such as vorolanib; IRAK4 inhibitors, such as CA-4948; anti-TLR-2 antibodies, such as OPN-305; Calmodulin modulators, such as CBP-501.

Glucocorticoid receptor antagonists, such as relacorilant (CORT-125134); Second mitochondria-derived activator of caspases (SMAC) protein inhibitors, such as BI-891065; Lactoferrin modulators, such as LTX-315; KIT proto-oncogene, receptor tyrosine kinase (KIT) inhibitors, such as PLX-9486; platelet derived growth factor receptor alpha (PDGFRA)/KIT proto-oncogene, receptor tyrosine kinase (KIT) mutant-specific antagonists/inhibitors such as BLU-285, DCC-2618; Exportin 1 inhibitors, such as eltanexor; CHST15 gene inhibitors, such as STNM-01; Somatostatin receptor antagonist, such as OPS-201; CEBPA gene stimulators, such as MTL-501; DKK3 gene modulators, such as MTG-201; Chemokine (CXCR1/CXCR2) inhibitors, such as SX-682; p70s6k inhibitors, such as MSC2363318A; methionine aminopeptidase 2 (MetAP2) inhibitors, such as M8891, APL-1202; arginine N-methyltransferase 5 inhibitors, such as GSK-3326595; CD71 modulators, such as CX-2029 (ABBV-2029); ATM (ataxia telangiectasia) inhibitors, such as AZD0156, AZD1390; CHK1 inhibitors, such as GDC-0575, LY2606368 (prexasertib), SRA737, RG7741 (CHK1/2); CXCR4 antagonists, such as BL-8040, LY2510924, burixafor (TG-0054), X4P-002, X4P-001-IO, Plerixafor; EXH2 inhibitors, such as GSK2816126; KDM1 inhibitors, such as ORY-1001, IMG-7289, INCB-59872, GSK-2879552; CXCR2 antagonists, such as AZD-5069; DNA dependent protein kinase inhibitors, such as MSC2490484A (nedisertib), VX-984, AsiDNA (DT-01); protein kinase C (PKC) inhibitors, such as LXS-196, sotrastaurin; selective estrogen receptor downregulators (SERD), such as fulvestrant (Faslodex®), RG6046, RG6047, RG6171, elacestrant (RAD-1901), SAR439859 and AZD9496; selective estrogen receptor covalent antagonists (SERCAs), such as H3B-6545; selective androgen receptor modulator (SARM), such as GTX-024, darolutamide; transforming growth factor-beta (TGF-beta) kinase antagonists, such as galunisertib, LY3200882; TGF-beta inhibitors described in WO 2019/103203; TGF beta receptor 1 inhibitors, such as PF-06952229; bispecific antibodies, such as ABT-165 (DLL4/VEGF), MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), FS-118 (LAG-3/PD-L1) MGD-019 (PD-1/CTLA-4), KN-046 (PD-1/CTLA-4), MEDI-5752 (CTLA-4/PD-1), RO-7121661 (PD-1/TIM-3), XmAb-20717 (PD-1/CTLA-4), AK-104 (CTLA-4/PD-1), AMG-420 (BCMA/CD3), BI-836880 (VEFG/ANG2), JNJ-63709178 (CD123/CD3), MGD-007 (CD3/gpA33), MGD-009 (CD3/B7H3), AGEN1223, IMCgp100 (CD3/gp100), AGEN-1423, ATOR-1015 (CTLA-4/OX40), LY-3415244 (TIM-3/PDL1), INHI-BRX-105 (4-1BB/PDL1), faricimab (VEGF-A/ANG-2), FAP-4-IBBL (4-1BB/FAP), XmAb-13676 (CD3/CD20), TAK-252 (PD-1/OX40L), TG-1801 (CD19/CD47), XmAb-18087 (SSTR2/CD3), catumaxomab (CD3/EpCAM), SAR-156597 (IL4/IL13), EMB-01 (EGFR/cMET), REGN-4018 (MUC16/CD3), REGN-1979 (CD20/CD3), RG-7828 (CD20/CD3), CC-93269 (CD3/BCMA), REGN-5458 (CD3/BCMA), navicixizumab (DLL4/VEGF), GRB-1302 (CD3/Erbb2), vanucizumab (VEGF-A/ANG-2), GRB-1342 (CD38/CD3), GEM-333 (CD3/CD33), IMM-0306 (CD47/CD20), RG6076, MEDI5752 (PD-1/CTLA-4), LY3164530 (MET/EGFR); Alpha-ketoglutarate dehydrogenase (KGDH) inhibitors, such as CPI-613; XPO1 inhibitors, such as selinexor (KPT-330); Isocitrate dehydrogenase 2 (IDH2) inhibitors, such as enasidenib (AG-221); IDH1 inhibitors such as AG-120, and AG-881 (IDH1 and IDH2), IDH-305, BAY-1436032; IDH1 gene inhibitors, such as ivosidenib; interleukin-3 receptor (IL-3R) modulators, such as SL-401; Arginine deiminase stimulators, such as pegargiminase (ADI-PEG-20); claudin-18 inhibitors, such as claudiximab; 3-catenin inhibitors, such as CWP-291; chemokine receptor 2 (CCR) inhibitors, such as PF-04136309, CCX-872, BMS-813160 (CCR2/CCR5); thymidylate synthase inhibitors, such as ONX-0801; ALK/ROS1 inhibitors, such as lorlatinib; tankyrase inhibitors, such as G007-LK; triggering receptor expressed on myeloid cells 1 (TREM1; NCBI Gene ID: 54210), such as PY159; triggering receptor expressed on myeloid cells 2 (TREM2; NCBI Gene ID: 54209), such as PY314; Mdm2 p53-binding protein inhibitors, such as CMG-097, HDM-201; c-PIM inhibitors, such as PIM447; sphingosine kinase-2 (SK2) inhibitors, such as Yeliva® (ABC294640); DNA polymerase inhibitors, such as sapacitabine; Cell cycle/Microtubule inhibitors, such as eribulin mesylate; c-MET inhibitors, such as AMG-337, savolitinib, tivantinib (ARQ-197), capmatinib, and tepotinib, ABT-700, AG213, AMG-208, JNJ-38877618 (OMO-1), merestinib, HQP-8361; c-Met/VEGFR inhibitors, such as BMS-817378, TAS-115; c-Met/RON inhibitors, such as BMS-777607; BCR/ABL inhibitors, such as rebastinib, asciminib, ponatinib (ICLUSIG®); MNK1/MNK2 inhibitors, such as eFT-508; Cytochrome P450 11B2/Cytochrome P450 17/AKT protein kinase inhibitors, such as LAE-201; Cytochrome P450 3A4 stimulators, such as mitotane; lysine-specific demethylase-1 (LSD1) inhibitors, such as CC-90011; CSF1R/KIT and FLT3 inhibitors, such as pexidartinib (PLX3397); Flt3 tyrosine kinase/Kit tyrosine kinase inhibitor and PDGF receptor antagonists, such as quizartinib dihydrochloride; kinase inhibitors, such as vandetanib; E selectin antagonists, such as GMI-1271; differentiation inducers, such as tretinoin; epidermal growth factor receptor (EGFR) inhibitors, such as osimertinib (AZD-9291), cetuximab; topoisomerase inhibitors, such as Adriamycin, doxorubicin, daunorubicin, dactinomycin, DaunoXome, Caelyx, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114); corticosteroids, such as cortisone, dexamethasone, hydrocortisone, methylprednisolone, prednisone, prednisolone; growth factor signal transduction kinase inhibitors; nucleoside analogs, such as DFP-10917; Axl inhibitors, such as BGB-324 (bemcentinib), SLC-0211; Axl/Flt3 inhibitors, such as gilteritinib; Inhibitors of bromodomain and extraterminal motif (BET) proteins, including ABBV-744, BRD2 (NCBI Gene ID: 6046), BRD3 (NCBI Gene ID: 8019), BRD4 (NCBI Gene ID: 23476), and bromodomain testis-specific protein (BRDT; NCBI Gene ID: 676), such as INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, CC-95775, mivebresib, BI-894999, PLX-2853, PLX-51107, CPI-0610, GS-5829; PARP inhibitors, such as olaparib (MK7339), rucaparib, veliparib, talazoparib, ABT-767, BGB-290, fluzolepali (SHR-3162), niraparib (JNJ-64091742), bendamustine hydrochloride; PARP/Tankyrase inhibitors such as 2X-121 (e-7499); IMP-4297, SC-10914, IDX-1197, HWH-340, CK-102, simmiparib; Proteasome inhibitors, such as ixazomib (NINLARO®), carfilzomib (Kyprolis®), marizomib, bortezomib; Glutaminase inhibitors, such as CB-839 (telaglenastat), bis-2-(5-phenylacetamido-1,3,4-thiadiazol-2-yl)ethyl sulfide (BPTES); mitochondrial complex I inhibitors, such as metformin, phenformin; vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131, peptide subunit vaccine (acute lymphoblastic leukemia, University Children's Hospital Tuebingen); bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, tapuldencel-T, eltrapuldencel-T, SL-701, BSK01TM, rocapuldencel-T (AGS-003), DCVAC, CVactm, stapuldencel-T, eltrapuldencel-T, SL-701, BSK01TM, ADXS31-142, autologous dendritic cell vaccine (metastatic malignant melanoma, intradermal/intravenous, Universitatsklinikum Erlangen); oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, CreaVax-BC, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; GI-4000; IO-103; Neoantigen peptide vaccines, such as AGEN-2017, GEN-010, NeoVax, RG-6180, GEN-009, PGV-001 (TLR-3 agonist), GRANITE-001, NEO-PV-01; Peptide vaccines that target heat shock proteins, such as PhosphoSynVax™; Vitespen (HSPPC-96-C), NANT Colorectal Cancer Vaccine containing aldoxorubicin, autologous tumor cell vaccine+systemic CpG-B+IFN-alpha (cancer), IO-120+IO-103 (PD-L1/PD-L2 vaccines), HB-201, HB-202, HB-301, TheraT®*-based vaccines; TLR-3 agonist/interferon inducers, such as Poly-ICLC (NSC-301463); STAT-3 inhibitors, such as napabucasin (BBI-608); ATPase p97 inhibitors, such as CB-5083; smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole; interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon); interferon gamma ligand modulators, such as interferon gamma (OH-6000, Ogamma 100); telomerase modulators, such as, tertomotide (GV-1001, HR-2802, Riavax) and imetelstat (GRN-163, JNJ-63935937); DNA methyltransferases inhibitors, such as temozolomide (CCRG-81045), decitabine, guadecitabine (S-110, SGI-110), KRX-0402, RX-3117, RRx-001, and azacytidine (CC-486); DNA gyrase inhibitors, such as pixantrone and sobuzoxane; DNA gyrase inhibitors/Topoisimerase II inhibitors, such as amrubicin; Bcl-2 family protein inhibitors, such as ABT-263, venetoclax (ABT-199), ABT-737, RG7601, and AT-101; Bcl-2/Bcl-XL inhibitors, such as novitoclax; Notch inhibitors, such as LY3039478 (crenigacestat), tarextumab (anti-Notch2/3), BMS-906024; hyaluronidase stimulators, such as PEGPH-20; Erbb2 tyrosine kinase receptor inhibitors/Hyaluronidase stimulators, such as Herceptin Hylecta; Wnt pathway inhibitors, such as SM-04755, PRI-724, WNT-974;

gamma-secretase inhibitors, such as PF-03084014, MK-0752, RO-4929097; Grb-2 (growth factor receptor bound protein-2) inhibitors, such as BP1001; TRAIL pathway-inducing compounds, such as ONC201, ABBV-621; TRAIL modulators, such as SCB-313; Focal adhesion kinase inhibitors, such as VS-4718, defactinib, GSK2256098; hedgehog inhibitors, such as saridegib, sonidegib (LDE225), glasdegib; Aurora kinase inhibitors, such as alisertib (MLN-8237), and AZD-2811, AMG-900, barasertib, ENMD-2076; HSPB1 modulators (heat shock protein 27, HSP27), such as brivudine, apatorsen; ATR inhibitors, such as BAY-937, AZD6738, AZD6783, VX-803, VX-970 (berzosertib) and VX-970; Hsp90 inhibitors, such as AUY922, onalespib (AT13387), SNX-2112, SNX5422; murine double minute (mdm2) oncogene inhibitors, such as DS-3032b, RG7775, AMG-232, HDM201, and idasanutlin (RG7388); CD137 agonists, such as urelumab, utomilumab (PF-05082566), AGEN2373, ADG-106, BT-7480, QL1806; STING agonists, such as ADU-S100 (MIW-815), SB-11285, MK-1454, SR-8291, AdVCA0848, GSK-532, SYN-STING, MSA-1, SR-8291, GSK3745417; FGFR inhibitors, such as FGF-401, INCB-054828, BAY-1163877, AZD4547, JNJ-42756493, LY2874455, Debio-1347; fatty acid synthase (FASN) inhibitors, such as TVB-2640; CD44 binders, such as A6; protein phosphateese 2A (PP2A) inhibitors, such as LB-100; CYP17 inhibitors, such as seviteronel (VT-464), ASN-001, ODM-204, CFG920, abiraterone acetate; RXR agonists, such as IRX4204; hedgehog/smoothened (hh/Smo) antagonists, such as taladegib, patidegib, vismodegib; complement C3 modulators, such as Imprime PGG; IL-15 agonists, such as ALT-803, NKTR-255, interleukin-15/Fc fusion protein, AM-0015, NIZ-985, and hetIL-15; EZH2 (enhancer of zeste homolog 2) inhibitors, such as tazemetostat, CPI-1205, GSK-2816126, PF-06821497; oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, OBP-301, IMLYGIC®; DOT1L (histone methyltransferase) inhibitors, such as pinometostat (EPZ-5676); toxins such as Cholera toxin, ricin, *Pseudomonas* exotoxin, *Bordetella pertussis* adenylate cyclase toxin, diphtheria toxin, and caspase activators; DNA plasmids, such as BC-819; PLK inhibitors of PLK 1, 2, and 3, such as volasertib (PLK1); WEE1 inhibitors, such as AZD-1775 (adavosertib); Rho kinase (ROCK) inhibitors, such as AT13148, KD025; Inhibition of Apoptosis Protein (IAP) inhibitors, such as ASTX660, debio-1143, birinapant, APG-1387, LCL-161; RNA polymerase inhibitors, such has lurbinectedin (PM-1183), CX-5461; Tubulin inhibitors, such as PM-184, BAL-101553 (lisavanbulin), and OXI-4503, fluorapacin (AC-0001), plinabulin, vinflunine; Toll-like receptor 4 (TLR-4) agonists, such as G100, GSK1795091, and PEPA-10; Elongation factor 1 alpha 2 inhibitors, such as plitidepsin; Elongation factor 2 inhibitors/Interleukin-2 ligands/NAD ADP ribosyltransferase stimulators, such as denileukin diftitox; CD95 inhibitors, such as APG-101, APO-010, asunercept; WT1 inhibitors, such as DSP-7888; splicing factor 3B subunit1 (SF3B1) inhibitors, such as H3B-8800; retinoid Z receptor gamma (RORγ) agonists, such as LYC-55716; and microbiome modulators, such as SER-401, EDP-1503, MRx-0518.

In some embodiments, an anti-CD47 agent or an anti-SIRPα agent as described herein, is co-administered with one or more additional therapeutic agents comprising an inhibitor or antagonist of: myeloid cell leukemia sequence 1 (MCL1) apoptosis regulator (NCBI Gene ID: 4170); mitogen-activated protein kinase 1 (MAP4K1) (also called Hematopoietic Progenitor Kinase 1 (HPK1), NCBI Gene ID: 11184); diacylglycerol kinase alpha (DGKA, DAGK, DAGK1 or DGK-alpha; NCBI Gene ID: 1606); 5'-nucleotidase ecto (NT5E or CD73; NCBI Gene ID: 4907); ecto-nucleoside triphosphate diphosphohydrolase 1 (ENTPD1 or CD39; NCBI Gene ID: 593); transforming growth factor beta 1 (TGFB1 or TGFβ; NCBI Gene ID: 7040); heme oxygenase 1 (HMOX1, HO-1 or HO1; NCBI Gene ID: 3162); heme oxygenase 2 (HMOX2, HO-2 or HO2; NCBI Gene ID: 3163); vascular endothelial growth factor A (VEGFA or VEGF; NCBI Gene ID: 7422); erb-b2 receptor tyrosine kinase 2 (ERBB2, HER2, HER2/neu or CD340; NCBI Gene ID: 2064), epidermal growth factor receptor (EGFR, ERBB, ERBB1 or HER1; NCBI Gene ID: 1956); ALK receptor tyrosine kinase (ALK, CD246; NCBI Gene ID: 238); poly(ADP-ribose) polymerase 1 (PARP1; NCBI Gene ID: 142); poly(ADP-ribose) polymerase 2 (PARP2; NCBI Gene ID: 10038); TCDD inducible poly(ADP-ribose) polymerase (TIPARP, PARP7; NCBI Gene ID: 25976); cyclin dependent kinase 4 (CDK4; NCBI Gene ID: 1019); cyclin dependent kinase 6 (CDK6; NCBI Gene ID: 1021); TNF receptor superfamily member 14 (TNFRSF14, HVEM, CD270; NCBI Gene ID: 8764); T cell immunoreceptor with Ig and ITIM domains (TIGIT; NCBI Gene ID: 201633); X-linked inhibitor of apoptosis (XIAP, BIRC4, IAP-3; NCBI Gene ID: 331); baculoviral IAP repeat containing 2 (BIRC2, cIAP1; NCBI Gene ID: 329); baculoviral IAP repeat containing 3 (BIRC3, cIAP2; NCBI Gene ID: 330); baculoviral IAP repeat containing 5 (BIRC5, surviving; NCBI Gene ID: 332); C—C motif chemokine receptor 2 (CCR2, CD192; NCBI Gene ID: 729230); C—C motif chemokine receptor 5 (CCR5, CD195; NCBI Gene ID: 1234); C—C motif chemokine receptor 8 (CCR8, CDw198; NCBI Gene ID: 1237); C—X—C motif chemokine receptor 2 (CXCR2, CD182; NCBI Gene ID: 3579); C—X—C motif chemokine receptor 3 (CXCR3, CD182, CD183; NCBI Gene ID: 2833); C—X—C motif chemokine receptor 4 (CXCR4, CD184; NCBI Gene ID: 7852); arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CASA (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240) and/or soluble epoxide hydrolase 2 (EPHX2, SEH; NCBI Gene ID: 2053); a secreted phospholipase A2 (e.g., PLA2G1B (NCBI Gene ID: 5319); PLA2G7 (NCBI Gene ID: 7941), PLA2G3 (NCBI Gene ID: 50487), PLA2G2A (NCBI Gene ID: 5320); PLA2G4A (NCBI Gene ID: 5321); PLA2G12A (NCBI Gene ID: 81579); PLA2G12B (NCBI Gene ID: 84647); PLA2G10 (NCBI Gene ID: 8399); PLA2G5 (NCBI Gene ID: 5322); PLA2G2D (NCBI Gene ID: 26279); PLA2G15 (NCBI Gene ID: 23659)); indoleamine 2,3-dioxygenase 1 (IDO1; NCBI Gene ID: 3620); indoleamine 2,3-dioxygenase 2 (IDO2; NCBI Gene ID: 169355); hypoxia inducible factor 1 subunit alpha (HIF1A; NCBI Gene ID: 3091); angiopoietin 1 (ANGPT1; NCBI Gene ID: 284); Endothelial TEK tyrosine kinase (TIE-2, TEK, CD202B; NCBI Gene ID: 7010); Janus kinase 1 (JAK1; NCBI Gene ID: 3716); catenin beta 1 (CTNNB1; NCBI Gene ID: 1499); histone deacetylase 9 (HDAC9; NCBI Gene ID: 9734), and/or 5'-3' exoribonuclease 1 (XRN1; NCBI Gene ID: 54464).

In various embodiments, an anti-CD47 agent or an anti-SIRPα agent as described herein, is combined with an agonist of fms related receptor tyrosine kinase 3 (FLT3; FLK2; STK1; CD135; FLK-2; NCBI Gene ID: 2322). Examples of FLT3 agonists include, but are not limited to, CDX-301 and GS-3583.

In various embodiments, an anti-CD47 agent or an anti-SIRPα agent as described herein, is combined with an anti-CD19 agent or antibody. Examples of anti-CD19 agents or antibodies that can be co-administered include without limitation: MOR00208, XmAb5574 (Xencor), AFM-11, Inebilizumab, MEDI 551 (Cellective Therapeutics); MDX-1342 (Medarexand) and blinatumomab (Amgen).

In various embodiments, an anti-CD47 agent or an anti-SIRPα agent as described herein, is combined with an anti-CD20 agent or antibody. Examples of anti-CD20 agents or antibodies that can be co-administered include without limitation: IGN-002, PF-05280586; Rituximab (Rituxan/Biogen Idec), Ofatumumab (Arzerra/Genmab), Obinutuzumab (Gazyva/Roche Glycart Biotech), Alemtuzumab, Veltuzumab, IMMU-106 (Immunomedics), Ocrelizumab (Ocrevus/Biogen Idec; Genentech), Ocaratuzumab, LY2469298 (Applied Molecular Evolution) and Ublituximab, LFB-R603 (LFB Biotech.; rEVO Biologics), IGN-002, PF-05280586.

In various embodiments, an anti-CD47 agent or an anti-SIRPα agent as described herein, is combined with an anti-CD22 agent or antibody. Examples of anti-CD22 agents or antibodies that can be co-administered include without limitation: Epratuzumab, AMG-412, IMMU-103 (Immunomedics).

In various embodiments, an anti-CD47 agent or an anti-SIRPα agent as described herein, is combined with an anti-CD30 agent or antibody. Examples of anti-CD30 agents or antibodies that can be co-administered include without limitation: Brentuximab vedotin (Seattle Genetics).

In various embodiments, an anti-CD47 agent or an anti-SIRPα agent as described herein, is combined with an anti-CD33 agent or antibody. Examples of anti-CD33 agents or antibodies that can be co-administered include without limitation: CIK-CAR.CD33; CD33CART, AMG-330 (CD33/CD3), AMG-673 (CD33/CD3), and GEM-333 (CD3/CD33), and IMGN-779.

In various embodiments, an anti-CD47 agent or an anti-SIRPα agent as described herein, is combined with an anti-CD37 agent or antibody. Examples of anti-CD37 agents or antibodies that can be co-administered include without limitation: BI836826 (Boehringer Ingelheim), Otlertuzumab, and TRU-016 (Trubion Pharmaceuticals).

In various embodiments, an anti-CD47 agent or an anti-SIRPα agent as described herein, is combined with an anti-CD38 agent or antibody. Examples of anti-CD38 agents or antibodies that can be co-administered include without limitation: CD38, such as T-007, UCART-38; Darzalex (Genmab), Daratumumab, JNJ-54767414 (Darzalex/Genmab), Isatuximab, SAR650984 (ImmunoGen), MOR202, MOR03087 (MorphoSys), TAK-079; and anti-CD38-attenukine, such as TAK573.

In various embodiments, an anti-CD47 agent or an anti-SIRPα agent as described herein, is combined with an anti-CD52 agent or antibody. Examples of anti-CD52 agents or antibodies that can be co-administered include without limitation: anti-CD52 antibodies, such as Alemtuzumab (Campath/University of Cambridge).

In various embodiments, an anti-CD47 agent or an anti-SIRPα agent as described herein, is combined with an anti-CD98 (4F2, FRP-1) agent or antibody. Examples of anti-CD98 agents or antibodies that can be co-administered include without limitation: IGN523 (Igenica).

In various embodiments, an anti-CD47 agent or an anti-SIRPα agent as described herein, is combined with an anti-CD157 (BST-1) agent or antibody. Examples of anti-CD157 agents or antibodies that can be co-administered include without limitation: OBT357, MEN1112 (Menarini; Oxford BioTherapeutics).

In various embodiments, an anti-CD47 agent or an anti-SIRPα agent as described herein, is combined with an anti-DKK-1 agent or antibody. Examples of anti-DKK-1 agents or antibodies that can be co-administered include without limitation: BHQ880 (MorphoSys; Novartis), and DKN-01, LY-2812176 (Eli Lilly).

In various embodiments, an anti-CD47 agent or an anti-SIRPα agent as described herein, is combined with an anti-GRP78 (BiP) agent or antibody. Examples of anti-GRP78 agents or antibodies that can be co-administered include without limitation: PAT-SM6 (OncoMab GmbH).

In various embodiments, an anti-CD47 agent or an anti-SIRPα agent as described herein, is combined with an anti-NOTCH1 agent or antibody. Examples of anti-NOTCH1 agents or antibodies that can be co-administered include without limitation: Brontictuzumab, OMP-52M51 (OncoMed Pharmaceuticals).

In various embodiments, an anti-CD47 agent or an anti-SIRPα agent as described herein, is combined with an anti-ROR1 agent or antibody. Examples of anti-ROR1 agents or antibodies that can be co-administered include without limitation: Mapatumumab, TRM1, and HGS-1012 (Cambridge Antibody Technology).

In various embodiments, an anti-CD47 agent or an anti-SIRPα agent as described herein, is combined with an anti-SLAMF7 (CS1, CD319) agent or antibody. Examples of anti-SLAMF7 agents or antibodies that can be co-administered include without limitation: Elotuzumab, HuLuc63, BMS-901608 (Empliciti/PDL BioPharma), Mogamulizumab (KW-0761).

In various embodiments, an anti-CD47 agent or an anti-SIRPα agent as described herein, is combined with an anti-TNFRSF10A (DR4; APO2; CD261; TRAILR1; TRAILR-1) agent or antibody. Examples of anti-TNFRSF10A agents or antibodies that can be co-administered include without limitation: Mapatumumab, TRM1, and HGS-1012 (Cambridge Antibody Technology).

In various embodiments, an anti-CD47 agent or an anti-SIRPα agent as described herein, is combined with an anti-Transferrin Receptor (TFRC; CD71) agent or antibody. Examples of anti-Transferrin Receptor agents or antibodies that can be co-administered include without limitation: E2.3/A27.15 (University of Arizona).

In various embodiments, an anti-CD47 agent or an anti-SIRPα agent as described herein, is combined with an anti-EPHA3 agent or antibody. Examples of anti-EPHA3 agents or antibodies that can be co-administered include without limitation: Ifabotuzumab, KB004 (Ludwig Institute for Cancer Research).

In various embodiments, an anti-CD47 agent or an anti-SIRPα agent as described herein, is combined with an anti-CCR4 agent or antibody. Examples of anti-CCR4 agents or antibodies that can be co-administered include without limitation: Mogamulizumab, KW-0761 (Poteligeo/Kyowa Hakko Kirin Co.)

In various embodiments, an anti-CD47 agent or an anti-SIRPα agent as described herein, is combined with an anti-CXCR4 agent or antibody. Examples of anti-CXCR4 agents or antibodies that can be co-administered include without limitation: Ulocuplumab, BMS-936564, MDX-1338 (Medarex), and PF-06747143 (Pfizer).

In various embodiments, an anti-CD47 agent or an anti-SIRPα agent as described herein, is combined with an anti-BAFF agent or antibody. Examples of anti-BAFF agents or antibodies that can be co-administered include without limitation: Tabalumab, LY2127399 (Eli Lilly).

In various embodiments, an anti-CD47 agent or an anti-SIRPα agent as described herein, is combined with an anti-BAFF Receptor (BAFF-R) agent or antibody. Examples of anti-BAFF-R agents or antibodies that can be co-administered include without limitation: VAY736 (MorphoSys; Novartis).

In various embodiments, an anti-CD47 agent or an anti-SIRPα agent as described herein, is combined with an anti-RANKL agent or antibody. Examples of anti-RANKL agents or antibodies that can be co-administered include without limitation: Denosumab, AMG-162 (Prolia; Ranmark; Xgeva/Amgen).

In various embodiments, an anti-CD47 agent or an anti-SIRPα agent as described herein, is combined with an anti-IL-6 agent or antibody. Examples of anti-IL-6 agents or antibodies that can be co-administered include without limitation: Siltuximab, CNTO-328 (Sylvant/Centocor).

In various embodiments, an anti-CD47 agent or an anti-SIRPα agent as described herein, is combined with an anti-IL-6 Receptor (IL-6R) agent or antibody. Examples of anti-IL-6R agents or antibodies that can be co-administered include without limitation: Tocilizumab, R-1569 (Actemra/Chugai Pharmaceutical; Osaka University), or AS-101 (CB-06-02, IVX-Q-101).

In various embodiments, an anti-CD47 agent or an anti-SIRPα agent as described herein, is combined with an anti-IL3RA (CD123) agent or antibody. Examples of anti-IL3RA (CD123) agents or antibodies that can be co-administered include without limitation: CSL360 (CSL), Talacotuzumab, JNJ-56022473, CSL362 (CSL); XmAb14045 (Xencor); KHK2823 (Kyowa Hakko Kirin Co.); APV0436 (CD123/CD3); flotetuzumab (CD123/CD3); JNJ-63709178 (CD123/CD3); and XmAb-14045 (CD123/CD3) (Xencor).

In various embodiments, an anti-CD47 agent or an anti-SIRPα agent as described herein, is combined with an anti-IL2RA (CD25) agent or antibody. Examples of anti-IL2RA agents or antibodies that can be co-administered include without limitation: Basiliximab, SDZ-CHI-621 (Simulect/Novartis), and Daclizumab.

In various embodiments, an anti-CD47 agent or an anti-SIRPα agent as described herein, is combined with an anti-IGF-1R (CD221) agent or antibody. Examples of anti-IGF-1R agents or antibodies that can be co-administered include without limitation: Ganitumab, AMG-479 (Amgen); Ganitumab, AMG-479 (Amgen), Dalotuzumab, MK-0646 (Pierre Fabre), and AVE1642 (ImmunoGen).

In various embodiments, an anti-CD47 agent or an anti-SIRPα agent as described herein, is combined with an anti-GM-CSF (CSF2) agent or antibody. Examples of anti-GM-CSF agents or antibodies that can be co-administered include without limitation: Lenzilumab, KB003 (KaloBios Pharmaceuticals).

In various embodiments, an anti-CD47 agent or an anti-SIRPα agent as described herein, is combined with an anti-HGF agent or antibody. Examples of anti-HGF agents or antibodies that can be co-administered include without limitation: Ficlatuzumab, AV-299 (AVEO Pharmaceuticals).

In various embodiments, an anti-CD47 agent or an anti-SIRPα agent as described herein, is combined with an anti-CD44 agent or antibody. Examples of anti-CD44 agents or antibodies that can be co-administered include without limitation: RG7356, RO5429083 (Chugai Biopharmaceuticals; Roche).

In various embodiments, an anti-CD47 agent or an anti-SIRPα agent as described herein, is combined with an anti-VLA-4 (CD49d) agent or antibody. Examples of anti-VLA-4 agents or antibodies that can be co-administered include without limitation: Natalizumab, BG-0002-E (Tysabri/Elan Corporation).

In various embodiments, an anti-CD47 agent or an anti-SIRPα agent as described herein, is combined with an anti-ICAM-1 (CD54) agent or antibody. Examples of anti-ICAM-1 agents or antibodies that can be co-administered include without limitation: BI-505 (BioInvent International)

In various embodiments, an anti-CD47 agent or an anti-SIRPα agent as described herein, is combined with an anti-VEGF-A agent or antibody. Examples of anti-VEGF-A agents or antibodies that can be co-administered include without limitation: Bevacizumab (Avastin/Genentech; Hackensack University Medical Center).

In various embodiments, an anti-CD47 agent or an anti-SIRPα agent as described herein, is combined with an anti-Endosialin (CD248, TEM1) agent or antibody. Examples of antiEndosialin agents or antibodies that can be co-administered include without limitation: Ontecizumab, MORAB-004 (Ludwig Institute for Cancer Research; Morphotek).

In various embodiments, an anti-CD47 agent or an anti-SIRPα agent as described herein, is combined with an anti-CD79 agent or antibody. Examples of anti-CD79 agents or antibodies that can be co-administered include without limitation: polatuzumab, DCDS4501A, RG7596 (Genentech).

In various embodiments, an anti-CD47 agent or an anti-SIRPα agent as described herein, is combined with an anti-Isocitrate dehydrogenase (IDH) agent or antibody. Examples of anti-IDH agents or antibodies that can be co-administered include without limitation: IDH1 inhibitor ivosidenib (Tibsovo; Agios) and the IDH2 inhibitor enasidenib (Idhifa; Celgene/Agios).

In various embodiments, an anti-CD47 agent or an anti-SIRPα agent as described herein, is combined with an antibody that targets tumor associated calcium signal transducer 2 (TACSTD2) (NCBI Gene ID: 4070; EGP-1, EGP1, GA733-1, GA7331, GP50, M1S1, TROP2), such as sacituzumab.

In various embodiments, an anti-CD47 agent or an anti-SIRPα agent as described herein, is combined with an anti-major histocompatibility complex, class I, G (HLA-G; NCBI Gene ID: 3135) antibody, such as TTX-080.

In various embodiments, an anti-CD47 agent or an anti-SIRPα agent as described herein, is combined with an anti-leukocyte immunoglobulin like receptor B2 (LILRB2, a.k.a., CD85D, ILT4; NCBI Gene ID: 10288) antibody, such as JTX-8064 or MK-4830.

TNF Receptor Superfamily (TNFRSF) Member Agonists or Activators

In various embodiments, an anti-CD47 agent or an anti-SIRPα agent as described herein, is combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Examples anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628, each of which is hereby incorporated by reference in its entirety.

Examples anti-TNF receptor superfamily member 10b (TNFRSF10B, DR5, TRAILR2) antibodies that can be co-administered include without limitation, such as DS-8273, CTB-006, INBRX-109, and GEN-1029.

Examples of anti-TNFRSF5 (CD40) antibodies that can be co-administered include without limitation selicrelumab (RO7009789), mitazalimab (a.k.a., vanalimab, ADC-1013, JNJ-64457107), RG7876, SEA-CD40, APX-005M and ABBV-428, ABBV-927, and JNJ-64457107.

Examples of anti-TNFRSF7 (CD27) that can be co-administered include without limitation varlilumab (CDX-1127).

Examples of anti-TNFRSF9 (4-1BB, CD137) antibodies that can be co-administered include without limitation urelumab, utomilumab (PF-05082566), AGEN2373, and ADG-106, BT-7480, and QL1806.

Examples of anti-TNFRSF17 (BCMA) that can be co-administered include without limitation GSK-2857916.

Examples of anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628, each of which is hereby incorporated by reference in its entirety.

Example anti-TRAILR1, anti-TRAILR2, anti-TRAILR3, anti-TRAILR4 antibodies that can be co-administered include without limitation ABBV-621.

Examples of Bi-specific antibodies targeting TNFRSF family members that can be co-administered include without limitation PRS-343 (CD-137/HER2), AFM26 (BCMA/CD16A), AFM-13 (CD16/CD30), REGN-1979 (CD20/CD3), AMG-420 (BCMA/CD3), INHIBRX-105 (4-1BB/PDL1), FAP-4-IBBL (4-1BB/FAP), XmAb-13676 (CD3/CD20), RG-7828 (CD20/CD3), CC-93269 (CD3/BCMA), REGN-5458 (CD3/BCMA), and IMM-0306 (CD47/CD20), and AMG-424 (CD38.CD3).

Examples of inhibitors of PVR related immunoglobulin domain containing (PVRIG, CD112R) that can be co-administered include without limitation: COM-701.

Examples of inhibitors of T cell immunoreceptor with Ig and ITIM domains (TIGIT; NCBI Gene ID: 201633) that can be co-administered include without limitation: BMS-986207, RG-6058, AGEN-1307, and COM-902, etigilimab, tiragolumab (a.k.a., MTIG-7192A; RG-6058; RO 7092284), AGEN1777, IBI-939, AB154, MG1131 and EOS884448 (EOS-448).

Examples of inhibitors of hepatitis A virus cellular receptor 2 (HAVCR2, TIMD3, TIM-3) that can be co-administered include without limitation: TSR-022, LY-3321367, MBG-453, INCAGN-2390, RO-7121661 (PD-1/TIM-3), LY-3415244 (TIM-3/PDL1), and RG7769 (PD-1/TIM-3).

Examples of inhibitors of lymphocyte activating 3 (LAG-3, CD223) that can be co-administered include without limitation: relatlimab (ONO-4482), LAG-525, MK-4280, REGN-3767, INCAGN2385, TSR-033, MGD-013 (PD-1/LAG-3), and FS-118 (LAG-3/PD-L1).

Examples of anti-killer cell immunoglobulin like receptor, three Ig domains and long cytoplasmic tail 1 (KIR3DL1; KIR; NCBI Gene ID: 3811) monoclonal antibodies, such as lirilumab (IPH-2102), and IPH-4102.

Examples of anti-NKG2a antibodies that can be co-administered include without limitation: monalizumab.

Examples of anti-V-set immunoregulatory receptor (VSIR, B7H5, VISTA) antibodies that can be co-administered include without limitation: HMBD-002, and CA-170 (PD-L1/VISTA).

Examples of anti-CD70 antibodies that can be co-administered include without limitation: AMG-172.

Examples of anti-ICOS antibodies that can be co-administered include without limitation: JTX-2011, GSK3359609.

Examples of ICOS agonists that can be co-administered include without limitation: ICOS-L.COMP (Gariepy, J. et al. 106th Annu Meet Am Assoc Immunologists (AAI) (May 9-13, San Diego) 2019, Abst 71.5).

Immune Checkpoint Inhibitors

In some embodiments, an anti-CD47 agent or an anti-SIRPα agent as described herein, is combined with one or more immune checkpoint inhibitors. In some embodiments, the one or more immune checkpoint inhibitors is a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, HBM-4003, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors/antibodies of PD-L1 (CD274) or PD-1 (PDCD1) that can be co-administered include without limitation pembrolizumab, nivolumab, cemiplimab, pidilizumab, AMG-404, AMP-224, MED10680 (AMP-514), spartalizumab, atezolizumab, avelumab, durvalumab, BMS-936559, CK-301, PF-06801591, BGB-A317 (tislelizumab), GEN-1046 (PD-L1/4-1BB), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), RO-7247669 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM-3/PDL1), RG7769 (PD-1/TIM-3) and INBRX-105 (4-1BB/PDL1), GNS-1480 (PD-L1/EGFR), RG-7446 (Tecentriq, atezolizumab), ABBV-181, nivolumab (OPDIVO®, BMS-936558, MDX-1106), pembrolizumab (KEYTRUDA, MK-3477, SCH-900475, lambrolizumab, CAS Reg. No. 1374853-91-4), pidilizumab, PF-06801591, BGB-A317 (tislelizumab), GLS-010 (WBP-3055), AK-103 (HX-008), CS-1003, HLX-10, MGA-012, BI-754091, REGN-2810 (cemiplimab), AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, AK-105, PD1-PIK, BAT-1306, BMS-936559, atezolizumab (MPDL3280A), durvalumab (MEDI-4736), avelumab, CK-301, (MSB0010718C), MEDI-0680, CX-072, CBT-502, PDR-001 (spartalizumab), PDR001+Tafinlar®+Mekinist®, MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, and MDX1105-01, and those described, e.g., in Intl. Patent Publ. Nos. WO2018195321, WO2020014643, W2019160882, and W2018195321.

In various embodiments, an anti-CD47 agent as described herein, is combined with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include AMG-176, AMG-397, S-64315, and AZD-5991, 483-LM, A-1210477, UMI-77, JKY-5-037, and those described in WO2018183418, WO2016033486, and WO2017147410.

Toll-Like Receptor (TLR) Agonists

In various embodiments, an anti-CD47 agent or an anti-SIRPα agent as described herein, is combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation DS-0509, GS-9620, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Examples of TLR8 inhibitors include, but are not limited to, E-6887, IMO-8400, IMO-9200 and VTX-763.

Examples of TLR8 agonists include, but are not limited to, MCT-465, motolimod, GS-9688, and VTX-1463.

Examples of TLR9 inhibitors include but are not limited to, AST-008, IMO-2055, IMO-2125, lefitolimod, litenimod, MGN-1601, and PUL-042.

Examples of TLR7/TLR8 agonist, such as NKTR-262, IMO-4200, MEDI-9197 (telratolimod), resiquimod.

Examples of TLR agonists include without limitation: lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.

In some embodiments, the therapeutic agent is a stimulator of interferon genes (STING) In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP), and cyclic-di-AMP.

TCR Signaling Modulators

In various embodiments, an anti-CD47 agent or an anti-SIRPα agent as described herein, is combined with one or more agonist or antagonist of T-Cell Receptor (TCR) signaling modulators. Activation of T cells through the TCR and is essential for thymocyte development and effector T cell function. TCR activation promotes signaling cascades that ultimately determine cell fate through regulating cytokine production, cell survival, proliferation, and differentiation. Examples of TCR signaling modulators include without limitation CD2 (cluster of differentiation 2, LFA-2, T11, LFA-3 receptor), CD3 (cluster of differentiation 3), CD4 (cluster of differentiation 4), CD8 (cluster of differentiation 8), CD28 (cluster of differentiation 28), CD45 (PTPRC, B220, GP180), LAT (Linker for activation of T cells, LAT1), Lck, LFA-1 (ITGB2, CD18, LAD, LCAMB), Src, Zap-70, SLP-76, DGKalpha, CBL-b, CISH, HPK1. Examples of agonist of cluster of differentiation 3 (CD3) that can be co-administered include without limitation MGD015.

In various embodiments, an anti-CD47 agent or an anti-SIRPα agent as described herein, is combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In various embodiments, the immune checkpoint proteins or receptors regulate T cell responses (e.g., reviewed in Xu, et al., *J Exp Clin Cancer Res*. (2018) 37:110). In various embodiments, the immune checkpoint proteins or receptors regulate NK cell responses (e.g., reviewed in Davis, et al., *Semin Immunol*. (2017) 31:64-75 and Chiossone, et al., *Nat Rev Immunol*. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (PDL1, PD-L1); programmed cell death 1 (PDCD1, PD-1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM-3); galectin 9 (LGALS9); lymphocyte activating 3 (LAG-3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript IE (RAETIE; ULBP4); retinoic acid early transcript 1G (RAETIG; ULBP5); retinoic acid early transcript 1L (RAETIL; ULBP6); lymphocyte activating 3 (CD223); killer cell immunoglobulin like receptor (KIR); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1.

In various embodiments, an anti-CD47 agent or an anti-SIRPα agent as described herein, is combined with one or more blockers or inhibitors of one or more T-cell inhibitory immune checkpoint proteins or receptors. Illustrative T-cell inhibitory immune checkpoint proteins or receptors include without limitation CD274 (PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG-3, CD223); hepatitis A virus cellular receptor 2 (HAVCR2, TIMD3, TIM-3); galectin 9 (LGALS9); killer cell immunoglobulin like receptor (KIR); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, an anti-CD47 agent or an anti-SIRPα agent as described herein, is combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res*. (2018) 37:110.

In various embodiments, an anti-CD47 agent or an anti-SIRPα agent as described herein, is combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94).

In various embodiments, an anti-CD47 agent or an anti-SIRPα agent as described herein, is combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol.* (2017) 31:64-75; Fang, et al., *Semin Immunol.* (2017) 31:37-54; and Chiossone, et al., *Nat Rev Immunol.* (2018) 18(11):671-688.

Adenosine Generation and Signaling

In various embodiments, an anti-CD47 agent or an anti-SIRPα agent as described herein, is combined with an agonist or antagonist of AIR, A2AR, A2BR, A3R, CD73, CD39, CD26; e.g., Adenosine A3 receptor (A3R) agonists, such as namodenoson (CF102); A2aR/A2bR antagonists, such as AB928; anti-CD73 antibodies, such as MEDI-9447 (oleclumab), CPX-006, IPH-53, BMS-986179, NZV-930, CPI-006; CD73 inhibitors, such as AB-680, PSB-12379, PSB-12441, PSB-12425, CB-708, and those described in Int Patent Publication No. WO19173692; CD39/CD73 inhibitors, such as PBF-1662; anti-CD39 antibodies, such as TTX-030; adenosine A2A receptor antagonists, such as CPI-444, AZD-4635, preladenant, PBF-509; and adenosine deaminase inhibitors, such as pentostatin, cladribine.

Bi-Specific T-Cell Engagers

In various embodiments, an anti-CD47 agent or an anti-SIRPα agent as described herein, is combined with a bi-specific T-cell engager (e.g., not having an Fc) or an anti-CD3 bi-specific antibody (e.g., having an Fc). Illustrative anti-CD3 bi-specific antibodies or BiTEs that can be co-administered include AMG-160 (PSMA/CD3), AMG-212 (PSMA/CD3), AMG-330 (CD33/CD3), AMG-420 (BCMA/CD3), AMG-427 (FLT3/CD3), AMG-562 (CD19/CD3), AMG-596 (EGFRvIII/CD3), AMG-701 (BCMA/CD3), AMG-757 (DLL3/CD3), JNJ-64052781 (CD19/CD3), AMG-211 (CEA/CD3), BLINCYTO® (CD19/CD3), RG7802 (CEA/CD3), ERY-974 (CD3/GPC3), huGD2-BsAb (CD3/GD2), PF-06671008 (Cadherins/CD3), APVO436 (CD123/CD3), ERY974, flotetuzumab (CD123/CD3), GEM333 (CD3/CD33), GEMoab (CD3/PSCA), REGN-1979 (CD20/CD3), REGN-5678 (PSMA/CD28), MCLA-117 (CD3/CLEC12A), JNJ-0819, JNJ-7564 (CD3/heme), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), XmAb-18087 (SSTR2/CD3), catumaxomab (CD3/EpCAM), REGN-4018 (MUC16/CD3), RG6026, RG6076, RG6194, RG-7828 (CD20/CD3), CC-93269 (CD3/BCMA), REGN-5458 (CD3/BCMA), GRB-1302 (CD3/Erbb2), GRB-1342 (CD38/CD3), PF-06863135 (BCMA/CD3), SAR440234 (CD3/CDwl23). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology.* (2017) May 17; 6(7):e1326437); PD-L1 (Horn, et al., *Oncotarget.* 2017 Aug. 3; 8(35):57964-57980); and EGFRvIII (Yang, et al., *Cancer Lett.* 2017 Sep. 10; 403:224-230).

Bi- and Tri-Specific Natural Killer (NK)-Cell Engagers

In various embodiments, a compound as described herein, is combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol.* (2016) 1441:333-346; Fang, et al., *Semin Immunol.* (2017) 31:37-54.

Hematopoietic Progenitor Kinase 1 (HPK1) Inhibitors

In various embodiments, an anti-CD47 agent or an anti-SIRPα agent as described herein, is combined with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO-2018183956, WO-2018183964, WO-2018167147, WO-2018183964, WO-2016205942, WO-2018049214, WO-2018049200, WO-2018049191, WO-2018102366, WO-2018049152, WO2020092528, WO2020092621 and WO-2016090300.

Apoptosis Signal-Regulating Kinase (ASK) Inhibitors

In various embodiments, an anti-CD47 agent or an anti-SIRPα agent as described herein, is combined with an inhibitor of an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include without limitation, those described in WO 2011/008709 (Gilead Sciences) and WO 2013/112741 (Gilead Sciences).

Bruton Tyrosine Kinase (BTK) Inhibitors

In various embodiments, an anti-CD47 agent or an anti-SIRPα agent as described herein, is combined with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include without limitation, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, Calquence+AZD6738, Calquence+danvatirsen.

Cyclin-Dependent Kinase (CDK) Inhibitors

In various embodiments, an anti-CD47 agent or an anti-SIRPα agent as described herein, is combined with an inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; MO15; STK1; CDKN7; p39MO15; NCBI Gene ID: 1022); cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include without limitation abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, PF-06873600, AZD4573, and TG-02.

Discoidin Domain Receptor (DDR) Inhibitors.

In various embodiments, an anti-CD47 agent or an anti-SIRPα agent as described herein, is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include without limitation, dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Histone Deacetylase (HDAC) Inhibitors

In various embodiments, an anti-CD47 agent or an anti-SIRPα agent as described herein, is combined with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, entinostat, romidepsin, tucidinostat.

Indoleamine-pyrrole-2,3-dioxygenase (IDO1) Inhibitors

In various embodiments, an anti-CD47 agent or an anti-SIRPα agent as described herein, is combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Janus Kinase (JAK) Inhibitors

In various embodiments, an anti-CD47 agent or an anti-SIRPα agent as described herein, is combined with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include without limitation, AT9283, AZD1480, baricitinib, BMS-911543, fedratinib, filgotinib (GLPG0634), gandotinib (LY2784544), INCB039110 (itacitinib), lestaurtinib, momelotinib (CYT0387), NS-018, pacritinib (SB1518), peficitinib (ASP015K), ruxolitinib, tofacitinib (formerly tasocitinib), INCB052793, and XL019.

Matrix Metalloprotease (MMP) Inhibitors

In various embodiments, an anti-CD47 agent or an anti-SIRPα agent as described herein, is combined with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include without limitation, marimastat (BB-2516), cipemastat (Ro 32-3555), GS-5745 (andecaliximab) and those described in WO 2012/027721 (Gilead Biologics).

RAS and RAS Pathway Inhibitors

In various embodiments, an anti-CD47 agent or an anti-SIRPα agent as described herein, is combined with an inhibitor of KRAS proto-oncogene, GTPase (KRAS; a.k.a., NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893); HRas proto-oncogene, GTPase (HRAS; a.k.a., CTLO; KRAS; HAMSV; HRAS1; KRAS2; RASH1; RASK2; Ki-Ras; p21ras; C-H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR.

In various embodiments, an anti-CD47 agent or an anti-SIRPα agent as described herein, is combined with an inhibitor of KRAS. Examples of KRAS inhibitors include AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras (G12D)-selective inhibitory peptides, including KRpep-2 (Ac-RRCPLYISYDPVCRR-NH$_2$) (SEQ ID NO: 152) and KRpep-2d (Ac-RRRRCPLYISYDPVCRRRR-NH$_2$) (SEQ ID NO: 153).

In various embodiments, an anti-CD47 agent or an anti-SIRPα agent as described herein, is combined with an inhibitor of KRAS mRNA. Illustrative KRAS mRNA inhibitors include anti-KRAS U1 adaptor, AZD-4785, siG12D-LODER™, and siG12D exosomes.

In various embodiments, an anti-CD47 agent or an anti-SIRPα agent as described herein, is combined with an inhibitor of MEK. Illustrative MEK inhibitors that can be co-administered include binimetinib, cobimetinib, PD-0325901, pimasertib, RG-7304, selumetinib, trametinib, and selumetinib.

In various embodiments, an anti-CD47 agent or an anti-SIRPα agent as described herein, is combined with an inhibitor of AKT. Illustrative AKT inhibitors that can be co-administered include RG7440, MK-2206, ipatasertib, afuresertib, AZD5363, and ARQ-092, capivasertib, triciribine, ABTL-0812 (PI3K/Akt/mTOR).

In various embodiments, an anti-CD47 agent or an anti-SIRPα agent as described herein, is combined with an inhibitor of Raf. Illustrative Raf inhibitors that can be co-administered BGB-283 (Raf/EGFR), HM-95573, LXH-254, LY-3009120, RG7304, TAK-580, dabrafenib, vemurafenib, encorafenib (LGX818), PLX8394. RAF-265 (Raf/VEGFR), ASN-003 (Raf/PI3K).

In various embodiments, an anti-CD47 agent or an anti-SIRPα agent as described herein, is combined with an inhibitor of ERK. Illustrative ERK inhibitors that can be co-administered include LTT-462, LY-3214996, MK-8353, ravoxertinib, GDC-0994, and ulixertinib.

In various embodiments, an anti-CD47 agent or an anti-SIRPα agent as described herein, is combined with an inhibitor of PI3K. Illustrative PI3K inhibitors that can be co-administered include idelalisib (Zydelig®), alpelisib, buparlisib, pictilisib, eganelisib (IPI-549). Illustrative PI3K/mTOR inhibitors that can be co-administered include dactolisib, omipalisib, voxtalisib, gedatolisib, GSK2141795, RG6114.

In various embodiments, an anti-CD47 agent or an anti-SIRPα agent as described herein, is combined with an inhibitor of mTOR. Illustrative mTOR inhibitors that can be co-administered include as sapanisertib, vistusertib (AZD2014), ME-344, sirolimus (oral nano-amorphous formulation, cancer), TYME-88 (mTOR/cytochrome P450 3A4).

In certain embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2):132-137.

In various embodiments, an anti-CD47 agent or an anti-SIRPα agent as described herein, is combined with an inhibitor of RAS. Examples of RAS inhibitors include NEO-100, rigosertib;

In various embodiments, an anti-CD47 agent or an anti-SIRPα agent as described herein, is combined with an antagonist of EGFR, such as AMG-595, necitumumab, ABBV-221, depatuxizumab mafodotin (ABT-414), tomuzotuximab, ABT-806, vectibix, modotuximab, RM-1929.

In various embodiments, an anti-CD47 agent or an anti-SIRPα agent as described herein, is combined with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, SAR442720 and those described in WO2018172984 and WO2017211303.

In various embodiments, an anti-CD47 agent or an anti-SIRPα agent as described herein, is combined with an inhibitor of mitogen-activated protein kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, CK-127, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib, TAK-733, CI-1040, RG7421.

In various embodiments, an anti-CD47 agent or an anti-SIRPα agent as described herein, is combined with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, pI10gamma, p120-PI3K; Gene ID: 5494); and/or phosphatidylinositol-4,5-bisphosphate 3-kinase catalytic subunit delta (PIK3CD, APDS, IMD14, PIODELTA, PI3K, p110D, NCBI Gene ID: 5293). In some embodiments, the PI3K inhibitor is a pan-PI3K inhibitor. Examples of PI3K inhibitors include without limitation, ACP-319, AEZA-129, AMG-319, AS252424, AZD8186, BAY 1082439, BEZ235, bimiralisib (PQR309), buparlisib (BKM120), BYL719 (alpelisib), carboxyamidotriazole orotate (CTO), CH5132799, CLR-457, CLR-1401, copanlisib (BAY 80-6946), DS-7423, dactolisib, duvelisib (IPI-145), fimepinostat (CUDC-907), gedatolisib (PF-05212384), GDC-0032, GDC-0084 (RG7666), GDC-0077, pictilisib (GDC-0941), GDC-0980, GSK2636771, GSK2269577, GSK2141795, idelalisib (Zydelig®), INCB040093, INCB50465, IPI-443, IPI-549, KAR4141, LY294002, LY3023414, NERLYNX® (neratinib), nemiralisib (GSK2269557), omipalisib (GSK2126458, GSK458), OXY111A, panulisib (P7170, AK151761), PA799, perifosine (KRX-0401), Pilaralisib (SAR245408; XL147), puquitinib mesylate (XC-302), SAR260301, seletalisib (UCB-5857), serabelisib (INK-1117, MLN-1117, TAK-117), SF1126, sonolisib (PX-866), RG6114, RG7604, rigosertib sodium (ON-01910 sodium), RP5090, tenalisib (RP6530), RV-1729, SRX3177, taselisib, TG100115, umbralisib (TGR-1202), TGX221, voxtalisib (SAR245409), VS-5584, WX-037, X-339, X-414, XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Spleen Tyrosine Kinase (SYK) Inhibitors

In various embodiments, an anti-CD47 agent or an anti-SIRPα agent as described herein, is combined with an inhibitor of spleen associated tyrosine kinase (SYK, p72-Syk, Gene ID: 6850). Examples of SYK inhibitors include without limitation, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Conn.) and those described in U.S. 2015/0175616.

Tyrosine-kinase Inhibitors (TKIs)

In various embodiments, an anti-CD47 agent or an anti-SIRPα agent as described herein, is combined with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation, axitinib, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, olmutinib, osimertinib (AZD-9291), pazopanib, ponatinib, poziotinib, quizartinib, radotinib, rociletinib, sulfatinib (HMPL-012), sunitinib, famitinib L-malate, (MAC-4), tivoanib, TH-4000, tivoanib, and MEDI-575 (anti-PDGFR antibody), TAK-659, Cabozantinib.

Chemotherapeutic Agents (Standard of Care)

In various embodiments, an anti-CD47 agent or an anti-SIRPα agent as described herein, is combined with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223, 177-Lu-PSMA-617; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors. Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®). Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®). Examples of anti-androgens include apalutamide, abiraterone, enzalutamide, flutamide, galeterone, nilutamide, bicalutamide, leuprolide, goserelin, ODM-201, APC-100, ODM-204. An example progesterone receptor antagonist includes onapristone.

Anti-Angiogenic Agents

In various embodiments, an anti-CD47 agent or an anti-SIRPα agent as described herein, is combined with an anti-angiogenic agent. Anti-angiogenic agents that can be co-administered include, but are not limited to, retinoid acid and derivatives thereof, 2-methoxyestradiol, ANGIOSTATIN®, ENDOSTATIN, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cishydroxyproline, d,I-3,4-dehydroproline, thiaproline, α,α'-dipyridyl, beta-aminopropionitrile fumarate, 4-propyl-5-(4-pyridinyl)-2 (3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other antiangiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

In various embodiments, an anti-CD47 agent or an anti-SIRPα agent as described herein, is combined with an anti-fibrotic agent. Anti-fibrotic agents that can be co-administered include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In various embodiments, an anti-CD47 agent or an anti-SIRPα agent as described herein, is combined with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include without limitation mofezolac, GLY-230, and TRK-700.

Examples of inhibitors of prostaglandin-endoperoxide synthase 2 (PTGS2, COX-2; NCBI Gene ID: 5743) that can be co-administered include without limitation diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, Anitrazafen, Apricoxib, Cimicoxib, Deracoxib, Flumizole, Firocoxib, Mavacoxib, NS-398, Pamicogrel, Parecoxib, Robenacoxib, Rofecoxib, Rutecarpine, Tilmacoxib, and Zaltoprofen. Examples of dual COX1/COX2 inhibitors that can be co-administered include without limitation, HP-5000, lornoxicam, ketorolac tromethamine, bromfenac sodium, ATB-346, HP-5000. Examples of dual COX-2/carbonic anhydrase (CA) inhibitors that can be co-administered include without limitation polmacoxib and imrecoxib.

Examples of inhibitors of secreted phospholipase A2, prostaglandin E synthase (PTGES, PGES; Gene ID: 9536) that can be co-administered include without limitation LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett.* (2017) 389:23-32; and Liu, et al., *Oncotarget.* (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include without limitation acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include without limitation meclofenamate sodium, zileuton.

Examples of inhibitors of soluble epoxide hydrolase 2 (EPHX2, SEH; NCBI Gene ID: 2053) that can be co-administered include without limitation compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include without limitation GS-4875, GS-5290, BHM-078 and those described, e.g., in WO2006124944, WO2006124692, WO2014064215, WO2018005435, Teli, et al., *J Enzyme Inhib Med Chem*. (2012) 27(4):558-70; Gangwall, et al., *Curr Top Med Chem*. (2013) 13(9):1015-35; Wu, et al., *Bioorg Med Chem Lett*. (2009) 19(13):3485-8; Kaila, et al., *Bioorg Med Chem*. (2007) 15(19):6425-42; and Hu, et al., *Bioorg Med Chem Lett*. (2011) 21(16):4758-61.

Tumor Oxygenation Agents

In various embodiments, an anti-CD47 agent or an anti-SIRPα agent as described herein, is combined with an agent that promotes or increases tumor oxygenation or reoxygenation, or prevents or reduces tumor hypoxia. Illustrative agents that can be co-administered include, e.g., Hypoxia inducible factor-1 alpha (HIF-1α) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO 2007/137767, WO 2007/139791, WO 2014/107171, and WO 2016/149562.

Immunotherapeutic Agents

In various embodiments, an anti-CD47 agent or an anti-SIRPα agent as described herein, is combined with an immunotherapeutic agent. Example immunotherapeutic agents that can be co-administered include without limitation abagovomab, ABP-980, adecatumumab, afutuzumab, alemtuzumab, altumomab, amatuximab, anatumomab, arcitumomab, bavituximab, bectumomab, bevacizumab biosimilar, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, emibetuzumab, ensituximab, ertumaxomab, etaracizumab, farletuzumab, figitumumab, flanvotumab, futuximab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, matuzumab, milatuzumab, minretumomab, mitumomab, moxetumomab, moxetumomab pasudotox, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, trastuzumab biosimilar, tucotuzumab, ubilituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative ADCs that can be co-administered include without limitation drug-conjugated antibodies, fragments thereof, or antibody mimetics targeting the proteins or antigens listed above and herein (e.g., in Table B). Example ADCs that can be co-administered include without limitation gemtuzumab, brentuximab, trastuzumab, inotuzumab, glembatumumab, anetumab, mirvetuximab, depatuxizumab, rovalpituzumab, vadastuximab, labetuzumab, sacituzumab, lifastuzumab, indusatumab, polatzumab, pinatuzumab, coltuximab, indatuximab, milatuzumab, rovalpituzumab, ABBV-011, ABBV-2029, ABBV-321, ABBV-647, MLN0264 (anti-GCC, guanylyl cyclase C), T-DM1 (trastuzumab emtansine, Kadcycla); SYD985 (anti-HER2, Duocarmycin), milatuzumab-doxorubicin (hCD74-DOX), DCDT2980S, belantamab mafodotin (GSK2857916), polatuzumab vedotin (RG-7596), SGN-CD70A, SGN-CD19A, inotuzumab ozogamicin (CMC-544), lorvotuzumab mertansine, SAR3419, isactuzumab govitecan, enfortumab vedotin (ASG-22ME), ASG-15ME, DS-8201 ((trastuzumab deruxtecan), 225Ac-lintuzumab, U3-1402, 177Lu-tetraxetan-tetuloma, tisotumab vedotin, anetumab ravtansine, CX-2009, SAR-566658, W-0101, ABBV-085, gemtuzumab ozogamicin, ABT-414, glembatumumab vedotin (CDX-011), labetuzumab govitecan (IMMU-130), sacituzumab govitecan (IMMU-132), lifastuzumab vedotin, (RG-7599), milatuzumab-doxorubicin (IMMU-110), indatuximab ravtansine (BT-062), pinatuzumab vedotin (RG-7593), SGN-LIV1A, SGN-CD33A, SAR566658, MLN2704, SAR408701, rovalpituzumab tesirine, ABBV-399, AGS-16C3F, ASG-22ME, AGS67E, AMG 172, AMG 595, AGS-15E, BAY1129980, BAY1187982, BAY94-934 (anetumab ravtansine), GSK2857916, Humax-TF-ADC (tisotumab vedotin), IMGN289, IMGN529; IMGN853 (mirvetuximab soravtansine), LOP628, PCA062, MDX-1203, MEDI-547, PF-06263507, PF-06647020, PF-06647263, PF-06664178, PF-06688992, PF-06804103, RG7450, RG7458, RG7598, SAR566658, SGN-CD33A, DS-1602 and DS-7300, DS-6157, DS-6000, TAK-164, MEDI2228, MEDI7247, AMG575, ADCs that can be co-administered are described, e.g., in Lambert, et al., *Adv Ther* (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a *vinca* alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein.

Cancer Gene Therapy and Cell Therapy

In various embodiments, an anti-CD47 agent or an anti-SIRPα agent as described herein, is combined with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In various embodiments, an anti-CD47 agent or an anti-SIRPα agent as described herein, is combined with one or more cellular therapies. Illustrative cellular therapies include without limitation co-administration of one or more of a population of immune cells. In some embodiments, the immune cells are natural killer (NK) cells, NK-T cells, T cells, gamma delta T cells, B-cells, cytokine-induced killer (CIK) cells, macrophage (MAC) cells, tumor infiltrating lymphocytes (TILs) a granulocyte, an innate lymphoid cell, a megakaryocyte, a monocyte, a macrophage, a platelet, a thymocyte, a myeloid cell, and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments, the cellular therapy entails co-administering immune cells engineered to express chimeric antigen receptors (CARs) or T cell receptors (TCRs) TCRs. In particular embodiments, a population of immune cells is engineered to express a CAR, wherein the CAR comprises a tumor antigen-binding domain. In other embodiments, a population of immune cells is engineered to express T cell receptors (TCRs) engineered to target tumor derived peptides presented on the surface of tumor cells. In one embodiment, the immune cell engineered to express chimeric antigen receptors (CARs) or T cell receptors (TCRs) TCRs is a T cell. In another embodiment, the immune cell engineered to express chimeric antigen receptors (CARs) or T cell receptors (TCRs) TCRs is an NK cell.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, lymphocyte function-associated antigen-1 (LFA-1), MYD88, B7-H3, a ligand that specifically binds with CD83, CDS, ICAM-1, GITR, BAFFR, HVEM (LIGHTR), SLAMF7, NKp80 (KLRF1), CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain derived from a protein selected from the group consisting of the alpha, beta or zeta chain of the T-cell receptor, CD28, CD3 epsilon, CD3 delta, CD3 gamma, CD45, CD4, CD5, CD7, CD8 alpha, CD8 beta, CD9, CD11a, CD11b, CD11c, CD11d, CD16, CD18, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD19, CD19a, IL2R beta, IL2R gamma, IL7R alpha, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, ITGB2, ITGB7, CD29, ITGB2 (LFA-1, CD18), ITGB7, TNFR2, DNAM1 (CD226), SLAMF4 (CD244, 2B4), CD84, CD96 (TACTILE), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C activating NK cell receptors, an Immunoglobulin protein, BTLA, CD247, CD276 (B7-H3), CD30, CD84, CDS, cytokine receptor, Fc gamma receptor, GADS, ICAM-1, Ig alpha (CD79a), integrins, LAT, a ligand that binds with CD83, LIGHT, MHC class 1 molecule, PAG/Cbp, TNFSF14, a Toll ligand receptor, TRANCE/RANKL, or a fragment, truncation, or a combination thereof.

In some embodiments, the CAR comprises a hinge domain. A hinge domain may be derived from a protein selected from the group consisting of the CD2, CD3 delta, CD3 epsilon, CD3 gamma, CD4, CD7, CD8.alpha., CD8.beta., CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, IgG1, IgG2, IgG3, IgG4, IgA, IgD, IgE, IgM or fragment or combination thereof.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3 (αNeuSAc(2-8)αNeuSAc(2-3)βDGaip(1-4)bDGlcp(1-1) Cer); ganglioside GM3 (αNeuSAc(2-3)βDGalp(I-4)βDGlcp (1-1)Cer); GM-CSF receptor; TNF receptor superfamily member 17 (TNFRSF17, BCMA); B-lymphocyte cell adhesion molecule; Tn antigen ((Tn Ag) or (GaINAcu-Ser/Thr)); prostate-specific membrane antigen (PSMA); Receptor tyrosine kinase-like orphan receptor 1 (ROR1); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); HLA class I antigen A-2 alpha; HLA antigen; Lewis(Y)antigen; CD24; Platelet-derived growth factor receptor beta (PDGFR-beta); Stage-specific embryonic antigen-4 (SSEA-4); CD20; delta like 3 (DLL3); Folate receptor alpha; Folate receptor beta, GDNF alpha 4 receptor, Receptor tyrosine-protein kinase, ERBB2 (Her2/neu); Mucin 1, cell surface associated (MUC1); APRIL receptor; ADP ribosyl cyclase-1; Ephb4 tyrosine kinase receptor, DCAMKL1 serine threonine kinase, Aspartate beta-hydroxylase, epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); ephrin type-A receptor 3 (EphA3), Fucosyl GM1; sialyl Lewis adhesion molecule (sLe); transglutaminase 5 (TGS5); high molecular weight-melanomaassociate-dantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); IL-15 receptor (IL-15); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma associated antigen 1 (MAGE-A1); Melanoma associated antigen 3 (MAGE-A3); Melanoma associated antigen 4 (MAGE-A4); T cell receptor beta 2 chain C; ETS translocation-variant gene 6, located on chromosome 12p (ETV6-AML); sperm protein 17 (SPA17); X Antigen Family, Member A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin-A1; Cyclin B; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); Peptidoglycan recognition protein, synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-2 (GPC2); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HLA class I antigen alpha G, HM1.24, K-Ras GTPase, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, Epstein-Barr nuclear antigen 1, Latent membrane protein 1, Secreted protein BARF1, P2X7 purinoceptor, Syndecan-1, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microglobulin, Fc Receptor-like 5 (FcRL5).

Examples of cell therapies include without limitation: AMG-119, Algenpantucel-L, ALOFISEL®, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, SNK-01, NEXI-001, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, CSG-005, LAAP T-cell therapy, PD-1 knockout T cell therapy (esophageal cancer/NSCLC), anti-MUC1 CAR T-cell therapy (esophageal cancer/NSCLC), anti-MUC1 CAR T-cell therapy+PD-1 knockout T cell therapy (esophageal cancer/NSCLC), anti-KRAS G12D mTCR PBL, anti-CD123 CAR T-cell therapy, anti-mutated neoantigen TCR T-cell therapy, tumor lysate/MUC1/survivin PepTivator-loaded dendritic cell vaccine, autologous dendritic cell vaccine (metastatic malignant melanoma, intradermal/intravenous), anti-LeY-scFv-CD28-zeta CAR T-cells, PRGN-3005, iC9-GD2-CAR-IL-15 T-cells, HSC-100, ATL-DC-101, MIDRIX4-LUNG, MIDRIXNEO, FCR-001, PLX stem cell therapy, MDR-101, GeniusVac-Mel4, ilixadencel, allogeneic mesenchymal stem cell therapy, romyelocel L, CYNK-001, ProTrans, ECT-100, MSCTRAIL, dilanubicel, FT-516, ASTVAC-2, E-CEL UVEC, CK-0801, allogenic alpha/beta CD3+ T cell and CD19+ B cell depleted stem cells (hematologic diseases, TBX-1400, HLCN-061, umbilical cord derived Hu-PHEC cells (hematological malignancies/aplastic anemia), AP-011, apceth-201, apceth-301, SENTI-101, stem cell therapy (pancreatic cancer), ICO-VIRiS-cBiTE, CD33HSC/CD33 CAR-T, PLX-Immune, SUBCUVAX, CRISPR allogeneic gamma-delta T-cell based gene therapy (cancer), ex vivo CRISPR allogeneic healthy donor NK-cell based gene therapy (cancer), ex-vivo allogeneic induced pluripotent stem cell-derived NK-cell based gene therapy (solid tumor), and anti-CD20 CAR T-cell therapy (non-Hodgkin's lymphoma).

Additional Agents for Targeting Tumors

Additional agents for targeting tumors include without limitation: Alpha-fetoprotein modulators, such as ET-1402, and AFP-TCR; Anthrax toxin receptor 1 modulator, such as anti-TEM8 CAR T-cell therapy; TNF receptor superfamily member 17 (TNFRSF17, BCMA), such as bb-2121 (idecel), bb-21217, JCARH125, UCART-BCMA, ET-140, MCM-998, LCAR-B38M, CART-BCMA, SEA-BCMA, BB212, ET-140, P-BCMA-101, AUTO-2 (APRIL-CAR), JNJ-68284528; Anti-CLL-1 antibodies, (see, for example, PCT/US2017/025573); Anti-PD-L-CAR tank cell therapy, such as KD-045; Anti-PD-L1 t-haNK, such as PD-L1 t-haNK; anti-CD45 antibodies, such as 131I-BC8 (lomab-B); anti-HER3 antibodies, such as LJM716, GSK2849330; APRIL receptor modulator, such as anti-BCMA CAR T-cell therapy, Descartes-011; ADP ribosyl cyclase-1/APRIL receptor modulator, such as dual anti-BCMA/anti-CD38 CAR T-cell therapy; CART-ddBCMA; B7 homolog 6, such as CAR-NKp30 and CAR-B7H6; B-lymphocyte antigen CD19, such as TBI-1501, CTL-119 huCART-19 T cells, iso-cell, JCAR-015 U.S. Pat. No. 7,446,190, JCAR-014, JCAR-017, (WO2016196388, WO2016033570, WO2015157386), axicabtagene ciloleucel (KTE-C19, Yescarta®), KTE-X19, U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110; anti-CD19 CAR T-cell therapy (B-cell acute lymphoblastic leukemia, Universiti Kebangsaan Malaysia); anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Bio-medicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem; UCAR-011, ICTCAR-014, GC-007F, PTG-01, CC-97540; allogeneic anti-CD19 CART cells, such as GC-007G; APRIL receptor modulator; SLAM family member 7 modulator, BCMA-CS1 cCAR; autologous dendritic cell tumor antigen (ADCTA), such as ADCTA-SSI-G; B-lymphocyte antigen CD20, such as ACTR707 ATTCK-20, PBCAR-20A; allogenic T cells expressing CD20 CAR, such as LB-1905; B-lymphocyte antigen CD19/B-lymphocyte antigen 22, such as TC-310; B-lymphocyte antigen 22 cell adhesion, such as UCART-22, JCAR-018 WO2016090190; NY-ESO-1 modulators, such as GSK-3377794, TBI-1301, GSK3537142; Carbonic anhydrase, such as DC-Ad-GMCAIX; Caspase 9 suicide gene, such as CaspaCIDe DLI, BPX-501; CCR5, such as SB-728; CCR5 gene inhibitor/TAT gene/TRIM5 gene stimulator, such as lentivirus vector CCR5 shRNA/TRIM5alpha/TAR decoy-transduced autologous CD34-positive hematopoietic progenitor cells; CDwl23, such as MB-102, IM-23, JEZ-567, UCART-123; CD4, such as ICG-122; CD5 modulators, such as CD5.28z CART cells; Anti-CD22, such as anti-CD22 CART; Anti-CD30, such as TT-11; Dual anti-CD33/anti-CLL1, such as LB-1910; CD40 ligand, such as BPX-201, MEDI5083; CD56, such as allogeneic CD56-positive CD3-negative natural killer cells (myeloid malignancies); CD19/CD7 modulator, such as GC-197; T-cell antigen CD7 modulator, such as anti-CD7 CAR T-cell therapy (CD7-positive hematological malignancies); CD123 modulator, such as Uni-CAR02-T-CD123; Anti-CD276, such as anti-CD276 CART; CEACAM protein 5 modulators, such as MG7-CART; Claudin 6, such as CSG-002; Claudin 18.2, such as LB-1904; Chlorotoxin, such as CLTX-CART; EBV targeted, such as CMD-003; MUC16EGFR, such as autologous 4H11-28z/fIL-12/EFGRt T cell; Endonuclease, such as PGN-514, PGN-201; Epstein-Barr virus specific T-lymphocytes, such as TT-10; Epstein-Barr nuclear antigen 1/Latent membrane protein 1/Secreted protein BARF1 modulator, such as TT-10X; Erbb2, such as CST-102, CIDeCAR; Ganglioside (GD2), such as 4SCAR-GD2; Gamma delta T cells, such as ICS-200; folate hydrolase 1 (FOLH1, Glutamate carboxypeptidase II, PSMA; NCBI Gene ID: 2346), such as CIK-CAR.PSMA, CART-PSMA-TGFORDN, P-PSMA-101; Glypican-3(GPC3), such as TT-16, GLYCAR; Hemoglobin, such as PGN-236; Hepatocyte growth factor receptor, such as anti-cMet RNA CAR T; HLA class I antigen A-2 alpha modulator, such as FH-MCVA2TCR; HLA class I antigen A-2 alpha/Melanoma associated antigen 4 modulator, such as ADP-A2M4CD8; HLA antigen modulator, such as FIT-001, NeoTCR-P1; Human papillomavirus E7 protein, such as KITE-439 (see, for example, PCT/US2015/033129); ICAM-1 modulator, such as AIC-100; Immunoglobulin gamma Fc receptor III, such as ACTR087; IL-12, such as DC-RTS-IL-12; IL-12 agonist/mucin 16, such as JCAR-020; IL-13 alpha 2, such as MB-101; IL-15 receptor agonist, such as PRGN-3006, ALT-803; interleukin-15/Fc fusion protein (e.g., XmAb24306); recombinant interleukin-15 (e.g., AM0015, NIZ-985); pegylated IL-15 (e.g., NKTR-255); IL-2, such as CST-101; Interferon alpha ligand, such as autologous tumor cell vaccine+systemic CpG-B+IFN-alpha (cancer); K-Ras GTPase, such as anti-KRAS G12V mTCR cell therapy; Neural cell adhesion molecule L1 LCAM (CD171), such as JCAR-023; Latent membrane protein 1/Latent membrane protein 2, such as Ad5f35-LMPd1-2-transduced autologous dendritic cells; MART-1 melanoma antigen modulator, such as MART-1 F5 TCR engineered PBMC; Melanoma associated antigen 10, such as MAGE-A10C796T MAGE-A10 TCR; Melanoma associated antigen 3/Melanoma associated antigen 6 (MAGE A3/A6) such as KITE-718 (see, for example, PCT/US2013/059608); Mesothelin, such as CSG-MESO, TC-210; Mucin 1 modulator, such as ICTCAR-052, Tn MUC-1 CAR-T, ICTCAR-053; Anti-MICA/MICB, such as CYAD-02; NKG2D, such as NKR-2; Ntrkr1 tyrosine kinase receptor, such as JCAR-024; PRAMET cell receptor, such as BPX-701; Prostate stem cell antigen modulator, such as MB-105; Roundabout homolog 1 modulator, such as ATCG-427; Peptidoglycan recognition protein modulator, such as Tag-7 gene modified autologous tumor cell vaccine; PSMA, such as PSMA-CAR T-cell therapy (lentiviral vector, castrate-resistant prostate cancer); SLAM family member 7 modulator, such as IC9-Luc90-CD828Z; TGF beta receptor modulator, such as DNR.NPC T-cells; T-lymphocyte, such as TT-12; T-lymphocyte stimulator, such as ATL-001; TSH receptor modulator, such as ICTCAR-051; Tumor infiltrating lymphocytes, such as LN-144, LN-145; and/or Wilms tumor protein, such as JTCR-016, WT1-CTL, ASP-7517.

MCL1 Apoptosis Regulator, BCL2 Family Member (MCL1) Inhibitors

In various embodiments, an anti-CD47 agent or an anti-SIRPα agent as described herein, is combined with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include AMG-176, AMG-397, S-64315, and AZD-5991, 483-LM, A-1210477, UMI-77, JKY-5-037, and those described in WO2018183418, WO2016033486, WO2019222112 and WO2017147410.

Cytokine Inducible SH2 Containing Protein (CISH) Inhibitors

In various embodiments, an anti-CD47 agent or an anti-SIRPα agent as described herein, is combined with an inhibitor of cytokine inducible SH2 containing protein (CISH; CIS; G18; SOCS; CIS-1; BACTS2; NCBI Gene ID: 1154). Examples of CISH inhibitors include those described in WO2017100861, WO2018075664 and W2019213610.

Gene Editors

In various embodiments, an anti-CD47 agent or an anti-SIRPα agent as described herein, is combined with gene editor. Illustrative gene editing system that can be co-administered include without limitation a CRISPR/Cas9 system, a zinc finger nuclease system, a TALEN system, a homing endonucleases system (e.g., an ARCUS), and a homing meganuclease system.

Others Drugs with Unspecified Targets

In various embodiments, an anti-CD47 agent or an anti-SIRPα agent as described herein, is combined with human immunoglobulin (10% liquid formulation), Cuvitru (human immunoglobulin (20% solution), levofolinate disodium, IMSA-101, BMS-986288, IMUNO BGC Moreau RJ, R-OKY-034F, GP-2250, AR-23, calcium levofolinate, porfimer sodium, RG6160, ABBV-155, CC-99282, polifeprosan 20 with carmustine, Veregen, gadoxetate disodium, gadobutrol, gadoterate meglumine, gadoteridol, 99mTc-sestamibi, pomalidomide, pacibanil, and/or valrubicin, Exemplified Combination Therapies Lymphoma or Leukemia Combination Therapy Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), pomalidomide (POMALYST®/IMNOVID®) lymphokineactivated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCl-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCI-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-cell Lymphoma Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and RICE.

Chronic Lymphocytic Leukemia Combination Therapy

Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

Myelofibrosis inhibiting agents include, but are not limited to, hedgehog inhibitors, histone deacetylase (HDAC) inhibitors, and tyrosine kinase inhibitors. Non-limiting examples of hedgehog inhibitors are saridegib and vismodegib. Examples of HDAC inhibitors include, but are not limited to, pracinostat and panobinostat. Non-limiting examples of tyrosine kinase inhibitors are lestaurtinib, bosutinib, imatinib, radotinib, and cabozantinib.

Hyperproliferative Disorder Combination Therapy

Gemcitabine, nab-paclitaxel, and gemcitabine/nab-paclitaxel may be used with a JAK inhibitor and/or PI3Kδ inhibitor to treat hyperproliferative disorders.

Hypomethylating Agents

The methods described herein include administration of a hypomethylating agent. Hypomethylating agents include, but are not limited to, azacitidine (Vidaza, also known as azacytidine) and decitabine (Dacogen). In some embodiments, the hypomethylating agent is azacitidine or decitabine. In some embodiments, the hypomethylating agent is azacitidine.

Azacitidine (5-azacytidine) is a chemical analogue of cytidine and is approved by the U.S. FDA for use in the treatment of myelodysplastic syndrome (MDS). Azacitidine removes methyl groups on DNA and also inhibits DNA methyltransferase, causing hypomethylation of DNA. At higher concentrations, azacitidine incorporates into DNA and RNA, resulting in direct cytotoxicity of abnormal hematopoietic cells in the bone marrow. The structure of azacitidine is shown below:

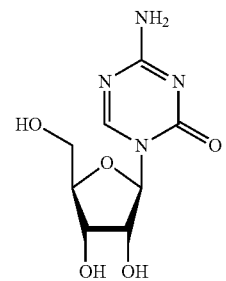

Decitabine (5-aza-2'deoxycitidine) is a chemical analogue of cytidine and is approved by the U.S. FDA for use in the treatment of myelodysplastic syndrome (MDS) and acute myeloid leukemia (AML). Similar to azacitidine, decitabine inhibits DNA methyltransferase, causing hypomethylation of DNA. However, decitabine is only integrated into DNA strands. Once integrated into DNA, decitabine binds irreversibly to DNA methyltransferases (DNMTs) and inhibits disengagement of the DNMTs from the DNA strand, resulting in inhibition of methylation of the DNA. The structure of decitabine is shown below:

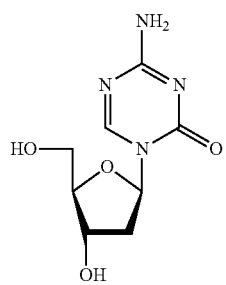 [SMILES: Nc1ncn([C@H]2C[C@@H](O)[C@@H](CO)O2)c(=O)n1]

Methods of Treatment

Methods are provided for treating a subject with a therapeutic dose of an anti-CD47 or anti-SIRPα agent. For example, a method can include (a) administering an isolated antibody that inhibits binding between CD47 and SIRPα and (b) administering a hypomethylating agent to the subject. In another example, a method can include (a) administering an isolated antibody that inhibits binding between CD47 and SIRPα; and (b) administering a hypomethylating agent to the subject, wherein the subject is determined or has been determined to have at least one p53 mutation. In a third example, a method can include determining or having determined the presence of at least one p53 mutation in the subject; and administering or having administered to the subject (i) an isolated antibody that inhibits binding between CD47 and SIRPα and (ii) a hypomethylating agent.

Methods can include a step of administering a primer agent to subject, followed by a step of administering a therapeutically effective dose of an anti-CD47 or anti-SIRPα agent to the subject. In some embodiments, the step of administering a therapeutically effective dose is performed after at least about 3 days (e.g., at least about 4 days, at least about 5 days, at least about 6 days, at least about 7 days, at least about 8 days, at least about 9 days, or at least about 10 days) after beginning the administration of a primer agent. This period of time is, for example, sufficient to provide for enhanced reticulocyte production by the individual. In some embodiments, the anti-CD47 agent is an isolated anti-CD47 antibody. In some embodiments, the anti-SIRPα agent is an isolated anti-SIRPα antibody.

The administration of a therapeutically effective dose of an anti-CD47 or anti-SIRPα agent can be achieved in a number of different ways. In some cases, two or more therapeutically effective doses are administered after a primer agent is administered. Suitable administration of a therapeutically effective dose can entail administration of a single dose, or can entail administration of doses daily, semi-weekly, weekly, once every two weeks, once a month, annually, etc. In some cases, a therapeutically effective dose is administered as two or more doses of escalating concentration (i.e., increasing doses), where (i) all of the doses are therapeutic doses, or where (ii) a sub-therapeutic dose (or two or more sub-therapeutic doses) is initially given and therapeutic doses are achieved by said escalation. As one non-limiting example to illustrate escalating concentration (i.e., increasing doses), a therapeutically effective dose can be administered weekly, beginning with a sub-therapeutic dose (e.g., a dose of less than 10 mg/kg, e.g., 5 mg/kg, 4 mg/kg, 3 mg/kg, 2 mg/kg or 1 mg/kg), and each subsequent dose can be increased by a particular increment (e.g., by 5 mg/kg, by 10 mg/kg, by 15 mg/kg), or by variable increments, until a therapeutic dose (e.g., 15 mg/kg, 30 mg/kg, 45 mg/kg, 60 mg/kg) is reached, at which point administration may cease or may continue with one or more additional therapeutic doses (e.g., continued therapeutic doses or escalated therapeutic doses, e.g., doses of 15 mg/kg, 30 mg/kg, 45 mg/kg, 60 mg/kg). As another non-limiting example to illustrate escalating concentration (i.e., increasing doses), a therapeutically effective dose can be administered weekly, beginning with one or more relatively lower therapeutic doses (e.g., a dose of 10 mg/kg, 15 mg/kg or 30 mg/kg), and each subsequent dose can be increased by a particular increment (e.g., by 10 mg/kg or 15 mg/kg), or by variable increments, until a relatively higher therapeutic dose (e.g., 30 mg/kg, 45 mg/kg, 60 mg/kg, 100 mg/kg, etc.) is reached, at which point administration may cease or may continue (e.g., one or more continued or escalated therapeutic doses, e.g., doses of 30 mg/kg, 45 mg/kg, 60 mg/kg, 100 mg/kg, etc.). In various embodiments, relatively lower therapeutic doses are administered more often (e.g., two or more doses of 15 mg/kg administered weekly (Q1W) or two or more doses of 30 mg/kg administered every two weeks (Q2W)), and relatively higher therapeutic doses are administered less often (e.g., two or more doses of 45 mg/kg administered every 3 weeks (Q3W) or two or more doses of 60 mg/kg administered monthly or every 4 weeks (Q4W)). In some embodiments, administration of a therapeutically effective dose can be a continuous infusion and the dose can altered (e.g., escalated) over time.

Dosage and frequency may vary depending on the half-life of the anti-CD47 or anti-SIRPα agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. intramuscular (i.m.), intraperitoneal (i.p.), intravenous (i.v.), subcutaneous (s.c.), and the like.

An initial dose of a CD47 or SIRPα binding agent, including but not limited to a priming dose, may lead to anemia or hemagglutination for a period of time immediately following infusion. Without being bound by the theory, it is believed that the initial dose of a multivalent CD47 or SIRPα binding agent may cause cross-linking of RBC bound to the agent. In certain embodiments of the invention, a CD47 or SIRPα binding agent is infused to a patient in an initial dose, and optionally in subsequent doses, over a period of time and/or concentration that reduces the possibility of hematologic microenvironments where there is a high local concentration of RBC and the agent.

In some embodiments, an initial dose of a CD47 or SIRPα binding agent is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example from about 3 hours to about 4 hours. In some such embodiments, the dose of agent in the infusate is from about 0.05 mg/ml to about 0.5 mg/ml; for example from about 0.1 mg/ml to about 0.25 mg/ml.

In other embodiments, an initial dose of a CD47 or SIRPα binding agent, e.g. a priming dose, is administered by continuous fusion, e.g. as an osmotic pump, delivery patch, etc., where the dose is administered over a period of at least about 6 hours, at least about 12 hours, at least about 24 hours, at least about 2 days, at least about 3 days. Many such systems are known in the art. For example DUROS technology, provides a bi-compartment system separated by a piston. One of the compartments consists of osmotic engine specifically formulated with an excess of solid NaCl, such that it remains present throughout the delivery period and results in a constant osmotic gradient. It also consists of a semi permeable membrane on one end through which water is drawn into the osmotic engine and establishes a large and constant osmotic gradient between the tissue water and the osmotic engine. Other compartment consists of a drug solution with an orifice from which the drug is released due to the osmotic gradient. This helps to provide site specific and systemic drug delivery when implanted in humans. The preferred site of implantation is subcutaneous placement in the inside of the upper arm.

Following administration of the priming agent, and allowing a period of time effective for an increase in reticulocyte production, a therapeutic dose of an anti-CD47 or anti-SIRPα agent is administered. The therapeutic dose can be administered in number of different ways. In some embodiments, two or more therapeutically effective doses are administered after a primer agent is administered, e.g. in a weekly dosing schedule. In some embodiments a therapeutically effective dose of an anti-CD47 agent is administered as two or more doses of escalating concentration, in others the doses are equivalent. There is reduced hemagglutination after the priming dose.

Additional agents can enhance the efficacy of anti-CD47 or anti-SIRPα agents. The anti-CD47 or anti-SIRPα antibody can be administered in combination or prior to the additional agent.

A combination of an anti-CD47 or anti-SIRPα antibody with an additional agent described herein is given to patients with tumors subtypes that are responsive to these therapies. These tumors may be defined by a higher frequency of mutations, resulting in more tumor antigens, therefore being more immunogenic, as described herein. In some embodiments patients treated with combination therapy are responsive to treatment with an immune activator or checkpoint inhibitor; however this represents a subset of approximately 25% of patients within a specific potentially responsive tumor subtype. In some embodiments, the individuals may be platinum therapy sensitive or resistant.

In some embodiments, the subject methods include a step of administering a primer agent to subject, followed by a step of administering a therapeutically effective dose of an anti-CD47 or anti-SIRPα antibody and an additional agent to the subject. In some embodiments, the step of administering a therapeutically effective dose is performed after at least about 3 days (e.g., at least about 4 days, at least about 5 days, at least about 6 days, at least about 7 days, at least about 8 days, at least about 9 days, or at least about 10 days) after beginning the administration of a primer agent. This period of time is, for example, sufficient to provide for enhanced reticulocyte production by the individual.

The administration of a therapeutically effective dose of an anti-CD47 or anti-SIRPα antibody and/or an additional agent can be achieved in a number of different ways. In some cases, two or more therapeutically effective doses are administered after a primer agent is administered. Suitable administration of a therapeutically effective dose can entail administration of a single dose, or can entail administration of doses daily, semi-weekly, weekly, once every two weeks, once a month, annually, etc. In some cases, a therapeutically effective dose is administered as two or more doses of escalating concentration (i.e., increasing doses), where (i) all of the doses are therapeutic doses, or where (ii) a sub-therapeutic dose (or two or more sub-therapeutic doses) is initially given and therapeutic doses are achieved by said escalation. As one non-limiting example to illustrate escalating concentration (i.e., increasing doses), a therapeutically effective dose can be administered weekly, beginning with a sub-therapeutic dose (e.g., a dose of less than 10 mg/kg, e.g., a dose of 5 mg/kg, 4 mg/kg, 3 mg/kg, 2 mg/kg, 1 mg/kg), and each subsequent dose can be increased by a particular increment (e.g., by 5 mg/kg, 10 mg/kg, 15 mg/kg), or by variable increments, until a therapeutic dose (e.g., 15 mg/kg, 30 mg/kg, 45 mg/kg, 60 mg/kg) is reached, at which point administration may cease or may continue (e.g., one or more continued therapeutic doses or additional escalated (i.e., increasing) doses, e.g., doses of 15 mg/kg, 30 mg/kg, 45 mg/kg, 60 mg/kg). As another non-limiting example to illustrate escalating concentration (i.e., increasing doses), a therapeutically effective dose can be administered weekly, beginning with one or more relatively lower therapeutic doses (e.g., a dose of 10 mg/kg, 15 mg/kg, 30 mg/kg), and each subsequent dose can be increased by a particular increment (e.g., by 10 mg/kg, 15 mg/kg), or by variable increments, until a relatively higher therapeutic dose (e.g., 30 mg/kg, 45 mg/kg, 60 mg/kg, 100 mg/kg, etc.) is reached, at which point administration may cease or may continue (e.g., one or more continued ore escalating therapeutic doses, e.g., doses of 30 mg/kg, 45 mg/kg, 60 mg/kg, 100 mg/kg, etc.). In various embodiments, relatively lower therapeutic doses are administered more often (e.g., two or more doses of 15 mg/kg administered weekly (Q1W) or two or more doses of 30 mg/kg administered every two weeks (Q2W)), and relatively higher therapeutic doses are administered less often (e.g., two or more doses of 45 mg/kg administered every 3 weeks (Q3W) or two or more doses of 60 mg/kg administered monthly or every 4 weeks (Q4W). In some embodiments, administration of a therapeutically effective dose can be a continuous infusion and the dose can altered (e.g., escalated) over time.

Dosage and frequency may vary depending on the half-life of the anti-CD47 or anti-SIRPα antibody and/or the additional agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. i.m., i.p., i.v., s.c., and the like.

In certain embodiments of the invention, the anti-CD47 or anti-SIRPα antibody is infused to a patient in an initial dose, and optionally in subsequent doses, over a period of time and/or concentration that reduces the possibility of hematologic microenvironments where there is a high local concentration of RBC and the agent.

In some embodiments of the invention, an initial dose of the anti-CD47 or anti-SIRPα antibody is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example from about 3 hours to about 4 hours. In some such embodiments, the dose of agent in the infusate is from about 0.05 mg/ml to about 0.5 mg/ml; for example from about 0.1 mg/ml to about 0.25 mg/ml.

Hematopoietic Disorders

Hematopoietic disorders include blood cancers, blood pre-cancers, blood disorders, blood dysplasia, blood hyperproliferative disorders, hematological cancers, hematologic malignancies, hematologic disorders, leukemias, pre-leukemias, acute myeloid leukemia (AML), myelodysplastic syndromes (MDS), clonal hematopoiesis (CH), clonal hematopoiesis of indeterminant potential (CHIP), age-related clonal hematopoiesis (ARCH), idiopathic cytopenias of undetermined significance (ICUS), and clonal cytopenia of undetermined significance (CCUS). A hematopoietic disorder can include a blood cancer or blood pre-cancer that includes one or more p53 mutations. A hematopoietic disorder can be a blood cancer. A hematopoietic disorder can be AML. A hematopoietic disorder can be MDS.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

In some embodiments, the patient has a low mutation burden. In some embodiments, the patient has a high mutation burden. As is known in the art, cancer types can vary in the average or specific degree of mutation, where higher levels of mutation are associated with increased expression of neoantigens. See, for example, Vogelstein et al., (2013), supra. A low mutation burden can be a cancer type with an average per tumor, or specific number for an individual tumor, of up to about 10, up to about 20, up to about 30, up to about 40, up to about 50 non-synonymous mutations per tumor. A high mutation burden can be a cancer type with greater than about 50, greater than about 75, greater than about 100, greater than about 125, greater than about 150 non-synonymous mutations per tumor.

In some embodiments, the hematopoietic disorder is myelodysplastic syndrome (MDS). In some embodiments, the hematopoietic disorder is acute myeloid leukemia (AML). In some embodiments, a cancer is a hematological or blood cancer.

In some embodiments, a hematopoietic disorder is associated with somatic mutations in the hematopoietic cells of a subject. In some embodiments, clonal hematopoiesis (CH), clonal hematopoiesis of indeterminant potential (CHIP), age-related clonal hematopoiesis (ARCH), idiopathic cytopenias of undetermined significance (ICUS), and clonal cytopenia of undetermined significance (CCUS) are associated with somatic mutations in the hematopoietic cells of a subject. Such mutations include, but are not limited to, mutations in DNMT3A, TET2, ASXL1, TP53, JAK2, SF3B1, GNB1, CBL, SRSF2, PPM1D, GNAS, BRCC3, CREBBP, NRAS, RAD21, SETDB1m, U2AF1, SETD2, or any combination thereof.

Exemplary mutations associated with pre-leukemias and progression to AML are generally disclosed in Desai P, et al, Nature Medicine, 24:1015-1023 (2018) and Jaiswal et al, NEJM 2014, both of which are hereby incorporated by reference in their entirety. Mutations associated with risk of AML in healthy subjects are disclosed in Abelson S et al, Nature, 559:400-404 (2018), hereby incorporated by reference in its entirety. Mutations associated with clonal hematopoiesis of indeterminate potential are disclosed in Gibson et al, J. Clin. Oncol, 2017 May 10; 35(14):1598-1605, Jaiswal et al, NEJM 2014, and Steensam D P, Blood Adv. 2018 Nov. 27; 2(22):3404-3410, each of which is hereby incorporated by reference in their entirety. Mutations associated with age-related clonal hematopoiesis (ARCH) are disclosed in Shlush L I, Blood (2018) 131 (5): 496-504, hereby incorporated by reference in its entirety.

P53 Mutations

Provided herein are methods of treating a hematopoietic disorder in a subject, wherein the subject has at least one p53 mutation, comprising: (a) administering an isolated antibody that inhibits binding between CD47 and SIRPα and (b) administering a hypomethylating agent to the subject.

Also provided herein are methods of treating a hematopoietic disorder in a subject comprising: (a) administering an isolated antibody that inhibits binding between CD47 and SIRPα; and (b) administering a hypomethylating agent to the subject, wherein the subject is determined or has been determined to have at least one p53 mutation.

Also provided herein are methods of treating a hematopoietic disorder in a subject comprising: determining or having determined the presence of at least one p53 mutation in the subject; and administering or having administered to the subject (i) an isolated antibody that inhibits binding between CD47 and SIRPα and (ii) a hypomethylating agent.

p53, also known as tumor protein 53 (TP53, UNIPROT P04637, NCBI Gene ID: 7157, NG_017013.2, p53 isoform a: NM_000546.6,), is a tumor suppressor protein that plays a crucial role in cell cycle regulation and apoptosis after cellular stress. A major role of p53 is at the G1/S regulation point during cell division. After cellular stress than results in DNA damage, the p53 protein is activated and initiates transcription of p53 responsive genes. p53 can activate DNA repair proteins, arrest cell growth by holding the cell cycle at the G/S point to allow DNA repair proteins time to repair any damaged DNA, and initiate apoptosis if the DNA damage is irreparable. This allows for the cell to maintain genetic stability. The p53 gene can create 12 different isoforms via multiple promoters, alternative slicing, and an internal ribosome entry site.

p53 is the most frequently mutated gene in human cancers. Loss of function mutations in p53 can occur in the DNA-binding core domain and result in the inability of p53 to bind its target DNA sequences and thus prevent transcription of those genes. Most cancer mutations are missense mutations in the DNA-binding core. In addition, N-terminal and C-terminal truncation mutations have also been associated with cancer. p53 isoforms and mutations are described in "p53 Isoforms and Their Implications in Cancer," Vieler M et al, Cancers (Basel). 2018 September; 10(9): 288, hereby incorporated by reference. Mutations in p53 in AML patients are described in "TP53 Mutations in Newly Diagnosed Acute Myeloid Leukemia," Kadia T M et al, Cancer. 2016 Nov. 15; 122(22):3484-3491, hereby incorporated by reference. p53 mutations can be grouped into various classes, such as early stop codon (C-terminal truncation), N-terminal domain deletion truncation, missense or hotspot mutations that compromise function, nonsense mutations, frameshift mutations, intronic mutations, mutations in the DNA binding domain (amino acid residues 98-293), and mutations in the tetramerization domain (amino acid residues 326-353).

In some embodiments, the p53 mutation comprises one or more amino acid mutations. In some embodiments, the p53 mutation comprises 2, 3, 4, 5, 6, 7, 8, 9, 10, or more amino acid mutations. In some embodiments, the p53 mutation comprises one or more nucleotide mutations. In some embodiments, the p53 mutation comprises 2, 3, 4, 5, 6, 7, 8, 9, 10, or more nucleotide mutations.

In some embodiments, the p53 mutation is an arginine to another amino acid mutation. In some embodiments, the p53 mutation is an arginine to histidine mutation. In some embodiments, the p53 mutation comprises a mutation in exon 4, 5, 6, 7, 8, or 10. In some embodiments, the p53 mutation comprises a mutation in exon 4. In some embodiments, the p53 mutation comprises a mutation in exon 5. In some embodiments, the p53 mutation comprises a mutation in exon 6. In some embodiments, the p53 mutation comprises a mutation in exon 7. In some embodiments, the p53 mutation comprises a mutation in exon 8. In some embodiments, the p53 mutation comprises a mutation in exon 10.

In some embodiments, the p53 mutation comprises a mutation in intron 5, 6, or 9. In some embodiments, the p53 mutation comprises a mutation in intron 5. In some embodiments, the p53 mutation comprises a mutation in intron 6. In some embodiments, the p53 mutation comprises a mutation in intron 9.

The amino acid sequence of wild type p53 is shown as SEQ ID NO: 129. The nucleic acid transcript sequence of wild type p53 isoform a is shown as SEQ ID NO: 130 (NM_000546.6). In some embodiments, the p53 mutation comprises a mutation in codon 248 of p53. In some embodiments, the p53 mutation comprises a nucleic acid mutation including one or more of a 559+1G>A mutation, a 589T>C mutation, a 672+1G>T mutation, a 673+1G>T mutation, a 659A>G mutation, a 517G>A mutation, a 658T>G mutation, a 405C>G mutation, a 298C>T mutation, a 993+1G>A mutation, a 736A>C mutation, an 824G>A mutation, a 584T>C mutation, a 710T>A mutation, and a 1024delC mutation, or any combination thereof. In some embodiments, the p53 mutation comprises a 559+1G>A mutation. In some embodiments, the p53 mutation comprises a 589 T>C mutation. In some embodiments, the p53 mutation comprises a 672+1G>T mutation. In some embodiments, the p53 mutation comprises a 673+1G>T mutation. In some embodiments, the p53 mutation comprises a 659A>G mutation. In some embodiments, the p53 mutation comprises a 517G>A mutation. In some embodiments, the p53 mutation comprises a 658T>G mutation. In some embodiments, the p53 mutation comprises a 405C>G mutation. In some embodiments, the p53 mutation comprises a 298C>T mutation. In some embodiments, the p53 mutation comprises a 993+1G>A mutation. In some embodiments, the p53 mutation comprises a 736A>C mutation. In some embodiments, the p53 mutation comprises an 824G>A mutation. In some embodiments, the p53 mutation comprises a 584T>C mutation. In some embodiments, the p53 mutation comprises a 710T>A mutation. In some embodiments, the p53 mutation comprises a 1024delC mutation.

In some embodiments, the p53 mutation comprises at least two mutations including one or more of a 673+1 G>T mutation and a 659A>C mutation; a 736A>C mutation and an 824G>A mutation; a 672+1G>T mutation and a 584T>C mutation; and a 710T>A mutation and a 1024delC mutation, or any combination thereof.

In some embodiments, the p53 mutation is a somatic mutation. In some embodiments, the p53 mutation is a genomic mutation.

In some embodiments, the p53 mutation comprises at least one amino acid mutation including one or more of Tyr220Cys, Val173Met, Tyr220Cys, Tyr220Asp, Cys135Trp, Gln100Ter (termination), Met248Leu, Cys275Tyr, Ile195Thr, Met237Lys, and Arg342Glu fsTer3, or any combination thereof.

In some embodiments, the p53 mutation comprises at least one of a missense mutation, a frameshift mutation, a nonsense mutation, a deletion mutation, an intronic mutation, or a truncating mutation. In some embodiments, the p53 mutation comprises a missense mutation or a truncating mutation. In some embodiments, the p53 mutation comprises a missense mutation. In some embodiments, the p53 mutation comprises a truncating mutation. In some embodiments, the p53 mutation comprises an N-terminus truncating mutation. In some embodiments, the p53 mutation comprises a C-terminus truncating mutation. In some embodiments, the p53 mutation comprises a frameshift mutation. In some embodiments, the p53 mutation comprises a nonsense mutation. In some embodiments, the p53 mutation comprises a deletion mutation. In some embodiments, the p53 mutation comprises an intronic mutation. In some embodiments, the p53 mutation comprises a mutation in the DNA binding domain. In some embodiments, the p53 mutation comprises a mutation in the tetramerization domain.

In one embodiment, determining the presence of at least one p53 mutation comprises a DNA assay, an RNA assay or a protein assay. In one embodiment, if the at least one p53 mutation is present, the antibody that inhibits binding between CD47 and SIRPα and azacytidine are administered to the subject.

In some embodiments, a p53 mutation in a subject is determined or has been determined by any appropriate method on a biological sample collected from the subject. Such methods include, but are not limited to, a nucleotide-based assay, a protein-based assay, PCR, RNA-seq, DNA-seq, next generation DNA sequencing, sequencing, whole exome sequencing, fluorescent in situ hybridization (FISH), DNA microarray analysis, RNA microarray analysis, mass spectrometry, western blot, immunoblot, or enzyme-linked immunosorbent assay (ELISA). Such methods are well known in the art to determine genetic or protein mutations. Biological samples include, but are not limited to, blood, peripheral blood, bone marrow, tumor biopsy, serum, saliva, skin, hair, buccal swab, or any combination thereof. In some aspects, the samples are assayed for a panel of common pre-leukemia, leukemia, AML, and MDS mutations.

In some embodiments, the p53 mutation status of the subject is or has been determined by a direct to consumer genetic test. Such tests are commercially available from multiple vendors, including, but not limited to, 23andMe, Ancestry.com, Futura Genetics, MyDNA, Pathway Genomics, Progenity, and Dante Labs.

In some embodiments, the p53 mutation status of the subject is or has been determined by a physician or healthcare provider ordered genetic test. Such tests can be provided by multiple vendors such as university internal labs, or a variety of established CLIA certified vendors, including but not limited to Invivoscribe, Cancer Genetics, Foundation Medicine, Centogene, and Quest Diagnostics.

In some embodiments, the p53 mutation status of the subject is or has been determined by a commercial assay panel. Multiple commercial panels are available to one of skill in the art from a variety of vendors, including but not limited to, the Illumina TruSight sequencing panel, the Foundation Medicine FoundationOne panel, the CleanPlex TP53 Panel by Paragon Genomics, and the Accel-Amplicon Comprehensive TP53 Panel by Swift BioSciences.

Subject Status and Selection

A subject with cancer that is administered an anti-CD47 agent and azacitidine can have a certain status. The status can be used for selection of the subject. A status can make a given subject more likely to benefit from administration of both agents.

In some embodiments, a subject that is administered an anti-CD47 agent and azacitidine has a p53 mutation.

A subject can be relapsed or refractory to at least 1, 2, 3, 4, 5, 6, 7, 8, 9, 10 or greater than 10 prior lines of cancer therapy.

A subject can be refractory to azacitidine. A subject can be resistant to azacitidine.

azacitidine refractory status can be a failure to respond to, or progression during, any previous azacitidine-containing regimen, or progression within 6 months of the last azacitidine dose.

Azacitidine refractory status can be a failure to respond to, or progression during, last previous azacitidine-containing regimen, or progression within 6 months of the last azacitidine dose.

In some aspects, a subject has AML or MDS and has received at least two prior systemic therapies. In some aspects, a subject has AML or MDS and relapsed after, or is refractory to, an azacitidine-containing regimen.

Selection and treatment of a subject having MDS with an anti-CD47 agent or an anti-SIRPα agent as described herein can be based on risk stratification of the subject. Cytogenetic abnormalities are seen in more than 80% of subjects with MDS and include translocations or aneuploidy (see Greenberg et al., Myelodysplastic Syndromes, Version 2.2017, NCCN Clinical Practice Guidelines in Oncology. *J Natl Compr Canc Netw.* 15(1):60-87, 2017, which is hereby incorporated by reference in its entirety). The International Prognostic Scoring System (IPSS) or revised IPSS (R-IPSS) are the the most common MDS classification systems (see Dotson and Lebowicz. Myelodysplastic Syndrome. In: StatPearls [Internet]. Treasure Island (FL): StatPearls Publishing; 2020. Available from: www.ncbi.nlm.nih.gov/books/NBK534126/, which is hereby incorporated by reference in its entirety).

The IPSS can be used to classify the MDS risk level of a subject for treatment with an anti-CD47 agent or an anti-SIRPα agent as described herein. The IPSS stratifies patient risk based on the percentage of blasts in bone marrow, karyotype, and number of cell lineages with cytopenias. Karyotype with a good prognosis can include a normal karyotype, —Y, deletion 5q, or deletion 20q. Karyotype with a poor prognosis can include complex cytogenetics (e.g., greater than three abnormalities) or chromosome 7 abnormalities. All other karyotypes can be categorized as intermediate risk. Based on these findings, a score can be calculated to determine a risk score of low, intermediate-1, intermediate-2, or high risk. In some embodiments, a subject is classified as having low risk MDS. In some embodiments, a subject is classified as having intermediate-1 risk MDS. In some embodiments, a subject is classified as having intermediate-2 risk MDS. In some embodiments, a subject is classified as having high risk MDS.

The R-IPSS can be used to classify the MDS risk level of a subject for treatment with an anti-CD47 agent or an anti-SIRPα agent as described herein. The newer R-IPSS stratifies patient risk based on cytogenetics, blast percentage, and has separate scores for absolute neutrophil count, hemoglobin value, and platelet value. The R-IPSS can be used to stratify subjects into one of five categories: very good, good, intermediate, high, and very-high risk. In some embodiments, a subject is classified as having a very good prognosis of MDS. In some embodiments, a subject is classified as having a good prognosis of MDS. In some embodiments, a subject is classified as having an intermediate risk of MDS. In some embodiments, a subject is classified as having a high risk of MDS. In some embodiments, a subject is classified as having a very high risk of MDS.

In some aspects, the expression level of CD47 in lymphoma tissue of a subject can be determined by an assay. CD47 expression can be protein expression by immunohistochemistry, flow cytometry, mass cytometry (CyTOF), or gene expression by RNA sequencing, microarray analysis or other gene expression profiling method.

Examples of assays for CD47 include DNA assays (including whole genome or exome sequencing), microarrays, polymerase chain reaction (PCR), RT-PCR, Southern blots, Northern blots, antibody-binding assays, enzyme-linked immunosorbent assays (ELISAs), flow cytometry, protein assays, Western blots, nephelometry, turbidimetry, chromatography, mass spectrometry, immunoassays, including, by way of example, but not limitation, RIA, immunofluorescence, immunochemiluminescence, immunoelectrochemiluminescence, or competitive immunoassays, and immunoprecipitation. The information from the assay can be quantitative and sent to a computer system of the invention. The information can also be qualitative, such as observing patterns or fluorescence, which can be translated into a quantitative measure by a user or automatically by a reader or computer system. In an embodiment, the subject can also provide information other than assay information to a computer system, such as race, height, weight, age, gender, eye color, hair color, family medical history and any other information that may be useful to a user, such as a clinical factor.

Protein detection assays are assays used to detect the expression level of a given protein from a sample. Protein detection assays are generally known in the art and can include an immunoassay, a protein-binding assay, an antibody-based assay, an antigen-binding protein-based assay, a protein-based array, an enzyme-linked immunosorbent assay (ELISA), flow cytometry, a protein array, a blot, a Western blot, nephelometry, turbidimetry, chromatography, mass spectrometry, enzymatic activity, and an immunoassays selected from RIA, immunofluorescence, immunochemiluminescence, immunoelectrochemiluminescence, immunoelectrophoretic, a competitive immunoassay, and immunoprecipitation.

Protein based analysis, using an antibody as described above that specifically binds to a polypeptide encoded by an altered nucleic acid or an antibody that specifically binds to a polypeptide encoded by a non-altered nucleic acid, or an antibody that specifically binds to a particular splicing variant encoded by a nucleic acid, can be used to identify the presence in a test sample of a particular splicing variant or of a polypeptide encoded by a polymorphic or altered nucleic acid, or the absence in a test sample of a particular splicing variant or of a polypeptide encoded by a non-polymorphic or non-altered nucleic acid. The presence of a polypeptide encoded by a polymorphic or altered nucleic acid, or the absence of a polypeptide encoded by a non-polymorphic or non-altered nucleic acid, is diagnostic for a susceptibility to coronary artery disease.

In one aspect, the level or amount of polypeptide encoded by a nucleic acid in a test sample is compared with the level or amount of the polypeptide encoded by the nucleic acid in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid, and is diagnostic. Alternatively, the composition of the polypeptide encoded by a nucleic acid in a test sample is compared with the composition of the polypeptide encoded by the nucleic acid in a control sample (e.g., the presence of different splicing variants). A difference in the composition of the polypeptide in the test sample, as compared with the composition of the polypeptide in the control sample, is diagnostic. In another aspect, both the level or amount and the composition of the polypeptide can be assessed in the test sample and in the control sample. A difference in the amount or level of the polypeptide in the test sample, compared to the control sample; a difference in composition in the test sample, compared to the control sample; or both a difference in the amount or level, and a difference in the composition, is indicative of whether a subject should be treated with an anti-CD47 antibody, either increased or decreased.

In addition, one of skill will also understand that the above described methods can also generally be used to detect markers that do not include a polymorphism.

Dosing

The methods described herein include administration of a therapeutically effective dose of compositions, e.g., a therapeutically effective dose of an isolated anti-CD47 or anti-SIRPα antibody and a hypomethylating agent.

Compositions are administered to a patient in an amount sufficient to substantially ablate targeted cells, as described above. An amount adequate to accomplish this is defined as a "therapeutically effective dose", which may provide for an improvement in overall survival rates. Single or multiple administrations of the compositions may be administered depending on the dosage and frequency as needed and tolerated by the patient. The particular dose used for a treatment will depend upon the medical condition and history of the mammal, as well as other factors such as age, weight, gender, administration route, efficiency, etc.

Effective doses of the combined agents of the present invention for the treatment of cancer vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

A therapeutically effective dose of the anti-CD47 antibody can depend on the specific agent used, but is usually about 10 mg/kg body weight or more (e.g., about 10 mg/kg or more, about 15 mg/kg or more, 20 mg/kg or more, about 25 mg/kg or more, about 30 mg/kg or more, about 35 mg/kg or more, about 40 mg/kg or more, about 45 mg/kg or more, about 50 mg/kg or more, or about 55 mg/kg or more, or about 60 mg/kg or more, or about 65 mg/kg or more, or about 70 mg/kg or more), or from about 10 mg/kg, from about 15 mg/kg to about 70 mg/kg (e.g., from about 10 mg/kg to about 67.5 mg/kg, or from about 10 mg/kg, from about 15 mg/kg to about 60 mg/kg).

In some embodiments, the therapeutically effective dose of the anti-CD47 antibody is 10, 15, 20, 25, 30, 35, 40, 45, 50, 55, 60, 65, or 67.5 mg/kg. In some embodiments, the therapeutically effective dose of the anti-CD47 antibody is 10 to 60 mg/kg. In some embodiments, the therapeutically effective dose of the anti-CD47 antibody is 10 to 67.5 mg/kg. In some embodiments, the anti-CD47 antibody is administered at a dose of at least 10-30, 20-30, 15-60, 30-60, 10, 15, 20, 30, 40, 45, 50, or 60 mg of antibody per kg of body weight.

A dose of an anti-CD47 antibody can be a flat dose. For example, a flat dose can be given irrespective of a particular subject's weight. Alternatively a flat dose can be given based on a particular subject's weight falling within a particular weight range, e.g., a first range of less than or equal to 100 kg; or a second range of greater than 100 kg. A flat dose can be, e.g., 1000-5000, 2000-4000, 2000-3500, 2400-3500, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000 mg, or an interim number of mg thereof.

A therapeutically effective dose of a hypomethylating agent can be from 10 to 150 mg/kg. In some embodiments, the therapeutically effective dose of a hypomethylating agent is from 10-20, 20-30, 30-40, 40-50, 50-60, 60-70, 75, 70-80, 80-90, 90-100, 100-110, 110-120, 120-130, 130-140, or 140-150 mg/kg. In some embodiments, the therapeutically effective dose of a hypomethylating agent is about 10, 15, 20, 25, 30, 35, 40, 45, 50, 55, 60, 65, 70, 75, 80, 85, 90, 95, 100, 110, 120, 130, 140, or 150 mg/kg.

A therapeutically effective dose of azacitidine can be from 10 to 150 mg/kg. In some embodiments, the therapeutically effective dose of azacitidine is from 10-20, 20-30, 30-40, 40-50, 50-60, 60-70, 75, 70-80, 80-90, 90-100, 100-110, 110-120, 120-130, 130-140, or 140-150 mg/kg. In some embodiments, the therapeutically effective dose of azacitidine is about 10, 15, 20, 25, 30, 35, 40, 45, 50, 55, 60, 65, 70, 75, 80, 85, 90, 95, 100, 110, 120, 130, 140, or 150 mg/kg. In some embodiments, the therapeutically effective dose of azacitidine is 75 mg/kg. In some embodiments, the azacitidine is administered at a dose of at least 75 mg/m².

The dose needed to achieve and/or maintain a particular serum level of the administered composition is proportional to the amount of time between doses and inversely proportional to the number of doses administered. Thus, as the frequency of dosing increases, the needed dose decreases. The optimization of dosing strategies will be readily understood and practiced by one of ordinary skill in the art. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is used. Dosage and frequency vary depending on the half-life of the polypeptide in the patient. In some embodiments, the interval between each single dose is a week. In some embodiments, the interval between each single dose is two weeks. In some embodiments, the interval between each single dose is three weeks. In some embodiments, the interval between each single dose is four weeks. In some embodiments, the interval between each single dose of anti-CD47 antibody is a week. In some embodiments, the interval between each single dose of anti-CD47 antibody is two weeks. In some embodiments, the interval between each single dose of anti-CD47 antibody is three weeks. In some embodiments, the interval between each single dose of anti-CD47 antibody is four weeks. In some embodiments, the interval between each single dose of Hu5F9-G4 is a week. In some embodiments, the interval between each single dose of Hu5F9-G4 is two weeks. In some embodiments, the interval between each single dose of Hu5F9-G4 is three weeks. In some embodiments, the interval between each single dose of Hu5F9-G4 is four weeks.

A "maintenance dose" is a dose intended to be a therapeutically effective dose. For example, in experiments to determine the therapeutically effective dose, multiple different maintenance doses may be administered to different subjects. As such, some of the maintenance doses may be therapeutically effective doses and others may be sub-therapeutic doses.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes used until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including carcinomas, hematologic cancers, melanomas, sarcomas, gliomas, etc. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Toxicity of the combined agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Primer Agents and Priming Dose

In some embodiments of the methods described herein, a primer agent is administered prior to administering a therapeutically effective dose of an anti-CD47 antibody to the individual. Suitable primer agents include an erythropoiesis-stimulating agent (ESA), and/or a priming dose of an anti-CD47 antibody. Following administration of the priming agent, and allowing a period of time effective for an increase in reticulocyte production, a therapeutic dose of an anti-CD47 antibody is administered. Administration may be made in accordance with the methods described in co-pending patent application U.S. Pat. No. 9,623,079, herein specifically incorporated by reference.

In some embodiments, administration of a combination of agents of the invention is combined with an effective dose of an agent that increases patient hematocrit, for example erythropoietin stimulating agents (ESA). Such agents are known and used in the art, including, for example, Aranesp® (darbepoetin alfa), Epogen® NF/Procrit® NF (epoetin alfa), Omontys® (peginesatide), Procrit®, etc.

The term "priming dose" or as used herein refers to a dose of an anti-CD47 antibody that primes a subject for administration of a therapeutically effective dose of anti-CD47 antibody such that the therapeutically effective dose does not result in a severe loss of RBCs (reduced hematocrit or reduced hemoglobin). The specific appropriate priming dose of an anti-CD47 antibody can vary depending on the nature of the agent used and on numerous subject-specific factors (e.g., age, weight, etc.). Examples of suitable priming doses of an anti-CD47 antibody include from about 0.5 mg/kg to about 5 mg/kg, from about 0.5 mg/kg to about 4 mg/kg, from about 0.5 mg/kg to about 3 mg/kg, from about 1 mg/kg to about 5 mg/kg, from about 1 mg/kg to about 4 mg/kg, from about 1 mg/kg to about 3 mg/kg, about 1 mg/kg, about 2 mg/kg, about 3 mg/kg, about 4 mg/kg, about 5 mg/kg. In some embodiments, the priming does is preferably 1 mg/kg.

In some embodiments of the methods described herein, the anti-CD47 antibody is administered to the subject as a priming dose ranging from about 0.5 mg to about 10 mg, e.g., from about 0.5 to about 5 mg/kg of antibody, optionally, 4 mg/kg, 3 mg/kg, 2 mg/kg, or 1 mg/kg of antibody. In some embodiments, the anti-CD47 antibody is administered to the subject as a therapeutic dose ranging from about 20 to about 67.5 mg/kg of antibody, optionally from 15 to 60 mg/kg of antibody, optionally from 30 to 60 mg/kg of antibody, optionally 15 mg/kg of antibody, 20 mg/kg of antibody, 30 mg/kg of antibody, 45 mg/kg of antibody, 60 mg/kg of antibody, or 67.5 mg/kg of antibody.

A priming dose of an anti-CD47 antibody can be a flat priming dose. For example, a flat priming dose can be given irrespective of a particular subject's weight. Alternatively a flat priming dose can be given based on a particular subject's weight falling within a particular weight range, e.g., a first range of less than or equal to 100 kg; or a second range of greater than 100 kg. A flat priming dose can be, e.g., 10-200, 50-100, 80-800, 80-400, 80-200, 70-90, 75-85, 10, 20, 30, 40, 50, 60, 70, 80, 90, 100, 110, 120, 130, 140, 150, 160, 170, 180, 190, 200, 240, 300, 320, 400, 500, 600, 700 or 800 mg, or an interim number of mg thereof.

In some embodiments, a primer agent is administered prior to administering a therapeutically effective dose of an anti-CD47 antibody to the individual. Suitable primer agents include an erythropoiesis-stimulating agent (ESA), and/or a priming dose of an anti-CD47 antibody. Following administration of the priming agent, and allowing a period of time effective for an increase in reticulocyte production, a therapeutic dose of an anti-CD47 antibody is administered. The therapeutic dose can be administered in number of different ways. In some embodiments, two or more therapeutically effective doses are administered after a primer agent is administered. In some embodiments a therapeutically effective dose of an anti-CD47 antibody is administered as two or more doses of escalating concentration, in others the doses are equivalent.

In some embodiments, an effective priming dose of Hu-5F9G4 is provided, where the effective priming dose for a human is around about 1 mg/kg, e.g. from at least about 0.5 mg/kg up to not more than about 5 mg/kg; from at least about 0.75 mg/kg up to not more than about 1.25 mg/kg; from at least about 0.95 mg/kg up to not more than about 1.05 mg/kg; and may be around about 1 mg/kg.

In some embodiments, an initial dose of an anti-CD47 antibody is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example, from about 3 hours to about 4 hours. In some such embodiments, the dose of an anti-CD47 antibody in the infusate is from about 0.05 mg/ml to about 0.5 mg/ml; for example from about 0.1 mg/ml to about 0.25 mg/ml.

In some embodiments a priming dose may be delivered through a sub-cutaneous route, by injection, patch, osmotic pump, and the like as known in the art.

Following administration of the priming agent, and allowing a period of time effective for an increase in reticulocyte production, a therapeutic dose of an anti-CD47 antibody is administered. The therapeutic dose can be administered in number of different ways. In some embodiments, two or more therapeutically effective doses are administered after a primer agent is administered, e.g. in a weekly dosing schedule. In some embodiments a therapeutically effective dose of an anti-CD47 antibody is administered as two or more doses of escalating concentration, in others the doses are equivalent.

In other embodiments, an initial dose of a CD47 antibody, e.g. a priming dose, is administered by continuous fusion, e.g. as an osmotic pump, delivery patch, etc., where the dose is administered over a period of at least about 6 hours, at least about 12 hours, at least about 24 hours, at least about 2 days, at least about 3 days. Many such systems are known in the art. For example DUROS technology, provides a bi-compartment system separated by a piston. One of the compartments consists of osmotic engine specifically formulated with an excess of solid NaCl, such that it remains present throughout the delivery period and results in a constant osmotic gradient. It also consists of a semi permeable membrane on one end through which water is drawn into the osmotic engine and establishes a large and constant osmotic gradient between the tissue water and the osmotic engine. Other compartment consists of a drug solution with an orifice from which the drug is released due to the osmotic gradient. This helps to provide site specific and systemic drug delivery when implanted in humans. The preferred site of implantation is subcutaneous placement in the inside of the upper arm.

Following administration of the priming agent, and allowing a period of time effective for an increase in reticulocyte production, a therapeutic dose of the anti-CD47 antibody is administered. The therapeutic dose can be administered in number of different ways. In some embodiments, two or more therapeutically effective doses are administered after a primer agent is administered, e.g. in a weekly dosing schedule. In some embodiments a therapeutically effective dose of the anti-CD47 antibody is administered as two or more doses of escalating concentration, in others the doses are equivalent. There is reduced hemagglutination after the priming dose.

Dosing Cycles

Provided herein are methods of treating a human subject having an MDS or AML cancer with a p53 mutation or reducing the size of the MDS or AML cancer with a p53 mutation or reducing the tumor burden of MDS or AML patients with a p53 mutation in the human subject can include at least one cycle of (a) administering an anti-CD47 antibody to the subject at a dose of greater than or equal to 10 mg of antibody per kg of body weight; and (b) administering azacitidine to the subject.

In another aspect, methods of treating a human subject having an MDS or AML cancer with a p53 mutation or reducing the size of the MDS or AML cancer with a p53 mutation or reducing the tumor burden of MDS or AML patients with a p53 mutation in the human subject provided herein can include at least one cycle of (a) administering an anti-CD47 agent (e.g., an anti-CD47 antibody, e.g., Hu5F9-G4) to the subject at a dose of greater than or equal to 10 mg of anti-CD47 agent (e.g., antibody) per kg of body weight; and (b) administering a hypomethylating agent to the subject.

Administration can occur in one or more cycles, for example, a first cycle can have a first dosing scheme and one or more subsequent cycles can have dosing scheme(s) that are distinct from (or the same as) the first cycle.

An anti-CD47 antibody can be administered to a subject in a given cycle as a dose ranging from about 10 to about 67.5 mg of antibody per kg of body weight, optionally 10 to 30 mg of antibody per kg of body weight, optionally 15 to 60 mg of antibody per kg of body weight, optionally 10 mg of antibody per kg of body weight, 15 mg of antibody per kg of body weight, 20 mg of antibody per kg of body weight, 30 mg of antibody per kg of body weight, 45 mg of antibody per kg of body weight, 60 mg of antibody per kg of body weight, or 67.5 mg of antibody per kg of body weight.

An anti-CD47 antibody can be administered to a subject in a given cycle, e.g., twice a week, once every week, once every two weeks, once every three weeks, or once every four weeks.

A priming dose of an anti-CD47 antibody to a subject in a given cycle prior to administering an anti-CD47 antibody to the subject at a dose of greater than or equal to 1 mg of antibody per kg of body weight. A priming dose can be 1 mg of antibody per kg of body weight. A priming dose can be administered to a subject for about 3 hours.

An anti-CD47 antibody can be administered to a subject in a first cycle comprising a priming dose of 1 mg of antibody per kg of body weight on day 1 followed by a dose of 30 mg of antibody per kg of body weight once every week. The first cycle can be 4 weeks in duration. Azacitidine can be administered to the subject in the first cycle on days 1-7 at a dose of 75 mg/m² of drug. Azacitidine can be administered to the subject in the first cycle on days 1-5 at a dose of 75 mg/m² of drug.

An anti-CD47 agent (e.g., antibody) can be administered in a second cycle and additional cycles as needed, e.g., as determined by a physician. The additional cycles can comprise a dose of at least 10 mg (e.g., 10-50, 10, 15, 20, 25, 30, 35, 40, 45, 50, 60 mg) of antibody per kg of body weight once every 2 weeks. The second cycle and additional cycles can be 4 weeks in duration. An anti-CD47 antibody can be administered in as many additional cycles as are determined beneficial by a physician. An anti-CD47 antibody can be administered in at least a second, third, fourth, fifth, sixth, seventh, eighth, ninth, tenth, or more cycles, e.g., as determined beneficial by a physician. In some embodiments, the at least second cycle comprises an administration of the antibody once every week. In some embodiments, the at least second cycle comprises administration of the antibody once every two weeks. In some embodiments, the at least second, third, fourth, fifth, sixth, seventh, eighth, ninth, tenth, or more cycles comprise a dose of at least 10 mg (e.g., 10-50, 15-60, 30-60, 10, 15, 20, 25, 30, 35, 40, 45, 50, 60 mg) of antibody per kg of body weight once every 2 weeks. In some embodiments, the at least third, fourth, fifth, sixth, seventh, eighth, ninth, tenth, or more cycles comprise a dose of at least 10 mg (e.g., 10-50, 10, 15, 20, 25, 30, 35, 40, 45, 50, 60 mg) of antibody per kg of body weight once every 2 weeks. For example, each 4-week cycle following the first cycle can continue as-needed for the subject and each include two total doses of anti-CD47 antibody administered once every two weeks and each at least 10 mg (e.g., 10-50, 10, 15, 20, 25, 30, 35, 40, 45, 50, 60 mg) of antibody per kg of body weight.

An anti-CD47 antibody can be administered in a second cycle comprising a dose of 30 mg of antibody per kg of body weight once every 2 weeks. The second cycle can be 4 weeks in duration. Azacitidine can be administered to the subject in the second cycle on days 1-5 or days 1-7 at a dose of 75 mg/m² of drug.

An anti-CD47 antibody can be administered in a third cycle comprising a dose of 30 mg of antibody per kg of body weight once every 2 weeks. The third cycle can be 4 weeks in duration. Azacitidine can be administered to the subject in the third cycle on days 1-5 or days 1-7 at a dose of 75 mg/m² of drug.

An anti-CD47 antibody can be administered in a fourth cycle comprising a dose of 30 mg of antibody per kg of body weight once every 2 weeks. The fourth cycle can be 4 weeks in duration. Azacitidine can be administered to the subject in the fourth cycle on days 1-5 or days 1-7 at a dose of 75 mg/m² of drug.

An anti-CD47 antibody can be administered in a fifth cycle comprising a dose of 30 mg of antibody per kg of body weight once every 2 weeks. The fifth cycle can be 4 weeks in duration. Azacitidine can be administered to the subject in the fifth cycle on days 1-5 or days 1-7 at a dose of 75 mg/m² of drug.

An anti-CD47 antibody can be administered in a sixth cycle comprising a dose of 30 mg of antibody per kg of body weight once every 2 weeks. The sixth cycle can be 4 weeks in duration. Azacitidine can be administered to the subject in the sixth cycle on days 1-5 or days 1-7 at a dose of 75 mg/m² of drug.

An anti-CD47 antibody can be administered in a seventh cycle comprising a dose of 30 mg of antibody per kg of body weight once every 2 weeks. The seventh cycle can be 4 weeks in duration. Azacitidine can be administered to the subject in the seventh cycle on days 1-5 or days 1-7 at a dose of 75 mg/m² of drug.

An anti-CD47 antibody can be administered in a eighth cycle comprising a dose of 30 mg of antibody per kg of body weight once every 2 weeks. The eighth cycle can be 4 weeks in duration. Azacitidine can be administered to the subject in the eighth cycle on days 1-5 or days 1-7 at a dose of 75 mg/m² of drug.

An anti-CD47 antibody can be administered in a ninth cycle comprising a dose of 30 mg of antibody per kg of body weight once every 2 weeks. The ninth cycle can be 4 weeks in duration. Azacitidine can be administered to the subject in the ninth cycle on days 1-5 or days 1-7 at a dose of 75 mg/m² of drug.

An anti-CD47 antibody can be administered in a tenth cycle comprising a dose of 30 mg of antibody per kg of body weight once every 2 weeks. The tenth cycle can be 4 weeks in duration. Azacitidine can be administered to the subject in the tenth cycle on days 1-5 or days 1-7 at a dose of 75 mg/m² of drug.

In some embodiments, no hypomethylating agent, such as azacitidine, is administered in combination with the anti-CD47 antibody. In some embodiments, a hypomethylating agent, such as azacitidine, is administered in combination with the anti-CD47 antibody. In some embodiments, the azacitidine can be administered to the subject in the second cycle, third cycle, fourth cycle, fifth cycle, sixth cycle, seventh cycle, eight cycle, ninth cycle, tenth cycle, or additional cycles (e.g., as determined beneficial by a physician), for example, on days 1-5 or days 1-7 at a dose of 75 mg/m² of drug.

Additional cycles can be used. For example, at least one additional cycle, optionally 1, 2, 3, 4, 5, 6, 7, 8, 9, 10, 11, 12, 13, 14, 15, 16, 17, 18, 19, 20, or greater than 20 additional cycles can be used. The dosing regimen of the at least one additional cycle can be the same as the second cycle, optionally wherein the azacitidine portion of the dosing regimen is discontinued after completing 6 total cycles. Optionally the azacitidine portion of a given cycle can be continued after completing 6 total cycles, e.g., by pursuing a once per month or a once every other month dosing protocol. An at least one additional cycle can be 4 weeks in duration.

In another example, the dosing intervals of the first cycle and second cycle are the same (e.g. the anti-CD47 agent is administered once a week) and the dosing intervals of the third cycle and further additional cycles are different from the first and second cycles (e.g., the anti-CD47 agent is administered once every two weeks). The dosing intervals of the third cycle and additional cycles can be the same. For example, an anti-CD47 antibody can be administered in a first cycle comprising a dose of antibody once every week; a second cycle comprising a dose of antibody once every week; a third cycle comprising a dose of antibody once every two weeks; a fourth cycle comprising a dose of antibody once every two weeks; and additional cycles comprising a dose of antibody once every two weeks as needed, e.g., as determined by a physician. The first cycle, second cycle, third cycle, and additional cycles can be 4 weeks in duration.

In some embodiments, an anti-CD47 antibody can be administered to the subject for at least three distinct cycles of four weeks each, the first cycle comprising (1) administering a dose of antibody once every week; the second cycle comprising (2) administering a dose of antibody once every week; and the third cycle comprising (3) administering a dose of antibody once every two weeks. Azacitidine can be administered to the subject in the second cycle on days 1-5 or days 1-7 at a dose of 75 mg/m$^2$ of drug.

Also disclosed herein is a method of treating or reducing the size of a cancer in a human subject, comprising administering an anti-CD47 antibody (e.g., Hu5F9-G4) and azacitidine to the subject for at least three distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight at time 0 (TO), (2) administering a dose of at least 30 mg (e.g., 30-50, 30, 35, 40, 45, 50, 60 mg) of anti-CD47 antibody per kg of body weight once every week beginning one week after TO with an additional (optional) loading dose of at least 15 mg/kg (e.g., 15-50, 15, 20, 25, 30, 35, 40, 45, 50, 60 mg) on Day 8 and/or an additional (optional) loading dose of at least 30 mg/kg (e.g., 30-50, 30, 35, 40, 45, 50, 60 mg) on Day 11 (week 2), and (3) administering a dose of 75 mg/m$^2$ of azacitidine on days 1-5 or days 1-7 of the first cycle; the second cycle comprising (1) administering a dose of at least 30 mg (e.g., 30-50, 30, 35, 40, 45, 50, 60 mg) of anti-CD47 antibody per kg of body weight once every week and (2) administering a dose of 75 mg/m$^2$ of azacitidine on days 1-5 or days 1-7 of the second cycle; and the third cycle comprising (1) administering a dose of at least 30 mg (e.g., 30-50, 30, 35, 40, 45, 50, 60 mg) of anti-CD47 antibody per kg of body weight once every two weeks and (2) administering a dose of 75 mg/m$^2$ of azacitidine on days 1-5 or days 1-7 of the third cycle. The third cycle can be repeated as additional cycles (e.g., fourth, fifth, sixth, seventh, eighth, ninth, tenth, etc.) without limit or, for example, until clinical benefit is reduced or lost or no longer observed.

Also disclosed herein is a method of treating or reducing the size of a cancer in a human subject, comprising administering an anti-CD47 antibody (e.g., Hu5F9-G4) and azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight at time 0 (TO), (2) administering a dose of at least 30 mg (e.g., 30-50, 30, 35, 40, 45, 50, 60 mg) of anti-CD47 antibody per kg of body weight once every week beginning one week after TO with an additional (optional) loading dose of at least 15 mg/kg (e.g., 15-50, 15, 20, 25, 30, 35, 40, 45, 50, 60 mg) on Day 8 and/or an additional (optional) loading dose of at least 30 mg/kg (e.g., 30-50, 30, 35, 40, 45, 50, 60 mg) on Day 11 (week 2), and (3) administering a dose of 75 mg/m$^2$ of azacitidine on days 1-5 or days 1-7 of the first cycle; and the second cycle comprising (1) administering a dose of at least 30 mg (e.g., 30-50, 30, 35, 40, 45, 50, 60 mg) of anti-CD47 antibody per kg of body weight once every two weeks, once every week, or twice weekly, and (2) administering a dose of 75 mg/m$^2$ of azacitidine on days 1-5 or days 1-7 of the second cycle. The second cycle can be repeated as additional cycles (e.g., third, fourth, fifth, sixth, seventh, eighth, ninth, tenth, etc.) without limit or, for example, until clinical benefit is reduced or lost or no longer observed. When reached and starting at Cycle 6 and beyond, azacitidine can instead be administered to the subject at a dose of 75 mg/m$^2$ for seven days every eight weeks. Generally, anti-CD47 antibody and azacitidine will continue to be administered to the subject as above until the subject loses clinical benefit, e.g., via CR or death. The anti-CD47 antibody can be Hu5F9-G4. The cancer can be at least one of: a myelodysplastic syndrome (MDS) with a p53 mutation (e.g., low, intermediate or high risk), or an acute myeloid leukemia (AML) with a p53 mutation.

In some embodiments, the subject is a human subject, and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on days 11, 15, and 22, and (3) administering a dose of at least 75 mg/m$^2$ of azacitidine on each of days 1-7; and the second cycle comprising (1) administering a dose of at least 30 mg of anti-CD47 antibody per kg of body weight once every week on days 1, 8, 15, and 22, and (2) administering a dose of at least 75 mg/m$^2$ of azacitidine on each of days 1-5 or days 1-7.

In some embodiments, the second cycle comprises administering a dose of at least 75 mg/m$^2$ of azacitidine on each of days 1-5. In some embodiments, the second cycle comprises administering a dose of at least 75 mg/m$^2$ of azacitidine on each of days 1-7.

In some embodiments, the second cycle is repeated as one or more additional cycles without limit or until a clinical benefit is reduced or lost.

In some embodiments, a third cycle of four weeks comprises (1) administering a dose of at least 30 mg of anti-CD47 antibody per kg of body weight once every four weeks on day 1, and (2) administering a dose of at least 75 mg/m$^2$ of azacitidine on each of days 1-5 or days 1-7.

In some embodiments, a third cycle of four weeks comprises (1) administering a dose of at least 30 mg of anti-CD47 antibody per kg of body weight once every two weeks on days 1 and 15, and (2) administering a dose of at least 75 mg/m$^2$ of azacitidine on each of days 1-5 or days 1-7.

In some embodiments, a third cycle of four weeks comprises (1) administering a dose of at least 30 mg of anti-CD47 antibody per kg of body weight once every week on days 1, 8, 15, and 22 and (2) administering a dose of at least 75 mg/m$^2$ of azacitidine on each of days 1-5 or days 1-7.

In some embodiments, the third cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In some embodiments, the subject is a human subject, and the method comprises administering the anti-CD47 antibody and the azacitidine to the subject for at least three distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on days 11, 15, and 22, and (4) administering a dose of at least 75 mg/m$^2$ of azacitidine on each of days 1-7; the second cycle comprising (1) administering a dose of at least 30 mg of anti-CD47 antibody per kg of body weight once every week on days 1, 8, 15, and 22, and (2) administering a dose of at least 75 mg/m² of azacitidine on each of days 1-7; and the third cycle comprising (1) administering a dose of at least 30 mg of anti-CD47 antibody per kg of body weight once every week on days 1, and 15, and (2) administering a dose of at least 75 mg/m² of azacitidine on each of days 1-7.

In some embodiments, the subject is a human subject, and the method comprises administering the anti-CD47 antibody and the azacitidine to the subject for at least three distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (3) administering a dose of at least 30 mg of anti-CD47 antibody per kg of body weight on days 15 and 22, and (4) administering a dose of at least 75 mg/m² of azacitidine on each of days 1-7; the second cycle comprising (1) administering a dose of at least 30 mg of anti-CD47 antibody per kg of body weight once every week on days 1, 8, 15, and 22, and (2) administering a dose of at least 75 mg/m² of azacitidine on each of days 1-7; and the third cycle comprising (1) administering a dose of at least 30 mg of anti-CD47 antibody per kg of body weight once every week on days 1, and 15, and (2) administering a dose of at least 75 mg/m² of azacitidine on each of days 1-7.

In some embodiments, the third cycle is repeated as one or more additional cycles without limit or until a clinical benefit is reduced or lost or no longer observed.

In some embodiments, a fourth cycle of four weeks comprises (1) administering a dose of at least 30 mg of anti-CD47 antibody per kg of body weight once every two weeks on days 1 and 15, and (2) administering a dose of at least 75 mg/m² of azacitidine on each of days 1-7.

In some embodiments, the fourth cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In some embodiments, the subject is a human subject having a myelodysplastic syndrome (MDS), wherein the wherein the subject has at least one p53 mutation, and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on days 11, 15, and 22, and (3) administering a dose of at least 75 mg/m² of azacitidine on each of days 1-7; and the second cycle comprising (1) administering a dose of at least 30 mg of anti-CD47 antibody per kg of body weight once every week on days 1, 8, 15, and 22, and (2) administering a dose of at least 75 mg/m² of azacitidine on each of days 1-7.

In some embodiments, the second cycle is repeated as one or more additional cycles without limit or until a clinical benefit is reduced or lost or no longer observed.

In some embodiments, a third cycle of four weeks comprises (1) administering a dose of at least 30 mg of anti-CD47 antibody per kg of body weight once every two weeks on days 1 and 15, and (2) administering a dose of at least 75 mg/m² of azacitidine on each of days 1-7.

In some embodiments, a third cycle of four weeks comprises (1) administering a dose of at least 30 mg of anti-CD47 antibody per kg of body weight once every week on days 1, 8, 15, and 22 and (2) administering a dose of at least 75 mg/m² of azacitidine on each of days 1-7.

In some embodiments, the third cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In some embodiments, the subject is a human subject having acute myeloid leukemia (AML), wherein the subject has at least one p53 mutation and the method comprises administering the anti-CD47 antibody and the azacitidine to the subject for at least two distinct cycles of four weeks each, the first cycle comprising (1) administering a priming dose of anti-CD47 antibody in the range of 1 mg to 10 mg (e.g., 1 mg to 5 mg, e.g., 1 mg, 2 mg, 3 mg, 4 mg, 5 mg) of antibody per kg of body weight on Day 1 and 4, (2) administering a dose of at least 15 mg of anti-CD47 antibody per kg of body weight on day 8, (3) administering a dose of at least 30 mg of anti-CD47 antibody per kg of body weight on days 11, 15, and 22, and (3) administering a dose of at least 75 mg/m² of azacitidine on each of days 1-7; and the second cycle comprising (1) administering a dose of at least 30 mg of anti-CD47 antibody per kg of body weight once every week on days 1, 8, 15, and 22, and (2) administering a dose of at least 75 mg/m² of azacitidine on each of days 1-7. In some embodiments, the second cycle comprises administering a dose of at least 75 mg/m² of azacitidine on each of days 1-5.

In some embodiments, the second cycle is repeated as one or more additional cycles without limit or until a clinical benefit is reduced or lost or no longer observed.

In some embodiments, a third cycle of four weeks comprises (1) administering a dose of at least 30 mg of anti-CD47 antibody per kg of body weight once every two weeks on days 1 and 15, and (2) administering a dose of at least 75 mg/m² of azacitidine on each of days 1-7.

In some embodiments, a fourth cycle of four weeks comprises (1) administering a dose of at least 30 mg of anti-CD47 antibody per kg of body weight once every two weeks on days 1 and 15, and (2) administering a dose of at least 75 mg/m² of azacitidine on each of days 1-7.

In some embodiments, a fifth cycle of four weeks comprises (1) administering a dose of at least 30 mg of anti-CD47 antibody per kg of body weight once every two weeks on days 1 and 15, and (2) administering a dose of at least 75 mg/m² of azacitidine on each of days 1-7.

In some embodiments, a sixth cycle of four weeks comprises (1) administering a dose of at least 30 mg of anti-CD47 antibody per kg of body weight once every two weeks on days 1 and 15, and (2) administering a dose of at least 75 mg/m² of azacitidine on each of days 1-7.

In some embodiments, a third cycle of four weeks comprises (1) administering a dose of at least 30 mg of anti-CD47 antibody per kg of body weight once every week on days 1, 8, 15, and 22 and (2) administering a dose of at least 75 mg/m² of azacitidine on each of days 1-7.

In some embodiments, the third cycle is repeated as one or more additional cycles without limit or until a clinical benefit is reduced or lost or no longer observed; optionally the anti-CD47 antibody and azacitidine are administered to the subject until the subject loses a clinical benefit; optionally the anti-CD47 antibody is Hu5F9-G4.

In some embodiments, a third cycle of four weeks comprises (1) administering a dose of at least 60 mg of anti-CD47 antibody per kg of body weight once every four weeks on day 1.

In some embodiments, a third cycle of four weeks comprises (1) administering a dose of at least 60 mg of anti-CD47 antibody per kg of body weight once every two weeks on days 1 and 15.

In some embodiments, a third cycle of four weeks comprises (1) administering a dose of at least 60 mg of anti-CD47 antibody per kg of body weight once every week on days 1, 8, 15, and 22.

In some embodiments, the third cycle of four weeks further comprises administering a dose of at least 75 mg/m$^2$ of azacitidine on each of days 1-7. In some embodiments, the third cycle of four weeks further comprises administering a dose of at least 75 mg/m$^2$ of azacitidine on each of days 1-5.

Administration

In the methods described herein, compositions, e.g., an anti-CD47 antibody and, optionally, an additional agent, are administered to a subject. The compositions can be administered by parenteral, topical, intravenous, intra-abdominal, intra-tumoral, oral, subcutaneous, intra-arterial, intracranial, intraperitoneal, intranasal or intramuscular means. A typical route of administration is intravenous or intra-tumoral, although other routes can be equally effective.

In some embodiments the anti-CD47 antibody and/or the additional agent is administered intra-abdominally. In some embodiments the anti-CD47 antibody and/or the additional agent is administered intravenously. In some embodiments the anti-CD47 antibody and/or the additional agent is administered intra-tumorally. In one embodiment, a priming dose of the anti-CD47 antibody is administered, and the priming dose is delivered subcutaneously. In some embodiments, the anti-CD47 antibody and the additional agent are administered concurrently. In some embodiments, the anti-CD47 antibody and the additional agent are administered sequentially.

The active agents are administered within a period of time to produce an additive or synergistic effect on depletion of cancer cells in the host. Methods of administration include, without limitation, systemic administration, intra-tumoral administration, etc. Usually the anti-CD47 antibody is administered within about a period of about 45 days, about 30 days, about 21 days, about 14 days, about 10 days, about 8 days, about 7 days, about 6 days, about 5 days, about 4 days, about 3 days, about 2 days, about 1 day or substantially the same day as the additional agent. In some embodiments the anti-CD47 antibody is administered prior to the additional agent. In some embodiments the anti-CD47 antibody is administered after the additional agent. The agents can be considered to be combined if administration scheduling is such that the serum level of both agents is at a therapeutic level at the same time. Administration may be repeated as necessary for depletion of the cancer cell population.

One or more antibodies disclosed herein can be administered by a medical professional, optionally a physician.

One or more antibodies disclosed herein can be administered by the subject.

Clinical Endpoints

The methods described herein result in at least one improved endpoint compared to baseline.

A method disclosed herein can result in an objective response (OR) in a subject. An objective response is a partial response or complete remission as defined by Cheson, Lugano, or similar NHL response criteria.

A method disclosed herein can result disease control in a subject. Disease control is stable disease plus objective response.

A method disclosed herein can result in a partial response (PR) in a subject. PR is a shrinkage of the tumor by at least 50% by imaging criteria (CT or PET/CT) without complete disappearance of tumor lesions. By PET/CT criteria, a PR is as described above or by reduced metabolic uptake compared with baseline and residual masses of any size (Lugano criteria, Cheson et al., JCO 2014).

A method disclosed herein can result in a complete response (CR) in a subject. Cheson et al., JCO 2014.

A method disclosed herein can result in stable disease (SD) in a subject. Cheson et al., JCO 2014.

A method disclosed herein can reduce the size of a subject's cancer relative to baseline where baseline is determined prior to administration of anti-CD47 antibody.

A method disclosed herein can result in a reversal of refractoriness to azacitidine in a subject.

Pharmaceutical Compositions

An antibody provided herein can be formulated in any appropriate pharmaceutical composition and administered by any suitable route of administration. Suitable routes of administration include, but are not limited to, the intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the Handbook of Pharmaceutical Excipients, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, propylene glycol, and combinations thereof.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, monosodium glutamate, and combinations thereof.

In some embodiments, the pharmaceutical composition comprises a carrier or filler. Illustrative examples of carriers or fillers include lactose, maltodextrin, mannitol, sorbitol, chitosan, stearic acid, xanthan gum, guar gum, and combinations thereof.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, vitamin E polyethylene(glycol) succinate, and combinations thereof.

In some embodiments, the pharmaceutical composition comprises an anti-caking agent. Illustrative examples of anti-caking agents include calcium phosphate (tribasic), hydroxymethyl cellulose, hydroxypropyl cellulose, magnesium oxide, and combinations thereof.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, sugars, and combinations thereof. Specific examples of each of these agents are described, for example, in the Handbook of Pharmaceutical Excipients, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody, since water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

In certain embodiments, an antibody provided herein is formulated as parenteral dosage forms. Parenteral dosage forms can be administered to subjects by various routes including, but not limited to, subcutaneous, intravenous (including infusions and bolus injections), intramuscular, and intra-arterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry (e.g., lyophilized) products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

In some embodiments, the parenteral dosage form is lyophilized. Exemplary lyophilized formulations are described, for example, in U.S. Pat. Nos. 6,267,958 and 6,171,586; and WO 2006/044908; each of which is incorporated by reference in its entirety.

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibody.

The amount of the antibody or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the dosage amounts and dose frequency schedules provided herein. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

As discussed in more detail elsewhere in this disclosure, an antibody provided herein may optionally be administered with one or more additional agents useful to prevent or treat a disease or disorder. The effective amount of such additional agents may depend on the amount of antibody present in the formulation, the type of disorder or treatment, and the other factors known in the art or described herein.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

Kits

Also described herein are kits comprising the active agents, e.g., an anti-CD47 antibody and, optionally, an additional agent, and formulations thereof, and instructions for use. The kit can further contain a least one additional reagent, e.g. azacitidine. Kits typically include a label indicating the intended use of the contents of the kit. The term label includes any writing, or recorded material supplied on or with the kit, or which otherwise accompanies the kit.

Also provided are kits for use in the various methods disclosed herein. The subject kits include a primer agent and an anti-CD47 agent. In some embodiments, a kit comprises two or more primer agents. In some embodiments, a kit comprises two or more anti-CD47 agents. In some embodiments, a primer agent is provided in a dosage form (e.g., a priming dosage form). In some embodiments, a primer agent is provided in two or more different dosage forms (e.g., two or more different priming dosage forms). In some embodiments, an anti-CD47 agent is provided in a dosage form (e.g., a therapeutically effective dosage form). In some embodiments, an anti-CD47 agent is provided in two or more different dosage forms (e.g., two or more different therapeutically effective dosage forms). In the context of a kit, a primer agent and/or an anti-CD47 agent can be provided in liquid or sold form in any convenient packaging (e.g., stick pack, dose pack, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B (1992).

Example 1: Hu5F9-G4 in Combination with Azacitidine in Patients with Hematological Malignancies Introduction Acute myeloid leukemia (AML) is a common hematological malignancy whose incidence rises from 3:100,000 in young adults to greater than 20:100,000 in older adults. For patients <60 years of age, overall survival (OS) is 40 to 50%, but is only 5% for patients >60 years of age. The majority of newly diagnosed patients with AML are over the age of 60. In this patient population, standard induction chemotherapy is often not an option due to increased treatment-related mortality as a result of age and co-morbidities. Standard of care for AML patients unfit for combination chemotherapy is treatment with hypomethylating agents (azacitidine or decitabine) or low dose cytarabine. Despite these frontline treatments, median overall survival (OS) is only about 10 months. In all types of AML, disease relapse is common despite an initial therapeutic response and is the most common reason for death. Standard chemotherapy and allogeneic stem cell transplant (when used) often fail to eradicate all tumor-propagating cells and select for chemotherapy-resistant leukemia-propagating subclones. Patients refractory to salvage therapy are treated palliatively, as current treatment options are extremely limited. These patients have a median survival of 2 months. In addition, patients with newly diagnosed intermediate or higher-risk myelodysplastic syndrome (MDS) and those who relapse after standard care have a poor prognosis and high risk of progression to AML. Therefore, there is an urgent need for new treatment modalities for relapsed/refractory (R/R) AML and MDS patients, newly diagnosed AML patients ineligible for induction chemotherapy based on age and co-morbidities, and newly diagnosed intermediate/high/very high risk MDS patients.

Hu5F9-G4 is a humanized monoclonal antibody that blocks the anti-phagocytic signal CD47, which is highly expressed on cancer cells including AML and serves as a key immune evasion signal for cancers. Hu5F9-G4 binds CD47 and blocks it from interacting with its ligand, signal regulatory protein alpha (SIRPα), on phagocytic cells, leading to phagocytic elimination of cancer cells. Hu5F9-G4 treatment in nonclinical xenograft models of human AML leads to robust elimination of leukemic disease in the peripheral blood and bone marrow which results in long term remissions in a high percentage of mice treated. Hu5F9-G4 has been tested in Phase 1 trials of solid tumors and AML. Hu5F9-G4 monotherapy has been well tolerated and a maximum tolerated dose (MTD) has not been reached in a Phase 1 trial. Based on nonclinical testing, it is hypothesized that Hu5F9-G4 will demonstrate significant anti-leukemic activity in patients with AML or intermediate/high/very high risk MDS. Furthermore, the addition of Hu5F9-G4 to standard-of-care hypomethylating agents (azacitidine) may enhance anti-leukemic activity. This trial will evaluate the anti-leukemic activity of Hu5F9-G4 monotherapy in patients with relapsed or refractory AML or MDS, and will provide continued treatment for patients on a Phase 1 AML trial who are deriving ongoing clinical benefit from Hu5F9-G4 monotherapy. In addition, the safety and anti-leukemic activity of Hu5F9-G4 in combination with azacitidine will be investigated in patients with R/R AML or MDS, previously untreated AML patients who are ineligible for standard induction chemotherapy, and newly diagnosed intermediate/high/very high risk MDS patients.

Study Design and Schema

FIG. 1 shows the study design schema for: Phase 1b Trial of Hu5F9-G4 Monotherapy or Hu5F9-G4 in Combination with Azacitidine in Patients with Hematological Malignancies.

The study included 3 groups of patients:
1. R/R Cohorts: Relapsed and/or refractory AML or MDS patients who have not previously received Hu5F9-G4, received Hu5F9-G4 monotherapy in the safety run-in cohort or Hu5F9-G4 in combination with azacitidine in the expansion cohort on this study (total N=up to 46).
2. TN/U Cohorts: AML patients ineligible for standard induction chemotherapy and previously untreated intermediate/high/very high risk MDS patients by IPSS-R, who received Hu5F9-G4 in combination with azacitidine on this study, with at least 91 intermediate to very high risk MDS patients treated (total N=up to 121). TN/U stands for treatment-naïve/unfit (for standard induction chemotherapy).
3. Rollover Cohort: Patients who received Hu5F9-G4 in the Phase 1 R/R AML study, who continue Hu5F9-G4 monotherapy on this study (total N=up to 8).

Study Design—R/R Cohort

The R/R Cohort was evaluated in 2 stages. 10 patients (the R/R Safety Cohort) were treated in a safety run-in to evaluate the safety profile of Hu5F9-G4 monotherapy in this R/R population. Based on aggregate clinical, safety, PK, and pharmacodynamic data in the R/R Safety Cohort, the Clinical Trial Steering Committee (CTSC) determined whether enrollment may begin in an Expansion stage of the initial R/R Cohort, in which a total of up to 36 additional patients in the R/R Expansion Cohort were treated to evaluate the clinical activity of Hu5F9-G4 in combination with azacitidine. In the R/R Expansion Cohort, Hu5F9-G4 was administered 1 mg/kg twice weekly for Week 1 (Day 1 and Day 4); 15 mg/kg on Day 8; 30 mg/kg on Day 11 and Day 15; and 30 mg/kg weekly on Day 22 through end of Cycle 2, then 30 mg/kg Q2 weeks starting Cycle 3 and thereafter as shown in Table 2 based on clinical, PK, and pharmacodynamic data and for evaluation of a more convenient dosing regimen. If a patient has only received Day 1 treatment for a cycle, the patient may transfer to the new dosing regimen with that cycle, for the balance of the cycle and beyond.

If an increased dose or frequency of dosing is explored, additional cohorts will use a standard 3+3 design. Based on emerging clinical data, including efficacy data, the R/R Expansion Cohort may be increased beyond 36 patients as determined by the CTSC.

TABLE 2

Dose and Schedule for R/R AML/MDS Cohorts

| | | Dose Schedule (Day per 28-day Cycle) | | |
|---|---|---|---|---|
| | | Cycle 1 | Cycle 2 | Cycle 3+ |
| R/R AML/ MDS (Safety Cohort) | Hu5F9-G4 - 1 mg/kg IV | Day 1, 4 | — | |
| | Hu5F9-G4 - 15 mg/kg IV | Day 8 | — | |
| | Hu5F9-G4 - 30 mg/kg IV | Day 11, 15, 22 | Day 1, 8, 15, 22 | Day 1, 8, 15, and 22 |
| R/R AML/ MDS (Expansion Cohort) | Hu5F9-G4 - 1 mg/kg IV | Day 1, 4 | — | |
| | Hu5F9-G4 - 15 mg/kg IV | Day 8 | — | |
| | Hu5F9-G4 - 30 mg/kg IV | Day 11, 15, 22 | Day 1, 8, 15, 22 | Day 1 and 15 |
| | Azacitidine - 75 mg/m2 SC or IV | Day 1-7 | Day 1-7 | Day 1-7 |

The Hu5F9-G4 maintenance dose in R/R Expansion was changed to Q2 weeks beginning at Cycle 3. Azacitidine administered per region-specific labeling: subcutaneous (SC) in UK or US; intravenous (IV) in US only.

Study Design—TN/U Cohort Dose Levels

All patients in the TN/U Cohort receive Hu5F9-G4 in combination with azacitidine. Hu5F9-G4 was administered twice weekly through Cycle 1, Day 11, and then weekly beginning Cycle 1, Day 15 and thereafter, as shown in Table 3. This dose regimen was selected based on emerging clinical, PK, and pharmacodynamic data. Because dosing is changed from twice weekly to weekly (beginning Week 3 of Cycle 1 and thereafter), patients who were treated under a previous regime transitioned to the new (weekly) dosing schedule at the next cycle, or as determined by the Investigator. If a patient has only received Day 1 treatment for a cycle, the patient may transfer to the new dosing regimen for the balance of the cycle and beyond.

Azacitidine was administered according to region-specific drug labeling, either SC or IV, at the standard dose of 75 mg/m2 on Days 1 to 7 of each 28-day cycle for both dose levels. Hu5F9-G4 was given at least 1 hour after the azacitidine infusion/injection was completed.

TABLE 3

Dose and Schedule for TN/U AML/MDS Cohorts

| | | Dose Schedule (Day per 28-day Cycle) | |
|---|---|---|---|
| | | Cycle 1 | Cycle 2 |
| TN/U Dose Evaluation Cohort: Level 1 | Hu5F9-G4 - 1 mg/kg IV | Day 1, 4 | — |
| | Hu5F9-G4 - 15 mg/kg IV | Day 8 | — |
| | Hu5F9-G4 - 30 mg/kg IV | Day 11, 15, 22 | Day 1, 8, 15, 22 |
| | Azacitidine - 75 mg/m2 SC or IV | Day 1-7 | Day 1-7 |
| TN/U Expansion Cohort: 30 mg/kg IV | Hu5F9-G4 - 30 mg/kg IV | Day 1, 4 | — |
| | | Day 8 | — |
| | | Day 11, 15, 22 | Day 1, 8, 15, 22 |
| | Azacitidine - 75 mg/m2 SC or IV | Day 1-7 | Day 1-7 |

Dose evaluation of Hu5F9-G4 began with the designated dose level shown in Table 2. Decisions related to potential dose escalation or de-escalation was based on the first 4 weeks of treatment in the current cohort, referred to as the "Dose-Limiting Toxicity (DLT) Assessment Period," in conjunction with ongoing assessments for patients on prior cohorts who continued therapy beyond 4 weeks. Decisions regarding additional cohorts to further refine the maximum tolerated dose (MTD) or recommended Phase 2 dose and schedule (RP2DS) were made by the CTSC. The CTSC may create additional dose cohorts to be evaluated using a 3+3 design including, but not limited to, adding additional dose cohorts, adding intermediate dose steps (e.g., an additional intra-patient dose escalation step), reducing intermediate dose steps (e.g., removal of an intra-patient dose escalation step), or exploring a dose schedule of weekly or up to every 4 weeks, if supported by emerging PK and clinical data.

Study Design—Rollover Cohort

In the Phase 1 trial of Hu5F9-G4 in R/R AML, patients who have derived clinical benefit from Hu5F9-G4 have been continuously receiving Hu5F9-G4 dosing. These patients may continue to receive Hu5F9-G4 therapy under this protocol in the Rollover Cohort. Patients in the Rollover Cohort may receive the same dose level and schedule (i.e., twice-weekly) of Hu5F9-G4 monotherapy as previously received in the Phase 1 AML study or may transition to once-weekly dosing at the discretion of the Investigator and with Sponsor approval. Patients who are receiving twice-weekly dosing may transition to the new (weekly) dosing schedule at the next cycle, or as determined by the Investigator. If a patient has only received Day 1 treatment for a cycle, the patient may transfer to the new dosing regimen with that cycle, for the balance of the cycle and beyond. Patients on the Rollover Cohort who progress on therapy, no longer derive clinical benefit, or demonstrate unacceptable toxicity to Hu5F9-G4 will be taken off study.

TABLE 4

Dose and Schedule for Rollover AML Cohort

| | | Dose Schedule (Day per 28-day Cycle) All Cycles |
|---|---|---|
| Rollover AML | Hu5F9-G4 - continue same dose level as previous study (up to 30 mg/kg) IV | Dosing schedule may be twice weekly (Day 1, 4, 8, 11, 15, 18, 22, and 25), once weekly (Day 1, 8, 15, 22), or in accordance with a modified recommended Phase 2 dose and schedule determined by the CTSC. |

Patient Eligibility

Inclusion Criteria

All Patients:

1. Met the criteria below for the appropriate cohort:
   a. All R/R Cohorts (met i or ii):
      i. Pathologically confirmed AML (defined by 2017 ELN classification; Döhner 2017) relapsed or refractory to a prior therapy with either a hypomethylating agent (such as azacitidine or decitabine), non-intensive chemotherapy (such as low-dose cytarabine arabinoside), and/or venetoclax. Treatment is limited to 1 prior line of therapy. Hematopoietic stem cell transplant for patients in remission would not be counted as a line of therapy for AML, or
      ii. Confirmed MDS defined according to World Health Organization (WHO) classification that is either refractory to hypomethylating agent (defined as disease progression per IWG 2006 criteria [Cheson 2006] at any time after initiation of a hypomethylating agent or failure to achieve an objective response by IWG 2006 criteria after 4 cycles) or is relapsed or intolerant to prior therapy with either a hypomethylating agent, non-intensive chemotherapy, or targeted therapy. Treatment is limited to 1 prior line of hypomethylating agent therapy (including investigational hypomethylating agents) for all R/R MDS patients.
   b. All TN/U Cohorts (met i or ii):
      i. Previously untreated patients with MDS defined according to WHO classification, with an IPSS-R (Greenberg 2012) risk category of intermediate, high, or very high risk. Prior and concurrent therapy with hydroxyurea, oral etoposide, erythroid, and/or myeloid growth factors is allowed.
      ii. Previously untreated patients with histological confirmation of AML by WHO criteria who are ineligible for treatment with a standard cytarabine and anthracycline induction regimen due to co-morbidity, age or other factors, or who refuse such therapy.

c. Rollover Cohort: Patients on active Hu5F9-G4 therapy on the Phase 1 AML (SCI-CD47-002) trial who are deriving clinical benefit by Investigator assessment.
2. WBC count ≤20×103/mcL pre-first dose of study treatment and prior to each Hu5F9-G4 dose for Cycle 1. Patients with WBC>20×103/mcL can be treated with hydroxyurea (up to 4 g/day) throughout the trial to reduce the WBC to ≤20×103/mcL. Oral etoposide (up to 200 mg orally [PO]/day) may be given as an alternative to hydroxyurea for patients who are intolerant to hydroxyurea or cannot achieve sufficient WBC lowering on hydroxyurea.
3. Patient has provided informed consent.
4. Must be willing and able to comply with clinic visits and procedures outlined in the study protocol.

R/R and TN/U Cohorts only (Criteria 5 through 9 DO NOT apply to the Rollover Cohort):

5. Male or female, age ≥18 years.
6. Eastern Cooperative Oncology Group (ECOG) performance score of 0 to 2.
7. Willing to undergo blood transfusions as deemed clinically necessary.
8. Pretreatment blood crossmatch completed (as detailed in Section 7.3.4).
9. Hematological and biochemical indices within the ranges shown below:
    a. Aspartate aminotransferase (AST)/serum glutamic oxaloacetic transaminase (SGOT) and alanine aminotransferase (ALT)/serum glutamic pyruvic transaminase (SGPT)≤5× upper limit of normal (ULN)
    b. Bilirubin ≤1.5×ULN, or 3.0×ULN and primarily unconjugated if patient has a documented history of Gilbert's syndrome or genetic equivalent
    c. Serum creatinine ≤1.5×ULN or calculated glomerular filtration rate (GFR)≥40 mL/min/1.73 m2
10. Female patients of childbearing potential must not be nursing or planning to be pregnant and must have a negative urine or serum pregnancy test within 30 days before enrollment and within 72 hours before the first administration of study drug.
11. Female patients of childbearing potential must be willing to use 1 highly effective method of contraception during the study and continue for 4 months after the last dose of Hu5F9-G4 or azacitidine, whichever ends later (Section 4.5.1).
12. Male patients who are sexually active with a WOCBP and who have not had vasectomies must be willing to use a barrier method of contraception during the study and for 4 months after the last dose of Hu5F9-G4 or azacitidine, whichever ends later (Section 4.5.2).
13. Willing to consent to mandatory pretreatment and on-treatment bone marrow biopsies (trephines), unless not feasible as determined by the Investigator. Exclusion Criteria 1. Prior treatment with CD47 or SIRPα-targeting agents (with exception of Hu5F9-G4 for patients in the Rollover Cohort).
2. Prior anti-leukemic therapies including, but not limited to, chemotherapy (with the exception of hydroxyurea or oral etoposide), targeted therapies, immunotherapy, or radiotherapy within 4 weeks prior to Day 1 Hu5F9-G4 dosing. NOTE: Localized non-central nervous system (non-CNS) radiotherapy, previous hormonal therapy with luteinizing hormone-releasing hormone (LHRH) agonists for prostate cancer, and treatment with bisphosphonates and receptor activator of nuclear factor kappa-B ligand (RANKL) inhibitors are not criteria for exclusion.
3. TN/U Cohorts Only: Any prior anti-leukemic therapy (excluding hydroxyurea or oral etoposide), prior treatment with hypomethylating agents and/or low dose cytarabine.
4. R/R Expansion Cohort and TN/U Cohorts Only: Contraindications to azacitidine, including advanced malignant hepatic tumors or known hypersensitivity to azacitidine or mannitol.
5. Acute promyelocytic leukemia.
6. Known inherited or acquired bleeding disorders.
7. Previous allogeneic hematopoietic stem cell transplant within 6 months prior to enrollment, active graft versus host disease (GVHD), or requiring transplant-related immunosuppression.
8. Clinical suspicion of active CNS involvement by leukemia.
9. Significant medical diseases or conditions, as assessed by the Investigators and Sponsor, that would substantially increase the risk-benefit ratio of participating in the study. This includes, but is not limited to, acute myocardial infarction within the last 6 months, unstable angina, uncontrolled diabetes mellitus, significant active infections, and congestive heart failure New York Heart Association (NYHA) Class III-IV.
10. Second malignancy, except treated basal cell or localized squamous skin carcinomas, localized prostate cancer, or other malignancies for which patients are not on active anti-cancer therapy as defined in Exclusion Criterion 2.
11. History of psychiatric illness or substance abuse likely to interfere with the ability to comply with protocol requirements or give informed consent.
12. Pregnancy or active breastfeeding.
13. Known active or chronic hepatitis B or C infection or human immunodeficiency virus (HIV).

Study Objectives

Primary Objectives

1) To confirm the safety and tolerability of Hu5F9-G4 monotherapy in this R/R AML and MDS population, and of Hu5F9-G4 in combination with azacitidine in previously untreated patients with AML or MDS and patients with R/R AML and MDS.

2) To evaluate the efficacy of Hu5F9-G4 monotherapy in R/R AML/MDS, and of Hu5F9-G4 in combination with azacitidine in previously untreated patients with AML/MDS or R/R AML/MDS as measured by complete remission (CR) rate for patients with AML, CR+partial remission (PR) rate for patients with MDS, duration of CR for patients with AML, and duration of CR+PR for patients with MDS.

Secondary Objectives

1) To evaluate the pharmacokinetic (PK) profile of Hu5F9-G4 alone and in combination with azacitidine.

2) To evaluate the immunogenicity of Hu5F9-G4.

3) To evaluate the efficacy of Hu5F9-G4 alone or in combination with azacitidine as measured by objective response rate, CR with partial hematologic recovery, duration of response (DOR) for patients with AML, DOR for patients with MDS, red blood cell (RBC) transfusion independence, progression-free survival (PFS), relapse-free survival (RFS), and OS.

4) To assess the level of minimal residual disease (MRD) negativity

Exploratory Objectives

1) To assess CD47 receptor occupancy (RO).

2) To assess biomarkers of immune cell efficacy and bone marrow penetration of Hu5F9-G4.

3) To assess efficacy in molecular subtypes of AML/MDS.

Endpoints

Primary Endpoints

The primary endpoints for this study were:

1) Measurement of adverse events (AEs) according to National Cancer Institute Common Terminology Criteria for Adverse Events (NCI CTCAE) Version 4.03 or customized AE severity grading for Hemagglutination and Microangiopathy as defined below.

2) Complete remission (CR) rate for patients with AML as defined by the Investigator according to protocol-specified criteria shown below which are based on European Leukemia Net (ELN) AML recommendations (Döhner 2017), CR+PR (complete remission and partial remission) rate for patients with MDS as defined by the IWG MDS response criteria, DCR for patients with AML, (Cheson 2006), and duration of CR+PR for patients with MDS.

Secondary Endpoints

The secondary endpoints for this study were:

1) Hu5F9-G4 concentration versus time measurements.

2) ADA to Hu5F9-G4.

3) Objective response in AML based on ELN AML recommendations (Döhner 2017) and IWG AML response criteria, or ORR (Cheson 2003) in MDS as defined by IWG MDS response criteria (Cheson 2006); complete remission with partial hematologic recovery (CRh); DOR for patients with AML; DOR for patients with MDS; RBC transfusion independence (no RBC transfusions for at least an 8-week consecutive period); and, where appropriate, progression-free survival (PFS), relapse-free survival (RFS), and OS for patients with AML or MDS.

4) Level of MRD negativity using a multiparameter flow cytometry-based assay for patients on therapy.

Exploratory Endpoints

The exploratory endpoints for this study were:

1) A US-only sub-study of RO on peripheral RBCs, white blood cells (WBCs), and leukemia cells.

2) Pharmacodynamic markers of Hu5F9-G4 biological activity potentially including, but not limited to, circulating cytokine profiles, T cell receptor sequencing on circulating T cells, mass cytometry (CyTOF)/flow cytometry of circulating leukocytes, and T cell activation studies.

3) Hu5F9-G4 saturation of tumor cells and changes in the tumor microenvironment potentially including, but not limited to, macrophage and T cell tumor infiltration.

4) Correlation of response to molecular subtypes of AML/MDS potentially including, but not limited to, cytogenetic and mutational profile and leukemia/dysplastic immunophenotyped.

5) Impact of Hu5F9-G4 on bone marrow cellularity and leukemic stem cell populations.

AE Severity Grading for Hemagglutination and Microangiopathy

Grade 1: Evidence of hemagglutination and/or microangiopathy on peripheral blood smear AND associated clinical sequelae that are asymptomatic or mild, not requiring intervention Grade 2: Evidence of hemagglutination and/or microangiopathy on peripheral blood smear AND associated clinical sequelae that require medical intervention Grade 3: Evidence of hemagglutination and/or microangiopathy on peripheral blood smear AND associated clinical sequelae that are medically significant, requiring hospitalization or prolongation of existing hospitalization, disabling, or limiting self-care activities of daily living Grade 4: Evidence of hemagglutination and/or microangiopathy on peripheral blood smear AND associated clinical sequelae that are life threatening or require urgent intervention Grade 5: Evidence of hemagglutination and/or microangiopathy on peripheral blood smear AND associated clinical sequelae that result in death Intervention and Mode of Delivery Disease Response Assessment Based on European Leukemianet And International Working Group Criteria Assessment of leukemia response in AML patients was conducted primarily using the European Leukemia Net (ELN) 2017 recommendations for AML (Döhner 2017) and the 2003 International Working Group (IWG) criteria (Cheson 2003). Response classifications include: complete remission (CR), complete remission without minimal residual disease (CRMRD-), cytogenetic complete remission (cCR), molecular complete remission (mCR), complete remission with incomplete hematologic recovery (CRi), partial remission (PR) and stable disease (SD).

In addition, CR with partial hematologic recovery was assessed for AML and MDS, defined as patients who achieve a CR per AML ELN 2017 recommendations (Döhner 2017) or MDS IWG 2006 criteria (Cheson 2006), with the exception of requiring partial hematologic recovery as defined by a platelet count of $>50\times10^9$/L and an absolute neutrophil count of $>500/\mu$L.

In addition, hematologic improvement (HI) was assessed by 2006 IWG criteria (Cheson 2006) to compare with disease response assessed by 2017 ELN criteria (Döhner 2017) and 2003 IWG criteria (Cheson 2003).

Response was assessed in MDS patients using the 2006 IWG criteria (Cheson 2006), with the added caveat that the impact of anemia must be deemed disease-related and not due to study treatment.

Study Drug Information

Hu5F9-G4

The active pharmaceutical ingredient (API) was Hu5F9-G4, a humanized IgG4 monoclonal antibody of the IgG4 kappa isotype containing a Ser-Pro (S-P) substitution in the hinge region (position 228) of the heavy chain to reduce Fab-arm exchange. It comprises a disulfide-linked glycosylated tetramer, consisting of two identical 444 amino acid heavy gamma chains and two identical 219 amino acid kappa light chains. Hu5F9-G4 targets the human CD47 antigen. Hu5F9-G4 drug product is a sterile, clear, colorless, preservative-free liquid intended for IV infusion.

Hu5F9-G4 API was manufactured under current Good Manufacturing Practices. Hu5F9-G4 was supplied in single-use, 10 mL vials containing 200 mg of the antibody in a formulation of 10 mM sodium acetate, 5% (w/v) sorbitol, 0.01% (w/v) polysorbate 20, at pH of 5.0. The labeling complied with the requirements of the applicable regulatory agencies.

Azacitidine

Azacitidine is a nucleoside metabolic inhibitor. Azacitidine is a white to off-white solid supplied in a sterile form for reconstitution as a suspension for SC injection or (in the US only) reconstitution as a solution with further dilution for IV infusion.

Single-use vials of azacitidine contained 100 mg of azacitidine and 100 mg mannitol as a sterile lyophilized powder.

Duration of Intervention and Evaluation

Study treatment (Hu5F9-G4 and/or azacitidine) was administered continuously until disease progression, loss of clinical benefit, or unacceptable toxicity. It should be noted that treatment with azacitidine as monotherapy is recommended for a minimum of 6 cycles. All patients in the TN/U Cohort without evidence of treatment failure, relapse after CR/CRi (complete remission/complete remission with incomplete blood count recovery), or unacceptable toxicity continued study treatment for at least 6 cycles. Patients were discontinued from the treatment per Investigator's discretion prior to reaching the recommended minimum cycles for any of these reasons detailed below:

Reasons for discontinuation of study drug treatment included, but were not limited to, the following: (i) Disease progression with confirmation in subsequent assessment at least 4 weeks apart (i.e., disease worsening compared to the previous assessment), (ii) Unacceptable toxicity, (iii) Clinically significant change in the patient's status that precludes further treatment (e.g., pregnancy or other AE), (iv) Patient request, with or without a stated reason, (v) Bone marrow transplant, or (vi) Investigator or treating physician decision in the absence of any of the above.

Number of Patients

The number of patients included in this trial was up to a total of up to 193 patients evaluable for efficacy, as follows:

R/R Safety Cohort: 10 patients
R/R Expansion Cohort: Up to 36 patients
TN/U Dose Evaluation Cohort: Up to 18 patients
TN/U Expansion Cohort: Up to 121 patients, including at least 91 MDS patients
Rollover Cohort: Up to 8 patients Statistical Methods Time-to-event data was analyzed by the Kaplan-Meier method. Continuous variables were summarized with descriptive statistics (n, mean, standard deviation, range, and median). Frequency counts and percentage of patients within each category were provided for categorical data.

The safety and efficacy analysis was conducted on all enrolled patients who received at least 1 dose of Hu5F9-G4. An evaluable patient efficacy analysis was also be performed on all patients who received at least 1 dose of Hu5F9-G4 and had at least 1 disease response assessment or who died before the first disease response assessment.

The PK analysis set (PAS), defined as all treated patients who have at least 1 blood sample that provides evaluable PK data, were used for summaries of PK concentration data and PK parameters.

The rate and magnitude of anti-Hu5F9-G4 antibody positivity was evaluated.

Pharmacodynamic and correlative studies were conducted on patient samples, and both tissue and blood samples were be biobanked for future analyses.

Sample Size Calculations

A total of up to 193 efficacy evaluable patients were enrolled. For the R/R Safety Cohort and Expansion Cohort, a total of 46 patients were enrolled, including 10 patients treated in the safety run-in cohort and 36 patients treated in the expansion cohort.

For the TN/U Dose Evaluation Cohort, up to 18 patients were enrolled based on a 3+3 dose de-escalation design assuming 3 potential dose cohorts with a maximum of 6 patients treated per cohort. For the TN/U Expansion Cohort, an initial sample size of 30 patients was proposed so that the 95% confidence interval of the desired 35% or higher CR rate would exclude a known CR rate of 17.85% for azacitidine alone. Based on Amendment 5 and the Food and Drug Administration (FDA) feedback for a single-arm trial to support potential accelerated approval, the sample size of the TN/U Expansion Cohort for untreated higher-risk MDS patients was further increased to include at least 91 patients with MDS (inclusive of patients previously treated in the Evaluation and Expansion Cohorts). A sample size of 91 patients provided 80% power to reject the null hypothesis that the CR+PR rate is 23.5% or lower at 2-sided 0.05 significant level, assuming the true CR+PR rate is at least 36.5% (i.e., a 13% improvement). The null CR+PR rate of 23.5% is based on the pivotal randomized trial leading to azacitidine approval in MDS, where the upper bound of the 1-sided 95% confidence interval for azacitidine CR+PR rate is 23.5%, with a point estimate of 15.7%.

For the Rollover Cohort, a maximum of 8 patients were enrolled, as only 8 eligible patients were expected to be continuing in the previous Phase 1 study at the initiation of this study.

Example 2: Human Results

Safety of Hu5F9-G4 Plus Azacitidine 43 patients were treated with Hu5F9-G4 plus azacitidine; 18 patients with MDS and 25 patients with AML. 1 patient (1/43: 2%) was discontinued due to adverse effects (AE) for Hu5F9-G4 plus azacitidine (hemagglutination). The most frequent treatment-related adverse effects (TRAEs) were >15%: anemia (37%), neutropenia (26%), thrombocytopenia (26%). TRAE: febrile neutropenia occurred in 1 patient (2%). No treatment-related infections were observed.

Efficacy of Hu5F9-G4 Plus Azacitidine

Shown in Table 5 are the MDS efficacy parameters and number of responsive patients in each parameter in the efficacy evaluable cohort and total treated patients.

TABLE 5

| Parameter | MDS Subjects (N = 13) Efficacy evaluable | MDS Subjects (N = 16) Total Treated |
|---|---|---|
| Objective Response Rate (ORR) | 13 (100%) | 13 (81%) |
| Complete Remission (CR) | 7 (54%) | 7 (44%) |
| Partial Remission (PR) | 0 | 0 |
| Marrow CR | 5 (39%) 3 with marrow CR + HI | 5 (31%) 3 with marrow CR + HI |
| hematologic improvement (HI) | 1 (9%) | 1 (6%) |
| Stable Disease (SD) | 0 | 0 |
| Progressive disease (PD) | 0 | 0 |

Shown in Table 6 are the AML efficacy parameters and number of responsive patients in each parameter in the efficacy evaluable cohort.

TABLE 6

| Parameter | AML Subjects (N = 16) Efficacy evaluable | AML Subjects (N = 19) Total Treated |
|---|---|---|
| Objective Response Rate (ORR) | 11 (69%) | 11 (58%) |
| Complete Remission (CR) | 6 (38%) | 6 (32%) |
| CR with incomplete blood count recovery (Cri) | 2 (13%) | 2 (11%) |
| Partial Remission (PR) | 2 (13%) | 2 (11%) |
| Morphologic Leukemia-free State (MLFS) | 1 (6%) | 1 (5%) |
| Stable Disease (SD) | 5 (31%) | 5 (26%) |
| Progressive disease (PD) | 0 | 0 |

Summarized in Table 7 is the depth of response (DOR) in the efficacy evaluable patients.

TABLE 7

| Parameter | 1L AML N = 16 | 1L MDS N = 13 |
|---|---|---|
| RBC transfusion independence | 11/16 (69%) | — |
| Complete cytogenetic response in responders* | 4/9 (44%) | 4/10 (40%) |
| MRD negativity in responders | 4/8 (50%) In CR/CRi | 2/13 (17%) In CR/marrow CR |
| Median duration of response (months) | NR | NR |
| Median follow-up [range] (months) | 5.8 (1.9-9.5) | 4.9 (3.1-8.8) |

The response parameters were similar for both the AML and the MDS cohorts. In addition, the MRD negativity rates with Hu5F9-G4 plus azacitidine were better (50%) than azacitidine/decitabine and venetoclax treatment in AML patients. The MRD negativity in responders (CR/CRi) for azacitidine/decitabine and venetoclax was previously shown to be 29% (DiNardo et al., Blood 2019).

TP53 Mutant Patient Response

Further analysis of the responders showed a high rate of response in a subset of AML and MDS patients with a TP53 mutation. Shown in Table 8 are the response rates of patients with TP53 mutations to Hu5F9-G4 and azacitidine treatment.

Table 8. Mutational Analysis and Response in TP53 mutant patients

TABLE 8

| TP53 mutant | 1L AML (N = 6) | 1L MDS (N = 2) | Combined AML/MDS (N = 8) | Aza/decitabine and venetoclax |
|---|---|---|---|---|
| Best Overall Response Rate | 5/6 (83%) | 2/2 (100%) | 7/8 (88%) | 17 (47%) |
| DOR/Overall survival | Not reached | Not reached | Not reached | 5.6 mo/7.2 mo |

Shown in Table 8 are the response rates of all patients to Hu5F9-G4 and azacitidine treatment.

Table 9. Mutational Analysis and Response in all patients

TABLE 9

| | 1L AML (N = 16) | 1L MDS (N = 13) | Combined AML/MDS (N = 29) | Aza/decitabine + venetoclax |
|---|---|---|---|---|
| Best Overall Response Rate | 11/16 (69%) 8 CR/CRi | 13/13 (100%) 7 CR | 24/29 (83%) | 17 (47%) |
| DOR/Overall survival | Not reached | Not reached | Not reached | 5.6 mo/7.2 mo |

Both AML and MDS patients with a TP53 mutation exhibited a high rate of response to the combination Hu5F9-G4 and azacitidine treatment (83% for AML patients and 100% for MDS patients). In contrast, AML patients with TP53 mutations did not respond well to azacitidine/decitabine and venetoclax treatment (47% response, DiNardo et al., Blood 2019). Furthermore, only 69% of all AML patients achieved a high rate of response to the combination Hu5F9-G4 and azacitidine treatment.

Figure 2A:
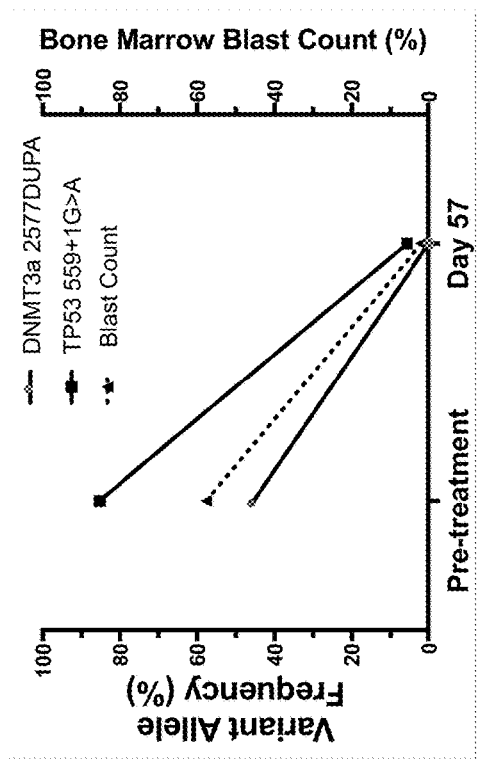
FIG. 2A shows a graph of the variant allele frequency and bone marrow blast cell counts before treatment and on Day 57 of treatment in a patient with a DNMT3a 2577DUPA and a TP53 559+1G>A phenotype.

FIG. 2A shows a graph of the variant allele frequency and bone marrow blast cell counts before treatment and on Day 57 of treatment in a patient with a DNMT3a 2577DUPA and a TP53 559+1G>A phenotype. Treatment with combination Hu5F9-G4 and azacitidine significantly reduced the percentage of cells with the variant mutant alleles of DNMTa and TP53. Treatment also significantly reduced the number of bone marrow blast cells in the patient.

Figure 2B:
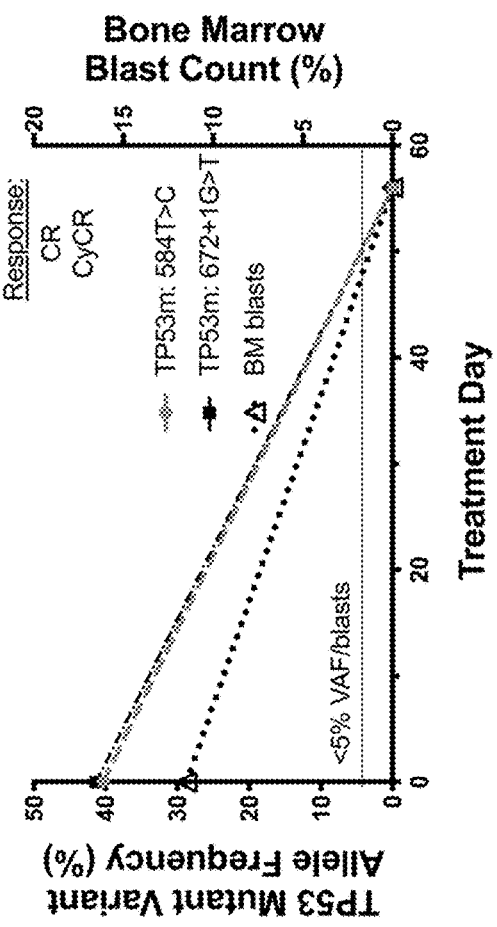
FIG. 2B shows the bone marrow blast count and TP53 mutational burden in a second representative patient over time after Hu5F9-G4 and azacytidine therapy.

An additional representative patient on study is shown in FIG. 2B. A 77 year old patient with very high risk and complex karyotype MDS and two TP53 mutations (584 T>C and 672+1G>T) was treated with Hu5F9-G4 and azacitidine. Bone marrow blast count and TP53 mutational burden is shown over time after three cycles of treatment. FIG. 2B shows a graph of the variant allele frequency and bone marrow blast cell counts before treatment and at the end of Cycle 3. The CR, CyCr, and clearance of TP53 mutations are also marked.

Conclusions

Treatment of Hu5F9-G4 plus azacitidine in untreated intermediate to very high risk MDS patients by IPSS-R and untreated AML (induction chemotherapy ineligible) patients was performed as described in Example 1. A Hu5F9-G4 priming/intrapatient dose escalation regimen (1-30 mg/kg weekly) was utilized to mitigate on target anemia. Azacitidine dosing was 75 mg/m$^2$ days 1-7 on a 28 day cycle. Responses were assessed by IWG 2006 and ELN 2017 criteria for MDS and AML patients, respectively.

43 patients (18 MDS and 25 AML) with a median of 73 years of age were treated with Hu5F9-G4 plus azacitidine. 19% were intermediate cytogenetic risk with 63% poor risk (19% unknown). 28% of patients harbored a TP53 mutation. Hu5F9-G4 plus azacitidine was well-tolerated with a safety profile similar to AZA monotherapy. Treatment-related AEs (>15% of patients) for Hu5F9-G4 plus azacitidine were anemia (37%), neutropenia (26%), and thrombocytopenia (26%). Treatment-related febrile neutropenia occurred in only 1 (2%) patient. Only 1 patient discontinued due to an AE. 29 patients were evaluable for efficacy at time of data cut. 13/13 (100%) untreated MDS patients had an objective response with 7 patients (54%) achieving a CR, 5 (39%) with marrow CR (3/5 also had hematologic improvement (HI)), and 1 (7%) with HI alone. In AML, 11/16 (69%) had an objective response; 8/16 (50%) with CR or CRi, 2 (13%) with PR, 1 (6%) with MLFS, and 5 (31%) with stable disease. Time to response was more rapid (median 1.9 mos) than expected for AZA alone. For those with abnormal cytogenetics at baseline, 40% and 44% of MDS and AML patients achieved a cytogenetic CR, respectively. 4/8 (50%) AML patients with CR/CRi and 2/12 (17%) MDS patients with CR or marrow CR were MRD negative by flow cytometry. 11/16 (69%) AML patients became RBC transfusion independent and 11/13 (85%) MDS patients had hematologic improvement.

Given that CD47 is an LSC marker on leukemic cells, CD34+CD38− putative LSC frequency was measured by flow cytometry in the bone marrow in 5F9+AZA treated AML/MDS patients. In data available for analysis, LSCs were completely eliminated in 10/16 (63%) of AML/MDS patients who had a clinical response. Lastly, mutational analyses are ongoing to correlate subgroups with response. 7/8 (88%) evaluable TP53 mutant patients (5/6 AML patients [5 CR/CRi], 2/2 MDS [1 CR, 1 marrow CR]) achieved an objective response, highlighting efficacy in a poor prognosis and therapy-refractory population. No median duration response or overall survival has been reached for either MDS or AML patients with a median follow-up of 4.9 months (range 3.1-8.8 months) for MDS and 5.8 months (range 1.9-9.5 months) for AML.

Hu5F9-G4 plus azacitidine is a novel immunotherapy regimen that blocks a key macrophage checkpoint. The combination therapy continues to be well tolerated with robust activity in MDS and AML patients with an ORR of 100% and 69%, respectively. High rates of putative LSC eradication suggest potential durable responses, with no median duration of response yet reached. Initial data indicate that Hu5F9-G4 plus azacitidine may be particularly effective in TP53 mutant patients, a treatment-refractory subgroup.

Example 3: Hu5F9-G4 and Azacytidine Reduces Disease in AML Patients with TP53 Mutation Clinical efficacy is shown in 9 untreated AML patients with TP53 mutation on treatment with Hu5F9-G4 and azacitidine. The overall response rate was 78% with 44% achieving CR and 33% achieving CRi. In addition, deep responses were observed as evidenced by a 67% cytogenetic CR rate and 57% of patients achieved minimal residual disease negativity by flow cytometry. The median duration of response has not been reached with a median follow up of 6.9 months. An additional 3 AML patients with TP53 mutations on treatment with Hu5F9-G4 and azacitidine were identified. Clinical efficacy is also shown in these 12 untreated AML patients with TP53 mutation. The overall response rate for the n=12 TP53 mutation AML patients was 78% with 44% achieving CR and 33% achieving CRi.

Clinical efficacy is also shown in 4 MDS patients with TP53 mutation on treatment with Hu5F9-G4 and azacitidine. The overall response rate for the n=4 TP53 mutation MDS patients was 75% with 50% achieving CR and 25% achieving CRi. The survival probability at 6 months for the n=12 AML patients and the MDS patients is 91% (AML) and 100% (MDS).

Table 10 provides further data on the efficacy of the combination of Hu5F9-G4 and azacytidine in AML and MDS patients with TP53 mutations.

TABLE 10

| Parameter | AML TP53 Subjects (N = 9) | AML TP53 Mutant (N = 12) | MDS TP53 Mutant (N = 4) |
|---|---|---|---|
| Objective Response Rate (ORR) | 7 (78%) | 9 (75%) | 3 (75%) |
| Complete Remission (CR) | 4 (44%) | 5 (42%) | 2 (50%) |
| CR with incomplete blood count recovery (Cri) | 3 (33%) | 4 (33%) | 1 (25%) |
| Complete cytogenetic response in responders (CCyR)* | 4/6 (67%) | 4/8 (50%) | 3/3 (100%) |
| MRD negative responders | 4/7 (57%) | 4/9 (44%) | 0 |
| Median duration of response (months) | Not reached (0.03+-15.1+) | Not reached (0.03+-15.1+) | Not reached (0.03+-5.2+) |
| Median overall survival (months) | Not reached (3.8+-16.9+) | Not reached | Not reached |
| Median follow-up [range] (months) | 6.9 [1.9-16.9] | 8.8 (1.9-16.9) | 7 (4.2-12.2) |

*CCyR is for patients with abnormal cytogenetics at baseline

The overall clinical efficacy in AML and MDS patients, regardless of p53 mutational status, is shown in Table 11. Treatment with Hu5F9-G4 and azacitidine induced a 91% ORR (42% CR) in MDS patients and 64% ORR (56% CR/CRi) in AML patients. Responses deepened over time with a 56% CR rate in MDS patients with at least 6 months follow-up and the median time to response was 1.9 months, which is more rapid than azacitidine alone.

TABLE 11

| Parameter | 1L MDS N = 33 | 1L AML N = 25 |
|---|---|---|
| ORR | 30 (91%) | 16 (64%) |
| CR | 14 (42%) | 10 (40%) |
| CRi | NA | 4 (16%) |
| PR | 1 (3%) | 1 (4%) |
| MLFS/marrow CR | 8 (24%) 4 with marrow CR + HI | 1 (4%) |
| Hematologic improvement (HI) | 3 (9%) | NA |
| SD | 3 (9%) | 8 (32%) |
| PD | 0 | 1 (4%) |
| RBC transfusion independence* | 11/19 (58%) | 9/14 (64%) |
| Complete cytogenetic response† | 9/26 (35%) | 6/12 (50%) |
| MRD negativity in responders | 6/30 (20%) | 8/16 (50%) |
| Median duration of response (months) | Not reached (0.03+-10.4+) | Not reached (0.03+-15.1+) |
| Median follow-up [range] (months) | 5.8 [2.0-15.0] | 9.4 [1.9-16.9] |

Figure 3A:
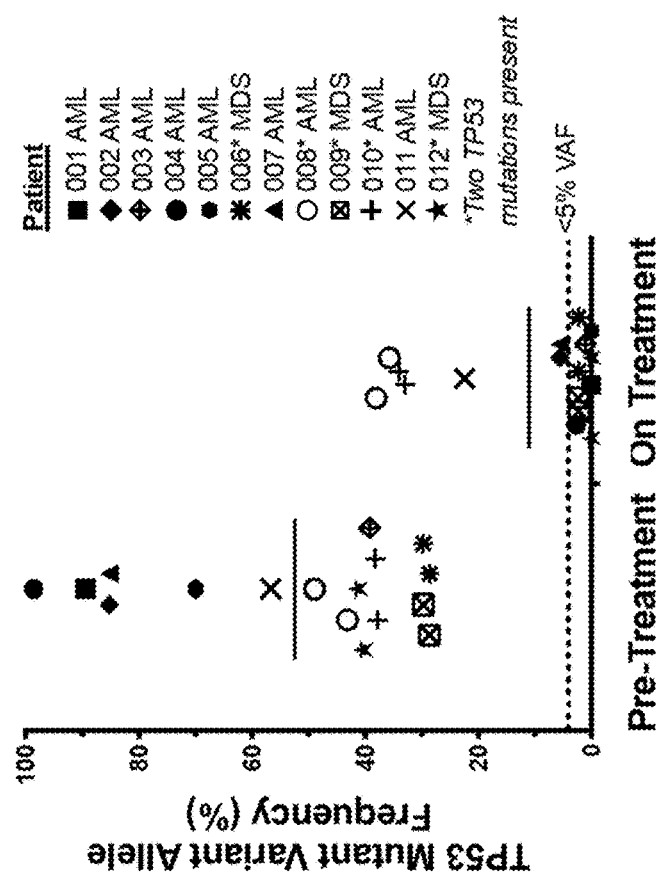
FIG. 3A shows the TP53 mutational burden for 9 patients pre-treatment and as a best overall response on Hu5F9-G4 and azacytidine therapy.
Figure 3B:
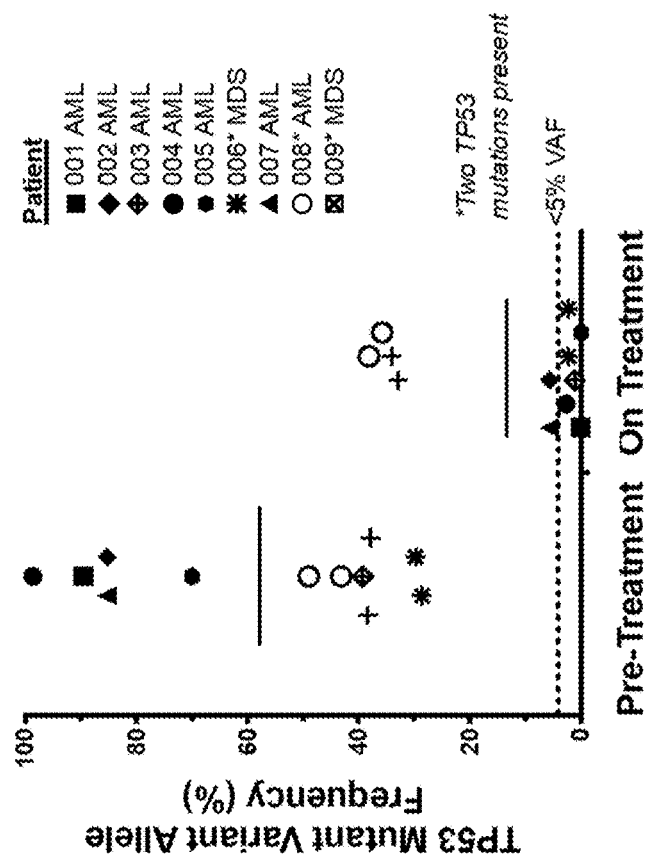
FIG. 3B shows the TP53 mutational burden for 12 patients pre-treatment and as a best overall response on Hu5F9-G4 and azacytidine therapy.

FIG. 3A shows the TP53 mutational burden for 9 AML patients, FIG. 3B shows the TP53 mutation burden for an additional 3 patients, for a total of 12 AML patients. TP53 mutation variant allele frequency is shown pre-treatment and as a best overall response on therapy. Treatment with Hu5F9 and azacytidine substantially reduced or eliminated the TP53 mutation burden in patients. Six patients had one TP53 mutation and the mutation burden was eliminated in all six patients. Three patients had two TP53 mutations and the mutation burden was eliminated in two of the patients with two TP53 mutations. Analysis of three additional patients showed that seven patients in total had at least one detected TP53 mutation and the mutation burden was reduced or eliminated in all seven patients; and that five patients had at least two detected TP53 mutations and the mutation burden was eliminated in three of the patients with at least two TP53 mutations. Thus, Hu5F9-G4 and azacytidine had a high response rate and MRD negativity in TP53 mutant AML patients, and the TP53 mutational burden was dramatically reduced in AML patients on therapy. In addition, the median duration and survival have not been reached, which compares favorably to current therapies such as venetoclax and azacitidine (ORR 47%, DOR 5.6 mo, OS 7.2 mo).

Figure 4:
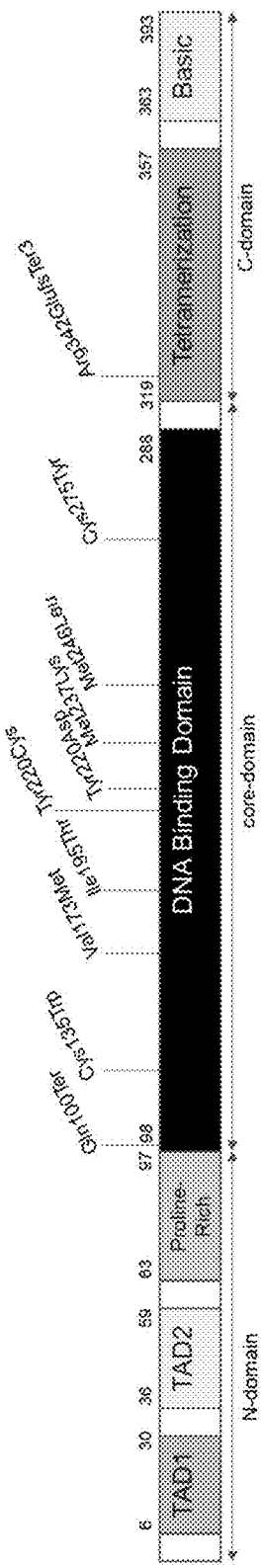
FIG. 4 shows a schematic of the p53 gene and p53 mutations identified in trial patients.

A diagram of the TP53 gene, indicating the various domains, and the TP53 mutations observed in trial patients is shown in FIG. 4. Table 12 also provides a summary of the nucleic acid mutations, amino acid mutations, gene targeted regions, and protein domains of the observed p53 mutations in trial patients.

TABLE 12

| Indication | Cohort | Objective Response | Survival Duration (months) | Mutation (Variant Freq) | Gene Targeted Region | AA mutation | Protein Domain | Known hot spot mutation in tumors? |
|---|---|---|---|---|---|---|---|---|
| AML | TN/U | CR | 12.8 | c.559 + 1G > A (86%) | Intron 5 | — | — | — |
| AML | TN/U | SD | 8.2 | c.673 − 1G > T (49%); c.659A > G (43%) | Intron 6; Exon 6 | Tyr220Cys | DBD | Yes |
| AML | TN/U | CRi | 16.9+ | c.517G > A (90%) | Exon 5 | Val173Met | DBD | Yes |
| AML | TN/U | CR | 13.6+ | c.658T > G (40%) | Exon 6 | Tyr220Asp | DBD | Yes |
| AML | TN/U | CR | 7.9+ | c.405C > G (99%) | Exon 5 | Cys135Trp | DBD | Yes |
| AML | TN/U | CR | 8.3+ | c.298C > T (70%) | Exon 4 | Gln100Ter | DBD | — |
| AML | TN/U | PD | 2.6 | c.993 + 1G > A (85%) | Intron 9 | — | — | — |
| MDS | TN/U | Marrow CR | 10.6+ | c.736A > C (30%); c.824G > A (29%) | Exon 7; Exon 8 | Met246Leu; Cys275Tyr | DBD | Yes |
| MDS | TN/U | CR | 9.8 | c.672 + 1G > T (41%); c.584T > C (40%) | Intron 6; Exon 6 | Ile195Thr | DBD | — |
| MDS | TN/U | CR | 1.0+ | c.710T > A (39%); c.1024delC (40%) | Exon 7; Exon 10 | Met237Lys; Arg342Glu fsTer3 | DBD; Tetra | — |

Example 4: Hu5F9-G4 and Azacytidine Depletes Leukemia Stem Cells

Figure 5B:
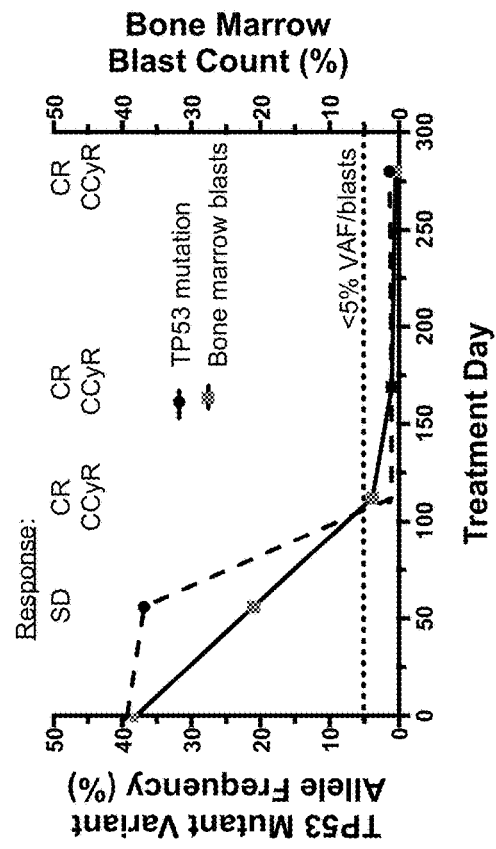
FIG. 5B shows the bone marrow blast count and TP53 mutational burden in a representative patient over time after Hu5F9-G4 and azacytidine therapy.
Figure 5A:
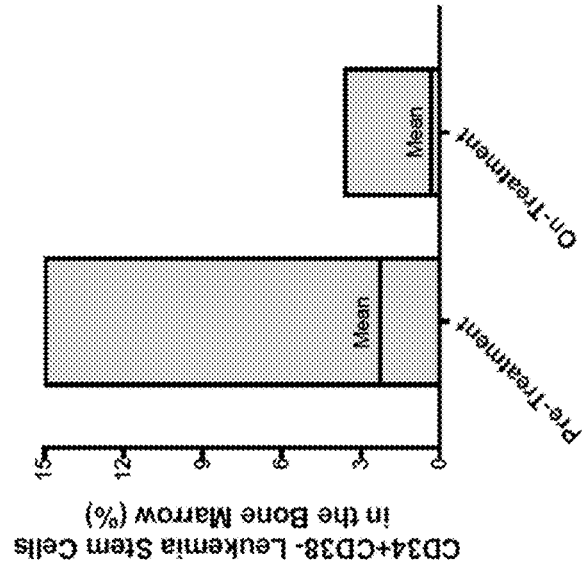
FIG. 5A shows depletion of CD34+CD38− leukemia stem cells in the bone marrow of responding MDS/AML patients before and after treatment with Hu5F9-G4 and azacytidine.

Putative CD34+CD38− LSC frequency was evaluated in AML/MDS patients treated with Hu5F9-G4 and azacitidine by flow cytometry. Mean and range cell frequency are shown pre-treatment and best response on treatment. As shown in FIG. 5A, treatment with Hu5F9-G4 and azacytidine depleted CD34+CD38− leukemia stem cells in the bone marrow of responding MDS/AML patients, regardless of TP53 mutation status. CD34+CD38− were eliminated in 40% of responding MDS/AML patients.

Treatment with Hu5F9-G4 and azacytidine also depleted CD34+CD38− leukemia stem cells and bone marrow blastocytes in the bone marrow of a representative TP53 mutant patient. A representative patient on study is shown in FIG. 5B. A 65 year old AML patient with high risk cytogenetics and a TP53 mutation was treated with Hu5F9-G4 and azacytidine. Bone marrow blast count and TP53 mutational burden is shown over time on therapy. At month 5 on treatment, the patient achieved a complete remission (CR) and complete cytogenetic CR (CCyR) with elimination of bone marrow blasts, TP53 mutational burden, and elimination of LSCs (FIG. 5B). The patient remains in deep CR with continued clearance of blasts and TP53 mutation over 280 days and ongoing.

Example 5: Hu5F9-G4 and Azacytidine Alters T Cell Infiltration in the Bone Marrow Bone marrow aspirates were collected from patients enrolled in our 5F9005 trial at baseline (BL), Cycle 3 day 1 (C3), Cycle 5 day 1 (C5), and Cycle 7 day 1 (C7). Viable nucleated marrow cells were isolated by density gradient centrifugation and cryopreserved. Expression of relevant immune cell regulatory or marker proteins was assessed using mass cytometry (cytometry by time of flight, CyToF). Regulatory or marker proteins assessed included CD45, CD8a, TIGIT, CD86, CD4, CD163, ICOS, OX40, PD-L1, CD3, TIM-3, CD86, PD-1, VISTA, FoxP3, LILRB1, CTLA-4, PD-L2, HLA-DR, CD11c, CD24, CD117, CD123, CD33, CD38, CD99, BCL2, CD47, CD206, SIRPα, CD56, MCL1, CD34, CLEC12A, FTL3, SIGLEC, and CD14. Total T cells (CD45+CD3+), helper T cells (CD45+CD3+CD4), cytotoxic T cells (CD45+CD3+CD8+), and regulatory T cells (Tregs; CD45+CD3+CD4+FOXP3) were quantified. Significance was assessed by one-way ANOVA in all cases.

A significant increase in total T cells at C3, C5, and C7 relative to baseline was observed across all AML patient samples (FIG. 6A). CD4+ T cells were significantly increased at C5 and C7 relative to baseline (FIG. 6B). CD8+ T cells were significantly increased at C7 relative to baseline (FIG. 6C). These changes in T cell populations strongly support a treatment-induced anti-cancer adaptive immune response and the opportunity for combination with checkpoint inhibitors. When separated by clinical response category into objective responders (FIG. 6D) and stable disease patients (FIG. 6E), no significant change in Treg populations was observed in the objective responders. However, in stable disease patients, a significant increase in Treg populations was observed at C5 and C7 relative to baseline.

Example 6: Antibody Receptor Occupancy in Q1W vs Q2W Dosing Regime

Antibody receptor occupancy (RO) was assessed in the once per week dosing (Q1W) and the once every two weeks dosing (Q2W) regime. Patients were dosed with Hu5F9-G4 once a week for all cycles (Q1W throughout) or once per week for cycles 1 and 2 and then once every two weeks (Q2W) in Cycle 3 and beyond. CD47 antibody receptor occupancy (RO) was assessed in the peripheral blood and bone marrow and compared against Q1W vs. Q2W dosing. Primary patient blood or bone marrow cells were stained with a Hu5F9-reactive fluorescent anti-IgG4 antibody, followed by quantitation via flow cytometry. Occupancy levels were calculated as a percent of maximum signal, defined by matched patient sample with saturating quantities of unlabeled Hu5F9-G4 added prior to anti-IgG4 antibody staining. Data for the Q2W dosing were normalized against the Q1W RO levels.

Figure 7A:
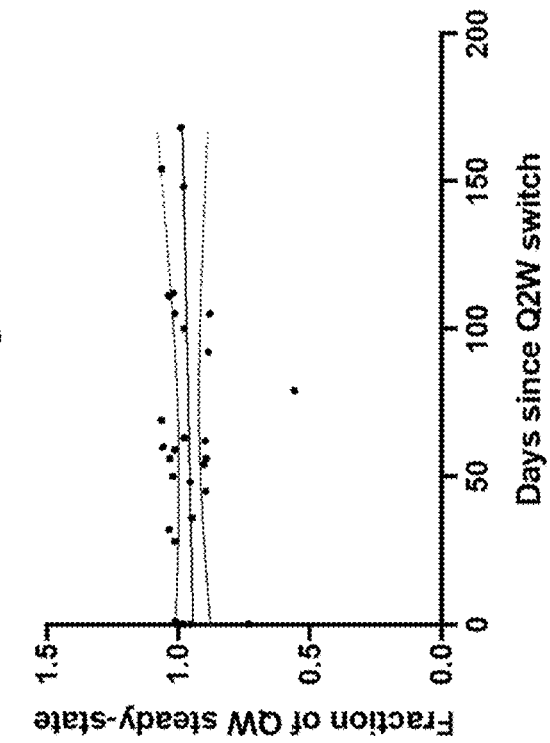
FIG. 7A shows CD47 receptor occupancy by Hu5F9-G4 in CD45+ peripheral blood cells over time after a transition from weekly Hu5F9 dosing (Q1W) to every other week Hu5F9-G4 dosing (Q2W). Receptor occupancy is expressed as a fraction of the steady-state Q1W level.
Figure 7B:
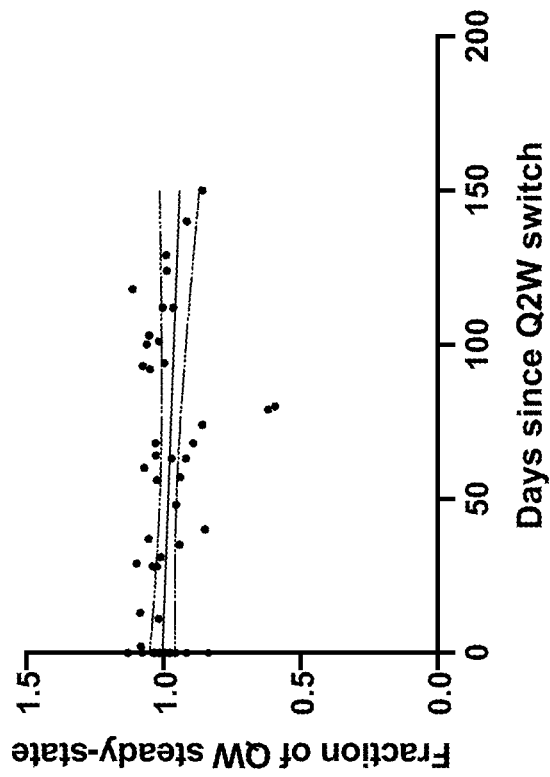
FIG. 7B shows CD47 receptor occupancy by Hu5F9-G4 in CD45+ bone marrow cells over time after a transition from weekly Hu5F9-G4 dosing (Q1W) to every other week Hu5F9-G4 dosing (Q2W). Receptor occupancy is expressed as a fraction of the steady-state Q1W level.

The patients rapidly achieved maximum occupancy during Cycle 1 and Cycle 2 (Q1W dosing, not shown). A similar CD47 antibody RO was observed in both the peripheral blood (FIG. 7A) or bone marrow (FIG. 7B) after Q2W dosing change in Cycle 3 and beyond. For both figures, the dots indicate the antibody occupancy level in patient samples taken over time from Cycle 3 and beyond normalized to the patient Q1W RO levels, while the middle line indicates the linear regression best fit, and the top and bottom lines indicate the 95% confidence intervals. Thus, Hu5F9-G4 Q2W (i.e., dose administration once every two weeks) dosing resulted in a similar CD47 receptor occupancy as Q1W (i.e., dose administration once every week) dosing.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE A

SEQUENCES

| SEQ ID NO | ID | Sequence |
|---|---|---|
| 1 | 1H9 CDR-H1 | SYWIT |
| 2 | 1H9 CDR-H2 | DIYPGSGSTNHIEKFKS |
| 3 | 1H9 CDR-H3 | GYGSSYGYFDY |
| 4 | 1H9 CDR-L1 | RASENIYSYLA |
| 5 | 1H9 CDR-L2 | TAKTLAE |
| 6 | 1H9 CDR-L3 | QHQYGPPFT |
| 7 | Humanized 1H9 $V_H$ | QVQLVQSGAE VKKPGASVKV SCKASGYTFT SYWITWVKQA PGQGLEWIGD IYPGSGSTNH IEKFKSKATL TVDTSISTAY MELSRLRSDD TAVYYCATGY GSSYGYFDYW GQGTLVTVSS |
| 8 | Humanized 1H9 $V_L$ | DIQMTQSPSS LSASVGDRVT ITCRASENIY SYLAWYQQKP GKAPKLLIYT AKTLAEGVPS RFSGSGSGTD FTLTISSLQP EDFATYYCQH QYGPPFTFGQ GTKLEIK |
| 9 | 3C2 CDR-H1 | SYWMH |
| 10 | 3C2 CDR-H2 | NIDPSDSDTHYNQKFKD |
| 11 | 3C2 CDR-H3 | GYSKYYAMDY |
| 12 | 3C2 CDR-L1 | RSSQSIVHSYGNTYLE |
| 13 | 3C2 CDR-L2 | KVSNRFS |
| 14 | 3C2 CDR-L3 | FQGSHVPYT |
| 15 | Humanized 3C2 $V_H$ | QVQLVQSGAE VKKPGASVKV SCKASGYTFT SYWMHWVRQA PGQGLEWMGN IDPSDSDTHY NQKFKDRVTM TRDTSTSTVY MELSSLRSED TAVYYCARGY SKYYAMDYWG QGTLVTVSS |
| 16 | Humanized 3C2 $V_L$ | DIVMTQTPLS LSVTPGQPAS ISCRSSQSIV HSYGNTYLEW YLQKPGQSPQ LLIYKVSNRF SGVPDRFSGS GSGTDFTLKI SRVEAEDVGV YYCFQGSHVP YTFGQGTKLE IK |
| 17 | Humanized 1H9 HC (full-length) | QVQLVQSGAEVKKPGASVKVSCKASGYTFTSYWITWVKQAPGQGLEWIGDIYPGSG STNHIEKFKSKATLTVDTSISTAYMELSRLRSDDTAVYYCATGYGSSYGYFDYWGQ GTLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFNW YVDGVEVHNAKTKPREEQYASTYRVVSVLTVLHQDWLNGKEYKCKVSNKALPAPIE KTISKAKGQPREPQVYTLPPSREEMTKNQVSLTCLVKGFYPSDIAVEWESNGQPEN NYKTTPPVLDSDGSFFLYSKLTVDKSRWQQGNVFSCSVMHEALHNHYTQKSLSLSP G |
| 18 | Humanized 1H9 LC (full-length) | DIQMTQSPSSLSASVGDRVTITCRASENIYSYLAWYQQKPGKAPKLLIYTAKTLAE GVPSRFSGSGSGTDFTLTISSLQPEDFATYYCQHQYGPPFTFGQGTKLEIKRTVAA PSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 19 | Humanized 3C2 HC (full-length) | QVQLVQSGAEVKKPGASVKVSCKASGYTFTSYWMHWVRQAPGQGLEWMGNIDPSDS DTHYNQKFKDRVTMTRDTSTSTVYMELSSLRSEDTAVYYCARGYSKYYAMDYWGQG TLVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPEVKFNWY VDGVEVHNAKTKPREEQYASTYRVVSVLTVLHQDWLNGKEYKCKVSNKALPAPIEK TISKAKGQPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQKSLSLSPG |

TABLE A-continued

SEQUENCES

| SEQ ID NO | ID | Sequence |
|---|---|---|
| 20 | Humanized 3C2 LC (full-length) | DIVMTQTPLSLSVTPGQPASISCRSSQSIVHSYGNTYLEWYLQKPGQSPQLLIYKV SNRFSGVPDRFSGSGSGTDFTLKISRVEAEDVGVYYCFQGSHVPYTFGQGTKLEIK RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 21 | 9B11 CDR-H1 | DYYIH |
| 22 | 9B11 CDR-H2 | RIDPEDGETKYAPKFQG |
| 23 | 9B11 CDR-H3 | GGFAY |
| 24 | 9B11 CDR-L1 | ASSSVSSSYLY |
| 25 | 9B11 CDR-L2 | STSNLAS |
| 26 | 9B11 CDR-L3 | HQWSSHPYT |
| 27 | 9B11 $V_H$ | EVQLQQSGAELVKPGASVKLSCTASGFNIKDYYIHWVKQRTEQGLEWIGRIDPEDG ETKYAPKFQGKATITADTSSNTAYLQLNSLTSEDTAVYSCAKGGFAYWGQGTLVTV SA |
| 28 | 9B11 $V_L$ | QIVLTQSPAIMSASPGEKVTLTCSASSSVSSSYLYWYQQKPGSSPKLWIYSTSNLA SGVPARFSGSGSGTSYSLTISSMEAEDAASYFCHQWSSHPYTFGGGTKLEIK |
| 29 | 7EI1 CDR-H1 | SYWMH |
| 30 | 7EI1 CDR-H2 | NIDPSDSDTHYNQKFKD |
| 31 | 7EI1 CDR-H3 | SYGNYGENAMDY |
| 32 | 7EI1 CDR-L1 | RSSQSIVHSYGNTYLE |
| 33 | 7EI1 CDR-L2 | KVSNRFS |
| 34 | 7EI1 CDR-L3 | FQGSHVPFT |
| 35 | 7EI1 $V_H$ | QVKLQESGAELVRPGSSVKLSCKASGYTFTSYWMHWVKQRPIQGLEWIGNIDPSDS DTHYNQKFKDKATLTVDNSSSTAYMQLSSLTSEDSAVYYCASYGNYGENAMDYWGQ GTSVTVSS |
| 36 | 7EI1 VL | DILMTQTPLSLPVSLGDQASISCRSSQSIVHSYGNTYLEWYLQKPGQSPKLLIYKV SNRFSGVPDRFSGSGSGTDFTLKISRVEAEDLGVYYCFQGSHVPFTFGSGTKLEIK |
| 37 | Humanized 1H9 heavy chain nucleic acid | CAGGTTCAGTTGGTTCAGTCTGGCGCCGAAGTGAAGAAACCTGGCGCCTCTGTGAA GGTGTCCTGCAAGGCTTCCGGCTACACCTTTACCAGCTACTGGATCACCTGGGTCA AGCAGGCTCCTGGACAGGGACTCGAGTGGATCGGCGATATCTATCCTGGCTCCGGC TCCACCAACCACATCGAGAAGTTCAAGTCCAAGGCTACCCTGACCGTGGACACCTC CATCTCCACCGCCTACATGGAACTGTCCCGGCTGAGATCTGACGACACCGCCGTGT ACTATTGCGCTACCGGCTACGGCTCCTCCTACGGCTACTTTGATTATTGGGGCCAG GGCACCCTGGTCACCGTGTCCTCTGCTTCTACCAAGGGACCCAGCGTGTTCCCTCT GGCTCCTTCCAGCAAGTCTACCTCTGGCGGAACAGCTGCTCTGGGCTGCCTGGTCA AGGACTACTTTCCTGAGCCTGTGACCGTGTCTTGGAACTCTGGCGCTCTGACATCT GGCGTGCACACATTCCCTGCTGTGCTGCAGTCCTCCGGCCTGTACTCTCTGTCCTC TGTCGTGACCGTGCCTTCCAGCTCTCTGGGAACCCAGACCTACATCTGCAATGTGA ACCACAAGCCTTCCAACACCAAGGTGGACAAGAAGGTGGAACCCAAGTCCTGCGAC AAGACCCACACCTGTCCTCCATGTCCTGCTCCAGAACTGCTCGGCGGACCTTCCGT GTTTCTGTTCCCTCCAAAGCCTAAGGACACCCTGATGATCTCTCGGACCCCTGAAG TGACCTGCGTGGTGGTGGATGTGTCTCACGAGGACCCCAGAAGTGAAGTTCAATTGG TACGTGGACGGCGTGGAAGTGCACAACGCCAAGACCAAGCCTAGAGAGGAACAGTA CGCCTCCACCTACAGAGTGGTGTCCGTGCTGACAGTGCTGCACCAGGATTGGCTGA ACGGCAAAGAGTACAAGTGCAAGGTGTCCAACAAGGCCCTGCCTGCTCCTATCGAA AAGACCATCTCCAAGGCCAAGGGCCAGCCTAGGGAACCCCAGGTTTACACCCTGCC ACCTAGCCGGGAAGAGATGACCAAGAACCAGGTGTCCCTGACCTGCCTCGTGAAGG GCTTCTACCCTTCCGATATCGCTGTGGAATGGGAGAGCAACGGCCAGCCTGAGAAC AACTACAAGACAACCCCTCCTGTGCTGGACTCCGACGGCTCATTCTTTCTGTACTC CAAGCTGACTGTGGACAAGTCCAGATGGCAGCAGGGCAACGTGTTCTCCTGCAGCG TGATGCACGAGGCCCTGCACAATCACTACACAGAAGTCTCTGTCTCTGAGCCCC GGC |
| 38 | Humanized 1H9 light chain nucleic acid | GACATCCAGATGACCCAGTCTCCATCCTCTCTGTCCGCCTCTGTGGGCGACAGAGT GACCATCACCTGTCGGGCCTCCGAGAACATCTACTCCTACCTGGCCTGGTATCAGC AGAAGCCTGGCAAGGCTCCCAAGCTGCTGATCTACACCGCTAAGACACTGGCCGAG GGCGTGCCCTCTAGATTTTCTGGCTCTGGAAGCGGCACCGACTTTACCCTGACAAT CTCCAGCCTGCAGCCTGAGGACTTCGCCACCTACTACTGCCAGCACCAGTACGGCC CTCCATTCACCTTTGGCCAGGGCACCAAGCTGGAAATCAAGCGGACAGTGGCCGCT |

TABLE A-continued

SEQUENCES

| SEQ ID NO | ID | Sequence |
|---|---|---|
| | | CCTTCCGTGTTCATCTTCCCACCTTCCGACGAGCAGCTGAAGTCTGGCACAGCCTC<br>TGTCGTGTGCCTGCTGAACAACTTCTACCCTCGGGAAGCCAAGGTGCAGTGGAAGG<br>TGGACAATGCCCTGCAGTCCGGCAACTCCCAAGAGTCTGTGACCGAGCAGGACTCC<br>AAGGACAGCACCTACAGCCTGTCCTCCACACTGACCCTGTCCAAGGCCGACTACGA<br>GAAGCACAAGGTGTACGCCTGCGAAGTGACCCATCAGGGCCTGTCTAGCCCTGTGA<br>CCAAGTCTTTCAACCGGGGCGAGTGC |
| 39 | Humanized 3C2 heavy chain nucleic acid | CAGGTTCAGTTGGTTCAGTCTGGCGCCGAAGTGAAGAAACCTGGCGCCTCTGTGAA<br>GGTGTCCTGCAAGGCTTCCGGCTACACCTTTACCAGCTACTGGATGCACTGGGTCC<br>GACAGGCTCCAGGACAAGGCTTGGAGTGGATGGGCAACATCGACCCCTCTGACAGC<br>GACACCCACTACAACCAGAAATTCAAGGACCGCGTGACCATGACCAGAGACACCTC<br>CACCAGCACCGTGTACATGGAACTGTCCAGCCTGAGATCCGAGGACACCGCCGTGT<br>ACTACTGTGCCAGAGGCTACTCCAAGTACTACGCCATGGACTACTGGGGCCAGGGC<br>ACACTGGTTACCGTGTCCTCTGCTTCCACCAAGGGACCCTCTGTGTTCCCTCTGGC<br>TCCTTCCAGCAAGTCTACCTCTGGCGGAACAGCTGCTCTGGGCTGCCTGGTCAAGG<br>ACTACTTTCCTGAGCCTGTGACCGTGTCTTGGAACTCTGGCGCTCTGACATCTGGC<br>GTGCACACATTCCCTGCTGTGCTGCAGTCCTCCGGCCTGTACTCTCTGTCCTCTGT<br>CGTGACCGTGCCTTCCAGCTCTCTGGGAACCCAGACCTACATCTGCAATGTGAACC<br>ACAAGCCTTCCAACACCAAGGTGGACAAGAAGGTGGAACCCAAGTCCTGCGACAAG<br>ACCCACACCTGTCCTCCATGTCCTGCTCCAGAACTGCTCGGCGGACCTTCCGTGTT<br>TCTGTTCCCTCCAAAGCCTAAGGACACCCTGATGATCTCTCGGACCCCTGAAGTGA<br>CCTGCGTGGTGGTGGATGTGTCCCACGAAGATCCAGAAGTGAAGTTCAATTGGTAC<br>GTGGACGGCGTGGAAGTGCACAACGCCAAGACCAAGCCTAGAGAGGAACAGTACGC<br>CTCCACCTACAGAGTGGTGTCCGTGCTGACAGTGCTGCACCAGGATTGGCTGAACG<br>GCAAAGAGTACAAGTGCAAGGTGTCCAACAAGGCCCTGCCTGCTCCTATCGAAAAG<br>ACCATCTCCAAGGCCAAGGGCCAGCCTAGGGAACCCCAGGTTTACACCCTGCCTCC<br>AAGCCGGGAAGAGATGACCAAGAACCAGGTGTCCCTGACCTGCCTCGTGAAGGGCT<br>TCTACCCTTCCGATATCGCCGTGGAATGGGAGAGCAATGGCCAGCCAGAGAACAAC<br>TACAAGACAACCCCTCCTGTGCTGGACTCCGACGGCTCATTCTTTCTGTACTCCAA<br>GCTGACCGTGGACAAGTCCAGATGGCAGCAGGGCAACGTGTTCTCCTGCAGCGTGA<br>TGCACGAGGCCCTGCACAATCACTATACCCAGAAGTCCCTGTCTCTGTCCCCTGGC |
| 40 | Humanized 3C2 light chain nucleic acid | GACATCGTGATGACCCAGACACCTCTGAGCCTGAGCGTGACACCTGGACAGCCTGC<br>CTCCATCTCCTGCAGATCCTCTCAGTCCATCGTGCACTCCTACGGCAACACCTACC<br>TGGAATGGTATCTGCAGAAGCCCGGCCAGTCTCCTCAGCTGCTGATCTACAAGGTG<br>TCCAACCGGTTCTCTGGCGTGCCCGACAGATTTTCCGGCTCTGGCTCTGGCACCGA<br>CTTCACCCTGAAGATCTCCAGAGTGGAAGCCGAGGACGTGGGCGTGTACTACTGCT<br>TCCAAGGCTCTCACGTGCCCTACACCTTTGGCCAGGGCACCAAGCTGGAAATCAAG<br>CGGACAGTGGCCGCTCCTTCCGTGTTCATCTTCCCACCTTCCGACGAGCAGCTGAA<br>GTCCGGCACAGCTTCCTGTCGTGTGCCTGCTGAACAACTTCTACCCTCGGGAAGCCA<br>AGGTGCAGTGGAAGGTGGACAATGCCCTGCAGTCCGGCAACTCCCAAGAGTCTGTG<br>ACCGAGCAGGACTCCAAGGACAGCACCTACAGCCTGTCCAGCACACTGACCCTGTC<br>CAAGGCCGACTACGAGAAGCACAAGGTGTACGCCTGCGAAGTGACCCATCAGGGCC<br>TGTCTAGCCCTGTGACCAAGTCTTTCAACCGGGGCGAGTGC |
| 41 | 9B11 VH nucleic acid | GAGGTTCAGCTGCAGCAGTCTGGGGCAGAGCTTGTGAAGCCAGGGGCCTCAGTCAA<br>GTTGTCCTGCACAGCTTCTGGCTTCAACATTAAAGACTACTATATACACTGGGTGA<br>AGCAGAGGACTGAACAGGGCCTGGAGTGGATTGGAAGGATTGATCCTGAGGATGGT<br>GAAACTAAATATGCCCCGAAATTCCAGGGCAAGGCCACTATAACAGCAGACACATC<br>CTCCAACACAGCCTACCTGCAGCTCAACAGCCTGACATCTGAGGACACTGCCGTCT<br>ATTCCTGTGCTAAGGGGGGGTTTGCTTACTGGGGCCAAGGGACTCTGGTCACTGTC<br>TCTGCA |
| 42 | 9B11 VL nucleic acid | CAAATTGTTCTCACCCAGTCTCCAGCAATCATGTCTGCATCTCCTGGGGAGAAGGT<br>CACCTTGACCTGCAGTGCCAGTTCAAGTGTAAGTTCCAGCTACTTGTACTGGTACC<br>AGCAGAAGCCAGGATCCTCCCCCAAACTCTGGATTTATAGCACATCCAACCTGGCT<br>TCTGGAGTCCCTGCTCGCTTCAGTGGCAGTGGGTCTGGGACCTCTTACTCTCTCAC<br>AATCAGCAGCATGGAGGCTGAAGATGCTGCCTCTTATTTCTGCCATCAGTGGAGTA<br>GTCACCCGTACACGTTCGGAGGGGGGACCAAGCTGGAAATAAAA |
| 43 | 7E11 VH nucleic acid | CAGGTCAAGCTGCAGGAGTCTGGGGCTGAGCTGGTGAGGCCTGGGTCTTCAGTGAA<br>GCTGTCCTGCAAGGCTTCTGGCTACACCTTCACCAGCTACTGGATGCATTGGGTGA<br>AGCAGAGGCCTATACAAGGCCTTGAATGGATTGGTAACATTGACCCTTCTGATAGT<br>GATACTCACTACAATCAAAAGTTCAAGGACAAGGCCACATTGACTGTGGACAACTC<br>CTCCAGCACAGCCTACATGCAGCTCAGCAGCCTGACCTCTGAGGACTCTGCGGTCT<br>ATTACTGTGCAAGCTATGGTAACTACGGGGAGAATGCTATGGACTACTGGGGTCAA<br>GGAACCTCAGTCACCGTCTCCTCA |
| 44 | 7E11 VL nucleic acid | GATATTTTGATGACCCAAACTCCACTCTCCCTGCCTGTCAGTCTTGGAGATCAAGC<br>CTCCATCTCTTGCAGATCTAGTCAGAGCATTGTACATAGTTATGGAAACACCTATT<br>TAGAATGGTACCTGCAGAAACCAGGCCAGTCTCCAAAACTCCTGATCTACAAAGTT<br>TCCAACCGATTTTCTGGGGTCCCAGACAGGTTCAGTGGCAGTGGATCAGGTACAGA<br>TTTCACACTCAAGATCAGCAGAGTGGAGGCTGAGGATCTGGGAGTTTATTACTGCT<br>TTCAAGGTTCACATGTTCCATTCACGTTCGGCTCGGGGACAAAGTTGGAAATAAAA |

TABLE A-continued

SEQUENCES

| SEQ ID NO | ID | Sequence |
|---|---|---|
| 45 | SIRPa | EEELQVIQPDKSVLVAAGETATLRCTATSLIPVGPIQWFRGAGPGRELIYNQKEGH<br>FPRVTTVSDLTKRNNMDFSIRIGNITPADAGTYYCVKFRKGSPDDVEFKSGAGTEL<br>SVRA |
| 46 | KWar VH | EVQLVQSGAEVKKPGATVKISCKVSGFNIKDYYIHWVQQAPGKGLEWIGRIDPEDG<br>ETKYAPKFQDRATITADTSTDTAYMELSSLRSEDTAVYYCARWGAYWGQGTLVTVS<br>S |
| 47 | KWar VL | QIVLTQSPPTLSLSPGERVTLTCSASSSVSSSYLYWYQQKPGQAPKLWIYSTSNLA<br>SGVPARFSGSGSGTSYTLTISSLQPEDFAVYFCHQWSSYPRTFGAGTKLEIK |
| 48 | SIRPa V1 | EEELQVIQPDKSVLVAAGETATLRCTATSLIPVGPIQWFRGAGPGRELIYNQKEGH<br>FPRVTTVSDLTKRNNMDFSIRIGNITPADAGTYYCVKFRKGSPDDVEFKSGAGTEL<br>SVRA |
| 49 | SIRPa V2 | EEELQVIQPDKSVSVAAGESAILHCTVTSLIPVGPIQWFRGAGPARELIYNQKEGH<br>FPRVTTVSESTKRENMDFSISISNITPADAGTYYCVKFRKGSPDTEFKSGAGTELS<br>VRA |
| 50 | Hu5f9-G4<br>Antibody<br>Heavy Chain | QVQLVQSGAEVKKPGASVKVSCKASGYTFTNYNMHWVRQAPGQRLEWMGTIYPGND<br>DTSYNQKFKDRVTITADTSASTAYMELSSLRSEDTAVYYCARGGYRAMDYWGQGTL<br>VTVSSASTKGPSVFPLAPCSRSTSESTAALGCLVKDYFPEPVTVSWNSGALTSGVH<br>TFPAVLQSSGLYSLSSVVTVPSSSLGTKTYTCNVDHKPSNTKVDKRVESKYGPPCP<br>PCPAPEFLGGPSVFLFPPKPKDTLMISRTPEVTCVVVDVSQEDPEVQFNWYVDGVE<br>VHNAKTKPREEQFNSTYRVVSVLTVLHQDWLNGKEYKCKVSNKGLPSSIEKTISKA<br>KGQPREPQVYTLPPSQEEMTKNQVSLTCLVKGFYPSDIAVEWESNGQPENNYKTTP<br>PVLDSDGSFFLYSRLTVDKSRWQEGNVFSCSVMHEALHNHYTQKSLSLSLGK |
| 51 | Hu5f9-G4<br>Antibody<br>Light chain | DIVMTQSPLSLPVTPGEPASISCRSSQSIVYSNGNTYLGWYLQKPGQSPQLLIYKV<br>SNRFSGVPDRFSGSGSGILFTLKISRVEAELVGVYYCFQGSHVPYTFGQGIKLEIK<br>RTVAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC |
| 52 | Hu5f9-G4 VH<br>CDR1 | NYNMH |
| 53 | Hu5f9-G4 VH<br>CDR2 | TIYPGNDDTSYNQKFKD |
| 54 | Hu5f9-G4 VH<br>CDR3 | GGYRAMDY |
| 133 | Hu5f9-G4 VL<br>CDR1 | RSSQSIVYSNGNTYLG |
| 56 | Hu5f9-G4 VL<br>CDR2 | KVSNRFS |
| 57 | Hu5f9-G4 VL<br>CDR3 | FQGSHVPYT |
| 58 | 5F9 VH | QVQLQQPGAELVKPGASVMMSCKASGYTFTNYNMHWVKQTPGQGLEWIGTIYPGND<br>DTSYNQKFKDKATLTADKSSSAAYMQLSSLTSEDSAVYYCARGGYRAMDYWGQTSV<br>TVSS |
| 59 | 5F9 VL | DVLMTQTPLSLPVSLGDQASISCRSSQSIVYSNGNTYLGWYLQKPGQSPKLLIYKV<br>SNRFSGVPDRFSGSGSGTDFTLKISRVEAEDLGVYHCFQGSHVPYTFGGGTKVEIK |
| 60 | HuB6H12 VH | EVQLVESGGGLVQPGGSLRLSCAASGFTFSGYGMSWVRQAPGKGLEWVATITSGGT<br>YTYYPDSVKGRFTISRDNAKNSLYLQMNSLRAEDTAVYYCARSLAGNAMDYWGQGT<br>LVTVSS |
| 61 | HuB6H12 VL | EIVLTQSPATLSLSPGERATLSCRASQTISDYLHWYQQKPGQAPRLLIKFASQSIS<br>GIPARFSGSGSGTDFTLTISSLEPEDFAVYYCQNGHGFPRTFGQGTKVEIK |
| 62 | 8B6 VH | EVQLVESGGGLVQPGGSLRLSCAASGFTFSSYWMSWVRQAPGKGLEWVANIKQDGS<br>EKYYVDSVKGRFTISRDNAKNSLYLQMNSLRAEDTAVYYCARWGQGTLVTVSS |
| 63 | 8B6 VL | DIVMTQSPATLSVTPGDRVSLSCRASQNFSDYLHWYQQKSHESPRLLIKYVSHSIS<br>GIPSRFSGSGSGSDFTLSINSVEPEDVGVYYCQNGHSFPPTFGGGTKLEIK |
| 64 | C3 VH | QVQLQQSGAELVKPGASVKLSCKASGYTFTNYYIFWVKERPGQGLEWIGDINPSNG<br>DTNFNEKFKIKATLTVDKSSSTTYMQLNSLTSEDSAVYFCTRGGYTMDYWGQGTSV<br>TVSS |

TABLE A-continued

SEQUENCES

| SEQ ID NO | ID | Sequence |
|---|---|---|
| 65 | C3 VL | DVVMTQTPLSLPVSLGDQASISCRSSQSLVHSNGNTYFHWYVQKPGQSPKLLIYKV<br>SYRFSGVPDRFSGSGSGTDFTLKISRVEAEDLGVYFCSQSTHVPRTFGGGTKLEIK |
| 66 | HuC3 VH (A) | QVQLVQSGAEVKKPGASVKVSCKASGYTFTNYYIFWVRQAPGQGLEWIGDINPSNG<br>DTNFNEKFKIKATLTVDKSTSTTYMELSSLRSEDTAVYYCTRGGYTMDYWGQGTLV<br>TVSS |
| 67 | HuC3 VH (B) | QVQLVQSGAEVKKPGASVKVSCKASGYTFTNYYIFWVRQAPGQGLEWMGDINPSNG<br>DTNFNEKFKIRVTMTRDTSTSTVYMELSSLRSEDTAVYYCTRGGYTMDYWGQGTLV<br>TVSS |
| 68 | HuC3 VL (C) | DVVMTQTPLSLSVTPGQPASISCRSSQSLVHSNGNTYFHWYLQKPGQPPKLLIYKV<br>SYRFSGVPDRFSGSGSGTDFTLKISRVEAEDVGVYFCSQSTHVPRTFGQGTKVEIK |
| 69 | HuC3 VL (D) | DIVMTQTPLSLSVTPGQPASISCRSSQSLVHSNGNTYFHWYLQKPGQPPQLLIYKV<br>SYRFSGVPDRFSGSGSGTDFTLKISRVEAEDVGVYYCSQSTHVPRTFGQGTKVEIK |
| 70 | Anti-CD47 VH | EVQLQQSGAELVRSGASVKLSCTASGFNIKDYYLHWVKQRPEQGLEWIGWIDPDNG<br>DTEFAPKFQGKATMTADTSSNTAYLQLSSLTSEDTAVYYCNAAYGSSSYPMDYWGQ<br>GTSVTV |
| 71 | Anti-CD47 VH | EVQLVQSGAEVKKPGATVKISCKVSGFNIKDYYLHWVQQAPGKGLEWMGWIDPDNG<br>DTEYAEKFQGRVTITADTSTDTAYMELSSLRSEDTAVYYCNAAYGSSSYPMDYWGQ<br>GTTVTV |
| 72 | Anti-CD47 VH | QMQLVQSGAEVKKTGSSVKVSCKASGFNIKDYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 73 | Anti-CD47 VH | EVQLVQSGAEVKKTGSSVKVSCKASGFNIKDYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 74 | Anti-CD47 VH | QMQLVQSGAEVKKTGSSVKVSCKASGFNIKDYYLHWVRQAPGQALEWMGWIDPDNG<br>DTEYAQKFQGRVTMTADTSSNTAYMELSSLRSEDTAMYYCNAAYGSSSYPMDYWGQ<br>GTTVTV |
| 75 | Anti-CD47 VH | QMQLVQSGAEVKKTGSSVKVSCKASGFNIKDYYLHWVRQAPGQALEWMGWIDPDNG<br>DTEYAQKFQGRVTMTEDTSTDTAYMELSSLRSEDTAMYYCNAAYGSSSYPMDYWGQ<br>GTTVTV |
| 76 | Anti-CD47 VH | QMQLVQSGAEVKKTGSSVKVSCKASGFNIKDYYLHWVRQAPGQALEWMGWIDPDQG<br>DTEYAQKFQDRVTITRDRSMSTAYMELSSLRSEDTAMYYCNAAYGSSSYPMDYWGQ<br>GTTVTV |
| 77 | Anti-CD47 VH | QMQLVQSGAEVKKTGSSVKVSCKASGFNIKDYYLHWVRQAPGQALEWMGWIDPDYG<br>DTEYAQKFQDRVTITRDRSMSTAYMELSSLRSEDTAMYYCNAAYGSSSYPMDYWGQ<br>GTTVTV |
| 78 | Anti-CD47 VH | QMQLVQSGAEVKKTGSSVKVSCKASGFNIKDYYLHWVRQAPGQALEWMGWIDPDSG<br>DTEYAQKFQDRVTITRDRSMSTAYMELSSLRSEDTAMYYCNAAYGSSSYPMDYWGQ<br>GTTVTV |
| 79 | Anti-CD47 VH | QMQLVQSGAEVKKTGSSVKVSCKASGFNIKDYYLHWVRQAPGQALEWMGWIDPDNA<br>DTEYAQKFQDRVTITRDRSMSTAYMELSSLRSEDTAMYYCNAAYGSSSYPMDYWGQ<br>GTTVTV |
| 80 | Anti-CD47 VH | QMQLVQSGAEVKKTGSSVKVSCKASGFNIKDYYLHWVRQAPGQALEWMGWIDPDNT<br>DTEYAQKFQDRVTITRDRSMSTAYMELSSLRSEDTAMYYCNAAYGSSSYPMDYWGQ<br>GTTVTV |
| 81 | Anti-CD47 VH | QMQLVQSGAEVKKTGSSVKVSCKASGFNIKDYYLHWVRQAPGQALEWMGWIDPDNG<br>DTEYAQKFQDRVTITRDRSMSTAYMELSSLRSEDTAMYYCNAAYGSSPYPMDYWGQ<br>GTTVTV |
| 82 | Anti-CD47 VH | QMQLVQSGAEVKKTGSSVKVSCKASGYTFTYYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 83 | Anti-CD47 VH | QMQLVQSGAEVKKTGSSVKVSCKASGFTFTYYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |

TABLE A-continued

SEQUENCES

| SEQ ID NO | ID | Sequence |
|---|---|---|
| 84 | Anti-CD47 VH | QMQLVQSGAEVKKTGSSVKVSCKASGYNFTYYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 85 | Anti-CD47 VH | QMQLVQSGAEVKKTGSSVKVSCKASGYTITYYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 86 | Anti-CD47 VH | QMQLVQSGAEVKKTGSSVKVSCKASGYTFKYYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 87 | Anti-CD47 VH | QMQLVQSGAEVKKTGSSVKVSCKASGYTFTDYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 88 | Anti-CD47 VH | QMQLVQSGAEVKKTGSSVKVSCKASGFTFTDYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 89 | Anti-CD47 VH | QMQLVQSGAEVKKTGSSVKVSCKASGFTITDYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 90 | Anti-CD47 VH | QMQLVQSGAEVKKTGSSVKVSCKASGYTFKDYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 91 | Anti-CD47 VH | QMQLVQSGAEVKKTGSSVKVSCKASGFTFKDYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 92 | Anti-CD47 VH | QMQLVQSGAEVKKTGSSVKVSCKASGFNIKDYYLHWVRQAPGQALEWMGWIDPDNG<br>DTEYAQKFQDRVTITRDRSMSTAYLQLSSLRSEDTAMYYCNAAYGSSSYPMDYWGQ<br>GTTVTV |
| 93 | Anti-CD47 VH | QMQLVQSGAEVKKTGSSVKVSCKASGFNIKDYYLHWVRQAPGQALEWMGWIDPDNG<br>DTEYAQKFQDRVTITRDRSMSTAYMELSSLTSEDTAVYYCNAAYGSSSYPMDYWGQ<br>GTTVTV |
| 94 | Anti-CD47 VH | EVQLVQSGAEVKKPGATVKISCKVSGFNIKDYYLHWVRQAPGQALEWMGWIDPDNG<br>DTEYAQKFQDRVTITRDRSMSTAYMELSSLRSEDTAMYYCNAAYGSSSYPMDYWGQ<br>GTTVTV |
| 95 | Anti-CD47 VH | EVQLVQSGAEVKKPGATVKISCKVSGFNIKDYYLHWVQQAPGKGLEWMGWIDPDNG<br>DTEYAQKFQDRVTITRDRSMSTAYMELSSLRSEDTAMYYCNAAYGSSSYPMDYWGQ<br>GTTVTV |
| 96 | Anti-CD47 VL | DIKMTQSPSSLYASLGERVTITCKASQDIHRYLSWFQQKPGKSPKILIYRANRLVD<br>GVPSRFSGSGSGQDYSLTISSLEYEDMGIYYCLQYDEFPYTFGGGTKLEMK |
| 97 | Anti-CD47 VL | DIKMTQSPSSLYASLGERVTITCKASQDIHRYLSWFQQKPGKSPKILIYRANRLVD<br>GVPSRFSGSGSGQDYSLTISSLEYEDMGIYYCLQYDEFPYTFGGGTKLEIK |
| 98 | Anti-CD47 VL | DIQMTQSPSSLSASVGDRVTITCKASQDIHRYLSWYQQKPGKAPKLLIYRANRLVD<br>GVPSRFSGSGSGTDFTFTISSLQPEDIATYYCLQYDEFPYTFGGGTKVEIK |
| 99 | Anti-CD47 VL | DIQMTQSPSSLSASVGDRVTITCKASQDIHRYLSWFQQKPGKAPKSLIYRANRLVD<br>GVPSRFSGSGSGTDFTLTISSLQPEDFATYYCLQYDEFPYTFGGGTKVEIK |
| 100 | Anti-CD47 VL | NIQMTQSPSAMSASVGDRVTITCKASQDIHRYLSWFQQKPGKVPKHLIYRANRLVD<br>GVPSRFSGSGSGTEFTLTISSLQPEDFATYYCLQYDEFPYTFGGGTKVEIK |
| 101 | Anti-CD47 VL | DIQMTQSPSSLSASVGDRVTITCKASQDIHRYLSWYQQKPGKAPKRLIYRANRLVD<br>GVPSRFSGSGSGTEFTLTISSLQPEDFATYYCLQYDEFPYTFGGGTKVEIK |
| 102 | Anti-CD47 VL | DIQMTQSPSSLSASVGDRVTITCRASQDIHRYLAWYQQKPGKVPKLLIYRANRLQS<br>GVPSRFSGSGSGTDFTLTISSLQPEDVATYYCLQYDEFPYTFGQGTKVEIK |
| 103 | Anti-CD47 VL | EIVLTQSPATLSLSPGERATLSCRASQDIHRYLAWYQQKPGQAPRLLIYRANRRAT<br>GIPARFSGSGSGTDFTLTISSLEPEDFAVYYCLQYDEFPYTGFQGTRLEIK |
| 104 | Anti-CD47 VL | DIQMTQSPSAMSASVGDRVTITCKASQDIHRYLSWFQQKPGKVPKHLIYRANRLVD<br>GVPSRFSGSGSGTEFTLTISSLQPEDFATYYCLQYDEFPYTFGGGTKVEIK |

TABLE A-continued

SEQUENCES

| SEQ ID NO | ID | Sequence |
|---|---|---|
| 105 | Anti-CD47 VL | NIQMTQSPSAMSASVGDRVTITCRARQGIHRYLSWFQQKPGKVPKHLIYRANRLVDGVPSRFSGSGSGTEFTLTISSLQPEDFATYYCLQYDEFPYTFGGGTKVEIK |
| 106 | Anti-CD47 VL | NIQMTQSPSAMSASVGDRVTITCKASQDIHRYLSWFQQKPGKVPKILIYRANRLVDGVPSRFSGSGSGTEFTLTISSLQPEDFATYYCLQYDEFPYTFGGGTKVEIK |
| 107 | Anti-CD47 VL | NIQMTQSPSAMSASVGDRVTITCKASQDIHRYLSWFQQKPGKVPKHLIYRANRLVSGVPSRFSGSGSGTEFTLTISSLQPEDFATYYCLQYDEFPYTFGGGTKVEIK |
| 108 | Anti-CD47 VL | NIQMTQSPSAMSASVGDRVTITCRARQGIHRYLSWFQQKPGKVPKILIYRANRLVDGVPSRFSGSGSGTEFTLTISSLQPEDFATYYCLQYDEFPYTFGGGTKVEIK |
| 109 | Anti-CD47 VL | NIQMTQSPSAMSASVGDRVTITCRARQGIHRYLSWFQQKPGKVPKHLIYRANRLVSGVPSRFSGSGSGTEFTLTISSLQPEDFATYYCLQYDEFPYTFGGGTKVEIK |
| 110 | Anti-CD47 VL | NIQMTQSPSAMSASVGDRVTITCKASQDIHRYLSWFQQKPGKVPKLLIYRANRLVDGVPSRFSGSGSGTEFTLTISSLQPEDFATYYCLQYDEFPYTFGGGTKVEIK |
| 111 | Anti-CD47 VL | NIQMTQSPSAMSASVGDRVTITCKASQDIHRYLSWFQQKPGKVPKLLIYRANRLVSGVPSRFSGSGSGTEFTLTISSLQPEDFATYYCLQYDEFPYTFGGGTKVEIK |
| 112 | Anti-CD47 VL | NIQMTQSPSAMSASVGDRVTITCRARQGIHRYLSWFQQKPGKVPKLLIYRANRLVSGVPSRFSGSGSGTEFTLTISSLQPEDFATYYCLQYDEFPYTFGGGTKVEIK |
| 113 | Anti-CD47 VH | QVQLVQSGAEVKKPGASVKVSCKASGYTFTNYNMHWVRQAPGQGLEWIGTIYPGNDDTSYNQKFKDKATLTADKSTSTAYMELSSLRSEDTAVYYCARGGYRAMDYWGQGTLVTVSS |
| 114 | Anti-CD47 VH | QVQLVQSGAEVKKPGASVKVSCKASGYTFTNYNMHWVRQAPGQRLEWMGTIYPGNDDTSYNQKFKDRVTITADTSASTAYMELSSLRSEDTAVYYCARGGYRAMDYWGQGTLVTVSS |
| 115 | Anti-CD47 VH | QVQLVQSGAEVKKPGASVKVSCKASGYTFTNYNMHWVRQAPGQRLEWIGTIYPGNDDTSYNQKFKDRATLTADKSASTAYMELSSLRSEDTAVYYCARGGYRAMDYWGQGTLVTVSS |
| 116 | Anti-CD47 VL | DVVMTQSPLSLPVTPGEPASISCRSSQSIVYSNGNTYLGWYLQKPGQSPKLLIYKVSNRFSGVPDRFSGSGSGTDFTLKISRVEAEDVGVYHCFQGSHVPYTFGGGTKVEIK |
| 117 | Anti-CD47 VL | DIVMTQSPLSLPVTPGEPASISCRSSQSIVYSNGNTYLGWYLQKPGQSPQLLIYKVSNRFSGVPDRFSGSGSGTDFTLKISRVEAEDVGVYYCFQGSHVPYTFGQGTKLEIK |
| 118 | Anti-CD47 VL | DVVMTQSPLSLPVTPGEPASISCRSSQSIVYSNGNTYLGWYLQKPGQSPQLLIYKVSNRFSGVPDRFSGSGSGTDFTLKISRVEAEDVGVYHCFQGSHVPYTFGQGTKLEIK |
| 119 | Anti-SIRPa VH | QVQLQQPGAELVRPGSSVKLSCKASGYTFTSYWVHWVKQRPIQGLEWIGNIDPSDSDTHYNQKFKDKASLTVDKSSSTAYMQLSSLTFEDSAVYYCVRGGTGTMAWFAYWGQGTLVTVSA |
| 120 | Anti-SIRPa VH | EVQLVQSGAEVKKPGESLRISCKASGYTFTSYWVHWVRQMPGKGLEWIGNIDPSDSDTHYNQKFKDHVTLSVDKSISTAYLQLSSLKASDTAMYYCVRGGTGTMAWFAYWGQGTLVTVSS |
| 121 | Anti-SIRPa VH | EVQLVQSGAEVKKPGESLRISCKASGYSFTSYWVHWVRQMPGKGLEWMGNIDPSDSDTHYNQKFKDHVTLSVDKSISTAYLQLSSLKASDTAMYYCVRGGTGTMAWFAYWGQGTLVTVSS |
| 122 | Anti-SIRPa VH | EVQLVQSGAEVKKPGESLRISCKASGYSFTSYWVHWVRQMPGKGLEWMGNIDPSDSDTHYSPSFQGHVTLSVDKSISTAYLQLSSLKASDTAMYYCVRGGTGTMAWFAYWGQGTLVTVSS |
| 123 | Anti-SIRPa VH | EVQLVQSGAEVKKPGESLRISCKASGYSFTSYWVHWVRQMPGKGLEWMGNIDPSDSDTHYSPSFQGHVTLSVDKSISTAYLQLSSLKASDTAMYYCVRGGTGTLAWFAYWGQGTLVTVSS |
| 124 | Anti-SIRPa VH | EVQLVQSGAEVKKPGESLRISCKASGYSFTSYWVHWVRQMPGKGLEWMGNIDPSDSDTHYSPSFQGHVTLSVDKSISTAYLQLSSLKASDTAMYYCVRGGTGTMAYFAYWGQGTLVTVSS |
| 125 | Anti-SIRPa VH | EVQLVQSGAEVKKPGESLRISCKASGYSFTSYWVHWVRQMPGKGLEWMGNIDPSDSDTHYSPSFQGHVTLSVDKSISTAYLQLSSLKASDTAMYYCVRGGTGTLAYFAYWGQGTLVTVSS |
| 126 | Anti-SIRPa VL | DVVMTQTPLSLPVSLGDQASISCRSSQSLVHSYGNTYLYWYLQKPGQSPKLLIYRVSNRFSGVPDRFSGSGSGTDFTLKISRVEAEDLGVYFCFQGTHVPYTFGSGTKLEIK |

TABLE A-continued

| SEQ ID NO | ID | Sequence |
|---|---|---|
| 127 | Anti-SIRPa VL | DVVMTQSPLSLPVTLGQPASISCRSSQSLVHSYGNTYLYWYQQRPGQSPRLLIYRV<br>SNRFSGVPDRFSGSGSGTDFTLKISRVEAEDVGVYFCFQGTHVPYTFGGGTKVEIK |
| 128 | Anti-SIRPa VL | DVVMTQSPLSLPVTLGQPASISCRSSQSLVHSYGNTYLYWFQQRPGQSPRLLIYRV<br>SNRFSGVPDRFSGSGSGTDFTLKISRVEAEDVGVYYCFQGTHVPYTFGGGTKVEIK |
| 129 | P53 amino acid sequence | MEEPQSDPSVEPPLSQETFSDLWKLLPENNVLSPLPSQAMDDLMLSPDDIEQWFTE<br>DPGPDEAPRMPEAAPPVAPAPAAPTPAAPAPAPSWPLSSSVPSQKTYQGSYGFRLG<br>FLHSGTAKSVTCTYSPALNKMFCQLAKTCPVQLWVDSTPPPGTRVRAMAIYKQSQH<br>MTEVVRRCPHHERCSDSDGLAPPQHLIRVEGNLRVEYLDDRNTFRHSVVVPYEPPE<br>VGSDCTTIHYNYMCNSSCMGGMNRRPILTIITLEDSSGNLLGRNSFEVRVCACPGR<br>DRRTEEENLRKKGEPHHELPPGSTKRALPNNTSSSPQPKKKPLDGEYFTLQIRGRE<br>RFEMFRELNEALELKDAQAGKEPGGSRAHSSHLKSKKGQSTSRHKKLMFKTEGPDS<br>D |
| 130 | P53 isoform a, DNA sequence NM_000546.6 | CTCAAAAGTCTAGAGCCACCGTCCAGGGAGCAGGTAGCTGCTGGGCTCCGGGGACA<br>CTTTGCGTTCGGGCTGGGAGCGTGCTTTCCACGACGGTGACACGCTTCCCTGGATT<br>GGCAGCCAGACTGCCTTCCGGGTCACTGCCATGGAGGAGCCGCAGTCAGATCCTAG<br>CGTCGAGCCCCCTCTGAGTCAGGAAACATTTTCAGACCTATGGAAACTACTTCCTG<br>AAAACAACGTTCTGTCCCCCTTGCCGTCCCAAGCAATGGATGATTTGATGCTGTCC<br>CCGGACGATATTGAACAATGGTTCACTGAAGACCCAGGTCCAGATGAAGCTCCCAG<br>AATGCCAGAGGCTGCTCCCCCCGTGGCCCCTGCACCAGCAGCTCCTACACCGGCGG<br>CCCCTGCACCAGCCCCCTCCTGGCCCCTGTCATCTTCTGTCCCTTCCCAGAAAACC<br>TACCAGGGCAGCTACGGTTTCCGTCTGGGCTTCTTGCATTCTGGGACAGCCAAGTC<br>TGTGACTTGCACGTACTCCCCTGCCCTCAACAAGATGTTTTGCCAACTGGCCAAGA<br>CCTGCCCTGTGCAGCTGTGGGTTGATTCCACACCCCCGCCCGGCACCCGCGTCCGC<br>GCCATGGCCATCTACAAGCAGTCACAGCACATGACGGAGGTTGTGAGGCGCTGCCC<br>CCACCATGAGCGCTGCTCAGATAGCGATGGTCTGGCCCCTCCTCAGCATCTTATCC<br>GAGTGGAAGGAAATTTGCGTGTGGAGTATTTGGATGACAGAAACACTTTTCGACAT<br>AGTGTGGTGGTGCCCTATGAGCCGCCTGAGGTTGGCTCTGACTGTACCACCATCCA<br>CTACAACTACATGTGTAACAGTTCCTGCATGGGCGGCATGAACCGGAGGCCCATCC<br>TCACCATCATCACACTGGAAGACTCCAGTGGTAATCTACTGGGACGGAACAGCTTT<br>GAGGTGCGTGTTTGTGCCTGTCCTGGGAGAGACCGGCGCACAGAGGAAGAGAATCT<br>CCGCAAGAAGGGGAGCCTCACCACGAGCTGCCCCCAGGGAGCACTAAGCGAGCAC<br>TGCCCAACAACACCAGCTCCTCTCCCCAGCCAAAGAAGAAACCACTGGATGGAGAA<br>TATTTCACCCTTCAGATCCGTGGGCGTGAGCGCTTCGAGATGTTCCGAGAGCTGAA<br>TGAGGCCTTGGAACTCAAGGATGCCCAGGCTGGGAAGGAGCCAGGGGGGAGCAGGG<br>CTCACTCCAGCCACCTGAAGTCCAAAAAGGGTCAGTCTACCTCCCGCCATAAAAAA<br>CTCATGTTCAAGACAGAAGGGCCTGACTCAGACTGACATTCTCCACTTCTTGTTCC<br>CCACTGACAGCCTCCCACCCCCATCTCTCCCTCCCCTGCCATTTTGGGTTTTGGGT<br>CTTTGAACCCTTGCTTGCAATAGGTGTGCGTCAGAAGCACCCAGGACTTCCATTTG<br>CTTTGTCCCGGGGCTCCACTGAACAAGTTGGCCTGCACTGGTGTTTTGTTGTGGGG<br>AGGAGGATGGGGAGTAGGACATACCAGCTTAGATTTTAAGGTTTTTACTGTGAGGG<br>ATGTTTGGGAGATGTAAGAAATGTTCTTGCAGTTAAGGGTTAGTTTACAATCAGCC<br>ACATTCTAGGTAGGGGCCCACTTCACCGTACTAACCAGGGAAGCTGTCCCTCACTG<br>TTGAATTTTCTCTAACTTCAAGGCCCATATCTGTGAAATGCTGGCATTTGCACCTA<br>CCTCACAGAGTGCATTGTGAGGGTTAATGAAATAATGTACATCTGGCCTTGAAACC<br>ACCTTTTATTACATGGGGTCTAGAACTTGACCCCCTTGAGGGTGCTTGTTCCCTCT<br>CCCTGTTGGTCGGTGGGTTGGTAGTTTCTACAGTTGGGCAGCTGGTTAGGTAGAGG<br>GAGTTGTCAAGTCTCTGCTGGCCCAGCCAAACCCTGTCTGACAACCTCTTGGTGAA<br>CCTTAGTACCTAAAAGGAAATCTCACCCCATCCCACACCCTGGAGGATTTCATCTC<br>TTGTATATGATGATCTGGATCCACCAAGACTTGTTTTATGCTCAGGGTCAATTTCT<br>TTTTTCTTTTTTTTTTTTTTTTCTTTTTCTTTGAGACTGGGTCTCGCTTTGTTG<br>CCCAGGCTGGAGTGGAGTGGCGTGATCTTGGCTTACTGCAGCCTTTGCCTCCCGG<br>CTCGAGCAGTCCTGCCTCAGCCTCCGGAGTAGCTGGGACCACAGGTTCATGCCACC<br>ATGGCCAGCCAACTTTTGCATGTTTTGTAGAGATGGGGTCTCACAGTGTTGCCCAG<br>GCTGGTCTCAAACTCCTGGGCTCAGGCGATCCACCTGTCTCAGCCTCCCAGAGTGC<br>TGGGATTACAATTGTGAGCCACCACGTCCAGCTGGAAGGGTCAACATCTTTTACAT<br>TCTGCAAGCACATCTGCATTTTCACCCCACCCTTCCCCTCCTTCTCCCTTTTTATA<br>TCCCATTTTTATATCGATCTCTTATTTTACAATAAAACTTTGCTGCCA |
| 131 | Hu5f9-G4 VH | QVQLVQSGAEVKKPGASVKVSCKASGYTFTNYNMHWVRQAPGQRLEWMGTIYPGND<br>DTSYNQKFKDRVTITADTSASTAYMELSSLRSEDTAVYYCARGGYRAMDYWGQGTL<br>VTVSS |
| 132 | Hu5f9-G4 VL | DIVMTQSPLSLPVTPGEPASISCRSSQSIVYSNGNTYLGWYLQKPGQSPQLLIYKV<br>SNRFSGVPDRFSGSGSGTDFTLKISRVEAEDVGVYYCFQGSHVPYTFGQGTKLEIK |
| 133 | Hu5f9-G4 VL CDR1 | RSSQSIVYSNGNTYLG |
| 134 | Hu5f9-G4 VH CDR1 | GYTFTNYN |
| 135 | Hu5f9-G4 VH CDR2 | IYPGNDDT |

TABLE A-continued

SEQUENCES

| SEQ ID NO | ID | Sequence |
|---|---|---|
| 136 | Hu5f9-G4 VH CDR3 | ARGGYRAMDY |
| 137 | Hu5f9-G4 VL CDR1 | QSIVYSNGNTY |
| 138 | Hu5f9-G4 VL CDR2 | KVS |
| 139 | Hu5f9-G4 VL CDR3 | FQGSHVPYT |
| 140 | Hu5f9-G4 VH CDR1 | GYTFTNY |
| 141 | Hu5f9-G4 VH CDR2 | PGND |
| 142 | Hu5f9-G4 VH CDR3 | GYRAMD |
| 143 | Hu5f9-G4 VL CDR1 | SQSIVYSNGNTY |
| 144 | Hu5f9-G4 VL CDR2 | KVS |
| 145 | Hu5f9-G4 VL CDR3 | GSHVPY |
| 146 | Hu5f9-G4 VH CDR1 | ASGYTFTNYN |
| 147 | Hu5f9-G4 VH CDR2 | IYPGNDDTSYNQKFKDR |
| 148 | Hu5f9-G4 VH CDR3 | GGYRAMD |
| 149 | Hu5f9-G4 VL CDR1 | SSQSIVYSNGNTY |
| 150 | Hu5f9-G4 VL CDR2 | KVSNRFSGVPDR |
| 151 | Hu5f9-G4 VL CDR3 | GSHVPY |

The invention claimed is:

1. A method of treating myelodysplastic syndrome (MDS) or acute myeloid leukemia (AML) in a subject comprising:
   a. determining or having determined the presence of at least one p53 mutation in the subject, before administering step;
   b. selecting the subject that has at least one p53 mutation; and
   c. administering to the subject (i) magrolimab and (ii) azacitidine;
   thereby treating the subject.

2. The method of claim 1, wherein the subject is relapsed or refractory to at least 1, 2, 3, 4, 5, 6, 7, 8, 9, 10 or greater than 10 prior lines of cancer therapy.

3. The method of claim 1, wherein the magrolimab is administered intravenously.

4. The method of claim 1, wherein the azacitidine is administered intravenously, subcutaneously, or orally.

5. The method of claim 1, wherein the administration of the magrolimab and the azacitidine reduces the p53 mutational burden in the subject relative to the p53 mutational burden present in the subject prior to the administration.

6. The method of claim 1, wherein the administration of the magrolimab and the azacitidine reduces the level of leukemia stem cells present in the bone marrow of the subject as compared to the level of leukemia stem cells present in the bone marrow of the subject before the administration.

7. The method of claim 1, wherein the method comprises administering the magrolimab and the azacitidine to the subject for at least two distinct cycles of four weeks each, the first cycle comprising (1) administering a priming dose of the magrolimab in the range of 1 mg to 10 mg of antibody per kg of body weight on Day 1 and 4, (2) administering a dose of at least 15 mg of the magrolimab per kg of body weight on day 8, (3) administering a dose of at least 30 mg of the magrolimab per kg of body weight on days 11, 15, and 22, and (4) administering a dose of at least 75 mg/m2 of the azacitidine on each of days 1-7; and the second cycle comprising (1) administering a dose of at least 30 mg of the magrolimab per kg of body weight once every week on days 1, 8, 15, and 22, and (2) administering a dose of at least 75 mg/m2 of the azacitidine on each of days 1-7.

8. The method of claim 7, wherein the second cycle is repeated as one or more additional cycles without limit or until a clinical benefit is reduced or lost or no longer observed.

9. The method of claim 7, wherein a third cycle of four weeks comprises (1) administering a dose of at least 30 mg of the magrolimab per kg of body weight once every two weeks on days 1 and 15, and (2) administering a dose of at least 75 mg/m2 of the azacitidine on each of days 1-7.

10. The method of claim 7, wherein a third cycle of four weeks comprises (1) administering a dose of at least 30 mg of the magrolimab per kg of body weight once every week on days 1, 8, 15, and 22 and (2) administering a dose of at least 75 mg/m2 of the azacitidine on each of days 1-7.

11. The method of claim 9, wherein the third cycle is repeated as one or more additional cycles without limit or until a clinical benefit is reduced or lost or no longer observed.

12. The method of claim 1, wherein the subject is a human subject.

\* \* \* \* \*

SEQUENCE LISTING

<160> NUMBER OF SEQ ID NOS: 153

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Trp Ile Thr
1               5

<210> SEQ ID NO 2
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 2

Asp Ile Tyr Pro Gly Ser Gly Ser Thr Asn His Ile Glu Lys Phe Lys
1               5                   10                  15

Ser

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Gly Ser Ser Tyr Gly Tyr Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Glu Asn Ile Tyr Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ala Lys Thr Leu Ala Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln His Gln Tyr Gly Pro Pro Phe Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ala
```

```
                1               5                   10                  15
Ser Val Lys Val Ser Cys Lys Ala Ser Gly Tyr Thr Phe Thr Ser Tyr
                20                  25                  30

Trp Ile Thr Trp Val Lys Gln Ala Pro Gly Gln Gly Leu Glu Trp Ile
            35                  40                  45

Gly Asp Ile Tyr Pro Gly Ser Gly Ser Thr Asn His Ile Glu Lys Phe
        50                  55                  60

Lys Ser Lys Ala Thr Leu Thr Val Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Thr Gly Tyr Gly Ser Ser Tyr Gly Tyr Phe Asp Tyr Trp Gly Gln
                100                 105                 110

Gly Thr Leu Val Thr Val Ser Ser
            115                 120

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
                20                  25                  30

Leu Ala Trp Tyr Gln Gln Lys Pro Gly Lys Ala Pro Lys Leu Leu Ile
            35                  40                  45

Tyr Thr Ala Lys Thr Leu Ala Glu Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Tyr Gly Pro Pro Phe
                85                  90                  95

Thr Phe Gly Gln Gly Thr Lys Leu Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Tyr Trp Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

```
Asn Ile Asp Pro Ser Asp Ser Asp Thr His Tyr Asn Gln Lys Phe Lys
1               5                   10                  15

Asp
```

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Gly Tyr Ser Lys Tyr Tyr Ala Met Asp Tyr
1               5                   10
```

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Arg Ser Ser Gln Ser Ile Val His Ser Tyr Gly Asn Thr Tyr Leu Glu
1               5                   10                  15
```

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Lys Val Ser Asn Arg Phe Ser
1               5
```

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Phe Gln Gly Ser His Val Pro Tyr Thr
1               5
```

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Trp Met His Trp Val Arg Gln Ala Pro Gly Gln Gly Leu Glu Trp Met
            35                  40                  45

Gly Asn Ile Asp Pro Ser Asp Ser Asp Thr His Tyr Asn Gln Lys Phe
 50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Gly Tyr Ser Lys Tyr Tyr Ala Met Asp Tyr Trp Gly Gln Gly
                100                 105                 110

Thr Leu Val Thr Val Ser Ser
            115
```

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Ile Val His Ser
            20                  25                  30

Tyr Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
                100                 105                 110
```

<210> SEQ ID NO 17
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Trp Ile Thr Trp Val Lys Gln Ala Pro Gly Gln Gly Leu Glu Trp Ile
        35                  40                  45

Gly Asp Ile Tyr Pro Gly Ser Gly Ser Thr Asn His Ile Glu Lys Phe
 50                  55                  60

Lys Ser Lys Ala Thr Leu Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95
```

Ala Thr Gly Tyr Gly Ser Ser Tyr Gly Tyr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 18
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Thr Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gln Tyr Gly Pro Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Asp Pro Ser Asp Ser Asp Thr His Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Lys Tyr Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Ala Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 20
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
                20                  25                  30

Tyr Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
```

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Tyr Tyr Ile His
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ile Asp Pro Glu Asp Gly Glu Thr Lys Tyr Ala Pro Lys Phe Gln
1               5                   10                  15

Gly

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Phe Ala Tyr
1               5

<210> SEQ ID NO 24
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ser Ser Ser Val Ser Ser Ser Tyr Leu Tyr
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Thr Ser Asn Leu Ala Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Gln Trp Ser Ser His Pro Tyr Thr
1               5

<210> SEQ ID NO 27
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Asn Ser Leu Thr Ser Glu Asp Thr Ala Val Tyr Ser Cys
                85                  90                  95

Ala Lys Gly Gly Phe Ala Tyr Trp Gly Gln Gly Thr Leu Val Thr Val
            100                 105                 110

Ser Ala

<210> SEQ ID NO 28
<211> LENGTH: 108
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 28

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser His Pro
                85                  90                  95

Tyr Thr Phe Gly Gly Gly Thr Lys Leu Glu Ile Lys
            100                 105

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Tyr Trp Met His
1               5

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Ile Asp Pro Ser Asp Ser Asp Thr His Tyr Asn Gln Lys Phe Lys
1               5                   10                  15

Asp

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Tyr Gly Asn Tyr Gly Glu Asn Ala Met Asp Tyr
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ser Ser Gln Ser Ile Val His Ser Tyr Gly Asn Thr Tyr Leu Glu
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Val Ser Asn Arg Phe Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Gln Gly Ser His Val Pro Phe Thr
1               5

<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Lys Leu Gln Glu Ser Gly Ala Glu Leu Val Arg Pro Gly Ser
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Ile Gln Gly Leu Glu Trp Ile
            35                  40                  45

Gly Asn Ile Asp Pro Ser Asp Ser Asp Thr His Tyr Asn Gln Lys Phe
        50                  55                  60

Lys Asp Lys Ala Thr Leu Thr Val Asp Asn Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Tyr Gly Asn Tyr Gly Glu Asn Ala Met Asp Tyr Trp Gly Gln
            100                 105                 110

Gly Thr Ser Val Thr Val Ser Ser
        115                 120

<210> SEQ ID NO 36
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Tyr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110
```

<210> SEQ ID NO 37
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
caggttcagt tggttcagtc tggcgccgaa gtgaagaaac tggcgcctc tgtgaaggtg      60 tcctgcaagg cttccggcta cacctttacc agctactgga tcacctgggt caagcaggct    120
cctggacagg gactcgagtg gatcggcgat atctatcctg ctccggctc accaaccac     180 atcgagaagt tcaagtccaa ggctaccctg accgtggaca cctccatctc caccgcctac    240
atggaactgt cccggctgag atctgacgac accgccgtgt actattgcgc taccggctac    300
ggctcctcct acggctactt tgattattgg ggccagggca cctggtcac cgtgtcctct     360 gcttctacca agggacccag cgtgttccct ctggctcctt ccagcaagtc tacctctggc    420
ggaacagctg ctctgggctg cctggtcaag gactactttc ctgagcctgt gaccgtgtct    480
tggaactctg gcgctctgac atctggcgtg cacacattcc ctgctgtgct gcagtcctcc    540
ggcctgtact ctctgtcctc tgtcgtgacc gtgccttcca gctctctggg aacccagacc    600
tacatctgca atgtgaacca caagccttcc aacaccaagg tggacaagaa ggtgaaccc    660 aagtcctgcg acaagaccca cacctgtcct ccatgtcctg ctccagaact gctcggcgga    720
ccttccgtgt ttctgttccc tccaaagcct aaggacaccc tgatgatctc tcggacccct    780
gaagtgacct gcgtggtggt ggatgtgtct cacgaggacc cagaagtgaa gttcaattgg    840
tacgtggacg gcgtggaagt gcacaacgcc aagaccaagc ctagagagga cagtacgcc    900 tccacctaca gagtggtgtc cgtgctgaca gtgctgcacc aggattggct gaacggcaaa    960
gagtacaagt gcaaggtgtc caacaaggcc ctgcctgctc tatcgaaaa gaccatctcc   1020 aaggccaagg gccagcctag ggaacccag gtttacaccc tgccacctag ccgggaagag    1080
atgaccaaga accaggtgtc cctgacctgc ctcgtgaagg gcttctaccc ttccgatatc    1140
gctgtggaat gggagagcaa cggccagcct gagaacaact acaagacaac ccctcctgtg    1200
ctggactccg acggctcatt ctttctgtac tccaagctga ctgtggacaa gtccagatgg    1260
cagcagggca acgtgttctc ctgcagcgtg atgcacgagg ccctgcacaa tcactacaca    1320
cagaagtctc tgtctctgag ccccggc                                       1347
```

<210> SEQ ID NO 38
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

| | | | | | |
|---|---|---|---|---|---|
| gacatccaga | tgacccagtc | tccatcctct | ctgtccgcct | ctgtgggcga | cagagtgacc | 60 |
| atcacctgtc | gggcctccga | aacatctac | tcctacctgg | cctggtatca | gcagaagcct | 120 |
| ggcaaggctc | ccaagctgct | gatctacacc | gctaagacac | tggccgaggg | cgtgccctct | 180 |
| agattttctg | gctctggaag | cggcaccgac | tttaccctga | caatctccag | cctgcagcct | 240 |
| gaggacttcg | ccacctacta | ctgccagcac | cagtacggcc | ctccattcac | ctttggccag | 300 |
| ggcaccaagc | tggaaatcaa | gcggacagtg | gccgctcctt | ccgtgttcat | cttcccacct | 360 |
| tccgacgagc | agctgaagtc | tggcacagcc | tctgtcgtgt | gcctgctgaa | caacttctac | 420 |
| cctcgggaag | ccaaggtgca | gtggaaggtg | gacaatgccc | tgcagtccgg | caactcccaa | 480 |
| gagtctgtga | ccgagcagga | ctccaaggac | agcacctaca | gcctgtcctc | cacactgacc | 540 |
| ctgtccaagg | ccgactacga | aagcacaag | gtgtacgcct | gcgaagtgac | ccatcagggc | 600 |
| ctgtctagcc | ctgtgaccaa | gtctttcaac | cggggcgagt | gc | | 642 |

<210> SEQ ID NO 39
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

| | | | | | |
|---|---|---|---|---|---|
| caggttcagt | tggttcagtc | tggcgccgaa | gtgaagaaac | ctggcgcctc | tgtgaaggtg | 60 |
| tcctgcaagg | cttccggcta | cacctttacc | agctactgga | tgcactgggt | ccgacaggct | 120 |
| ccaggacaag | gcttggagtg | gatgggcaac | atcgacccct | ctgacagcga | cacccactac | 180 |
| aaccagaaat | tcaaggaccg | cgtgaccatg | accagagaca | cctccaccag | caccgtgtac | 240 |
| atggaactgt | ccagcctgag | atccgaggac | accgccgtgt | actactgtgc | cagaggctac | 300 |
| tccaagtact | acgccatgga | ctactggggc | cagggcacac | tggttaccgt | gtcctctgct | 360 |
| tccaccaagg | gaccctctgt | gttccctctg | gctccttcca | gcaagtctac | ctctggcgga | 420 |
| acagctgctc | tgggctgcct | ggtcaaggac | tactttcctg | agcctgtgac | cgtgtcttgg | 480 |
| aactctggcg | ctctgacatc | tggcgtgcac | acattccctg | ctgtgctgca | gtcctccggc | 540 |
| ctgtactctc | tgtcctctgt | cgtgaccgtg | ccttccagct | ctctgggaac | ccagacctac | 600 |
| atctgcaatg | tgaaccacaa | gccttccaac | accaaggtgg | acaagaaggt | ggaacccaag | 660 |
| tcctgcgaca | agacccacac | ctgtcctcca | tgtcctgctc | cagaactgct | cggcggacct | 720 |
| tccgtgtttc | tgttccctcc | aaagcctaag | gacaccctga | tgatctctcg | gacccctgaa | 780 |
| gtgacctgcg | tggtggtgga | tgtgtcccac | gaagatccag | aagtgaagtt | caattggtac | 840 |
| gtggacggcg | tggaagtgca | caacgccaag | accaagccta | gagaggaaca | gtacgcctcc | 900 |
| acctacagag | tggtgtccgt | gctgacagtg | ctgcaccagg | attggctgaa | cggcaaagag | 960 |
| tacaagtgca | aggtgtccaa | caaggccctg | cctgctccta | tcgaaaagac | catctccaag | 1020 |
| gccaagggcc | agcctaggga | accccaggtt | tacaccctgc | ctccaagccg | ggaagagatg | 1080 |

```
accaagaacc aggtgtccct gacctgcctc gtgaagggct tctacccttc cgatatcgcc    1140
gtggaatggg agagcaatgg ccagccagag aacaactaca agacaacccc tcctgtgctg    1200
gactccgacg gctcattctt tctgtactcc aagctgaccg tggacaagtc cagatggcag    1260
cagggcaacg tgttctcctg cagcgtgatg cacgaggccc tgcacaatca ctatacccag    1320
aagtccctgt ctctgtcccc tggc                                           1344
```

<210> SEQ ID NO 40
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
gacatcgtga tgacccagac acctctgagc ctgagcgtga cacctggaca gcctgcctcc     60
atctcctgca gatcctctca gtccatcgtg cactcctacg gcaacaccta cctggaatgg    120
tatctgcaga agcccggcca gtctcctcag ctgctgatct acaaggtgtc caaccggttc    180
tctggcgtgc ccgacagatt ttccggctct ggctctggca ccgacttcac cctgaagatc    240
tccagagtgg aagccgagga cgtgggcgtg tactactgct tccaaggctc tcacgtgccc    300 tacaccttg gccagggcac caagctggaa atcaagcgga cagtggccgc tccttccgtg    360
ttcatcttcc caccttccga cgagcagctg aagtccggca gcttctgt cgtgtgcctg    420 ctgaacaact ctacccctcg ggaagccaag gtgcagtgga aggtggacaa tgccctgcag    480
tccggcaact cccaagagtc tgtgaccgag caggactcca aggacagcac ctacagcctg    540
tccagcacac tgaccctgtc caaggccgac tacgagaagc acaaggtgta cgcctgcgaa    600
gtgacccatc agggcctgtc tagccctgtg accaagtctt tcaaccgggg cgagtgc      657
```

<210> SEQ ID NO 41
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
gaggttcagc tgcagcagtc tggggcagag cttgtgaagc caggggcctc agtcaagttg     60
tcctgcacag cttctggctt caacattaaa gactactata tacactgggt gaagcagagg    120
actgaacagg gcctggagtg gattggaagg attgatcctg aggatggtga aactaaatat    180
gccccgaaat ccagggcaa ggccactata acagcagaca catcctccaa cacagcctac    240
ctgcagctca acagcctgac atctgaggac actgccgtct attcctgtgc taaggggggg    300
tttgcttact ggggccaagg gactctggtc actgtctctg ca                       342
```

<210> SEQ ID NO 42
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
caaattgttc tcacccagtc tccagcaatc atgtctgcat ctcctgggga gaaggtcacc     60
```

```
ttgacctgca gtgccagttc aagtgtaagt tccagctact tgtactggta ccagcagaag    120
ccaggatcct cccccaaact ctggatttat agcacatcca acctggcttc tggagtccct    180
gctcgcttca gtggcagtgg gtctgggacc tcttactctc tcacaatcag cagcatggag    240
gctgaagatg ctgcctctta tttctgccat cagtggagta gtcacccgta cacgttcgga    300
ggggggacca agctggaaat aaaa                                           324

<210> SEQ ID NO 43
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
caggtcaagc tgcaggagtc tggggctgag ctggtgaggc ctgggtcttc agtgaagctg     60
tcctgcaagg cttctggcta caccttcacc agctactgga tgcattgggt gaagcagagg    120
cctatacaag gccttgaatg gattggtaac attgaccctt ctgatagtga tactcactac    180
aatcaaaagt tcaaggacaa ggccacattg actgtggaca actcctccag cacagcctac    240
atgcagctca gcagcctgac ctctgaggac tctgcggtct attactgtgc aagctatggt    300
aactacgggg agaatgctat ggactactgg ggtcaaggaa cctcagtcac cgtctcctca    360

<210> SEQ ID NO 44
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gatattttga tgacccaaac tccactctcc ctgcctgtca gtcttggaga tcaagcctcc     60
atctcttgca gatctagtca gagcattgta catagttatg gaaacaccta tttagaatgg    120
tacctgcaga aaccaggcca gtctccaaaa ctcctgatct acaaagtttc caaccgattt    180
tctggggtcc cagacaggtt cagtggcagt ggatcaggta cagatttcac actcaagatc    240
agcagagtgg aggctgagga tctgggagtt tattactgct ttcaaggttc acatgttcca    300
ttcacgttcg gctcggggac aaagttggaa ataaaa                              336

<210> SEQ ID NO 45
<211> LENGTH: 116
<212> TYPE: PRT
<213> ORGANISM: Homo sapiens

<400> SEQUENCE: 45

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80
```

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala
        115

<210> SEQ ID NO 46
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Tyr
            20                  25                  30

Tyr Ile His Trp Val Gln Gln Ala Pro Gly Lys Gly Leu Glu Trp Ile
        35                  40                  45

Gly Arg Ile Asp Pro Glu Asp Gly Glu Thr Lys Tyr Ala Pro Lys Phe
    50                  55                  60

Gln Asp Arg Ala Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Ala Tyr Trp Gly Gln Gly Thr Leu Val Thr Val Ser
            100                 105                 110

Ser

<210> SEQ ID NO 47
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Ile Val Leu Thr Gln Ser Pro Pro Thr Leu Ser Leu Ser Pro Gly
1               5                   10                  15

Glu Arg Val Thr Leu Thr Cys Ser Ala Ser Ser Ser Val Ser Ser Ser
            20                  25                  30

Tyr Leu Tyr Trp Tyr Gln Gln Lys Pro Gly Gln Ala Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Thr Leu Thr Ile Ser Ser Leu Gln
65                  70                  75                  80

Pro Glu Asp Phe Ala Val Tyr Phe Cys His Gln Trp Ser Ser Tyr Pro
                85                  90                  95

Arg Thr Phe Gly Ala Gly Thr Lys Leu Glu Ile Lys
            100                 105

<210> SEQ ID NO 48
<211> LENGTH: 116
<212> TYPE: PRT

<213> ORGANISM: Homo sapiens

<400> SEQUENCE: 48

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala
        115

<210> SEQ ID NO 49
<211> LENGTH: 115
<212> TYPE: PRT
<213> ORGANISM: Homo sapiens

<400> SEQUENCE: 49

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala
    115

<210> SEQ ID NO 50
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

-continued

```
Gly Thr Ile Tyr Pro Gly Asn Asp Asp Thr Ser Tyr Asn Gln Lys Phe
 50                  55                  60
Lys Asp Arg Val Thr Ile Thr Ala Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Tyr Arg Ala Met Asp Tyr Trp Gly Gln Gly Thr Leu
                100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
        195                 200                 205
Thr Lys Val Asp Lys Arg Val Glu Ser Lys Tyr Gly Pro Pro Cys Pro
210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
            260                 265                 270
Asn Trp Tyr Val Asp Gly Val Glu Val His Asn Ala Lys Thr Lys Pro
        275                 280                 285
Arg Glu Glu Gln Phe Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
            420                 425                 430
Tyr Thr Gln Lys Ser Leu Ser Leu Ser Leu Gly Lys
        435                 440

<210> SEQ ID NO 51
<211> LENGTH: 219
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gly
                85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asn Tyr Asn Met His
1               5

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ile Tyr Pro Gly Asn Asp Asp Thr Ser Tyr Asn Gln Lys Phe Lys
1               5                   10                  15

Asp

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Tyr Arg Ala Met Asp Tyr
1               5

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ser Ser Gln Ser Ile Val Tyr Ser Asn Gly Asn Thr Tyr Leu
1               5                   10                  15

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Val Ser Asn Arg Phe Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Gln Gly Ser His Val Pro Tyr Thr
1               5

<210> SEQ ID NO 58
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Gln Gln Pro Gly Ala Glu Leu Val Lys Pro Gly Ala
1               5                   10                  15

Ser Val Met Met Ser Cys Lys Ala Ser Gly Tyr Thr Phe Thr Asn Tyr
            20                  25                  30

Asn Met His Trp Val Lys Gln Thr Pro Gly Gln Gly Leu Glu Trp Ile
        35                  40                  45

Gly Thr Ile Tyr Pro Gly Asn Asp Asp Thr Ser Tyr Asn Gln Lys Phe
    50                  55                  60

```
Lys Asp Lys Ala Thr Leu Thr Ala Asp Lys Ser Ser Ala Ala Tyr
 65                  70                  75                  80

Met Gln Leu Ser Ser Leu Thr Ser Glu Asp Ser Ala Val Tyr Tyr Cys
                 85                  90                  95

Ala Arg Gly Gly Tyr Arg Ala Met Asp Tyr Trp Gly Gln Thr Ser Val
            100                 105                 110

Thr Val Ser Ser
        115

<210> SEQ ID NO 59
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr His Cys Phe Gln Gly
                85                  90                  95

Ser His Val Pro Tyr Thr Phe Gly Gly Gly Thr Lys Val Glu Ile Lys
            100                 105                 110

<210> SEQ ID NO 60
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Thr Tyr Thr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Leu Val Thr Val Ser Ser
        115
```

<210> SEQ ID NO 61
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Ser Asp Tyr
            20                  25                  30

Leu His Trp Tyr Gln Gln Lys Pro Gly Gln Ala Pro Arg Leu Leu Ile
        35                  40                  45

Lys Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Gly Phe Pro Arg
                85                  90                  95

Thr Phe Gly Gln Gly Thr Lys Val Glu Ile Lys
            100                 105

<210> SEQ ID NO 62
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Asn Phe Ser Asp Tyr
            20                  25                  30

Leu His Trp Tyr Gln Gln Lys Ser His Glu Ser Pro Arg Leu Leu Ile
        35                  40                  45

Lys Tyr Val Ser His Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Pro
                85                  90                  95

Thr Phe Gly Gly Gly Thr Lys Leu Glu Ile Lys
            100                 105

<210> SEQ ID NO 64
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Tyr Ile Phe Trp Val Lys Glu Arg Pro Gly Gln Gly Leu Glu Trp Ile
        35                  40                  45

Gly Asp Ile Asn Pro Ser Asn Gly Asp Thr Asn Phe Asn Glu Lys Phe
    50                  55                  60

Lys Ile Lys Ala Thr Leu Thr Val Asp Lys Ser Ser Ser Thr Thr Tyr
65                  70                  75                  80

Met Gln Leu Asn Ser Leu Thr Ser Glu Asp Ser Ala Val Tyr Phe Cys
                85                  90                  95

Thr Arg Gly Gly Tyr Thr Met Asp Tyr Trp Gly Gln Gly Thr Ser Val
            100                 105                 110

Thr Val Ser Ser
        115

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Phe His Trp Tyr Val Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Leu Gly Val Tyr Phe Cys Ser Gln Ser
            85                  90                  95

Thr His Val Pro Arg Thr Phe Gly Gly Gly Thr Lys Leu Glu Ile Lys
            100                 105                 110
```

<210> SEQ ID NO 66
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile Phe Trp Val Arg Gln Ala Pro Gly Gln Gly Leu Glu Trp Ile
        35                  40                  45

Gly Asp Ile Asn Pro Ser Asn Gly Asp Thr Asn Phe Asn Glu Lys Phe
    50                  55                  60

Lys Ile Lys Ala Thr Leu Thr Val Asp Lys Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Thr Met Asp Tyr Trp Gly Gln Gly Thr Leu Val
            100                 105                 110

Thr Val Ser Ser
        115
```

<210> SEQ ID NO 67
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile Phe Trp Val Arg Gln Ala Pro Gly Gln Gly Leu Glu Trp Met
        35                  40                  45

Gly Asp Ile Asn Pro Ser Asn Gly Asp Thr Asn Phe Asn Glu Lys Phe
    50                  55                  60

Lys Ile Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Thr Met Asp Tyr Trp Gly Gln Gly Thr Leu Val
            100                 105                 110

Thr Val Ser Ser
        115
```

<210> SEQ ID NO 68
<211> LENGTH: 112

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Phe His Trp Tyr Leu Gln Lys Pro Gly Gln Pro
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Arg Thr Phe Gly Gln Gly Thr Lys Val Glu Ile Lys
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Phe His Trp Tyr Leu Gln Lys Pro Gly Gln Pro
        35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Arg Thr Phe Gly Gln Gly Thr Lys Val Glu Ile Lys
            100                 105                 110

<210> SEQ ID NO 70
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
```

```
                35                  40                  45

Gly Trp Ile Asp Pro Asp Asn Gly Asp Thr Glu Phe Ala Pro Lys Phe
 50                  55                  60

Gln Gly Lys Ala Thr Met Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asn Ala Ala Tyr Gly Ser Ser Tyr Pro Met Asp Tyr Trp Gly Gln
                100                 105                 110

Gly Thr Ser Val Thr Val
                115

<210> SEQ ID NO 71
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Gln Ser Gly Ala Glu Val Lys Lys Pro Gly Ala
 1                   5                  10                  15

Thr Val Lys Ile Ser Cys Lys Val Ser Gly Phe Asn Ile Lys Asp Tyr
                 20                  25                  30

Tyr Leu His Trp Val Gln Gln Ala Pro Gly Lys Gly Leu Glu Trp Met
             35                  40                  45

Gly Trp Ile Asp Pro Asp Asn Gly Asp Thr Glu Tyr Ala Glu Lys Phe
 50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Asn Ala Ala Tyr Gly Ser Ser Tyr Pro Met Asp Tyr Trp Gly Gln
                100                 105                 110

Gly Thr Thr Val Thr Val
                115

<210> SEQ ID NO 72
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Met Gln Leu Val Gln Ser Gly Ala Glu Val Lys Lys Thr Gly Ser
 1                   5                  10                  15

Ser Val Lys Val Ser Cys Lys Ala Ser Gly Phe Asn Ile Lys Asp Tyr
                 20                  25                  30

Tyr Leu His Trp Val Arg Gln Ala Pro Gly Gln Ala Leu Glu Trp Met
             35                  40                  45

Gly Trp Ile Asp Pro Asp Asn Gly Asp Thr Glu Tyr Ala Gln Lys Phe
 50                  55                  60

Gln Asp Arg Val Thr Ile Thr Arg Asp Arg Ser Met Ser Thr Ala Tyr
 65                  70                  75                  80

Met Glu Leu Ser Ser Leu Arg Ser Glu Asp Thr Ala Met Tyr Tyr Cys
```

85                  90                  95

Asn Ala Ala Tyr Gly Ser Ser Tyr Pro Met Asp Tyr Trp Gly Gln
                100                 105                 110

Gly Thr Thr Val Thr Val
        115

<210> SEQ ID NO 73
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
        115

<210> SEQ ID NO 74
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
    50                  55                  60

Gln Gly Arg Val Thr Met Thr Ala Asp Thr Ser Ser Asn Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
        115

```
<210> SEQ ID NO 75
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
            115

<210> SEQ ID NO 76
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Gln Gly Asp Thr Glu Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
            115

<210> SEQ ID NO 77
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77
```

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Tyr Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
        115

<210> SEQ ID NO 78
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Ser Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
        115

<210> SEQ ID NO 79
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Ala Asp Thr Glu Tyr Ala Gln Lys Phe
            50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
        115

<210> SEQ ID NO 80
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Thr Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val
        115

<210> SEQ ID NO 81
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Pro Tyr Pro Met Asp Tyr Trp Gly Gln
            100                 105                 110

Gly Thr Thr Val Thr Val
        115

<210> SEQ ID NO 82
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 83
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Met Gln Leu Val Gln Ser Gly Ala Glu Val Lys Lys Thr Gly Ser
1               5                   10                  15

Ser Val Lys Val Ser Cys Lys Ala Ser Gly Phe Thr Phe Thr Tyr Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 84

<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Asn Phe Thr Tyr Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
        115

<210> SEQ ID NO 85
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Ile Thr Tyr Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
        50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
        115

<210> SEQ ID NO 86
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Lys Tyr Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 87
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 88
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Met Gln Leu Val Gln Ser Gly Ala Glu Val Lys Lys Thr Gly Ser
1               5                   10                  15

Ser Val Lys Val Ser Cys Lys Ala Ser Gly Phe Thr Phe Thr Asp Tyr
            20                  25                  30

Tyr Leu His Trp Val Arg Gln Ala Pro Gly Gln Ala Leu Glu Trp Met
        35                  40                  45

```
Gly Trp Ile Asp Pro Asp Asn Gly Asp Thr Glu Tyr Ala Gln Lys Phe
         50                  55                  60

Gln Asp Arg Val Thr Ile Thr Arg Asp Arg Ser Met Ser Thr Ala Tyr
 65                  70                  75                  80

Met Glu Leu Ser Ser Leu Arg Ser Glu Asp Thr Ala Met Tyr Tyr Cys
                 85                  90                  95

Asn Ala Ala Tyr Gly Ser Ser Ser Tyr Pro Met Asp Tyr Trp Gly Gln
             100                 105                 110

Gly Thr Thr Val Thr Val
        115

<210> SEQ ID NO 89
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Met Gln Leu Val Gln Ser Gly Ala Glu Val Lys Lys Thr Gly Ser
  1               5                  10                  15

Ser Val Lys Val Ser Cys Lys Ala Ser Gly Phe Thr Ile Thr Asp Tyr
                 20                  25                  30

Tyr Leu His Trp Val Arg Gln Ala Pro Gly Gln Ala Leu Glu Trp Met
             35                  40                  45

Gly Trp Ile Asp Pro Asp Asn Gly Asp Thr Glu Tyr Ala Gln Lys Phe
         50                  55                  60

Gln Asp Arg Val Thr Ile Thr Arg Asp Arg Ser Met Ser Thr Ala Tyr
 65                  70                  75                  80

Met Glu Leu Ser Ser Leu Arg Ser Glu Asp Thr Ala Met Tyr Tyr Cys
                 85                  90                  95

Asn Ala Ala Tyr Gly Ser Ser Ser Tyr Pro Met Asp Tyr Trp Gly Gln
             100                 105                 110

Gly Thr Thr Val Thr Val
        115

<210> SEQ ID NO 90
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Met Gln Leu Val Gln Ser Gly Ala Glu Val Lys Lys Thr Gly Ser
  1               5                  10                  15

Ser Val Lys Val Ser Cys Lys Ala Ser Gly Tyr Thr Phe Lys Asp Tyr
                 20                  25                  30

Tyr Leu His Trp Val Arg Gln Ala Pro Gly Gln Ala Leu Glu Trp Met
             35                  40                  45

Gly Trp Ile Asp Pro Asp Asn Gly Asp Thr Glu Tyr Ala Gln Lys Phe
         50                  55                  60

Gln Asp Arg Val Thr Ile Thr Arg Asp Arg Ser Met Ser Thr Ala Tyr
 65                  70                  75                  80

Met Glu Leu Ser Ser Leu Arg Ser Glu Asp Thr Ala Met Tyr Tyr Cys
                 85                  90                  95
```

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 91
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Met Gln Leu Val Gln Ser Gly Ala Glu Val Lys Lys Thr Gly Ser
1               5                   10                  15

Ser Val Lys Val Ser Cys Lys Ala Ser Gly Phe Thr Phe Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 92
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Leu Gln Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val
        115

<210> SEQ ID NO 93
<211> LENGTH: 118

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Thr Ser Glu Asp Thr Ala Val Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
        115

<210> SEQ ID NO 94
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Tyr
                20                  25                  30

Tyr Leu His Trp Val Arg Gln Ala Pro Gly Gln Ala Leu Glu Trp Met
            35                  40                  45

Gly Trp Ile Asp Pro Asp Asn Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
                100                 105                 110

Gly Thr Thr Val Thr Val
        115

<210> SEQ ID NO 95
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Gln Ser Gly Ala Glu Val Lys Lys Pro Gly Ala
```

```
                1               5                  10                 15
            Thr Val Lys Ile Ser Cys Lys Val Ser Gly Phe Asn Ile Lys Asp Tyr
                            20                  25                  30

Tyr Leu His Trp Val Gln Gln Ala Pro Gly Lys Gly Leu Glu Trp Met
                        35                  40                  45

Gly Trp Ile Asp Pro Asp Asn Gly Asp Thr Glu Tyr Ala Gln Lys Phe
                    50                  55                  60

Gln Asp Arg Val Thr Ile Thr Arg Asp Arg Ser Met Ser Thr Ala Tyr
            65                  70                  75                  80

Met Glu Leu Ser Ser Leu Arg Ser Glu Asp Thr Ala Met Tyr Tyr Cys
                            85                  90                  95

Asn Ala Ala Tyr Gly Ser Ser Tyr Pro Met Asp Tyr Trp Gly Gln
                            100                 105                 110

Gly Thr Thr Val Thr Val
                    115
```

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Asp Ile Lys Met Thr Gln Ser Pro Ser Ser Leu Tyr Ala Ser Leu Gly
1               5                   10                  15

Glu Arg Val Thr Ile Thr Cys Lys Ala Ser Gln Asp Ile His Arg Tyr
                20                  25                  30

Leu Ser Trp Phe Gln Gln Lys Pro Gly Lys Ser Pro Lys Ile Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys
            100                 105
```

<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Asp Ile Lys Met Thr Gln Ser Pro Ser Ser Leu Tyr Ala Ser Leu Gly
1               5                   10                  15

Glu Arg Val Thr Ile Thr Cys Lys Ala Ser Gln Asp Ile His Arg Tyr
                20                  25                  30

Leu Ser Trp Phe Gln Gln Lys Pro Gly Lys Ser Pro Lys Ile Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
```

```
            65                  70                  75                  80
Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105
```

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105
```

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105
```

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Asp Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 101
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Tyr Gln Gln Lys Pro Gly Lys Ala Pro Lys Arg Leu Ile
        35                  40                  45

Tyr Arg Ala Asn Arg Leu Val Asp Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Arg Tyr
            20                  25                  30

Leu Ala Trp Tyr Gln Gln Lys Pro Gly Lys Val Pro Lys Leu Leu Ile
        35                  40                  45

Tyr Arg Ala Asn Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105

<210> SEQ ID NO 103
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Ile His Arg Tyr
                20                  25                  30

Leu Ala Trp Tyr Gln Gln Lys Pro Gly Gln Ala Pro Arg Leu Leu Ile
            35                  40                  45

Tyr Arg Ala Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Leu Gln Tyr Asp Glu Phe Pro Tyr
                85                  90                  95

Thr Gly Phe Gln Gly Thr Arg Leu Glu Ile Lys
            100                 105

<210> SEQ ID NO 104
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
                20                  25                  30

Leu Ser Trp Phe Gln Gln Lys Pro Gly Lys Val Pro Lys His Leu Ile
            35                  40                  45

Tyr Arg Ala Asn Arg Leu Val Asp Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 105
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Asp Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys Ile Leu Ile
        35                  40                  45

Tyr Arg Ala Asn Arg Leu Val Asp Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys His Leu Ile
        35                  40                  45

```
Tyr Arg Ala Asn Arg Leu Val Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105
```

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Asn Ile Gln Met Thr Gln Ser Pro Ser Ala Met Ser Ala Ser Val Gly
 1               5                  10                  15

Asp Arg Val Thr Ile Thr Cys Arg Ala Arg Gln Gly Ile His Arg Tyr
                20                  25                  30

Leu Ser Trp Phe Gln Gln Lys Pro Gly Lys Val Pro Lys Ile Leu Ile
            35                  40                  45

Tyr Arg Ala Asn Arg Leu Val Asp Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105
```

<210> SEQ ID NO 109
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Asn Ile Gln Met Thr Gln Ser Pro Ser Ala Met Ser Ala Ser Val Gly
 1               5                  10                  15

Asp Arg Val Thr Ile Thr Cys Arg Ala Arg Gln Gly Ile His Arg Tyr
                20                  25                  30

Leu Ser Trp Phe Gln Gln Lys Pro Gly Lys Val Pro Lys His Leu Ile
            35                  40                  45

Tyr Arg Ala Asn Arg Leu Val Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105
```

<210> SEQ ID NO 110
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys Leu Leu Ile
        35                  40                  45

Tyr Arg Ala Asn Arg Leu Val Asp Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 111
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys Leu Leu Ile
        35                  40                  45

Tyr Arg Ala Asn Arg Leu Val Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 112
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile His Arg Tyr
            20                  25                  30

Leu Ser Trp Phe Gln Gln Lys Pro Gly Lys Val Pro Lys Leu Leu Ile
```

```
                35                  40                  45
Tyr Arg Ala Asn Arg Leu Val Ser Gly Val Pro Ser Arg Phe Ser Gly
             50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105
```

<210> SEQ ID NO 113
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Asn Met His Trp Val Arg Gln Ala Pro Gly Gln Gly Leu Glu Trp Ile
            35                  40                  45

Gly Thr Ile Tyr Pro Gly Asn Asp Asp Thr Ser Tyr Asn Gln Lys Phe
        50                  55                  60

Lys Asp Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
        115
```

<210> SEQ ID NO 114
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Asn Met His Trp Val Arg Gln Ala Pro Gly Gln Arg Leu Glu Trp Met
            35                  40                  45

Gly Thr Ile Tyr Pro Gly Asn Asp Asp Thr Ser Tyr Asn Gln Lys Phe
        50                  55                  60

Lys Asp Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
```

```
                100             105             110
Val Thr Val Ser Ser
        115

<210> SEQ ID NO 115
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Ile
        35                  40                  45

Gly Thr Ile Tyr Pro Gly Asn Asp Asp Thr Ser Tyr Asn Gln Lys Phe
    50                  55                  60

Lys Asp Arg Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
        115

<210> SEQ ID NO 116
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Phe Gln Gly
                85                  90                  95

Ser His Val Pro Tyr Thr Phe Gly Gly Gly Thr Lys Val Glu Ile Lys
            100                 105                 110

<210> SEQ ID NO 117
<211> LENGTH: 112
<212> TYPE: PRT
<213> ORGANISM: Artificial Sequence
<220> FEATURE:
<223> OTHER INFORMATION: Description of Artificial Sequence: Synthetic
```

```
                          polypeptide

<400> SEQUENCE: 117

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110

<210> SEQ ID NO 118
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Phe Gln Gly
                85                  90                  95

Ser His Val Pro Tyr Thr Phe Gly Gln Gly Thr Lys Leu Glu Ile Lys
            100                 105                 110

<210> SEQ ID NO 119
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60
```

```
Lys Asp Lys Ala Ser Leu Thr Val Asp Lys Ser Ser Thr Ala Tyr
 65                  70                  75                  80

Met Gln Leu Ser Ser Leu Thr Phe Glu Asp Ser Ala Val Tyr Tyr Cys
                 85                  90                  95

Val Arg Gly Gly Thr Gly Thr Met Ala Trp Phe Ala Tyr Trp Gly Gln
            100                 105                 110

Gly Thr Leu Val Thr Val Ser Ala
        115                 120

<210> SEQ ID NO 120
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser
        115                 120

<210> SEQ ID NO 121
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110
```

Gly Thr Leu Val Thr Val Ser Ser
        115                 120

<210> SEQ ID NO 122
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
        50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser
        115                 120

<210> SEQ ID NO 123
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
        50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Trp Phe Ala Tyr Trp Gly Gln
            100                 105                 110

Gly Thr Leu Val Thr Val Ser Ser
        115                 120

<210> SEQ ID NO 124
<211> LENGTH: 120
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 124

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Tyr Phe Ala Tyr Trp Gly Gln
            100                 105                 110

Gly Thr Leu Val Thr Val Ser Ser
        115                 120

<210> SEQ ID NO 125
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
            100                 105                 110

Gly Thr Leu Val Thr Val Ser Ser
        115                 120

<210> SEQ ID NO 126
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Val Val Met Thr Gln Thr Pro Leu Ser Leu Pro Val Ser Leu Gly
1               5                   10                  15
```

Asp Gln Ala Ser Ile Ser Cys Arg Ser Ser Gln Ser Leu Val His Ser
                20                  25                  30

Tyr Gly Asn Thr Tyr Leu Tyr Trp Tyr Leu Gln Lys Pro Gly Gln Ser
            35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

<210> SEQ ID NO 127
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Tyr Gly Asn Thr Tyr Leu Tyr Trp Tyr Gln Gln Arg Pro Gly Gln Ser
            35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Lys Val Glu Ile Lys
            100                 105                 110

<210> SEQ ID NO 128
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Tyr Gly Asn Thr Tyr Leu Tyr Trp Phe Gln Gln Arg Pro Gly Gln Ser
            35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

```
Thr His Val Pro Tyr Thr Phe Gly Gly Gly Thr Lys Val Glu Ile Lys
            100                 105                 110
```

<210> SEQ ID NO 129
<211> LENGTH: 393
<212> TYPE: PRT
<213> ORGANISM: Homo sapiens

<400> SEQUENCE: 129

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365
```

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 130
<211> LENGTH: 2512
<212> TYPE: DNA
<213> ORGANISM: Homo sapiens

<400> SEQUENCE: 130

| | | | | |
|---|---|---|---|---|
| ctcaaaagtc | tagagccacc | gtccagggag | caggtagctg | ctgggctccg gggacacttt | 60 |
| gcgttcgggc | tgggagcgtg | cttttccacga | cggtgacacg | cttccctgga ttggcagcca | 120 |
| gactgccttc | cgggtcactg | ccatggagga | gccgcagtca | gatcctagcg tcgagccccc | 180 |
| tctgagtcag | gaaacatttt | cagacctatg | gaaactactt | cctgaaaaca cgttctgtc | 240 |
| cccttgccg | tcccaagcaa | tgatgatttt | gatgctgtcc | ccggacgata ttgaacaatg | 300 |
| gttcactgaa | gacccaggtc | cagatgaagc | tcccagaatg | ccagaggctg ctcccccgt | 360 |
| ggcccctgca | ccagcagctc | ctacaccggc | ggccctgca | ccagccccct cctggccct | 420 |
| gtcatcttct | gtcccttccc | agaaaaccta | ccagggcagc | tacggtttcc gtctgggctt | 480 |
| cttgcattct | gggacagcca | agtctgtgac | ttgcacgtac | tccctgccc tcaacaagat | 540 |
| gttttgccaa | ctggccaaga | cctgccctgt | gcagctgtgg | gttgattcca ccccccgcc | 600 |
| cggcacccgc | gtccgcgcca | tggccatcta | caagcagtca | cagcacatga cggaggttgt | 660 |
| gaggcgctgc | ccccaccatg | agcgctgctc | agatagcgat | ggtctggccc tcctcagca | 720 |
| tcttatccga | gtggaaggaa | atttgcgtgt | ggagtatttg | gatgacagaa acactttcg | 780 |
| acatagtgtg | gtggtgccct | atgagccgcc | tgaggttggc | tctgactgta ccaccatcca | 840 |
| ctacaactac | atgtgtaaca | gttcctgcat | gggcggcatg | aaccggaggc catcctcac | 900 |
| catcatcaca | ctggaagact | ccagtggtaa | tctactggga | cggaacagct ttgaggtgcg | 960 |
| tgtttgtgcc | tgtcctggga | gagaccggcg | cacagaggaa | gagaatctcc gcaagaaagg | 1020 |
| ggagcctcac | cacgagctgc | ccccagggag | cactaagcga | gcactgccca caacaccag | 1080 |
| ctcctctccc | cagccaaaga | gaaaaccact | ggatggagaa | tatttcaccc ttcagatccg | 1140 |
| tgggcgtgag | cgcttcgaga | tgttccgaga | gctgaatgag | gccttggaac tcaaggatgc | 1200 |
| ccaggctggg | aaggagccag | gggggagcag | ggctcactcc | agccacctga gtccaaaaa | 1260 |
| gggtcagtct | acctcccgcc | ataaaaaact | catgttcaag | acagaagggc ctgactcaga | 1320 |
| ctgacattct | ccacttcttg | ttccccactg | acagcctccc | accccatct ctccctcccc | 1380 |
| tgccattttg | ggttttgggt | ctttgaaccc | ttgcttgcaa | taggtgtgcg tcagaagcac | 1440 |
| ccaggacttc | catttgcttt | gtcccggggc | tccactgaac | aagttggcct gcactggtgt | 1500 |
| tttgttgtgg | ggaggaggat | ggggagtagg | acataccagc | ttagatttta aggttttac | 1560 |
| tgtgagggat | gtttgggaga | tgtaagaaat | gttcttgcag | ttaagggtta gtttacaatc | 1620 |
| agccacattc | taggtagggg | cccacttcac | cgtactaacc | agggaagctg tccctcactg | 1680 |
| ttgaattttc | tctaacttca | aggcccatat | ctgtgaaatg | ctggcatttg cacctacctc | 1740 |
| acagagtgca | ttgtgagggt | taatgaaata | atgtacatct | ggccttgaaa ccaccttta | 1800 |
| ttacatgggg | tctagaactt | gaccccttg | agggtgcttg | ttccctctcc ctgttggtcg | 1860 |
| gtgggttggt | agtttctaca | gttgggcagc | tggttaggta | gagggagttg tcaagtctct | 1920 |

```
gctggcccag ccaaaccctg tctgacaacc tcttggtgaa ccttagtacc taaaaggaaa    1980
tctcacccca tcccacaccc tggaggattt catctcttgt atatgatgat ctggatccac    2040
caagacttgt tttatgctca gggtcaattt cttttttctt tttttttttt tttttctttt    2100
ttctttgaga ctgggtctcg ctttgttgcc caggctggag tggagtggcg tgatcttggc    2160
ttactgcagc ctttgcctcc ccggctcgag cagtcctgcc tcagcctccg gagtagctgg    2220
gaccacaggt tcatgccacc atggccagcc aacttttgca tgttttgtag agatggggtc    2280
tcacagtgtt gcccaggctg gtctcaaact cctgggctca ggcgatccac ctgtctcagc    2340
ctcccagagt gctgggatta caattgtgag ccaccacgtc cagctggaag ggtcaacatc    2400
ttttacattc tgcaagcaca tctgcatttt cacccacacc cttccctcct tctcccttttt   2460 tatatcccat ttttatatcg atctcttatt ttacaataaa actttgctgc ca            2512
```

<210> SEQ ID NO 131
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
        115
```

<210> SEQ ID NO 132
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Phe Gln Gly
                    85                  90                  95
Ser His Val Pro Tyr Thr Phe Gly Gln Gly Thr Lys Leu Glu Ile Lys
                100                 105                 110

<210> SEQ ID NO 133
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Arg Ser Ser Gln Ser Ile Val Tyr Ser Asn Gly Asn Thr Tyr Leu Gly
1               5                   10                  15

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Tyr Thr Phe Thr Asn Tyr Asn
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ile Tyr Pro Gly Asn Asp Asp Thr
1               5

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Arg Gly Gly Tyr Arg Ala Met Asp Tyr
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Ser Ile Val Tyr Ser Asn Gly Asn Thr Tyr
1               5                   10
```

```
<210> SEQ ID NO 138
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys Val Ser
1

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Phe Gln Gly Ser His Val Pro Tyr Thr
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Tyr Thr Phe Thr Asn Tyr
1               5

<210> SEQ ID NO 141
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Pro Gly Asn Asp
1

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Tyr Arg Ala Met Asp
1               5

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143
```

```
Ser Gln Ser Ile Val Tyr Ser Asn Gly Asn Thr Tyr
1               5                   10
```

<210> SEQ ID NO 144
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

```
Lys Val Ser
1
```

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

```
Gly Ser His Val Pro Tyr
1               5
```

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

```
Ala Ser Gly Tyr Thr Phe Thr Asn Tyr Asn
1               5                   10
```

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

```
Ile Tyr Pro Gly Asn Asp Asp Thr Ser Tyr Asn Gln Lys Phe Lys Asp
1               5                   10                  15

Arg
```

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Gly Gly Tyr Arg Ala Met Asp
1               5
```

<210> SEQ ID NO 149
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Ser Gln Ser Ile Val Tyr Ser Asn Gly Asn Thr Tyr
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Lys Val Ser Asn Arg Phe Ser Gly Val Pro Asp Arg
1               5                   10

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Ser His Val Pro Tyr
1               5

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Arg Arg Cys Pro Leu Tyr Ile Ser Tyr Asp Pro Val Cys Arg Arg
1               5                   10                  15

<210> SEQ ID NO 153
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Arg Arg Arg Arg Cys Pro Leu Tyr Ile Ser Tyr Asp Pro Val Cys Arg
1               5                   10                  15

Arg Arg Arg
```